(12) United States Patent
Kajino et al.

(10) Patent No.: US 10,308,605 B2
(45) Date of Patent: *Jun. 4, 2019

(54) PROTON PUMP INHIBITORS

(71) Applicant: Takeda Pharmaceutical Company Limited

(72) Inventors: Masahiro Kajino, Osaka (JP); Atsushi Hasuoka, Kanagawa (JP); Naoki Tarui, Kanagawa (JP); Terufumi Takagi, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/450,191

(22) Filed: Aug. 1, 2014

(65) Prior Publication Data

US 2014/0343070 A1 Nov. 20, 2014

Related U.S. Application Data

(60) Continuation of application No. 12/873,971, filed on Sep. 1, 2010, now abandoned, which is a division of
(Continued)

(30) Foreign Application Priority Data

Sep. 30, 2004 (JP) .................. 2004-289169
Feb. 21, 2005 (JP) .................. 2005-044740

(51) Int. Cl.
| | |
|---|---|
| *C07D 207/48* | (2006.01) |
| *C07D 409/04* | (2006.01) |
| *C07D 401/12* | (2006.01) |
| *C07D 403/12* | (2006.01) |
| *C07D 417/12* | (2006.01) |
| *C07D 401/04* | (2006.01) |
| *C07D 405/12* | (2006.01) |
| *A61K 31/4439* | (2006.01) |
| *A61K 31/4025* | (2006.01) |
| *A61K 31/41* | (2006.01) |
| *A61K 31/501* | (2006.01) |

(Continued)

(52) U.S. Cl.
CPC ........ *C07D 207/48* (2013.01); *A61K 31/4025* (2013.01); *A61K 31/41* (2013.01); *A61K 31/4439* (2013.01); *A61K 31/501* (2013.01); *A61K 31/506* (2013.01); *C07D 207/335* (2013.01); *C07D 401/04* (2013.01); *C07D 401/12* (2013.01); *C07D 403/04* (2013.01); *C07D 403/12* (2013.01); *C07D 405/04* (2013.01); *C07D 405/12* (2013.01); *C07D 409/04* (2013.01); *C07D 409/12* (2013.01); *C07D 417/12* (2013.01); *C07D 487/04* (2013.01)

(58) Field of Classification Search
None
See application file for complete search history.

(56) References Cited

U.S. PATENT DOCUMENTS

| 5,286,742 A | 2/1994 | Henegar et al. |
| 5,331,006 A | 7/1994 | Horwell et al. |

(Continued)

FOREIGN PATENT DOCUMENTS

| EP | 0259085 A1 | 3/1988 |
| EP | 0464845 A1 | 1/1992 |

(Continued)

*Primary Examiner* — Bong-Sook Baek
(74) *Attorney, Agent, or Firm* — Mintz Levin Cohn Ferris Glovsky and Popeo, P.C.; David G. Conlin; Joohee Lee

(57) ABSTRACT

A proton pump inhibitor containing a compound represented by the formula (I)

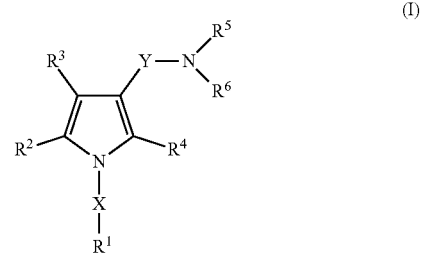

wherein X and Y are the same or different and each is a bond or a spacer having 1 to 20 carbon atoms in the main chain, $R^1$ is an optionally substituted hydrocarbon group or an optionally substituted heterocyclic group, $R^2$, $R^3$ and $R^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, $R^5$ and $R^6$ are the same or different and each is a hydrogen atom or an optionally substituted hydrocarbon group, which has a superior proton pump action and shows an antiulcer activity and the like after conversion to a proton pump inhibitor in the body, or a salt thereof, or a prodrug thereof is provided.

3 Claims, No Drawings

Related U.S. Application Data application No. 11/664,346, filed as application No. PCT/JP2005/018572 on Sep. 30, 2005, now Pat. No. 8,048,909.

(51) Int. Cl.

| | |
|---|---|
| *A61K 31/506* | (2006.01) |
| *C07D 207/335* | (2006.01) |
| *C07D 403/04* | (2006.01) |
| *C07D 405/04* | (2006.01) |
| *C07D 409/12* | (2006.01) |
| *C07D 487/04* | (2006.01) |

(56) References Cited

U.S. PATENT DOCUMENTS

| | | | |
|---|---|---|---|
| 5,480,902 A | 1/1996 | Addor et al. | |
| 5,510,320 A * | 4/1996 | Tseng | A01N 47/38 504/273 |
| 6,365,620 B2 | 4/2002 | Eberle et al. | |
| 7,932,272 B2 | 4/2011 | Nakamoto et al. | |
| 2002/0193410 A1 | 12/2002 | Burns et al. | |
| 2007/0105943 A1 | 5/2007 | Nakamoto et al. | |
| 2008/0139639 A1 | 6/2008 | Kajino et al. | |
| 2009/0227799 A1 | 9/2009 | Nakamoto et al. | |
| 2011/0195999 A1 | 8/2011 | Nakamoto et al. | |

FOREIGN PATENT DOCUMENTS

| | | |
|---|---|---|
| EP | 0538231 A1 | 4/1993 |
| EP | 0597291 A1 | 5/1994 |
| EP | 1061075 A2 | 12/2000 |
| EP | 1284260 A1 | 2/2003 |
| EP | 1432693 A2 | 6/2004 |
| EP | 1466902 A1 | 10/2004 |
| JP | 63-63678 | 3/1988 |
| JP | 08-119936 | 5/1996 |
| JP | 09-030967 | 2/1997 |
| JP | 9-30967 | 2/1997 |
| JP | 11-209344 | 8/1999 |
| JP | 2004-315511 A | 11/2004 |
| WO | 92-04025 A1 | 3/1992 |
| WO | 93/09100 A1 | 5/1993 |
| WO | 98/28269 A1 | 7/1998 |
| WO | 00/058285 A1 | 10/2000 |
| WO | 02/02524 | 1/2002 |
| WO | 02/02554 | 1/2002 |
| WO | 03/28641 A2 | 4/2003 |
| WO | 03/040147 A1 | 5/2003 |
| WO | 03/044011 A1 | 5/2003 |
| WO | 03/068738 A1 | 8/2003 |
| WO | 03/068740 A1 | 8/2003 |
| WO | 04/014368 A1 | 2/2004 |
| WO | 04/103968 A1 | 12/2004 |
| WO | WO 2004/103968 * | 12/2004 |

* cited by examiner

PROTON PUMP INHIBITORS

CROSS REFERENCE TO RELATED APPLICATIONS

This application is a continuation of U.S. patent application Ser. No. 12/873,971, filed Sep. 1, 2010, pending, which is a divisional of U.S. patent application Ser. No. 11/664,346, filed Mar. 30, 2007, now U.S. Pat. No. 8,048,909, issued Nov. 1, 2011, which is the National Phase application of PCT International Application No. PCT/JP2005/018572, filed Sep. 30, 2005, which claims priority to Japanese Patent Application No. 2005-044740, filed Feb. 21, 2005, and Japanese Patent Application No. 2004-289169, filed Sep. 30, 2004. The contents of the foregoing applications are incorporated herein by reference in their entirety.

TECHNICAL FIELD

The present invention relates to pyrrole compounds having a proton pump inhibitory activity.

BACKGROUND ART

Proton pump inhibitors represented by omeprazole, which suppress secretion of gastric acid for the treatment of peptic ulcer, reflux esophagitis and the like, have been widely used in clinical situations. However, the existing proton pump inhibitors are associated with problems in terms of effect and side effects. To be specific, since the existing proton pump inhibitors are unstable under acidic conditions, they are often formulated as enteric preparations, in which case several hours are required before expression of the effect. In addition, since the existing proton pump inhibitors show inconsistent treatment effects due to metabolic enzyme polymorphism and drug interaction with pharmaceutical agents such as diazepam and the like, an improvement has been desired.

As pyrrole compounds having a proton pump inhibitory action, EP-A-0259085 describes a compound represented by the formula:

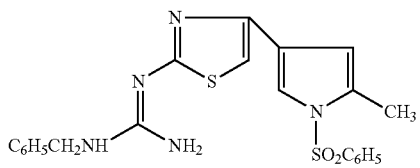

and the like.

As a production intermediate for a compound having a CCK antagonistic action, WO92/04025 describes a compound represented by the formula:

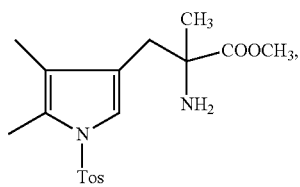

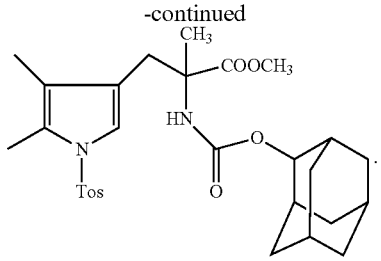

As compounds having a thromboxane A2 (TXA2) antagonistic action and a TXA2 synthase inhibitory action, JP-A-8-119936 describes a compound represented by the formula:

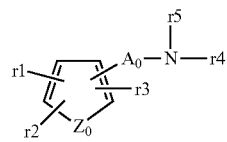

wherein r1 is carboxy, protected carboxy, carboxy(lower)alkyl, protected carboxy(lower)alkyl, carboxy(lower)alkenyl or protected carboxy(lower)alkenyl, r2 is hydrogen; lower alkyl; heterocyclic (lower)alkyl optionally having aminoimino or protected aminoimino; heterocyclic (lower)alkenyl; or heterocyclic carbonyl, r3 is hydrogen or lower alkyl, r4 is acyl, r5 is hydrogen, $A_0$ is lower alkylene, and $Z_0$ is S or NH, provided when r1 is carboxy or protected carboxy, then $Z_0$ is NH.

Moreover, as a therapeutic drug for neoplastic diseases or autoimmune diseases, WO2004/103968 describes a compound represented by the formula:

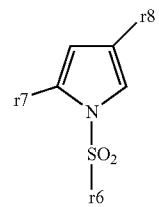

wherein r6 is aryl, aralkyl or heteroaryl, r7 is aryl or heteroaryl, and r8 is aryl, heteroaryl or an optionally substituted aminomethyl.

A pharmaceutical agent that effectively suppresses gastric acid secretion as known proton pump inhibitors, which is improved in instability under acidic conditions, dispersion of effects due to metabolic enzyme polymorphism and drug interaction, which are problems of known proton pump inhibitors, is expected to show more superior treatment effect on peptic ulcer, reflux esophagitis and the like. As the situation stands, however, a proton pump inhibitor capable of sufficiently satisfying these requirements has not been found. It is therefore an object of the present invention to provide a compound having a superior acid secretion suppressive effect (particularly, an acid secretion suppressive effect based on proton pump inhibition), which has been improved in these problems.

DISCLOSURE OF THE INVENTION

The present inventors have conducted various studies and found that a compound represented by the formula (I):

3

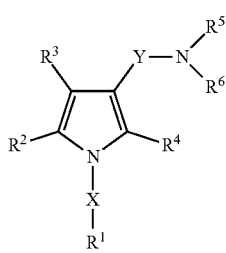

(I)

wherein
X and Y are the same or different and each is a bond or a spacer having 1 to 20 atoms in the main chain,
$R^1$ is an optionally substituted hydrocarbon group or an optionally substituted heterocyclic group,
$R^2$, $R^3$ and $R^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and
$R^5$ and $R^6$ are the same or different and each is a hydrogen atom or an optionally substituted hydrocarbon group,
or a salt thereof [hereinafter to be abbreviated as compound (I)] unexpectedly has a very strong proton pump inhibitory effect, and is fully satisfactory as a pharmaceutical agent, which resulted in the completion of the present invention.

Accordingly, the present invention relates to the following.

[1] A proton pump inhibitor comprising a compound represented by the formula (I)

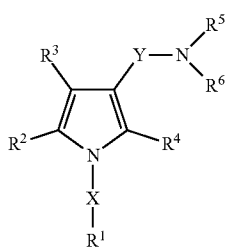

(I)

wherein
X and Y are the same or different and each is a bond or a spacer having 1 to 20 atoms in the main chain,
$R^1$ is an optionally substituted hydrocarbon group or an optionally substituted heterocyclic group,
$R^2$, $R^3$ and $R^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and
$R^5$ and $R^6$ are the same or different and each is a hydrogen atom or an optionally substituted hydrocarbon group,
or a salt thereof, or a prodrug thereof,

4

[2] the inhibitor of the above-mentioned [1], wherein X is $-SO_2-$, $-SO_2-N(R^7)-$ (wherein $R^7$ is a hydrogen atom or an optionally substituted hydrocarbon group), $-N(R^8)-SO_2-$ (wherein $R^8$ is a hydrogen atom or an optionally substituted hydrocarbon group), $-N(R^9)-$ (wherein $R^9$ is a hydrogen atom or an optionally substituted hydrocarbon group) or $-O-$,

[3] the inhibitor of the above-mentioned [1], wherein X is $-SO_2-$,

[4] an agent for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal anti-inflammatory agent or gastric hyperacidity and ulcer due to postoperative stress; an inhibitor of upper gastrointestinal hemorrhage due to peptic ulcer, acute stress ulcer, hemorrhagic gastritis or invasive stress, which comprises the proton pump inhibitor of the above-mentioned [1],

[5] a compound represented by the formula (II-a)

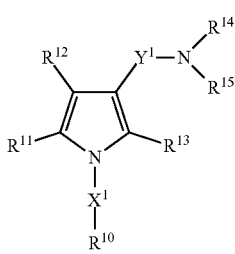

(II-a)

wherein
$X^1$ is $-SO_2-$, $-SO_2-N(R^7)-$ (wherein $R^7$ is a hydrogen atom or an optionally substituted hydrocarbon group), $-N(R^8)-SO_2-$ (wherein $R^8$ is a hydrogen atom or an optionally substituted hydrocarbon group), $-N(R^9)-$ (wherein $R^9$ is a hydrogen atom or an optionally substituted hydrocarbon group) or $-O-$,
$Y^1$ is an optionally substituted alkylene group, $R^{10}$ is an optionally substituted hydrocarbon group or an optionally substituted heterocyclic group,
$R^{11}$ is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group,
$R^{12}$ and $R^{13}$ are each independently a hydrogen atom, an optionally substituted hydrocarbon group, an acyl group, a halogen atom, a cyano group or a nitro group (provided that $R^{12}$ and $R^{13}$ are not simultaneously hydrogen atoms), and $R^{14}$ and $R^{15}$ are each independently a hydrogen atom or an optionally substituted hydrocarbon group,
with the proviso that 3-[[2,3-dimethyl-1-(4-methylphenyl)sulfonyl]-1H-pyrrol-4-yl]-2-methyl-alanine methyl ester is excluded,
or a salt thereof,

[6] a compound represented by the formula (II-b)

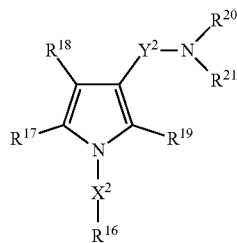

(II-b)

wherein
X² is a —SO₂—N(R⁷)— (wherein R⁷ is a hydrogen atom or an optionally substituted hydrocarbon group), —N(R⁸)—SO₂— (wherein R⁸ is a hydrogen atom or an optionally substituted hydrocarbon group), —N(R⁹)— (wherein R⁹ is a hydrogen atom or an optionally substituted hydrocarbon group) or —O—,
Y² is an optionally substituted alkylene group,
R¹⁶ is an optionally substituted hydrocarbon group or an optionally substituted heterocyclic group,
R¹⁷ is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group,
R¹⁸ and R¹⁹ are each a hydrogen atom, and
R²⁰ and R²¹ are each independently a hydrogen atom or an optionally substituted hydrocarbon group,
provided that R¹⁷ should not be a 1,3-dioxaindan-6-yl group, or a salt thereof,
[7] a compound represented by the formula (II-c)

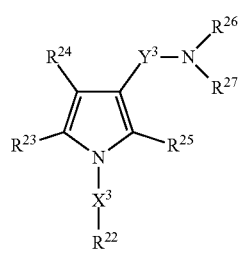

(II-c)

wherein
X³ is a —SO₂—,
Y³ is a methylene group (—CH₂—),
R²² is an alkyl group, an optionally substituted phenyl group or an optionally substituted thienyl group,
R²³ is an optionally substituted C₆₋₁₄ aryl group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group,
R²⁴ and R²⁵ are each a hydrogen atom,
R²⁶ is a hydrogen atom or a methyl group, and
R²⁷ is a methyl group,
or a salt thereof,

[8] a compound selected from
N-methyl-1-[1-(phenylsulfonyl)-5-(3-thienyl)-1H-pyrrol-3-yl]methanamine,
N-methyl-1-[5-phenyl-1-(3-thienylsulfonyl)-1H-pyrrol-3-yl]methanamine,
N-methyl-1-(1-{[3-(methylsulfonyl)phenyl]sulfonyl}-5-phenyl-1H-pyrrol-3-yl)methanamine,
1-[1-(1-benzothien-2-ylsulfonyl)-5-phenyl-1H-pyrrol-3-yl]-N-methylmethanamine,
1-[5-(2-fluorophenyl)-1-{[3-(methylsulfonyl)phenyl]sulfonyl}-1H-pyrrol-3-yl]-N-methylmethanamine,
1-{5-(2-fluorophenyl)-1-[(2-fluorophenyl)sulfonyl]-1H-pyrrol-3-yl}-N-methylmethanamine and
N-methyl-3-({4-[(methylamino)methyl]-2-phenyl-1H-pyrrol-1-yl}sulfonyl)benzamide,
or a salt thereof,
[9] a prodrug of the compound of any of the abovementioned [5] to [7],
[10] a pharmaceutical agent comprising the compound of any of the above-mentioned [5] to [7] or a prodrug thereof,
[11] the pharmaceutical agent of the above-mentioned [10], which is an agent for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal anti-inflammatory agent or gastric hyperacidity and ulcer due to postoperative stress; or an inhibitor of upper gastrointestinal hemorrhage due to peptic ulcer, acute stress ulcer, hemorrhagic gastritis or invasive stress,
[12] a method for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal anti-inflammatory agent or gastric hyperacidity and ulcer due to postoperative stress; or a method of inhibiting upper gastrointestinal hemorrhage due to peptic ulcer, acute stress ulcer, hemorrhagic gastritis or invasive stress, which comprises administering an effective amount of the compound of any of the abovementioned [5] to [7] or a prodrug thereof to the mammal, and
[13] use of the compound of any of the above-mentioned [5] to [7] or a prodrug thereof, for the production of an agent for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal antiinflammatory agent or gastric hyperacidity and ulcer due to postoperative stress; an inhibitor of upper gastrointestinal hemorrhage due to peptic ulcer, acute stress ulcer, hemorrhagic gastritis or invasive stress.

In another embodiment, the present invention relates to [13] a proton pump inhibitor comprising a compound represented by the formula (I⁰)

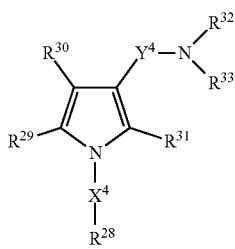

$(I^0)$ wherein $X^4$ and $Y^4$ are the same or different and each is a bond or a spacer having 1 to 20 atoms in the main chain, $R^{28}$ is an optionally substituted hydrocarbon group, $R^{29}$, $R^{30}$ and $R^{31}$ are the same or different and each is a hydrogen atom or an optionally substituted hydrocarbon group, an acyl group, a halogen atom, a cyano group or a nitro group, $R^{32}$ and $R^{33}$ are the same or different and each is a hydrogen atom or an optionally substituted hydrocarbon group, or a salt thereof, or a prodrug thereof,

[14] the inhibitor of the above-mentioned [13], wherein $X^4$ is $-SO_2-$, $-SO_2-N(R^7)-$ (wherein $R^7$ is a hydrogen atom or an optionally substituted hydrocarbon group), $-N(R^8)-SO_2-$ (wherein $R^8$ is a hydrogen atom or an optionally substituted hydrocarbon group), $-N(R^9)-$ (wherein $R^9$ is a hydrogen atom or an optionally substituted hydrocarbon group) or $-O-$,

[15] the inhibitor of the above-mentioned [13], wherein $X^4$ is $-SO_2-$,

[16] an agent for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal anti-inflammatory agent or gastric hyperacidity and ulcer due to postoperative stress; an inhibitor of upper gastrointestinal hemorrhage due to peptic ulcer, acute stress ulcer, hemorrhagic gastritis or invasive stress, which comprises the proton pump inhibitor of the above-mentioned [13],

[17] a compound represented by the formula (II)

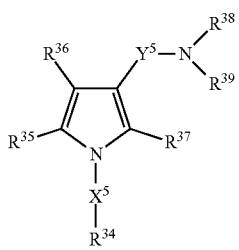

(II)

wherein $X^5$ is $-SO_2-$, $-SO_2-N(R^7)-$ (wherein $R^7$ is a hydrogen atom or an optionally substituted hydrocarbon group), $-N(R^8)-SO_2-$ (wherein $R^8$ is a hydrogen atom or an optionally substituted hydrocarbon group), $-N(R^9)-$ (wherein $R^9$ is a hydrogen atom or an optionally substituted hydrocarbon group) or $-O-$, $Y^5$ is an optionally substituted alkylene group, $R^{34}$ is an optionally substituted hydrocarbon group, $R^{35}$ is a hydrogen atom or an optionally substituted hydrocarbon group, $R^{36}$ and $R^{37}$ are each independently a hydrogen atom, an optionally substituted hydrocarbon group, an acyl group, a halogen atom, a cyano group or a nitro group, $R^{38}$ and $R^{39}$ are each independently a hydrogen atom or an optionally substituted hydrocarbon group, Provided that $R^{35}$ and/or $R^{37}$ should not be a 1,3-dioxaindan-6-yl group, with the proviso that 3-[[2,3-dimethyl-1-(4-methylphenyl)sulfonyl]-1H-pyrrol-4-yl]-2-methyl-alanine methyl ester is excluded, or a salt thereof,

[18] the compound of the above-mentioned [17], wherein $X^5$ is $-SO_2-$,

[19] a prodrug of the compound of the above-mentioned [17],

[20] a pharmaceutical agent comprising the compound of the above-mentioned [17] or a prodrug thereof,

[21] the pharmaceutical agent of the above-mentioned [20], which is an agent for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal anti-inflammatory agent or gastric hyperacidity and ulcer due to postoperative stress; or an inhibitor of upper gastrointestinal hemorrhage due to peptic ulcer, acute stress ulcer, hemorrhagic gastritis or invasive stress,

[22] a method for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal anti-inflammatory agent or gastric hyperacidity and ulcer due to postoperative stress; or a method of inhibiting upper gastrointestinal hemorrhage due to peptic ulcer, acute stress ulcer, hemorrhagic gastritis or invasive stress, which comprises administering an effective amount of the compound of any of the above-mentioned [17] or a prodrug thereof to the mammal, and

[23] use of the compound of any of the above-mentioned [17] or a prodrug thereof, for the production of an agent for the prophylaxis or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by a non-steroidal anti-inflammatory agent or gastric hyperacidity and ulcer due to postoperative stress; an inhibitor of upper gastrointestinal hemorrhage due to peptic ulcer, acute stress ulcer, hemorrhagic gastritis or invasive stress.

BEST MODE FOR EMBODYING THE INVENTION

In the formula (I), the "spacer having 1 to 20 atoms in the main chain" for X or Y means a divalent group having 1 to 20 contiguous atoms in the main chain. Here, the "atoms in the main chain" is counted such that the number of atoms in the main chain becomes minimum.

As the "spacer having 1 to 20 atoms in the main chain", for example, a divalent group that can be formed with 1 to 5 (preferably 1 to 3) contiguous groups selected from
—O—;
—S—;
—CO—;
—SO—;
—SO$_2$—;
—NR$^{40}$— (wherein R$^{40}$ is a hydrogen atom, an optionally substituted hydrocarbon group, an optionally substituted (e.g., halogenated) C$_{1-6}$ alkyl-carbonyl, or an optionally substituted (e.g., halogenated) C$_{1-6}$ alkylsulfonyl); and a divalent C$_{1-6}$ aliphatic hydrocarbon group optionally having substituent(s)
and the like can be mentioned.

As the "hydrocarbon group" of the "optionally substituted hydrocarbon group" for R$^{40}$, for example, a chain or cyclic hydrocarbon group (e.g., alkyl, alkenyl, alkynyl, cycloalkyl, aryl, aralkyl etc.) can be mentioned. Of these, a chain or cyclic hydrocarbon group having 1 to 16 carbon atoms and the like are preferable.

As the "alkyl", for example, C$_{1-6}$ alkyl (e.g., methyl, ethyl, propyl, isopropyl, butyl, isobutyl, sec-butyl, tert-butyl, pentyl, hexyl etc.) and the like can be mentioned.

As the "alkenyl", for example, C$_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like can be mentioned.

As the "alkynyl", for example, C$_{2-6}$ alkynyl (e.g., ethynyl, propargyl, 1-butynyl, 2-butynyl, 3-butynyl, 1-hexynyl etc.) and the like can be mentioned.

As the "cycloalkyl", for example, C$_{3-7}$ cycloalkyl (e.g., cyclopropyl, cyclobutyl, cyclopentyl, cyclohexyl, cycloheptyl etc.) and the like can be mentioned.

As the "aryl", for example, C$_{6-14}$ aryl (e.g., phenyl, 1-naphthyl, 2-naphthyl, 2-biphenylyl, 3-biphenylyl, 4-biphenylyl, 2-anthryl etc.) and the like can be mentioned.

As the "aralkyl", for example, C$_{7-16}$ aralkyl (e.g., phenyl-C$_{1-6}$ alkyl, naphthyl-C$_{1-6}$ alkyl or diphenyl-C$_{1-4}$ alkyl etc. such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like can be mentioned.

When the above-mentioned hydrocarbon group is an alkyl, an alkenyl or an alkynyl, the hydrocarbon group is optionally substituted by 1 to 3 substituents selected from (1) a halogen atom (e.g., a fluorine atom, a chlorine atom, a bromine atom, an iodine atom etc.), (2) nitro, (3) cyano, (4) hydroxy, (5) C$_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., a fluorine atom, a chlorine atom, a bromine atom, an iodine atom), (6) C$_{6-14}$ aryloxy (e.g., phenyloxy, naphthyloxy etc.), (7) C$_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) C$_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., a fluorine atom, a chlorine atom, a bromine atom, an iodine atom), (10) C$_{6-14}$ arylthio (e.g., phenylthio, naphthylthio etc.), (11) C$_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-C$_{1-6}$ alkylamino (e.g., methylamino, ethylamino etc.), (14) mono-C$_{6-14}$ arylamino (e.g., phenylamino, 1-naphthylamino, 2-naphthylamino etc.), (15) mono-C$_{7-16}$ aralkylamino (e.g., benzylamino etc.), (16) di-C$_{1-6}$ alkylamino (e.g., dimethylamino, diethylamino etc.), (17) di-C$_{6-14}$ arylamino (e.g., diphenylamino etc.), (18) di-C$_{7-16}$ aralkylamino (e.g., dibenzylamino etc.), (19) formyl, (20) C$_{1-6}$ alkyl-carbonyl (e.g., acetyl, propionyl etc.), (21) C$_{6-14}$ aryl-carbonyl (e.g., benzoyl, 1-naphthoyl, 2-naphthoyl etc.), (22) carboxyl, (23) C$_{1-6}$ alkoxy-carbonyl (e.g., methoxycarbonyl, ethoxycarbonyl, propoxycarbonyl, tert-butoxycarbonyl etc.), (24) C$_{6-14}$ aryloxy-carbonyl (e.g., phenoxycarbonyl etc.), (25) carbamoyl, (26) thiocarbamoyl, (27) mono-C$_{1-6}$ alkyl-carbamoyl (e.g., methylcarbamoyl, ethylcarbamoyl etc.), (28) di-C$_{1-6}$ alkyl-carbamoyl (e.g., dimethylcarbamoyl, diethylcarbamoyl, ethylmethylcarbamoyl etc.), (29) C$_{6-14}$ aryl-carbamoyl (e.g., phenylcarbamoyl, 1-naphthylcarbamoyl, 2-naphthylcarbamoyl etc.), (30) C$_{1-6}$ alkylsulfonyl (e.g., methylsulfonyl, ethylsulfonyl etc.), (31) C$_{6-14}$ arylsulfonyl (e.g., phenylsulfonyl, 1-naphthylsulfonyl, 2-naphthylsulfonyl etc.), (32) C$_{1-6}$ alkylsulfinyl (e.g., methylsulfinyl, ethylsulfinyl etc.), (33) C$_{6-14}$ arylsulfinyl (e.g., phenylsulfinyl, 1-naphthylsulfinyl, 2-naphthylsulfinyl etc.), (34) formylamino, (35) C$_{1-6}$ alkyl-carbonylamino (e.g., acetylamino etc.), (36) C$_{6-14}$ aryl-carbonylamino (e.g., benzoylamino, naphthoylamino etc.), (37) C$_{1-6}$ alkoxy-carbonylamino (e.g., methoxycarbonylamino, ethoxycarbonylamino, propoxycarbonylamino, butoxycarbonylamino etc.), (38) C$_{1-6}$ alkylsulfonylamino (e.g., methylsulfonylamino, ethylsulfonylamino etc.), (39) C$_{6-14}$ arylsulfonylamino (e.g., phenylsulfonylamino, 2-naphthylsulfonylamino, 1-naphthylsulfonylamino etc.), (40) C$_{1-6}$ alkyl-carbonyloxy (e.g., acetoxy, propionyloxy etc.), (41) C$_{6-14}$ aryl-carbonyloxy (e.g., benzoyloxy, naphthylcarbonyloxy etc.), (42) C$_{1-6}$ alkoxy-carbonyloxy (e.g., methoxycarbonyloxy, ethoxycarbonyloxy, propoxycarbonyloxy, butoxycarbonyloxy etc.), (43) mono-C$_{1-6}$ alkyl-carbamoyloxy (e.g., methylcarbamoyloxy, ethylcarbamoyloxy etc.), (44) di-C$_{1-6}$ alkyl-carbamoyloxy (e.g., dimethylcarbamoyloxy, diethylcarbamoyloxy etc.), (45) C$_{6-14}$ aryl-carbamoyloxy (e.g., phenylcarbamoyloxy, naphthylcarbamoyloxy etc.), (46) a 5- to 7-membered saturated cyclic amino (e.g., pyrrolidin-1-yl, piperidino, piperazin-1-yl, morpholino, thiomorpholino, hexahydroazepin-1-yl etc.) optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) containing, besides carbon atom, 1 or 2 kinds of 1 to 4 hetero atoms selected from a nitrogen atom, a sulfur atom and an oxygen atom, (48) C$_{1-3}$ alkylenedioxy (e.g., methylenedioxy, ethylenedioxy etc.), and (49) C$_{3-7}$ cycloalkyl (e.g., cyclopropyl, cyclobutyl, cyclopentyl, cyclohexyl, cycloheptyl etc.) and the like.

When the above-mentioned hydrocarbon group is a cycloalkyl, an aryl or an aralkyl, the hydrocarbon group is optionally substituted by 1 to 5 (preferably 1 to 3) substituents selected from (1) a halogen atom (e.g., a fluorine atom, a chlorine atom, a bromine atom, an iodine atom etc.), (2) nitro, (3) cyano, (4) hydroxy, (5) C$_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., a fluorine atom, a chlorine atom, a bromine atom, an iodine atom), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., a fluorine atom, a chlorine atom, a bromine atom, an iodine atom), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl, trifluoromethylsulfonyl etc.) optionally having 1 to 3 halogen atoms (e.g., a fluorine atom, a chlorine atom, a bromine atom, an iodine atom), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino (e.g., pyrrolidin-1-yl, piperidino, piperazin-1-yl, morpholino, thiomorpholino, hexahydroazepin-1-yl etc.) optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) containing, besides carbon atom, 1 or 2 kinds of 1 to 4 hetero atoms selected from a nitrogen atom, a sulfur atom and an oxygen atom, (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., a fluorine atom, a chlorine atom, a bromine atom, an iodine atom) or hydroxy groups, (51) a $C_{2-6}$ alkenyl group (e.g., allyl, isopropenyl, isobutenyl, 1-methylallyl, 2-pentenyl, 2-hexenyl etc.) optionally having 1 to 3 halogen atoms (e.g., a fluorine atom, a chlorine atom, a bromine atom, an iodine atom), (52) a $C_{2-46}$ alkynyl group (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), and (54) a 5 to 10-membered heterocyclyl-carbonyl (e.g., 4-morpholinocarbonyl etc.) containing, besides carbon atom, one or two kinds of 1 to 4 heteroatoms selected from a nitrogen atom, a sulfur atom and an oxygen atom and the like.

In the present specification, the substituent of the "optionally substituted hydrocarbon group" does not include an oxo group.

As the "optionally halogenated $C_{1-6}$ alkyl-carbonyl" for $R^{40}$, for example, $C_{1-6}$ alkyl-carbonyl optionally having 1 to 5, preferably 1 to 3 halogen atoms (e.g., a fluorine atom, a chlorine atom, a bromine atom, an iodine atom and the like) at substitutable positions and the like can be mentioned. Specific examples include, for example, acetyl, monochloroacetyl, trifluoroacetyl, trichloroacetyl, propanoyl, butanoyl, pentanoyl, hexanoyl and the like can be mentioned.

As the "optionally halogenated $C_{1-6}$ alkylsulfonyl" for $R^{40}$, for example, $C_{1-6}$ alkylsulfonyl optionally having 1 to 5, preferably 1 to 3 halogen atoms (e.g., a fluorine atom, a chlorine atom, a bromine atom, an iodine atom and the like) at substitutable positions and the like can be mentioned. Specific examples include, for example, methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, sec-butylsulfonyl, tert-butylsulfonyl, pentylsulfonyl, hexylsulfonyl and the like can be mentioned.

As the "divalent $C_{1-6}$ aliphatic hydrocarbon group" of the aforementioned "divalent $C_{1-6}$ aliphatic hydrocarbon group optionally having substituent(s)", an alkylene group, an alkenylene group, an alkynylene group can be mentioned, for example, (1) a $C_{1-6}$ alkylene (e.g., —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$(CH(CH_3))_2$—, —$(CH_2)_2C(CH_3)_2$—, —$(CH_2)_3C(CH_3)_2$— and the like);

(2) a $C_{2-6}$ alkenylene (e.g., —CH=CH—, —$CH_2$—CH=CH—, —CH=CH—$CH_2$—, —CH=CH—$CH_2$—$CH_2$—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— and the like);

(3) a $C_{2-6}$ alkynylene (e.g., —C≡C—, —$CH_2$—C≡C—, —$CH_2$—C≡C—$CH_2$—$CH_2$— and the like) and the like can be mentioned.

As the "substituent" of the "divalent $C_{1-6}$ aliphatic hydrocarbon group optionally having substituent(s)", for example, those similar to the substituents of the alkyl, alkenyl or alkynyl exemplified as the aforementioned "optionally substituted hydrocarbon group" for $R^{40}$, can be mentioned, particularly, halogen atom (e.g., a fluorine atom, a chlorine atom, a bromine atom, an iodine atom), hydroxy and the like are preferable. The number of the substituents is, for example, 1 to 5, preferably 1 to 3.

As preferable examples of the "spacer having 1 to 20 atoms in the main chain"
(1) an optionally substituted alkylene group:
specifically, a $C_{1-20}$ alkylene (e.g., —$CH_2$—, —$(CH_2)_2$—, —$(CH_2)_3$—, —$CH(OH)$—$(CH_2)_2$—, —$(CH_2)_4$—, —$(CH_2)_5$—, —$(CH_2)_6$—, —$CHCH_3$—, —$C(CH_3)_2$—, —$CH(CF_3)$—, —$(CH(CH_3))_2$—, —$(CF_2)_2$—, —$(CH_2)_2C(CH_3)_2$—, —$(CH_2)_3C(CH_3)_2$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, —$(CH_2)_{20}$— and the like) optionally having 1 to 3 substituents (preferably, halogen atom, hydroxy and the like); (2) an optionally substituted alkenylene group:
specifically, a $C_{2-20}$ alkenylene (e.g., —CH=CH—, —$CH_2$—CH=CH—, —CH=CH—$CH_2$—, —CH=CH—$CH_2$—$CH_2$—, —$CH_2$—CF=CH—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— and the like) optionally having 1 to 3 substituents (preferably, halogen atom, hydroxy and the like); (3) an optionally substituted alkynylene group:
specifically, a $C_{2-20}$ alkynylene (e.g., —C≡C—, —$CH_2$—C≡C—, —$CH_2$—C≡C—$CH_2$—$CH_2$— and the like) optionally having 1 to 3 substituents (preferably, halogen atom, hydroxy and the like); (4) —$(CH_2)_{w1a}O(CH_2)_{w2a}$—, —$(CH_2)_{w1a}S(CH_2)_{w2a}$—, —$(CH_2)_{w1a}CO(CH_2)_{w2a}$—, —$(CH_2)_{w1a}SO(CH_2)_{w2a}$—, —$(CH_2)_{w1a}SO_2(CH_2)_{w2a}$—, —$(CH_2)_{w1a}NR^{40}(CH_2)_{w2a}$—; (5) —$(CH_2)_{w3a}CO$—, —$(CH_2)_{w3a}CONR^{40}(CH_2)_{w4a}$—, —$(CH_2)_{w3a}NR^{40}CO(CH_2)_{w4a}$—, —$(CH_2)_{w3a}SO_2NR^{40}(CH_2)_{w4a}$—, —$(CH_2)_{w3a}NR^{40}SO_2(CH_2)_{w4a}$—, —$(CH_2)_{w3a}COO(CH_2)_{w4a}$—; (6) —$(CH_2)_{w5a}NR^{40}CONR^{40b}(CH_2)_{w6a}$—;
wherein $R^{40}$ is as defined above; $R^{40b}$ is as defined as $R^{40}$; w1a and w2a are each an integer of 0 to 19, and w1a+w2a is 0 to 19; w3a and w4a are each an integer of 0 to 18, and w3a+w4a is 0 to 18; w5a and w6a are each an integer of 0 to 17, and w5a+w6a is 0 to 17,
and the like can be mentioned.

As the aforementioned "spacer having 1 to 20 atoms in the main chain", the following "spacer having 1 to 8 atoms in the main chain" is preferable.
(1) a $C_{1-8}$ alkylene (e.g., —$CH_2$—, —$(CH_2)_2$—, —$(CH_2)_3$—, —$CH(OH)$—$(CH_2)_2$—, —$(CH_2)_4$—, —$(CH_2)_5$—, —$(CH_2)_6$—, —$CHCH_3$—, —$C(CH_3)_2$—, —$CH(CF_3)$—, —$(CH(CH_3))_2$—, —$(CF_2)_2$—, —$(CH_2)_2C(CH_3)_2$—, —$(CH_2)_3C(CH_3)_2$— and the like) optionally having 1 to 3 substituents (preferably, halogen atom, hydroxy and the like); (2) a $C_{2-8}$ alkenylene (e.g., —CH=CH—, —$CH_2$—CH=CH—, —CH=CH—$CH_2$—, —CH=CH—$CH_2$—$CH_2$—, —$CH_2$—CF=CH—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— and the like) optionally having 1 to 3 substituents (preferably, halogen atom, hydroxy and the like); (3) a $C_{2-8}$ alkynylene (e.g., —C≡C—, —$CH_2$—C≡C—, —$CH_2$—C≡C—$CH_2$— and the like) optionally having 1 to 3 substituents (preferably, halogen atom, hydroxy and the like); (4) —$(CH_2)_{w1}O(CH_2)_{w2}$—, —$(CH_2)_{w1}S(CH_2)_{w2}$—, —$(CH_2)_{w1}CO(CH_2)_{w2}$—, —$(CH_2)_{w1}SO(CH_2)_{w2}$—, —$(CH_2)_{w1}SO_2(CH_2)_{w2}$—, —$(CH_2)_{w1}NR^{40}(CH_2)_{w2}$—; (5) —$(CH_2)_{w3}CO$—, —$(CH_2)_{w3}CONR^{40}(CH_2)_{w4}$—, —$(CH_2)_{w3}NR^{40}CO(CH_2)_{w4}$—, —$(CH_2)_{w3}SO_2NR^{40}(CH_2)_{w4}$—, —$(CH_2)_{w3}NR^{40}SO_2(CH_2)_{w4}$—, —$(CH_2)_{w3}COO(CH_2)_{w4}$—; (6) —$(CH_2)_{w5}NR^{40}CONR^{40b}(CH_2)_{w6}$—;
wherein $R^{40}$ is as defined above; $R^{40b}$ is as defined as $R^{40}$; w1 and w2 are each an integer of 0 to 5, and w1+w2 is 0 to 7; w3 and w4 are each an integer of 0 to 4, and w3+w4 is 0 to 6; w5 and w6 are each an integer of 0 to 3, and w5+w6 is 0 to 5, and the like can be mentioned.

The "spacer having 1 to 20 atoms in the main chain" is preferably the following (1) to (6).
(1) —$SO_2$—; (2) —$SO_2$—$N(R^7)$— wherein $R^7$ is a hydrogen atom or an optionally substituted hydrocarbon group, and as the "optionally substituted hydrocarbon group" for $R^7$, those similar to the aforementioned "optionally substituted hydrocarbon group" for $R^{40}$ can be mentioned; (3) —$N(R^8)$—$SO_2$— wherein $R^8$ is a hydrogen atom or an optionally substituted hydrocarbon group, and as the "optionally substituted hydrocarbon group" for $R^8$, those similar to the aforementioned "optionally substituted hydrocarbon group" for $R^{40}$ can be mentioned; (4) —$N(R^9)$— wherein $R^9$ is a hydrogen atom or an optionally substituted hydrocarbon group, and as the "optionally substituted hydrocarbon group" for $R^9$, those similar to the aforementioned "optionally substituted hydrocarbon group" for $R^{40}$ can be mentioned; (5) —O—; (6) an optionally substituted alkylene group, preferably a $C_{1-8}$ alkylene (e.g., —$CH_2$—, —$(CH_2)_2$—, —$(CH_2)_3$—, —$CH(OH)$—$(CH_2)_2$—, —$(CH_2)_4$—, —$(CH_2)_5$—, —$(CH_2)_6$—, —$CHCH_3$—, —$C(CH_3)_2$—, —$CH(CF_3)$—, —$(CH(CH_3))_2$—, —$(CF_2)_2$—, —$(CH_2)_2C(CH_3)_2$—, —$(CH_2)_3C(CH_3)_2$— and the like) optionally having 1 to 3 substituents (preferably, halogen atom, hydroxy and the like).

In the formula (I), X is preferably —$SO_2$—, —$SO_2$—N($R^7$)— (wherein $R^7$ is as defined above), —N($R^8$)—$SO_2$— (wherein $R^8$ is as defined above), —N($R^9$)— (wherein $R^9$ is as defined above) or —O—, particularly preferably —$SO_2$—.

Y is preferably a bond or a $C_{1-8}$ alkylene (e.g., —$CH_2$—, —$(CH_2)_2$—, —$(CH_2)_3$—, —$(CH_2)_4$—, —$(CH_2)_5$—, —$(CH_2)_6$—, —$CHCH_3$—, —$C(CH_3)_2$—, —$(CH(CH_3))_2$—, —$(CH_2)_2C(CH_3)_2$—, —$(CH_2)_3C(CH_3)_2$— and the like).

In the aforementioned formula (I), $R^1$ is an optionally substituted hydrocarbon group or an optionally substituted heterocyclic group.

As the "optionally substituted hydrocarbon group", those similar to the aforementioned "optionally substituted hydrocarbon group" for $R^{40}$ can be mentioned.

As the "heterocyclic group" of the "optionally substituted heterocyclic group", for example, a 3 to 8-membered heterocyclic group (preferably 5 or 6-membered heterocyclic group) containing 1 to 4 heteroatoms selected from a nitrogen atom (optionally oxidized), an oxygen atom, a sulfur atom (optionally mono- or di-oxidized) and the like; or a group formed by condensing a 3 to 8-membered heterocyclic group (preferably 5 or 6-membered heterocyclic group) containing 1 to 4 heteroatoms selected from a nitrogen atom (optionally oxidized), an oxygen atom, a sulfur atom (optionally mono- or di-oxidized) and the like, and a benzene ring or a 3 to 8-membered heterocyclic group (preferably 5 or 6-membered heterocyclic group) containing 1 to 4 heteroatoms selected from a nitrogen atom (optionally oxidized), an oxygen atom, a sulfur atom (optionally mono- or di-oxidized) and the like, preferably a group formed by condensing the 5 or 6-membered heterocyclic group and a 5 or 6-membered ring containing 1 to 4 heteroatoms selected from a nitrogen atom (optionally oxidized), an oxygen atom, a sulfur atom (optionally mono- or di-oxidized) and the like, can be mentioned.

To be specific, aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-1-, 4- or -5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein the sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), triazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein the nitrogen atom is oxidized (e.g., 2-, 3- or 4-pyridyl-N-oxide), pyridazinyl (e.g., 3- or 4-pyridazinyl), pyridazinyl wherein one or both of the nitrogen atom is oxidized (e.g., 3-, 4-, 5- or 6-pyridazinyl-N-oxide), pyrimidinyl (e.g., 2-, 4- or 5-pyrimidinyl), pyrimidinyl wherein one or both of the nitrogen atoms is(are) oxidized (e.g., 2-, 4-, 5- or 6-pyrimidinyl-N-oxide), pyrazinyl, piperidinyl (e.g., 1-, 2-, 3- or 4-piperidinyl), piperazinyl (e.g., 1- or 2-piperazinyl), indolyl (e.g., 3H-indol-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein the sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl, 2,3-dihydro-1-benzofuranyl, 2,1,3-benzothiadiazolyl, 2,3-dihydro-1,4-benzodioxin-5- or -6-yl, 1,3-benzothiazol-6-yl, 1,1-dioxido-2,3-dihydro-1-benzothien-6-yl, 1-benzothienyl and the like can be used.

As the "substituent" of the heterocyclic group, those similar to the substituents of the cycloalkyl, aryl or aralkyl exemplified as the above-mentioned "hydrocarbon group" for $R^{40}$, can be mentioned. The number of the substituents is, for example, 1 to 5, preferably 1 to 3.

$R^1$ is preferably an optionally substituted alkyl group, an optionally substituted aryl group, an optionally substituted aralkyl group or an optionally substituted thienyl group, more preferably an optionally substituted alkyl group, an optionally substituted aryl group or an optionally substituted aralkyl group, particularly preferably an optionally substituted aryl group. To be specific, $R^1$ is preferably [1] $C_{1-6}$ alkyl (e.g., methyl, ethyl, propyl, isopropyl, butyl, isobutyl, sec-butyl, tert-butyl, pentyl, hexyl etc.), [2] a $C_{6-14}$ aryl group (e.g., phenyl etc.) optionally substituted by 1 to 5 (preferably 1 to 3) substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) phenyl, or [3] an (unsubstituted) thienyl group, particularly preferably a $C_{6-14}$ aryl group (e.g., phenyl etc.) optionally substituted by 1 to 5 (preferably 1 to 3) substituents selected from halogen, hydroxy and $C_{1-6}$ alkyl.

In the aforementioned formula (I), $R^2$, $R^3$ and $R^4$ are the same or different and each is a hydrogen atom or an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, preferably, a hydrogen atom or an optionally substituted hydrocarbon group, an optionally substituted thienyl group, an optionally substituted benzo[b]thienyl group, an optionally substituted furyl group, an optionally substituted pyridyl group, an acyl group, a halogen atom, a cyano group or a nitro group.

As the "optionally substituted hydrocarbon group" for $R^2$, $R^3$ or $R^4$, those similar to the aforementioned "optionally substituted hydrocarbon group" for $R^{40}$ can be mentioned.

As the "thienyl group" of the "optionally substituted thienyl group" for $R^2$, $R^3$ or $R^4$, 2- or 3-thienyl can be mentioned.

As the "substituent" of the thienyl group, those similar to the substituents of the cycloalkyl, aryl or aralkyl exemplified as the above-mentioned "hydrocarbon group" for $R^{40}$ can be mentioned. The number of the substituents is 1 to 3.

As the "benzo[b]thienyl group" of the "optionally substituted benzo[b]thienyl group" for $R^2$, $R^3$ or $R^4$, 2- or 3-benzo[b]thienyl can be mentioned.

As the "substituent" of the benzo[b]thienyl group, those similar to the substituents of the cycloalkyl, aryl or aralkyl exemplified as the above-mentioned "hydrocarbon group" for $R^{40}$ can be mentioned. The number of the substituents is, for example, 1 to 5, preferably 1 to 3.

As the "furyl group" of the "optionally substituted furyl group" for $R^2$, $R^3$ or $R^4$, 2- or 3-furyl can be mentioned.

As the "substituent" of the furyl group, those similar to the substituents of the cycloalkyl, aryl or aralkyl exemplified as the above-mentioned "hydrocarbon group" for $R^{40}$ can be mentioned. The number of the substituents is 1 to 3.

As the "pyridyl group" of the "optionally substituted pyridyl group" for $R^2$, $R^3$ or $R^4$, 2-, 3- or 4-pyridyl can be mentioned.

As the "substituent" of the pyridyl group, those similar to the substituents of the cycloalkyl, aryl or aralkyl exemplified as the above-mentioned "hydrocarbon group" for $R^{40}$ can be mentioned. The number of the substituents is 1 to 3.

As the "pyrazolyl group" of the "optionally substituted pyrazolyl group" for $R^2$, $R^3$ or $R^4$, 3- or 4-pyrazolyl can be mentioned.

As the "substituent" of the pyrazolyl group, those similar to the substituents of the cycloalkyl, aryl or aralkyl exemplified as the above-mentioned "hydrocarbon group" for $R^{40}$ can be mentioned. The number of the substituents is 1 to 3.

As the "pyrimidinyl group" of the "optionally substituted pyrimidinyl group" for $R^2$, $R^3$ or $R^4$, 2-, 4- or 5-pyrimidinyl can be mentioned.

As the "substituent" of the pyrimidinyl group, those similar to the substituents of the cycloalkyl, aryl or aralkyl exemplified as the above-mentioned "hydrocarbon group" for $R^{40}$ can be mentioned. The number of the substituents is 1 to 3.

As the "acyl group" for $R^2$, $R^3$ or $R^4$, an acyl group having 1 to 20 carbon atoms, which is derived from an organic carboxylic acid can be mentioned. For example, $C_{1-7}$ alkanoyl groups (e.g., formyl; $C_{1-6}$ alkyl-carbonyl such as acetyl, propionyl, butyryl, isobutyryl, pentanoyl, hexanoyl, heptanoyl and the like; etc.), $C_{6-14}$ aryl-carbonyl groups (e.g., benzoyl, naphthalenecarbonyl etc.), $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), $C_{6-14}$ aryloxy-carbonyl groups (e.g., phenoxycarbonyl group), $C_{7-19}$ aralkyl-carbonyl groups (e.g., phenyl-$C_{1-4}$ alkylcarbonyl such as benzylcarbonyl, phenethylcarbonyl, phenylpropylcarbonyl and the like, naphthyl-$C_{1-4}$ alkylcarbonyl such as benzhydrylcarbonyl, naphthylethylcarbonyl and the like, etc.), $C_{7-19}$ aralkyloxycarbonyl groups (e.g., phenyl-$C_{1-4}$ alkyloxycarbonyl such as benzyloxycarbonyl and the like, etc.), 5- or 6-membered heterocyclyl-carbonyl group or condensed heterocyclyl-carbonyl groups thereof (e.g., pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein nitrogen atom is oxidized such as 2-, 3- or 4-pyridyl-N-oxidocarbonyl and the like; pyridazinylcarbonyl such as 3- or 4-pyridazinylcarbonyl and the like; pyridazinyl wherein one or both nitrogen atoms are oxidized, such as 3-, 4-, 5- or 6-pyridazinyl-N-oxidocarbonyl and the like; pyrimidinylcarbonyl such as 2-, 4- or 5-pyrimidinylcarbonyl and the like; pyrimidinylcarbonyl wherein one or both nitrogen atoms are oxidized, such as 2-, 4-, 5- or 6-pyrimidinyl-N-oxidocarbonyl and the like; pyrazinylcarbonyl; piperidinylcarbonyl such as 2-, 3- or 4-piperidinylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl (e.g., 1,5-naphthyridin-2- or 3-ylcarbonyl) such as 1,5-, 1,6-, 1,7-, 1,8-, 2,6- or 2,7-naphthyridinylcarbonyl and the like; thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); a 5- or 6-membered heterocyclylcarbonyl group (e.g., chromenylcarbonyl (e.g., 2H-chromen-2- or 3-ylcarbonyl etc.) and the like) containing 1 to 4 hetero atoms such as nitrogen atom (optionally oxidized), oxygen atom, sulfur atom (optionally mono or dioxidized) and the like), a 5- or 6-membered heterocyclyl-acetyl group (e.g., 5- or 6-membered heterocyclyl-acetyl group containing 1 to 4 hetero atoms such as nitrogen atom (optionally oxidized), oxygen atom, sulfur atom (optionally mono or dioxidized) and the like), such as 2-pyrrolylacetyl, 3-imidazolylacetyl, 5-isoxazolylacetyl and the like, and the like can be used.

As regards the substituent of acyl group, for example, when the above-mentioned acyl group is an alkanoyl group or alkoxy-carbonyl group, the acyl group is optionally substituted by 1 to 3 selected from alkylthio groups (e.g., $C_{1-4}$ alkylthio such as methylthio, ethylthio, n-propylthio, isopropylthio and the like, and the like), halogen (e.g., fluorine, chlorine, bromine, iodine), alkoxy groups (e.g., $C_{1-6}$ alkoxy such as methoxy, ethoxy, n-propoxy, tert-butoxy, n-hexyloxy and the like, and the like), a nitro group, alkoxy-carbonyl groups (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), alkylamino group (e.g., mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino, di-(n-butyl)amino and the like, and the like), alkoxyimino groups (e.g., $C_{1-6}$ alkoxyimino such as methoxyimino, ethoxyimino, n-propoxyimino, tert-butoxyimino, n-hexyloxy-imino and the like, and the like) and hydroxyimino.

When the above-mentioned acyl group is an aryl-carbonyl group, an aryloxy-carbonyl group, an aralkyl-carbonyl group, an aralkyloxycarbonyl group, a 5- or 6-membered heterocyclyl-carbonyl group or a 5- or 6-membered heterocyclyl-acetyl group, the acyl group is optionally substituted by 1 to 5 (preferably 1 to 3) selected from alkyl groups (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like, $C_{3-6}$ cycloalkyl such as cyclohexyl and the like, and the like), alkenyl groups (e.g., $C_{2-6}$ alkenyl such as allyl, isopropenyl, isobutenyl, 1-methylallyl, 2-pentenyl, 2-hexenyl and the like, and the like), alkynyl groups (e.g., $C_{2-6}$ alkynyl such as propargyl, 2-butynyl, 3-butynyl, 3-pentynyl, 3-hexynyl and the like, and the like), alkoxy groups (e.g., $C_{1-6}$ alkoxy such as methoxy, ethoxy, n-propoxy, tert-butoxy, n-hexyloxy and the like, and the like), acyl groups [e.g., $C_{1-7}$ alkanoyl such as formyl, acetyl, propionyl, butyryl, isobutyryl, pentanoyl, hexanoyl, heptanoyl and the like; $C_{6-14}$ aryl-carbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxy-carbonyl such as phenoxycarbonyl and the like; $C_{7-19}$ aralkyl-carbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like], nitro, amino, hydroxy, cyano, sulfamoyl, mercapto, halogen (e.g., fluorine, chlorine, bromine, iodine), and alkylthio groups ($C_{1-4}$ alkylthio such as methylthio, ethylthio, n-propylthio, isobutylthio and the like, and the like).

As the "halogen atom" for $R^2$, $R^3$ or $R^4$, fluorine atom, chlorine atom, bromine atom and iodine atom can be mentioned.

$R^2$ is preferably a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group, more preferably a hydrogen atom, an optionally substituted hydrocarbon group, an optionally substituted thienyl group, an optionally substituted benzo[b]thienyl group, an optionally substituted furyl group or an optionally substituted pyridyl group, further more preferably a hydrogen atom or an optionally substituted hydrocarbon group, particularly preferably a hydrogen atom or an optionally substituted aryl group.

To be specific, $R^2$ is preferably
[1] a hydrogen atom, [2] $C_{6-14}$ aryl group (e.g., phenyl group) optionally substituted by 1 to 5 (preferably 1 to 3) substituents selected from (i) a halogen atom (e.g., a fluorine atom, a chlorine atom, a bromine atom, an iodine atom), (ii) cyano, (iii) amino optionally substituted by 1 or 2 selected from $C_{1-6}$ alkyl (e.g., methyl, ethyl etc.) and acetyl, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) phenoxy, (vii) $C_{1-6}$ alkylthio (e.g., methylthio, ethylthio etc.) optionally substituted by 1 to 5 (preferably 1 to 3) halogens (e.g., fluorine, chlorine, bromine, iodine), (viii) acetyl and (ix) aminocarbonyl, or [3] thienyl group, benzo[b]thienyl group, furyl group, pyridyl group, pyrazolyl group or pyrimidinyl group, each of which is optionally substituted by 1 to 3 substituents selected from $C_{1-6}$ alkoxy (e.g., methoxy, ethoxy etc.) and $C_{1-6}$ alkyl (e.g., methyl, ethyl, n-propyl, isobutyl etc.) (preferably 1 to 3 $C_{1-6}$ alkoxy) [preferably thienyl group, benzo[b]thienyl group, furyl group or pyridyl group, each of which is optionally substituted by 1 to 3 $C_{1-6}$ alkoxy],
particularly preferably (i) a hydrogen atom or (ii) a $C_{6-14}$ aryl group (e.g., phenyl group) optionally substituted by 1 to 5 (preferably 1 to 3) halogens atoms (e.g., a fluorine atom, a chlorine atom, a bromine atom, an iodine atom).

$R^3$ and $R^4$ are preferably the same or different and each is a hydrogen atom or an optionally substituted hydrocarbon group, an acyl group, a halogen atom, a cyano group or a nitro group.

Of these, a hydrogen atom, a $C_{1-6}$ alkyl group (e.g., methyl, ethyl, n-propyl, isobutyl etc.), a $C_{6-14}$ aryl group (e.g., phenyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group and a nitro group are preferable, particularly a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group and a nitro group are preferable.

In the aforementioned formula (I), $R^5$ and $R^6$ are the same or different and each is a hydrogen atom or an optionally substituted hydrocarbon group.

As the "optionally substituted hydrocarbon group" for $R^5$ or $R^6$, the groups similar to the "optionally substituted hydrocarbon group" for the aforementioned $R^{40}$ can be mentioned.

Particularly preferably, $R^5$ and $R^6$ are each independently a hydrogen atom or a $C_{1-6}$ alkyl group (e.g., methyl, ethyl, n-propyl, isobutyl etc.).

In the aforementioned formula ($I^0$), the "optionally substituted hydrocarbon group" for $R^{28}$ is the same as the "optionally substituted hydrocarbon group" for $R^1$ of the formula (I).

The "optionally substituted hydrocarbon group", "acyl group" or "halogen atom" for $R^{29}$, $R^{30}$ or $R^{31}$ in the aforementioned formula ($I^0$) is the same as the "optionally substituted hydrocarbon group", "acyl group" or "halogen atom" for $R^2$, $R^3$ or $R^4$ in the formula (I).

The "optionally substituted hydrocarbon group" for $R^{32}$ or $R^{33}$ in the aforementioned formula ($I^0$) is the same as the "optionally substituted hydrocarbon group" for $R^5$ or $R^6$ in the formula (I).

The "spacer having 1 to 20 atoms in the main chain" for $X^4$ or $Y^4$ in the aforementioned formula ($I^0$) is the same as the "spacer having 1 to 20 atoms in the main chain" for X or Y in the formula (I).

Preferable embodiment of each substituent in the aforementioned formula ($I^0$) is according to the preferable embodiment of the substituent in the formula (I).

That is, $R^{28}$ is preferably an optionally substituted alkyl group, an optionally substituted aryl group or an optionally substituted aralkyl group, and an optionally substituted aryl group is particularly preferable. Of these, a $C_{6-14}$ aryl group (e.g., phenyl etc.) optionally substituted by 1 to 5 (preferably 1 to 3) substituents selected from halogen, hydroxy and $C_{1-6}$ alkyl is particularly preferable.

As $R^{29}$, a hydrogen atom or an optionally substituted hydrocarbon group is preferable, and a hydrogen atom or an optionally substituted aryl group is particularly preferable.

Of these, a hydrogen atom or a $C_{6-14}$ aryl group (e.g., phenyl group) optionally substituted by 1-5 (preferably 1-3) halogen atoms (e.g., a fluorine atom, a chlorine atom, a bromine atom, an iodine atom) is preferable.

$R^{30}$ and $R^{31}$ are the same or different and each is preferably a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group or a nitro group.

Preferably, $R^{32}$ and $R^{33}$ are each independently a hydrogen atom or a $C_{1-6}$ alkyl group (e.g., methyl, ethyl, n-propyl, isobutyl etc.).

A preferable embodiment of $X^4$ or $Y^4$ is the same as the preferable embodiment of X or Y in the aforementioned formula (I).

As $X^4$, —$SO_2$—, —$SO_2$—N($R^7$)— ($R^7$ is as defined above), —N($R^8$)—$SO_2$—($R^8$ is as defined above), —N($R^9$)— ($R^9$ is as defined above) or —O— is preferable. Particularly, —$SO_2$— is preferable.

As $Y^4$, a bond or $C_{1-8}$ alkylene (e.g., —$CH_2$—, —$(CH_2)_2$—, —$(CH_2)_3$—, —$(CH_2)_4$—, —$(CH_2)_5$—, —$(CH_2)_6$—, —$CHCH_3$—, —$C(CH_3)_2$—, —$(CH(CH_3))_2$—, —$(CH_2)_2C(CH_3)_2$—, —$(CH_2)_3C(CH_3)_2$— and the like) is preferable.

As compound (I), a compound represented by the following formula (II)

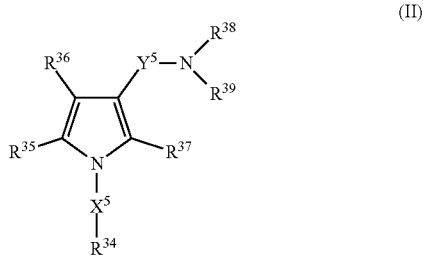

wherein $X^5$ is —$SO_2$—, —$SO_2$—$N(R^7)$— ($R^7$ is as defined above), —$N(R^8)$—$SO_2$— ($R^8$ is as defined above), —$N(R^9)$— ($R^9$ is as defined above) or —O—,
$Y^5$ is an optionally substituted alkylene group,
$R^{34}$ is an optionally substituted hydrocarbon group,
$R^{35}$ is a hydrogen atom or an optionally substituted hydrocarbon group,
$R^{36}$ and $R^{37}$ are each independently a hydrogen atom, an optionally substituted hydrocarbon group, an acyl group, a halogen atom, a cyano group or a nitro group,
$R^{38}$ and $R^{39}$ are each independently a hydrogen atom or an optionally substituted hydrocarbon group, and $R^{35}$ and/or $R^{37}$ are/is not a 1,3-dioxaindan-6-yl group] or a salt thereof (hereinafter abbreviated as compound (II)) is preferable. However, 3-[[2,3-dimethyl-1-(4-methylphenyl)sulfonyl]-1H-pyrrol-4-yl]-2-methyl-alanine methyl ester is excluded.

As an embodiment of preferable substituent for $X^5$, a group similar to the aforementioned X can be mentioned, and —$SO_2$— is particularly preferable.

As the "optionally substituted alkylene group" for $Y^5$, a group similar to the aforementioned "optionally substituted alkylene group" exemplified for Y can be mentioned. As $Y^5$, $C_{1-8}$ alkylene (e.g., —$CH_2$—, —$(CH_2)_2$—, —$(CH_2)_3$—, —$(CH_2)_4$—, —$(CH_2)_5$—, —$(CH_2)_6$—, —$CHCH_3$—, —$C(CH_3)_2$—, —$(CH(CH_3))_2$—, —$(CH_2)_2C(CH_3)_2$—, —$(CH_2)_3C(CH_3)_2$— and the like) are preferable.

As the "optionally substituted hydrocarbon group" for $R^{34}$, a group similar to the aforementioned "optionally substituted hydrocarbon group" for $R^{40}$ can be mentioned.

As $R^{34}$, an optionally substituted alkyl group, an optionally substituted aryl group or an optionally substituted aralkyl group is preferable, and an optionally substituted aryl group is more preferable.

Of these, [1] a $C_{6-14}$ aryl group (e.g., phenyl etc.) optionally substituted by 1 to 5 (preferably 1 to 3) substituents selected from (1) halogen (e.g., fluorine, chlorine, bromine, iodine), (2) hydroxy, (3) $C_{1-6}$ alkyl (e.g., methyl, ethyl, n-propyl, isobutyl etc.) optionally substituted by 1 to 5 (preferably 1 to 3) halogens (e.g., fluorine, chlorine, bromine, iodine) and (4) $C_{1-6}$ alkoxy (e.g., methoxy, ethoxy, n-propoxy, isobutoxy etc.), or [2] a $C_{1-6}$ alkyl group (e.g., methyl, ethyl, n-propyl, isobutyl etc.) is particularly preferable.

As the "optionally substituted hydrocarbon group" for $R^{35}$, a group similar to the aforementioned "optionally substituted hydrocarbon group" for $R^{40}$ can be mentioned. However, it is not a 1,3-dioxaindan-6-yl group.

As $R^{35}$, a hydrogen atom or an optionally substituted aryl group (substituent of aryl group is not a —O—$CH_2$—O— group) is preferable.

Of these, (i) a hydrogen atom, or (ii) a $C_{6-14}$ aryl group (e.g., phenyl etc.) optionally substituted by 1 to 5 (preferably 1 to 3) substituents selected from halogen (e.g., fluorine, chlorine, bromine, iodine) and $C_{1-6}$ alkyl (e.g., methyl, ethyl, n-propyl, isobutyl etc.) is preferable.

As the "optionally substituted hydrocarbon group" for $R^{36}$ or $R^{37}$, a group similar to the aforementioned "optionally substituted hydrocarbon group" for $R^{40}$ can be mentioned. However, $R^{37}$ is not a 1,3-dioxaindan-6-yl group.

As the "acyl group" for $R^{36}$ or $R^{37}$, a group similar to the aforementioned "acyl group" for $R^2$, $R^3$ or $R^4$ can be mentioned.

As $R^{36}$ or $R^{37}$, a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group or a nitro group is preferable.

As the "optionally substituted hydrocarbon group" for $R^{38}$ or $R^{39}$, a group similar to the aforementioned "optionally substituted hydrocarbon group" for $R^{40}$ can be mentioned.

Preferably, $R^{38}$ and $R^{39}$ are each independently a hydrogen atom or a $C_{1-6}$ alkyl group (e.g., methyl, ethyl, n-propyl, isobutyl etc.).

In addition, as a preferable embodiment of compound (I), a compound represented by the following formula can be mentioned. A compound represented by

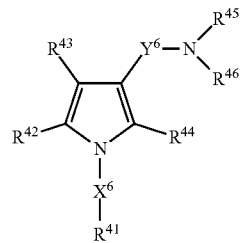

wherein $X^6$ is sulfonyl,
$Y^6$ is a $C_{1-6}$ alkylene group (e.g., —$CH_2$—, —$(CH_2)_2$—, —$(CH_2)_3$—, —$(CH_2)_4$—, —$(CH_2)_5$—, —$(CH_2)_6$—, —$CHCH_3$—, —$C(CH_3)_2$—, —$(CH(CH_3))_2$—, —$(CH_2)_2C(CH_3)_2$—, —$(CH_2)_3C(CH_3)_2$— etc.),
$R^{41}$ is [1] a $C_{6-14}$ aryl group (e.g., phenyl etc.) optionally substituted by 1 to 5 (preferably 1 to 3) substituents selected from (1) halogen (e.g., fluorine, chlorine, bromine, iodine), (2) hydroxy, (3) $C_{1-6}$ alkyl (e.g., methyl, ethyl, n-propyl, isobutyl etc.) optionally substituted by 1 to 5 (preferably 1 to 3) halogens (e.g., fluorine, chlorine, bromine, iodine) and (4) $C_{1-6}$ alkoxy (e.g., methoxy, ethoxy, n-propoxy, isobutoxy etc.) or [2] a $C_{1-6}$ alkyl group (e.g., methyl, ethyl, n-propyl, isobutyl etc.),
$R^{42}$ is a hydrogen atom, a $C_{6-14}$ aryl group (e.g., phenyl etc.) optionally substituted by 1 to 5 (preferably 1 to 3) substituents selected from halogen (e.g., fluorine, chlorine, bromine, iodine) and $C_{1-6}$ alkyl (e.g., methyl, ethyl, n-propyl, isobutyl etc.),
$R^{43}$ and $R^{44}$ are each independently a hydrogen atom, and
$R^{45}$ and $R^{46}$ are each independently a hydrogen atom or a $C_{1-6}$ alkyl group (e.g., methyl, ethyl, n-propyl, isobutyl etc.) is preferable.

In another embodiment, of the compounds encompassed in compound (I), particularly preferable compounds are the following [a], [b], [c] and [d].

[a] A compound represented by the formula (II-a)

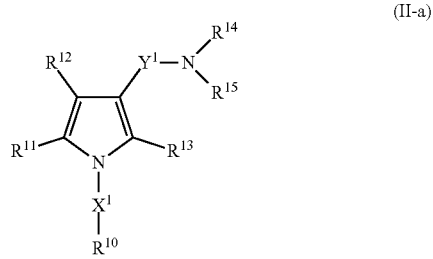

(II-a)

wherein $X^1$ is —$SO_2$—, —$SO_2$—N($R^7$)— ($R^7$ is a hydrogen atom or an optionally substituted hydrocarbon group), —N($R^8$)—$SO_2$— ($R^8$ is a hydrogen atom or an optionally substituted hydrocarbon group), —N($R^9$)— ($R^9$ is a hydrogen atom or an optionally substituted hydrocarbon group) or —O—, $Y^1$ is an optionally substituted alkylene group, $R^{10}$ is an optionally substituted hydrocarbon group or an optionally substituted heterocyclic group, $R^{11}$ is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group [preferably, a hydrogen atom, an optionally substituted hydrocarbon group, an optionally substituted thienyl group, an optionally substituted benzo[b]thienyl group, an optionally substituted furyl group or an optionally substituted pyridyl group], $R^{12}$ and $R^{13}$ are each independently a hydrogen atom, an optionally substituted hydrocarbon group, an acyl group, a halogen atom, a cyano group or a nitro group (provided that $R^{12}$ and $R^{13}$ are not simultaneously hydrogen atoms), and $R^{14}$ and $R^{15}$ are each independently a hydrogen atom or an optionally substituted hydrocarbon group] (provided that 3-[[2,3-dimethyl-1-(4-methylphenyl)sulfonyl]-1H-pyrrol-4-yl]-2-methyl-alanine methyl ester is excluded) or a salt thereof.

The "optionally substituted hydrocarbon group" and "optionally substituted heterocyclic group" for $R^{10}$ mean the same as the "optionally substituted hydrocarbon group" and "optionally substituted heterocyclic group" for $R^1$ in the formula (I).

The "optionally substituted hydrocarbon group", "optionally substituted thienyl group", "optionally substituted benzo[b]thienyl group", "optionally substituted furyl group", "optionally substituted pyridyl group", "optionally substituted pyrazolyl group" and "optionally substituted pyrimidinyl group" for $R^{11}$ mean the same as the "optionally substituted hydrocarbon group", "optionally substituted thienyl group", "optionally substituted benzo[b]thienyl group", "optionally substituted furyl group", "optionally substituted pyridyl group", "optionally substituted pyrazolyl group" and "optionally substituted pyrimidinyl group" each for $R^2$ in the formula (I).

The "optionally substituted hydrocarbon group", "acyl group" or "halogen atom" for $R^{12}$ or $R^{13}$ means the same as the "optionally substituted hydrocarbon group", "acyl group" or "halogen atom" for $R^3$ or $R^4$ in the formula (I).

The "optionally substituted hydrocarbon group" for $R^{14}$ or $R^{15}$ means the same as the "optionally substituted hydrocarbon group" for $R^5$ or $R^6$ in the formula (I).

As a preferable embodiment of $X^1$, a group similar to X in the aforementioned formula (I) can be mentioned.

As the "optionally substituted alkylene group" for $Y^1$, a group similar to the "optionally substituted alkylene group" for Y in the aforementioned formula (I) can be mentioned.

A preferable embodiment of each substituent in the aforementioned formula (II-a) is similar to the preferable embodiment of the corresponding substituent in the formula (I).

That is, as $R^{10}$, an optionally substituted alkyl group, an optionally substituted aryl group, an optionally substituted aralkyl group or an optionally substituted thienyl group is preferable, an optionally substituted alkyl group, optionally substituted aryl group, optionally substituted aralkyl group or (unsubstituted) thienyl group is more preferable, and an optionally substituted aryl group is particularly preferable.

Specifically,

[1] a $C_{6-14}$ aryl group (e.g., phenyl etc.) optionally substituted by 1 to 5 (preferably 1 to 3) substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) phenyl, or

[2] an (unsubstituted) thienyl group, is particularly preferable.

As $R^{11}$, (i) a hydrogen atom, (ii) an optionally substituted hydrocarbon group, or (iii) a thienyl group, a benzo[b]thienyl group, a furyl group, a pyridyl group, a pyrazolyl group or a pyrimidinyl group optionally substituted by 1 to 3 substituents selected from $C_{1-6}$ alkoxy (e.g., methoxy, ethoxy etc.) and $C_{1-6}$ alkyl (e.g., methyl, ethyl etc.) [particularly, a thienyl group, a benzo[b]thienyl group, a furyl group or a pyridyl group, which is optionally substituted by 1 to 3 $C_{1-6}$ alkoxy] is preferable. Of the above-mentioned groups, an optionally substituted hydrocarbon group is more preferable, and an optionally substituted aryl group is particularly preferable.

Specifically, as $R^{11}$,

[1] a hydrogen atom, [2] a $C_{6-14}$ aryl group (e.g., phenyl group, naphthyl group) optionally substituted by 1 to 5 (preferably 1 to 3) substituents selected from (i) a halogen atom (e.g., a fluorine atom, a chlorine atom, a bromine atom, an iodine atom), (ii) cyano, (iii) amino optionally substituted by one or two $C_{1-6}$ alkyl (e.g., methyl, ethyl etc.) or acetyl, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) phenoxy, (vii) $C_{1-6}$ alkylthio (e.g., methylthio, ethylthio etc.) optionally substituted by 1 to 5 (preferably 1 to 3) halogens (e.g., fluorine, chlorine, bromine, iodine), (viii) acetyl and (ix) aminocarbonyl, or [3] a thienyl group, a benzo[b]thienyl group, a furyl group, a pyridyl group, a pyrazolyl group or a pyrimidinyl group optionally substituted by 1 to 3 substituents selected from $C_{1-6}$ alkoxy (e.g., methoxy, ethoxy etc.) and $C_{1-6}$ alkyl (e.g., methyl, ethyl etc.) [particularly, a thienyl group, a benzo[b]thienyl group, a furyl group or a pyridyl group, which is optionally substituted by 1 to 3 $C_{1-6}$ alkoxy] is preferable, and particularly, a $C_{6-14}$ aryl group (e.g., phenyl group) optionally substituted by 1 to 5 (preferably 1 to 3) substituents selected from (i) a halogen atom and (ii) $C_{1-6}$ alkyl optionally substituted by 1-5 (preferably 1-3) halogens is preferable.

$R^{12}$ and $R^{13}$ are the same or different and each is preferably a hydrogen atom, a $C_{1-6}$ alkyl group (e.g., methyl, ethyl, n-propyl, isobutyl etc.), a $C_{6-14}$ aryl group (e.g., phenyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group or a nitro group. However, $R^{12}$ and $R^{13}$ are not simultaneously hydrogen atoms.

$R^{12}$ is preferably a hydrogen atom, a $C_{1-6}$ alkyl group (e.g., methyl, ethyl, n-propyl, isobutyl etc.) or a $C_{6-14}$ aryl group (e.g., phenyl etc.).

$R^{13}$ is preferably a hydrogen atom or a $C_{1-6}$ alkyl group (e.g., methyl, ethyl, n-propyl, isobutyl etc.).

Preferably, $R^{14}$ and $R^{15}$ are each independently a hydrogen atom or a $C_{1-6}$ alkyl group (e.g., methyl, ethyl, n-propyl, isobutyl etc.).

As a preferable embodiment of $X^1$ or $Y^1$, the preferable embodiment of X or Y in the aforementioned formula (I) can be mentioned.

As $X^1$, —$SO_2$— is particularly preferable.

As $Y^1$, $C_{1-8}$ alkylene (e.g., —$CH_2$—, —$(CH_2)_2$—, —$(CH_2)_3$—, —$(CH_2)_4$—, —$(CH_2)_5$—, —$(CH_2)_6$—, —$CHCH_3$—, —$C(CH_3)_2$—, —$(CH(CH_3))_2$—, —$(CH_2)_2C(CH_3)_2$—, —$(CH_2)_3C(CH_3)_2$— and the like) is preferable.

[b] A compound represented by the formula (II-b)

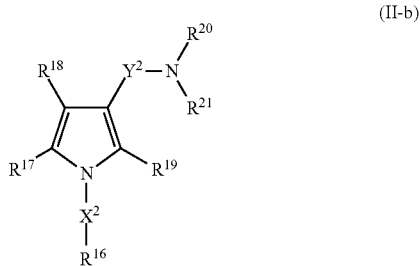

(II-b)

wherein $X^2$ is —$SO_2$—$N(R^7)$— ($R^7$ is a hydrogen atom or an optionally substituted hydrocarbon group), —$N(R^8)$—$SO_2$— ($R^8$ is a hydrogen atom or an optionally substituted hydrocarbon group), —$N(R^9)$— ($R^9$ is a hydrogen atom or an optionally substituted hydrocarbon group) or —O—, $Y^2$ is an optionally substituted alkylene group, $R^{16}$ is an optionally substituted hydrocarbon group or an optionally substituted heterocyclic group, $R^{17}$ is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group, $R^{18}$ and $R^{19}$ are each independently a hydrogen atom, $R^{20}$ and $R^{21}$ are each independently a hydrogen atom or an optionally substituted hydrocarbon group, and $R^{17}$ is not a 1,3-dioxaindan-6-yl group, or a salt thereof.

The "optionally substituted hydrocarbon group" and "optionally substituted heterocyclic group" for $R^{16}$ mean the same as the "optionally substituted hydrocarbon group" and "optionally substituted heterocyclic group" for $R^1$ in the formula (I).

The "optionally substituted hydrocarbon group", "optionally substituted thienyl group", "optionally substituted benzo[b]thienyl group", "optionally substituted furyl group", "optionally substituted pyridyl group", "optionally substituted pyrazolyl group" or "optionally substituted pyrimidinyl group" for $R^{17}$ means the same as the "optionally substituted hydrocarbon group", "optionally substituted thienyl group", "optionally substituted benzo[b]thienyl group", "optionally substituted furyl group", "optionally substituted pyridyl group", "optionally substituted pyrazolyl group" or "optionally substituted pyrimidinyl group" for $R^2$ in the formula (I).

The "optionally substituted hydrocarbon group" for $R^{20}$ or $R^{21}$ means the same as the "optionally substituted hydrocarbon group" for $R^5$ or $R^6$ in the formula (I).

As a preferable embodiment of $X^2$, a group similar to X in the aforementioned formula (I) can be mentioned.

As the "optionally substituted alkylene group" for $Y^2$, a group similar to the "optionally substituted alkylene group" for Y in the aforementioned formula (I) can be mentioned.

A preferable embodiment of each substituent in the aforementioned formula (II-b) is similar to the preferable embodiment of the corresponding substituent in the formula (I).

That is, as $R^{16}$, an optionally substituted alkyl group, an optionally substituted aryl group, an optionally substituted aralkyl group or an optionally substituted thienyl group is preferable, an optionally substituted alkyl group, an optionally substituted aryl group, an optionally substituted aralkyl group or an (unsubstituted) thienyl group is more preferable, and an optionally substituted aryl group is particularly preferable.

Specifically,

[1] a $C_{6-14}$ aryl group (e.g., phenyl etc.) optionally substituted by 1 to 5 (preferably 1 to 3) substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) phenyl, or

[2] an (unsubstituted) thienyl group, is particularly preferable.

As $R^{17}$, (i) a hydrogen atom, (ii) an optionally substituted hydrocarbon group, or (iii) a thienyl group, a benzo[b]thienyl group, a furyl group, a pyridyl group, a pyrazolyl group or a pyrimidinyl group optionally substituted by 1 to 3 substituents selected from $C_{1-6}$ alkoxy (e.g., methoxy, ethoxy etc.) and $C_{1-6}$ alkyl (e.g., methyl, ethyl etc.) [particularly, a thienyl group, a benzo[b]thienyl group, a furyl group or a pyridyl group, which is optionally substituted by 1 to 3 $C_{1-6}$ alkoxy] is preferable, and of those mentioned above, an optionally substituted hydrocarbon group is more preferable, and an optionally substituted aryl group is particularly preferable.

Specifically, as $R^{17}$,

[1] a hydrogen atom, [2] a $C_{6-14}$ aryl group (e.g., phenyl group) optionally substituted by 1 to 5 (preferably 1 to 3) substituents selected from (i) a halogen atom (e.g., a fluorine atom, a chlorine atom, a bromine atom, an iodine atom), (ii) cyano, (iii) amino optionally substituted by one or two $C_{1-6}$ alkyl (e.g., methyl, ethyl etc.) or acetyl, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) phenoxy, (vii) $C_{1-6}$ alkylthio (e.g., methylthio, ethylthio etc.) optionally substituted by 1 to 5 (preferably 1 to 3) halogens (e.g., fluorine, chlorine, bromine, iodine), (viii) acetyl and (ix) aminocarbonyl, or [3] a thienyl group, a benzo[b]thienyl group, a furyl group, a pyridyl group, a pyrazolyl group or a pyrimidinyl group optionally substituted by 1 to 3 substituents selected from $C_{1-6}$ alkoxy (e.g., methoxy, ethoxy etc.) and $C_{1-6}$ alkyl (e.g., methyl, ethyl etc.) [particularly, a thienyl group, a benzo[b]thienyl group, a furyl group or a pyridyl group, which is optionally substituted by 1 to 3 $C_{1-6}$ alkoxy]

is preferable, and particularly, a $C_{6-14}$ aryl group (e.g., a phenyl group) optionally substituted by 1 to 5 (preferably 1 to 3) substituents selected from (i) a halogen atom and (ii) $C_{1-6}$ alkyl optionally substituted by 1-5 (preferably 1-3) halogens is preferable.

Preferably, $R^{20}$ and $R^{21}$ are each independently a hydrogen atom or a $C_{1-6}$ alkyl group (e.g., methyl, ethyl, n-propyl, isobutyl etc.).

As a preferable embodiment of $Y^2$, the preferable embodiment of Y in the aforementioned formula (I) can be mentioned, and $C_{1-8}$ alkylene (e.g., —$CH_2$—, —$(CH_2)_2$—, —$(CH_2)_3$—, —$(CH_2)_4$—, —$(CH_2)_5$—, —$(CH_2)_6$—, —$CHCH_3$—, —$C(CH_3)_2$—, —$(CH(CH_3))_2$—, —$(CH_2)_2C(CH_3)_2$—, —$(CH_2)_3C(CH_3)_2$— and the like) is preferable.

[c] A compound represented by the formula (II-c)

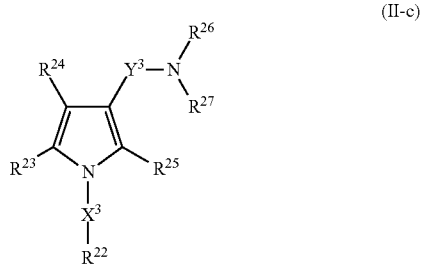

(II-c)

wherein $X^3$ is —$SO_2$—,
$Y^3$ is a methylene group (—$CH_2$—),
$R^{22}$ is an alkyl group, an optionally substituted phenyl group or an optionally substituted thienyl group,
$R^{23}$ is an optionally substituted $C_{6-14}$ aryl group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group, $R^{24}$ and $R^{25}$ are each individually a hydrogen atom,
$R^{26}$ is a hydrogen atom or a methyl group, and
$R^{27}$ is a methyl group, or a salt thereof.

As the "alkyl group" for $R^{22}$, for example, $C_{1-6}$ alkyl (e.g., methyl, ethyl, propyl, isopropyl, butyl, isobutyl, sec-butyl, tert-butyl, pentyl, hexyl etc.) and the like can be mentioned.

As the substituent of the "phenyl group" for $R^{22}$, those similar to the substituents of the "aryl" exemplified as the aforementioned "hydrocarbon group" of the "optionally substituted hydrocarbon group" for $R^{40}$ can be mentioned. The number of the substituents is 1-5 (preferably 1-3).

As the substituent of the "phenyl group", (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) phenyl and the like are preferable.

As the "thienyl group" for $R^{22}$, 2- or 3-thienyl can be mentioned.

As the substituent of the thienyl group, those similar to the substituents of the cycloalkyl, aryl or aralkyl exemplified as the aforementioned "hydrocarbon group" for $R^{40}$ can be mentioned. The number of the substituents is 1-3.

As the $C_{6-14}$ aryl group of the "optionally substituted $C_{6-14}$ aryl group" for $R^{23}$, phenyl and naphthyl can be mentioned. Particularly, phenyl is preferable.

As the substituent of the "$C_{6-14}$ aryl group" for $R^{23}$, those similar to the substituents of the "aryl" exemplified as the aforementioned "hydrocarbon group" of the "optionally substituted hydrocarbon group" for $R^{40}$ can be mentioned. The number of the substituents is 1-5 (preferably 1-3).

As the substituent of the "$C_{6-14}$ aryl group", (i) a halogen atom (e.g., a fluorine atom, a chlorine atom, a bromine atom, an iodine atom), (ii) cyano, (iii) amino optionally substituted by one or two $C_{1-6}$ alkyl (e.g., methyl, ethyl etc.) or acetyl, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) phenoxy, (vii) $C_{1-6}$ alkylthio (e.g., methylthio, ethylthio etc.) optionally substituted by 1 to 5 (preferably 1 to 3) halogens (e.g., fluorine, chlorine, bromine, iodine), (viii) acetyl, (ix) aminocarbonyl and the like are preferable.

As the "optionally substituted thienyl group" for $R^{23}$, those similar to the above-mentioned "optionally substituted thienyl group" for $R^{22}$ can be mentioned.

As the "benzo[b]thienyl group" of the "optionally substituted benzo[b]thienyl group" for $R^{23}$, 2- or 3-benzo[b]thienyl can be mentioned.

As the substituent of the benzo[b]thienyl group, those similar to the substituents of the cycloalkyl, aryl or aralkyl exemplified as the aforementioned "hydrocarbon group" for $R^{40}$ can be mentioned. The number of the substituents is 1 to 5, preferably 1 to 3.

As the "furyl group" of the "optionally substituted furyl group" for $R^{23}$, 2- or 3-furyl can be mentioned.

As the "substituent" of the furyl group, those similar to the substituents of the cycloalkyl, aryl or aralkyl exemplified as the aforementioned "hydrocarbon group" for $R^{40}$ can be mentioned. The number of the substituents is 1 to 3.

As the "pyridyl group" of the "optionally substituted pyridyl group" for $R^{23}$, 2-, 3- or 4-pyridyl can be mentioned.

As the "substituent" of the pyridyl group, those similar to the substituents of the cycloalkyl, aryl or aralkyl exemplified as the aforementioned "hydrocarbon group" for $R^{40}$ can be mentioned. The number of the substituents is 1 to 3.

As the "pyrazolyl group" of the "optionally substituted pyrazolyl group" for $R^{23}$, 3- or 4-pyrazolyl can be mentioned.

As the "substituent" of the pyrazolyl group, those similar to the substituents of the cycloalkyl, aryl or aralkyl exemplified as the aforementioned "hydrocarbon group" for $R^{40}$ can be mentioned. The number of the substituents is 1 to 3.

As the "pyrimidinyl group" of the "optionally substituted pyrazolyl group" for $R^{23}$, 2-, 4- or 5-pyrimidinyl can be mentioned.

As the substituent of the "pyrimidinyl group", those similar to the substituents of the "cycloalkyl, aryl or aralkyl" exemplified as the aforementioned "hydrocarbon group" for $R^{40}$ can be mentioned. The number of the substituents is 1 to 3.

As the substituent of the above-mentioned thienyl group, benzo[b]thienyl group, furyl group, pyridyl group, pyrazolyl group, pyrimidinyl group, $C_{1-6}$ alkoxy (e.g., methoxy, ethoxy etc.) and $C_{1-6}$ alkyl (e.g., methyl, ethyl, n-propyl, isobutyl etc.) and the like are preferable, and $C_{1-6}$ alkoxy (e.g., methoxy, ethoxy etc.) is particularly preferable. The number of the substituents is 1 to 3.

As $R^{22}$,

[1] a $C_{6-14}$ aryl group (e.g., phenyl etc.) optionally substituted by 1 to 5 (preferably 1 to 3) substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) phenyl, or

[2] an (unsubstituted) thienyl group, is particularly preferable.

As $R^{23}$, [1] a phenyl group optionally substituted by 1 to 5 (preferably 1 to 3) substituents selected from (i) a halogen atom (e.g., a fluorine atom, a chlorine atom, a bromine atom, an iodine atom), (ii) cyano, (iii) amino optionally substituted by one or two $C_{1-6}$ alkyl (e.g., methyl, ethyl etc.) or acetyl, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) phenoxy, (vii) $C_{1-6}$ alkylthio (e.g., methylthio, ethylthio etc.) optionally substituted by 1 to 5 (preferably 1 to 3) halogens (e.g., fluorine, chlorine, bromine, iodine), (viii) acetyl and (ix) aminocarbonyl,

[2] a naphthyl group, or [3] a thienyl group, a benzo[b]thienyl group, a furyl group, a pyridyl group, a pyrazolyl group or a pyrimidinyl group optionally substituted by 1 to 3 substituents (preferably 1 to 3 $C_{1-6}$ alkoxy) selected from $C_{1-6}$ alkoxy (e.g., methoxy, ethoxy etc.) and $C_{1-6}$ alkyl (e.g., methyl, ethyl, n-propyl, isobutyl etc.), [particularly, a thienyl group, a benzo[b]thienyl group, a furyl group or a pyridyl group, which is optionally substituted by 1 to 3 $C_{1-6}$ alkoxy]

is preferable.

[d] A compound represented by the formula (II-d)

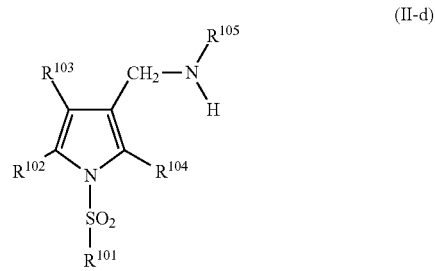

(II-d)

wherein $R^{101}$ is a monocyclic nitrogen-containing heterocyclic group optionally condensed with a benzene ring or heterocycle, the monocyclic nitrogen-containing heterocyclic group optionally condensed with the benzene ring or heterocycle may have a substituent, $R^{102}$ is an optionally substituted $C_{6-14}$ aryl group or an optionally substituted thienyl group, $R^{103}$ and $R^{104}$ are each a hydrogen atom, or one of $R^{103}$ and $R^{104}$ is a hydrogen atom and the other is an optionally substituted lower alkyl group, acyl group, halogen atom, cyano group or nitro group, and $R^{105}$ is an alkyl group, or a salt thereof.

In the formula (II-d), as the "nitrogen-containing monocyclic heterocyclic group optionally condensed with a benzene ring or a heterocycle" for $R^{101}$, (1) a nitrogen-containing monocyclic heterocyclic group, and (2) a fused ring group represented by the formula:

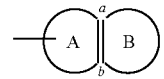

wherein ring A is a nitrogen-containing monocyclic heterocyclic group, ring B is a benzene ring or a heterocycle, a and b are each a bridgehead ring-constituting atom (e.g., a carbon atom, a nitrogen atom and the like), and ═ shows a single bond or a double bond, provided that a bond to an —SO₂— group in the formula (II-d) is present in a ring A-constituting atom (ring atom) other than the bridgehead ring-constituting atoms a and b, can be mentioned.

As used herein, ring A needs only to contain, as a ring A-constituting atom (ring atom), at least one (preferably 1 to 4, more preferably 1 or 2) nitrogen atom, and one or both of the bridgehead ring-constituting atoms a and b may be nitrogen atoms.

The "nitrogen-containing monocyclic heterocyclic group optionally condensed with a benzene ring or a heterocycle" optionally has substituent(s), and the substituent(s) may be present in any of ring A and ring B.

As the "nitrogen-containing monocyclic heterocyclic group" of the "nitrogen-containing monocyclic heterocyclic group optionally condensed with a benzene ring or a heterocycle" and the above-mentioned ring A, for example, an aromatic nitrogen-containing monocyclic heterocyclic group, a saturated or unsaturated non-aromatic nitrogen-containing monocyclic heterocyclic group (aliphatic nitrogen-containing monocyclic heterocyclic group) and the like containing, as a ring-constituting atom (ring atom), at least one (preferably 1 to 4, more preferably 1 or 2) nitrogen atom can be mentioned.

As the "aromatic nitrogen-containing monocyclic heterocyclic group", for example, aromatic nitrogen-containing monocyclic heterocyclic groups such as pyrrolyl, oxazolyl, isoxazolyl, thiazolyl, isothiazolyl, imidazolyl (1H-imidazol-1-yl, 1H-imidazol-4-yl etc.), pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl (1,2,4-triazol-1-yl, 1,2,4-triazol-4-yl etc.), tetrazolyl, pyridyl (2-, 3- or 4-pyridyl etc.), pyridazinyl, pyrimidinyl, pyrazinyl, triazinyl and the like, and N-oxide forms thereof and the like can be mentioned. Of these, a 5- or 6-membered aromatic nitrogen-containing monocyclic heterocyclic group is preferable, and thiazolyl, imidazolyl, pyrazolyl, pyridyl, pyrimidinyl and pyridazinyl are preferable, and pyridyl is particularly preferable.

As the "saturated or unsaturated non-aromatic nitrogen-containing monocyclic heterocyclic group", partially reduced forms (e.g., imidazolinyl, tetrahydropyrimidinyl and the like) of the above-mentioned "aromatic nitrogen-containing monocyclic heterocyclic group" and, for example, azetidinyl, pyrrolidinyl, piperidyl (2-, 3- or 4-piperidyl), morpholinyl, thiomorpholinyl, piperazinyl (1-piperazinyl etc.), homopiperazinyl and the like can be mentioned. Of these, a 5- or 6-membered non-aromatic nitrogen-containing monocyclic heterocyclic group is preferable.

As the "heterocycle" optionally condensed with a nitrogen-containing monocyclic heterocyclic group, for example, an aromatic heterocycle or non-aromatic heterocycle can be mentioned.

As the "aromatic heterocycle", for example, 5- or 6-membered aromatic monocyclic heterocycle such as a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, tetrazole ring, pyridine ring, pyridazine ring, pyrimidine ring, pyrazine ring, triazine ring and the like and, for example, 8- to 12-membered aromatic fused heterocycles such as a benzofuran ring, an isobenzofuran ring, a benzo[b]thiophene ring, an indole ring, an isoindole ring, a 1H-indazole ring, a benzindazole ring, a benzoxazole ring, a 1,2-benzoisoxazole ring, a benzothiazole ring, a benzopyran ring, a 1,2-benzoisothiazole ring, a 1H-benzotriazole ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an α-carboline ring, a β-carboline ring, a γ-carboline ring, an acridine ring, a phenoxazine ring, a phenothiazine ring, a phenazine ring, a phenoxathiine ring, a thianthrene ring, a phenanthridine ring, a phenanthrone ring, an indolizine ring, a pyrrolo[1,2-b]pyridazine ring, a pyrazolo[1,5-a]pyridine ring, an imidazo[1,2-a]pyridine ring, an imidazo[1,5-a]pyridine ring, an imidazo[1,2-b]pyridazine ring, an imidazo[1,2-a]pyrimidine ring, a 1,2,4-triazolo[4,3-a]pyridine ring, a 1,2,4-triazolo[4,3-b]pyridazine ring and the like (preferably, a heterocycle wherein the aforementioned 5- or 6-membered aromatic monocyclic heterocycle is condensed with a benzene ring or a heterocycle wherein the same or different two heterocycles of the aforementioned 5- or 6-membered aromatic monocyclic heterocycle are condensed, more preferably a heterocycle wherein the aforementioned 5- or 6-membered aromatic monocyclic heterocyclic group is condensed with a benzene ring, preferably imidazopyrimidinyl etc.) and the like can be mentioned.

As the "non-aromatic heterocycle", for example, 3- to 8-membered saturated or unsaturated non-aromatic heterocycles such as an oxirane ring, an azetidine ring, an oxetane ring, a thietane ring, a pyrrolidine ring, a tetrahydrofuran ring, a thioran ring, a piperidine ring, a tetrahydropyran ring, a morpholine ring, a thiomorpholine ring, a piperazine ring, a 3-hexahydrocyclopenta[c]pyrrole ring, a homopiperidine ring, a homopiperazine ring and the like, or non-aromatic heterocycles wherein the double bonds of the aforementioned aromatic monocyclic heterocycle or aromatic fused heterocycle are partly or entirely saturated such as a dihydropyridine ring, a dihydropyrimidine ring, a 1,2,3,4-tetrahydroquinoline ring, a 1,2,3,4-tetrahydroisoquinoline ring and the like, and the like can be mentioned.

As preferable nitrogen-containing monocyclic heterocyclic group condensed with a benzene ring or a heterocycle, for example, nitrogen-containing aromatic fused heterocyclic groups such as 8- to 16-membered (preferably 8- to 12-membered) nitrogen-containing aromatic bicyclic fused heterocyclic groups such as 2- or 3-indolyl, 1- or 3-isoindolyl, 1H-indazol-3-yl, 2-benzimidazolyl, 2-benzoxazolyl, 3-benzoisoxazolyl, 2-benzothiazolyl, 3-benzoisothiazolyl, 2-, 3- or 4-quinolyl, 1-, 3- or 4-isoquinolyl, 3- or 4-cinnolinyl, 2- or 4-quinazolinyl, 2- or 3-quinoxalinyl, 1- or 4-phthalazinyl, naphthyridinyl, purinyl, pteridinyl, 1,7-phenanthrolin-2-, 3- or 4-yl, 1-, 2- or 3-indolizinyl, pyrrolo[1,2-b]pyridazinyl, pyrazolo[1,5-a]pyridyl, imidazo[1,2-a]pyridyl, imidazo[1,2-b]pyrazolyl, imidazo[1,5-a]pyridyl, imidazo[4,5-c]pyridyl, pyrazolo[1,5-a]pyrimidinyl, pyrazolo[1,5-c]pyrimidinyl, pyrazolo[3,4-d]pyrimidinyl, imidazo[1,2-b]pyridazinyl, imidazo[1,5-b]pyridazinyl, pyrazolo[3,4-b]pyridyl, imidazo[1,2-a]pyrimidinyl, 1,2,4-triazolo[4,3-a]pyridyl, 1,2,4-triazolo[4,3-b]pyridazinyl, [1,2,4]triazolo[1,2-a]pyridazinyl, [1,2,3]triazolo[1,5-a]pyrimidinyl, [1,2,4]triazolo[1,5-c]pyrimidinyl, [1,2,4]triazolo[1,5-a]pyridyl, [1,2,4]triazolo[4,3-a]pyridyl, pyrazolo[5,1-b]thiazolyl, pyrrolo[2,1-f][1,2,4]triazinyl, pyrrolo[1,2-b]pyridazinyl, pyrrolo[2,3-d]pyrimidinyl, pyrrolo[2,3-b]pyridyl, thieno[3,2-b]pyrimidinyl, thieno[2,3-b]pyridyl, thieno[2,3-c]pyridyl, thieno[3,2-b]pyridyl, thieno[3,2-c]pyridyl, pyrido[2,3-b]pyrazyl, pyrido[3,4-b]pyrazyl, pyrido[2,3-d]pyrimidinyl, pyrido[3,2-d]pyrimidinyl, pyrido[4,3-d]pyrimidinyl and the like, and the like, and the like can be mentioned. As the nitrogen-containing aromatic fused heterocycle, fused pyridine wherein a pyridine ring is condensed with one or two (preferably one) of the aforementioned 5- or 6-membered nitrogen-containing aromatic monocyclic heterocycles or one or two (preferably one) benzene rings (when condensed with a benzene ring, the pyridine ring has a bond), fused pyrimidine wherein a pyrimidine ring is condensed with one or two (preferably one) of the aforementioned 5 or 6-membered heterocycles, or one or two (preferably one) benzene rings (when condensed with a benzene ring, the pyrimidine ring has a bond) and the like are preferable.

As the "non-aromatic nitrogen-containing heterocycle", for example, 3- to 8-membered (preferably 5- or 6-membered) nitrogen-containing saturated or unsaturated (preferably saturated) non-aromatic heterocycle (aliphatic nitrogen-containing heterocycle) such as azetidine, pyrrolidine, imidazolidine, thiazolidine, oxazolidine, piperidine, morpholine, thiomorpholine, piperazine and the like, or nitrogen-containing non-aromatic heterocycle wherein the double bonds of the aforementioned nitrogen-containing aromatic monocyclic heterocycle or nitrogen-containing aromatic fused heterocycle are partly or entirely saturated, such as 1,2,3,4-tetrahydroquinoline, 1,2,3,4-tetrahydroisoquinoline and the like, and the like can be mentioned.

As the "nitrogen-containing monocyclic heterocyclic group optionally condensed with a benzene ring or a heterocycle", a 5- or 6-membered aromatic nitrogen-containing monocyclic heterocyclic group is preferable from among those mentioned above. Of them, a 6-membered aromatic nitrogen-containing heterocyclic group such as pyridyl (e.g., 2-, 3- or 4-pyridyl etc.), pyrimidinyl (e.g., 2-, 4- or 5-pyrimidinyl etc.), pyridazinyl (e.g., 3- or 4-pyridazinyl etc.) and the like is preferable, and pyridyl is particularly preferable.

As the substituent that the "nitrogen-containing monocyclic heterocyclic group optionally condensed with a benzene ring or a heterocycle" may have, those similar to the substituents of the cycloalkyl, aryl or aralkyl exemplified as the aforementioned "hydrocarbon group" for $R^{40}$ can be mentioned. The position of the substituent is not particularly limited as long as it is a substitutable position, and the number of the substituents is, for example, 1 to 5, preferably 1 to 3.

As the "$C_{6-14}$ aryl group" of the "optionally substituted $C_{6-14}$ aryl group" for $R^{102}$, for example, phenyl, 1-naphthyl, 2-naphthyl, 2-biphenylyl, 3-biphenylyl, 4-biphenylyl, 2-anthryl and the like can be mentioned.

As the substituent that the "$C_{6-14}$ aryl group" optionally has, groups similar to the substituents that the "nitrogen-containing monocyclic heterocyclic group optionally condensed with a benzene ring or a heterocycle" for the aforementioned $R^{101}$ optionally has can be mentioned. The number of the substituents is 1 to 5, preferably 1 to 3.

As the "thienyl group" of the "optionally substituted thienyl group" for $R^{102}$, 2- or 3-thienyl can be mentioned.

As the substituent that the "thienyl group" optionally has, groups similar to the substituents that the "nitrogen-containing monocyclic heterocyclic group optionally condensed with a benzene ring or a heterocycle" for the aforementioned $R^{101}$ optionally has can be mentioned. The number of the substituents is 1 to 4, preferably 1 to 3.

As the "lower alkyl group" of the "optionally substituted lower alkyl group" for $R^{103}$ or $R^{104}$, for example, $C_{1-4}$ alkyl groups such as methyl, ethyl, propyl, isopropyl, butyl, isobutyl, sec-butyl, tert-butyl and the like, and the like can be mentioned.

As the substituent that the "lower alkyl group" optionally has, those similar to the substituents of the alkyl, alkenyl or alkynyl exemplified as the aforementioned "hydrocarbon group" for $R^{40}$ can be mentioned. The number of the substituents is 1 to 3.

As the "acyl group" for $R^{103}$ or $R^{104}$, a group similar to the above-mentioned "acyl group" for $R^2$, $R^3$ or $R^4$ can be mentioned.

As the "halogen atom" for $R^{103}$ or $R^{104}$, fluorine, chlorine, bromine and iodine can be mentioned.

As the "alkyl group" for $R^{105}$, for example, $C_{1-6}$ alkyl (e.g., methyl, ethyl, propyl, isopropyl, butyl, isobutyl, sec-butyl, tert-butyl, pentyl, hexyl etc.) and the like can be mentioned.

As $R^{101}$, a "nitrogen-containing monocyclic heterocyclic group optionally condensed with a benzene ring or a heterocycle" (e.g., 5-6-membered aromatic nitrogen-containing monocyclic heterocyclic groups such as thiazolyl, imidazolyl, pyrazolyl, pyridyl, pyrimidinyl, pyridazinyl and the like, and the like) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.) and (vii) oxo is preferable.

Of these, a 6-membered nitrogen-containing aromatic heterocyclic group (e.g., pyridyl groups (e.g., 2-, 3- or 4-pyridyl etc.), pyrimidinyl groups (e.g., 2-, 4- or 5-pyrimidinyl etc.), pyridazinyl groups (e.g., 3- or 4-pyridazinyl etc.) etc.) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) an amino group optionally substituted by $C_{1-6}$ alkyl (e.g., methyl, ethyl, propyl, isopropyl, butyl, isobutyl, sec-butyl, tert-butyl, pentyl, hexyl etc.) is preferable, and a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) is particularly preferable.

As $R^{102}$, [1] a $C_{6-14}$ aryl group (e.g., phenyl group) optionally substituted by 1 to 5 (preferably 1 to 3) substituents selected from (i) a halogen atom (e.g., a fluorine atom, a chlorine atom, a bromine atom, an iodine atom), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl, or

[2] a thienyl group optionally substituted by 1 to 3 substituents selected from (i) a halogen atom (e.g., a fluorine atom, a chlorine atom, a bromine atom, an iodine atom), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl, and particularly, [1] a phenyl group optionally substituted by 1 to 5 (preferably 1 to 3) substituents selected from (i) a halogen atom (e.g., a fluorine atom, a chlorine atom, a bromine atom, an iodine atom) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or

[2] a thienyl group optionally substituted by 1 to 3 substituents selected from (i) a halogen atom (e.g., a fluorine atom, a chlorine atom, a bromine atom, an iodine atom) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) is preferable.

As $R^{102}$, a phenyl group, a 2-fluorophenyl group or a 2-methylphenyl group is particularly preferable.

Preferably, $R^{103}$ and $R^{104}$ are each a hydrogen atom, or one of $R^{103}$ and $R^{104}$ is a hydrogen atom and the other is a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group or a nitro group. A compound wherein both $R^{103}$ and $R^{104}$ are hydrogen atoms is particularly preferable.

As $R^{105}$, methyl or ethyl is preferable, and methyl is particularly preferable.

Of the compounds represented by the formula (II-d), a particularly preferable compound is, for example,
a compound wherein, for example,
$R^{101}$ is a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine),
$R^{102}$ is [1] a phenyl group optionally substituted by 1 to 5 (preferably 1 to 3) substituents selected from (i) a halogen atom (e.g., a fluorine atom, a chlorine atom, a bromine atom, an iodine atom) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or
[2] a thienyl group optionally substituted by 1 to 3 substituents selected from (i) a halogen atom (e.g., a fluorine atom, a chlorine atom, a bromine atom, an iodine atom) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine),
$R^3$ and $R^4$ are each a hydrogen atom, and $R^5$ is methyl.

As compound (I),
N-methyl-1-[1-(phenylsulfonyl)-5-(3-thienyl)-1H-pyrrol-3-yl]methanamine,
N-methyl-1-[5-phenyl-1-(3-thienylsulfonyl)-1H-pyrrol-3-yl]methanamine,
N-methyl-1-(1-{[3-(methylsulfonyl)phenyl]sulfonyl}-5-phenyl-1H-pyrrol-3-yl)methanamine,
1-[1-(1-benzothien-2-ylsulfonyl)-5-phenyl-1H-pyrrol-3-yl]-N-methylmethanamine,
1-[5-(2-fluorophenyl)-1-{[3-(methylsulfonyl)phenyl]sulfonyl}-1H-pyrrol-3-yl]-N-methylmethanamine,
1-{5-(2-fluorophenyl)-1-[(2-fluorophenyl)sulfonyl]-1H-pyrrol-3-yl}-N-methylmethanamine,
N-methyl-3-({4-[(methylamino)methyl]-2-phenyl-1H-pyrrol-1-yl}sulfonyl)benzamide,
or a salt thereof is particularly preferable, and especially, as a compound represented by the formula (II-d), N-methyl-1-[5-phenyl-1-(pyridin-3-ylsulfonyl)-1H-pyrrol-3-yl] methanamine, 1-[5-(2-fluorophenyl)-1-(pyridin-3-ylsulfonyl)-1H-pyrrol-3-yl]-N-methylmethanamine, N-methyl-1-[4-methyl-1-(pyridin-3-ylsulfonyl)-5-phenyl-1H-pyrrol-3-yl]methanamine, N-methyl-1-[1-(pyridin-3-ylsulfonyl)-5-(3-thienyl)-1H-pyrrol-3-yl]methanamine, N-methyl-1-[5-(2-methylphenyl)-1-(pyridin-3-ylsulfonyl)-1H-pyrrol-3-yl]methanamine, 1-[5-(2,4-difluorophenyl)-1-(pyridin-3-ylsulfonyl)-1H-pyrrol-3-yl]-N-methylmethanamine, or a salt thereof is particularly preferable.

As a salt of compound (I), metal salt, ammonium salt, salts with organic bases, salts with inorganic acids, salts with organic acids, salts with basic or acidic amino acids and the like can be mentioned. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

Of these, pharmaceutically acceptable salts are preferable. For example, when a compound contains an acidic functional group, inorganic salts such as alkali metal salt (e.g., sodium salt, potassium salt etc.), alkaline earth metal salt (e.g., calcium salt, magnesium salt, barium salt etc.) and the like, ammonium salt and the like; and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

compound (I) can be produced, for example, according to the methods described in JP application No. 2005-044740, *Eur. J. Org. Chem.*, p. 2283 (2001), *J. Med. Chem.*, vol. 43, p. 1886 (2000), *J. Pharm. Pharmacol.*, vol. 46, p. 740 (1994), WO92/04025, *J. Heterocycl. Chem.*, vol. 25, p. 635 (1988), *J. Med. Chem.*, vol. 14, p. 328 (1971), *J. Med. Chem.*, vol. 35, p. 4195 (1992) or *Tetrahedron Lett.*, vol. 26, p. 4047 (1985), or a method analogous thereto.

The production methods of compound (I) in the present invention are explained by referring to the production methods of compound (VIII), (XI), (XIV), (XVI) and (XVII).

The compounds (VIII), (XI), (XIV), (XVI) and (XVII) of the present invention can be produced, for example, by the method shown by the following scheme or a method analogous thereto and the like.

The compounds (III)-(XVII) in the formulas may form salts, and as such salts, for example, those similar to the salts of compound (I) can be mentioned.

While the compounds obtained in respective steps can be used for the next reaction in the form of a reaction mixture or a crude product, they can also be easily isolated and purified from the reaction mixture by a known separation and purification means, such as recrystallization, distillation, chromatography and the like.

Compound (III) wherein $R^2$, $R^3$ and $R^4$ are as defined above, and $R^{47}$ is a $C_{1-4}$ alkyl group such as methyl, ethyl, propyl, isopropyl, butyl and the like can be produced according to a method known per se, such as the method described in *Chem. Pharm. Bull.*, vol. 49, p. 1406 (2001), *Tetrahedron Letters*, vol. 35, p. 5989 (1994) and the like or a method analogous thereto.

By acylation, alkylation and the like of compound (III), compound (IV) (wherein each symbol is as defined above)

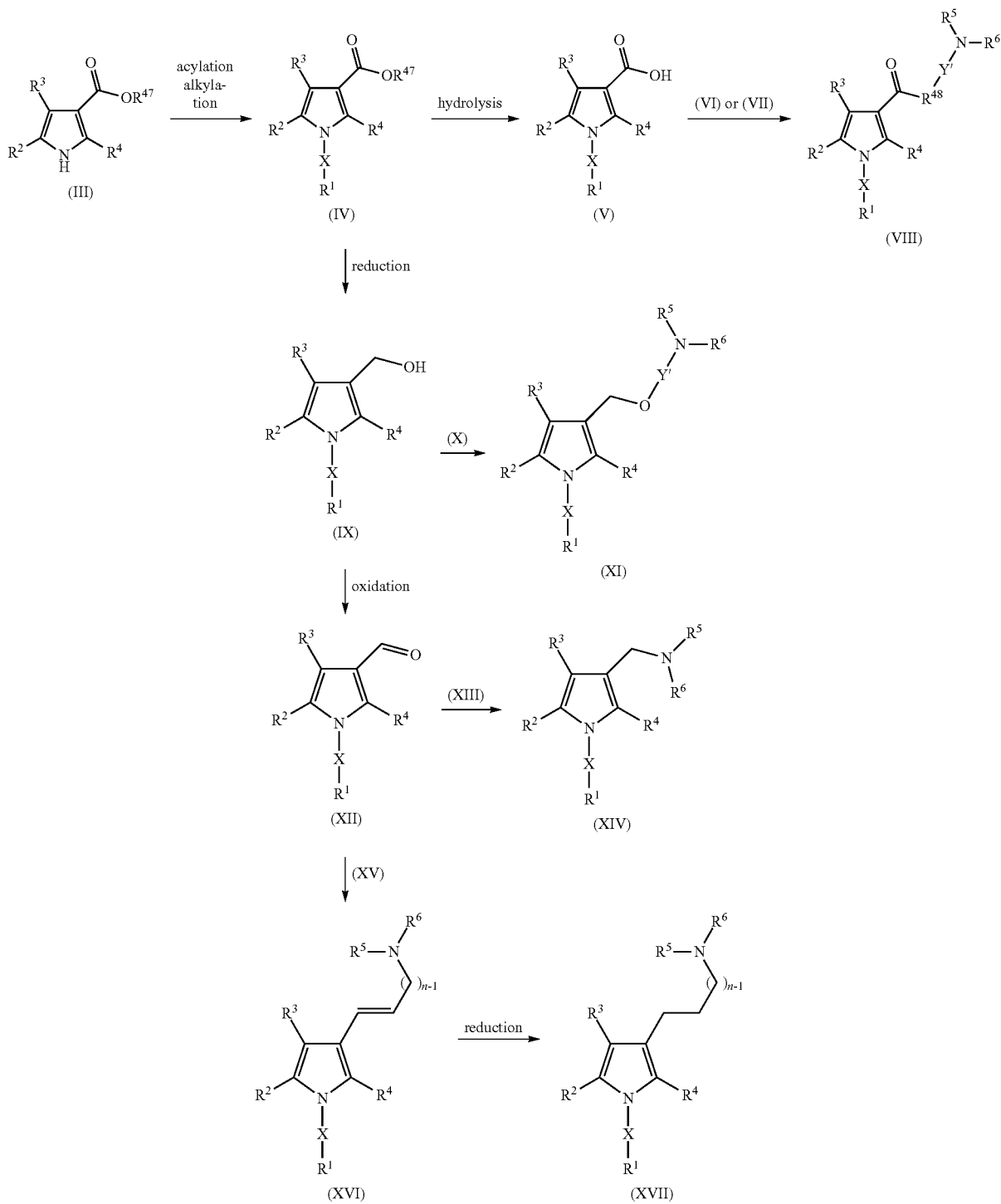

can be produced, which is a compound (III) wherein the 1-position of pyrrole ring is substituted by —X—R¹.

The acylation can be conducted using an acylating agent such as acid halide (e.g., carbonyl halide, sulfonyl halide and the like (e.g., benzoyl chloride)), acid anhydride (e.g., benzoic anhydride), chlorocarbonate (e.g., chlorobenzyl formate), carbamoyl chloride (e.g., phenylcarbamoyl chloride), sulfamoyl chloride (e.g., benzylsulfamoyl chloride) and the like. The alkylation can be conducted using an alkylating agent having a leaving group such as a halogen atom (e.g., a chlorine atom, a bromine atom, an iodine atom), an alkylsulfonyloxy group (e.g., a mesyloxy group), an arylsulfonyloxy group (e.g., a tosyloxy group) and the like (e.g., benzyl bromide, benzyl methanesulfonate or benzyl 4-methylbenzenesulfonate etc.).

This reaction is advantageously carried out using a solvent inert to the reaction. While the solvent is not particularly limited as long as the reaction proceeds, hydrocarbons such as benzene, toluene and the like, tetrahydrofuran, amides such as N,N-dimethylformamide, N,N-dimethylacetamide and the like, and the like or a mixed solvent thereof and the like are preferable.

Use of a base is effective for the reaction. As the base, for example, inorganic bases such as sodium hydroxide, potassium hydroxide and the like, basic salts such as sodium carbonate, potassium carbonate, cesium carbonate, sodium hydrogencarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 0.1-about 10 mol, preferably about 1-about 5 mol, per 1 mol of compound (III).

While the reaction time varies depending on the reagents and solvents to be used, it is generally about 30 min-about 24 hr, preferably about 30 min-about 8 hr.

The reaction temperature is generally about 0° C.-about 250° C., preferably about 25° C.-about 100° C.

The compound (IV) can be easily converted to compound (V) (wherein each symbol is as defined above) by hydrolysis.

The hydrolysis can be conducted according to the method described in *Shin Jikken Kagaku Koza*, vol. 14-II, page 930-941 (Maruzen Press).

By esterification or amidation reaction of the present compound (V) and a compound represented by the formula (VI)

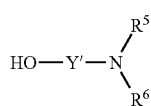

(VI)

wherein Y' is a bond or a spacer having 1 to 20 atoms in the main chain, and other symbols are as defined above, or a compound represented by the formula (VII)

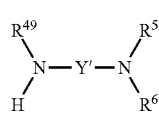

(VII)

wherein R⁴⁹ is a hydrogen atom or an alkyl group (preferably a C₁₋₆ alkyl group) such as methyl group, ethyl group and the like, and other symbols are as defined above, compound (VIII) wherein R⁴⁸ is —O— or —NR⁴⁹— (R⁴⁹ is as defined above), and other symbols are as defined above can be produced.

As the "spacer having 1 to 20 carbon atoms in the main chain" for Y', a group similar to the above-mentioned Y can be mentioned, and —(CH₂)₂₋₆— and the like are preferable.

As compound (VI), for example, N,N-dimethylethanolamine, 3-dimethylamino-1-propanol, 4-dimethylamino-1-butanol and the like, and as compound (VII), for example, N,N-dimethylethylenediamine, N,N,N'-trimethylethylenediamine, N,N-dimethyl-N'-ethylethylenediamine and the like can be mentioned.

This synthetic reaction can be conducted in a solvent inert to the reaction, for example, by a coupling reaction using N,N'-dicyclohexylcarbodiimide and N-hydroxysuccinimide or 1-hydroxybenzotriazole and the like in combination. While the solvent is not particularly limited as long as the reaction proceeds, solvents such as tetrahydrofuran, amides (e.g., N,N-dimethylformamide, N,N-dimethylacetamide and the like), halogenated hydrocarbons such as dichloromethane and the like, and the like or a mixed solvent thereof and the like are preferable.

While the reaction time varies depending on the reagents and solvents to be used, it is generally about 30 min-about 24 hr, preferably about 30 min-about 8 hr.

The reaction temperature is generally about −20° C.-about 50° C., preferably about 0° C.-about 25° C.

By subjecting compound (IV) to a reduction reaction according to the method described in *Shin Jikken Kagaku Koza*, vol. 14-I, pages 474-476 (Maruzen Press), the compound can be easily converted to compound (IX) wherein each symbol is as defined above.

By reacting the present compound (IX) with a compound represented by the formula (X)

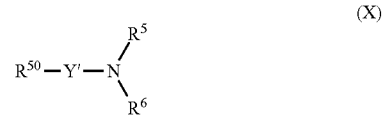

(X)

wherein R⁵⁰ is a leaving group such as a halogen atom (e.g., a chlorine atom, a bromine atom, an iodine atom), an alkylsulfonyloxy group (e.g., mesyloxy group), an arylsulfonyloxy group (e.g., tosyloxy group) and the like, and other symbols are as defined above, compound (XI) wherein each symbol is as defined above can be produced.

As compound (X), for example, 2-dimethylaminoethyl chloride, 3-dimethylaminopropyl chloride and the like can be mentioned.

This reaction can be conducted under conditions as in the production method of the aforementioned compound (IV).

Compound (IX) can be easily converted to a compound (XII) wherein each symbol is as defined above by a method known per se, for example, oxidation reaction described in *Synthesis*, page 639 (1994). By subjecting the present compound (XII) and a compound represented by the formula (XIII)

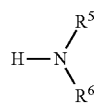

(XIII)

wherein each symbol is as defined above to a reductive amination reaction according to the method described in *Shin Jikken Kagaku Koza*, vol. 14-III, pages 1380-1385 (Maruzen Press), the compound can be converted to compound (XIV) (wherein the symbols in the formula are as defined above).

Compound (XVI) wherein n is an integer of 2 to 10, and other symbols are as defined above can be produced by subjecting compound (XII) and a compound represented by the formula (XV)

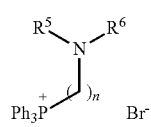

(XV)

wherein each symbol is as defined above and Ph is phenyl, to a Wittig reaction according to the method described in, for example, *J. Am. Chem. Soc.*, vol. 107, page 217 (1985) or *Shin Jikken Kagaku Koza*, vol. 14-I, pages 224-243 (Maruzen Press).

Compound (XV) can be produced according to a method known per se, for example, the method described in *J. Am. Chem. Soc.*, vol. 107, page 217 (1985) and the like, or a method analogous thereto.

Compound (XVI) can be converted to compound (XVII) (the symbols in the formula are as defined above) by subjecting the compound to a reduction reaction according to the method described in *Shin Jikken Kagaku Koza*, vol. 14-I, pages 1-5 (Maruzen Press).

The production methods of compound (II) of the present invention are described in more detail in the following.

Compound (II) of the present invention can be obtained, for example, by the method shown in the following scheme or a method analogous thereto and the like.

Compound (XVIII)-(XXIII) in the formulas may form a salt, and as such salts, for example, those similar to the salts of compound (I) can be used.

In addition, the compound obtained in each step can be used for the next reaction in the form of a reaction mixture as it is or as a crude product. However, it can also be isolated from the reaction mixture according to a conventional method, and easily purified by a separation means such as recrystallization, distillation, chromatography and the like.

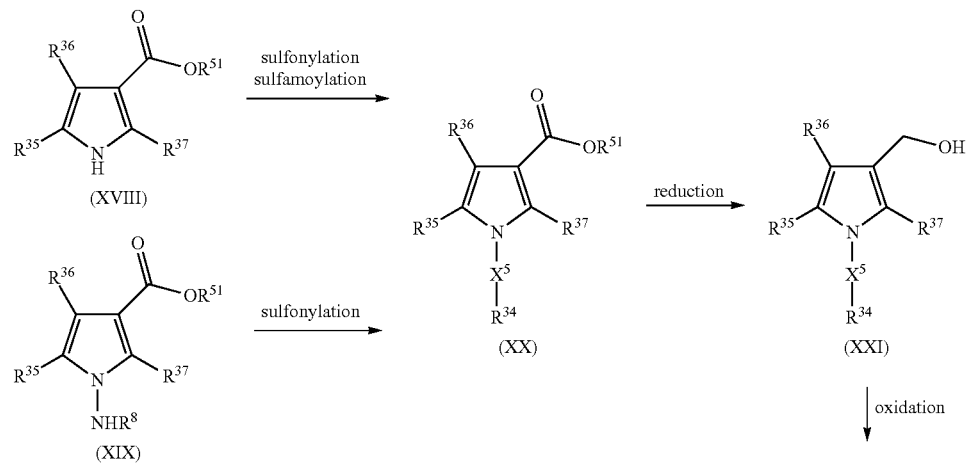

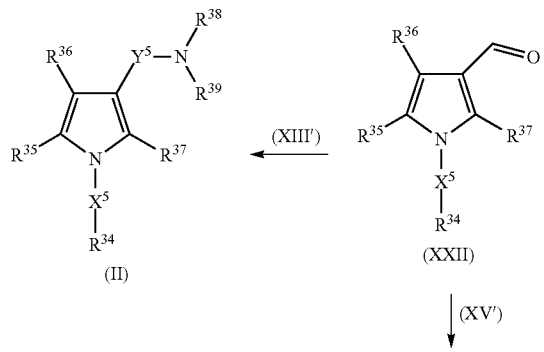

-continued

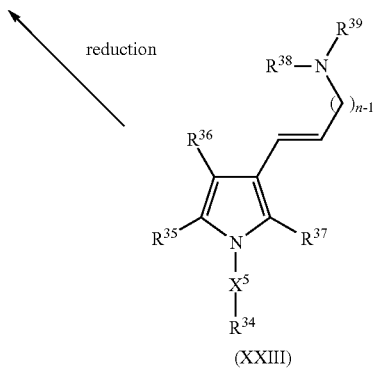

(XXIII)

Compound (XVIII) wherein $R^{51}$ is a $C_{1-4}$ alkyl group such as methyl, ethyl, propyl, isopropyl or butyl and the like, and other symbols are as defined above can be produced according to a method known per se, for example, the method described in *Chem. Pharm. Bull.*, vol. 49, page 1406 (2001), Tetrahedron Letters, vol. 35, page 5989 (1994) and the like, or a method analogous thereto. Compound (XIX) wherein each symbol is as defined above can be produced according to a method known per se, for example, the method described in *Chem. Ber.*, vol. 114, page 564 (1981) and the like, or a method analogous thereto.

Compound (XX) wherein each symbol is as defined above can be produced by sulfonylation of compound (XVIII) or compound (XIX) using $C_{1-5}$ alkylsulfonyl chloride (e.g., mesyl chloride), arylsulfonyl chloride (e.g., tosyl chloride) and the like, or sulfamoylation of compound (XVIII) using $C_{1-5}$ alkylsulfamoyl chloride (e.g., methylsulfamoyl chloride, ethylsulfamoyl chloride etc.) or arylsulfamoyl chloride (e.g., phenylsulfamoyl chloride etc.) and the like.

This reaction is advantageously carried out in a solvent inert to the reaction. While the solvent is not particularly limited as long as the reaction proceeds, solvents such as hydrocarbons (e.g., benzene, toluene and the like), tetrahydrofuran and amides (e.g., N,N-dimethylformamide, N,N-dimethylacetamide and the like) and the like or a mixed solvent thereof and the like are preferable.

In a certain reaction, the use of a base may be effective. As the base, for example, inorganic bases such as sodium hydroxide, potassium hydroxide and the like, basic salts such as sodium carbonate, potassium carbonate, cesium carbonate, sodium hydrogencarbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like and the like can be mentioned. The amount of the base to be used is about 0.1-about 10 mol, preferably about 1-about 5 mol, per 1 mol of compound (XVIII) or (XIX).

In addition, for this reaction, addition of crown ether may be effective. As the crown ether, for example, 15-crown-5-ether, 18-crown-6-ether and the like can be mentioned. The amount of crown ether to be used is about 1-about 10 mol, preferably about 1-about 5 mol, per 1 mol of compound (II).

While the reaction time varies depending on the reagents and solvents to be used, it is generally about 30 min-about 24 hr, preferably about 30 min-about 8 hr.

The reaction temperature is generally about 0° C.-about 250° C., preferably about 25° C.-about 100° C.

A compound (XX) wherein spacer $X^5$ is an oxygen atom can be produced according to a method known per se, for example, the method described in *J. Org. Chem.*, vol. 53, page 2268 (1988) and the like, or a method analogous thereto.

Compound (XXI) (each symbol in the formula is as defined above) can be synthesized by reducing compound (XX) with a reducing agent such as lithium aluminum hydride, diisobutyl aluminum hydride, sodium tetrahydroborate, calcium bis(tetrahydroborate) and the like. As the reducing agent, diisobutyl aluminum hydride is particularly preferable.

This reaction is advantageously carried out using a solvent inert to the reaction. While the solvent is not particularly limited as long as the reaction proceeds, solvents such as hydrocarbons (e.g., benzene, toluene and the like) and ethers (e.g., tetrahydrofuran, diethyl ether and the like), and the like, a mixed solvent thereof and the like are preferable.

While the reaction time varies depending on the reagents and solvent to be used, it is generally about 30 min-about 24 hr, preferably about 30 min-about 8 hr.

The reaction temperature is generally about −78° C. to about 100° C., preferably about −78° C. to about 25° C.

compound (XXII) (each symbol in the formula is as defined above) can be synthesized by reacting compound (XXI) with an oxidant such as chromic acid-pyridine complex, pyridinium chlorochromate, manganese dioxide, sulfur trioxide-pyridine complex or tetra-n-propylammonium perruthenate and the like. As the oxidant, manganese dioxide, sulfur trioxide-pyridine complex or tetra-n-propylammonium perruthenate is particularly preferable. The oxidation reaction can be carried out, for example, according to the method described in *Synthesis*, p. 639 (1994).

Compound (II) wherein $Y^5$ is a methylene chain can be produced by subjecting compound (XXII) and a compound represented by the formula (XIII'):

(XIII')

wherein each symbol in the formula is as defined above, to a reductive amination reaction according to the methods described in *Shin Jikken Kagaku Koza*, Vols. 14-III, pp. 1380-1385 (Maruzen Press).

By reacting compound (XXII) with a compound represented by the formula (XV')

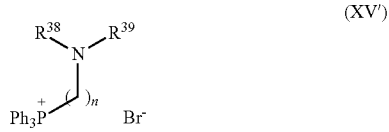

wherein each symbol is as defined above by an operation similar to the production method of the aforementioned compound (XVI), the compound can be converted to compound (XXIII) (wherein each symbol is as defined above), and compound (XXIII) can be converted to a compound (II) wherein $Y^5$ is an alkylene chain by conducting a reduction reaction according to an operation similar to the production method of the aforementioned compound (XVII).

The production method of compound (I) wherein X is —$SO_2$— is further explained in detail by referring to the production methods of compounds (XXXIII) and (XXXX).

se, for example, the method described in *Tetrahedron Letters*, vol. 13, page 5337 (1972), Heterocycles, vol. 7, page 77 (1977), Chem. Pharm. Bull., vol. 27, page 2857 (1979), J. Org. Chem., vol. 62, page 2649 (1997) and the like, or a method analogous thereto.

By reacting N-bromosuccinimide (NBS) with compound (XXIV), compound (XXV) wherein each symbol is as defined above can be produced.

This reaction is advantageously carried out using a solvent inert to the reaction. While the solvent is not particularly limited as long as the reaction proceeds, solvents such as ethers (e.g., tetrahydrofuran, diethyl ether and the like), amides (e.g., N,N-dimethylformamide, N,N-dimethylacetamide and the like) and the like or a mixed solvent thereof and the like are preferable.

While the reaction time varies depending on the reagents and solvents to be used, it is generally about 30 min-about 24 hr, preferably about 5-12 hr.

The reaction temperature is generally about −78° C.-about 25° C., preferably about −40° C.-about 0° C.

N-bromosuccinimide (NBS) is preferably used in about 1 equivalent amount relative to compound (XXIV), and the

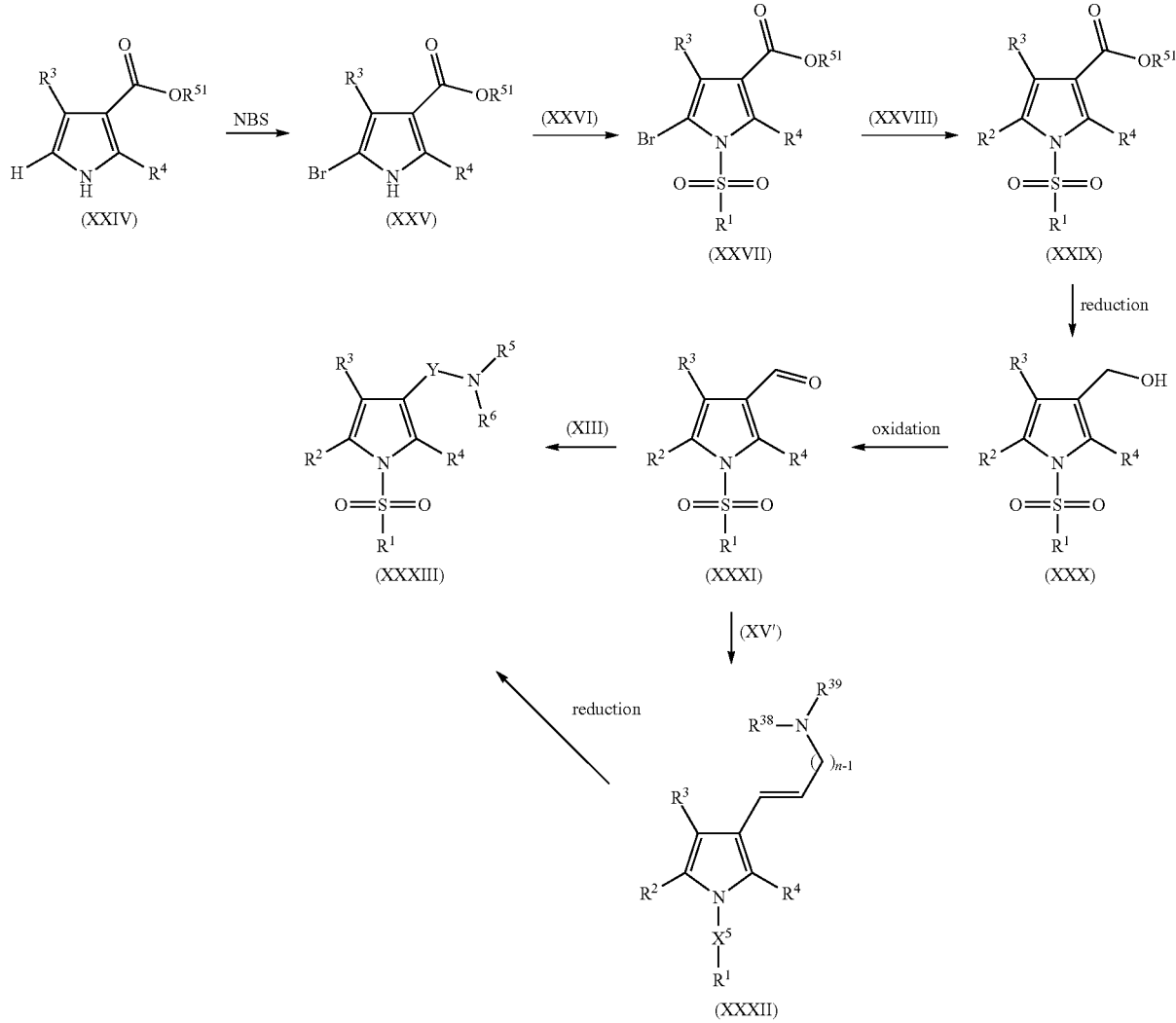

Compound (XXIV) (wherein each symbol is as defined above) can be produced according to a method known per reaction is preferably carried out in an inert gas atmosphere of nitrogen, argon and the like.

In this reaction, addition of a base may sometimes be effective. While the base to be used is not limited as long as the reaction proceeds, organic bases such as pyridine, picoline, lutidine and the like, and the like can be mentioned. The amount of the organic base to be used is about 0.001-about 10 equivalents, preferably about 0.001-about 0.1 equivalent, per 1 mol of compound (XXIV).

By reacting compound (XXV) with a compound represented by the formula (XXVI)

(XXVI)

wherein each symbol is as defined above, compound (XXVII) wherein each symbol is as defined above can be produced.

This reaction is advantageously carried out using a solvent inert to the reaction. While the solvent is not particularly limited as long as the reaction proceeds, solvents such as hydrocarbons (e.g., benzene, toluene and the like), ethers (e.g., tetrahydrofuran and the like), amides (e.g., N,N-dimethylformamide, N,N-dimethylacetamide and the like) and the like or a mixed solvent thereof and the like are preferable.

For this reaction, the use of a base is effective. As the base, for example, inorganic bases such as sodium hydride, sodium hydroxide, potassium hydroxide and the like, basic salts such as sodium carbonate, potassium carbonate, cesium carbonate, sodium hydrogencarbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 1-about 10 mol, preferably about 1-about 5 mol, per 1 mol of compound (XXV).

This reaction can also be carried out in the co-presence of crown ethers. As the crown ether, for example, 15-crown-5-ether, 18-crown-6-ether and the like can be mentioned. The amount of the crown ether to be used is, about 1-about 10 mol, preferably about 1-about 5 mol, per 1 mol of compound (XXV).

While the reaction time varies depending on the reagents and solvents to be used, it is generally about 30 min-about 24 hr, preferably about 30 min-about 8 hr.

The reaction temperature is generally about 0° C.-about 100° C., preferably about 10° C.-about 50° C.

By reacting compound (XXVII) with a compound represented by the formula (XXVIII)

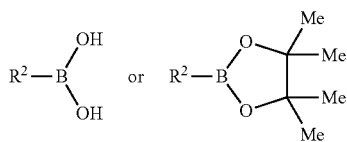

(XXVIII)

wherein each symbol is as defined above, according to the method described in *Synthetic Communications*, vol. 11, page 513 (1981), or a method analogous thereto, compound (XXIX) wherein each symbol is as defined above can be produced.

Compound (XXIX) can be converted to compound (XXX) wherein each symbol is as defined above, by a method similar to the production method of compound (XXI).

Compound (XXX) can be converted to compound (XXXI) wherein each symbol is as defined above by a method similar to the production method of compound (XXII).

Compound (XXXI) can be converted to compound (XXXIII) wherein each symbol is as defined above and Y is an alkylene chain by a method similar to the production method of compound (XIV) from compound (XII).

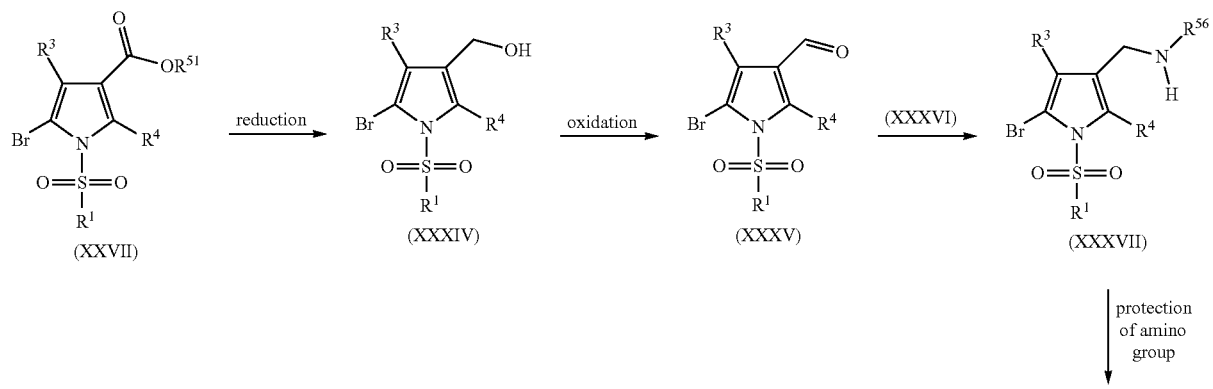

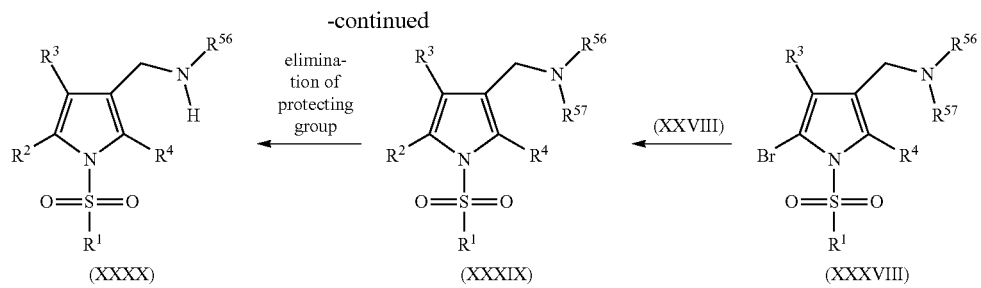

Compound (XXVII) can be converted to compound (XXXIV) by a method similar to the production method of compound (XXI).

Compound (XXXIV) (wherein each symbol is as defined above) can be converted to compound (XXXV) (wherein each symbol is as defined above) by a method similar to the production method of compound (XXII).

By reacting compound (XXXV) with a compound represented by the formula (XXXVI)

$$R^{56}-NH_2 \quad (XXXVI)$$

wherein $R^{56}$ is an optionally substituted hydrocarbon group, compound (XXXVII) (wherein each symbol is as defined above) can be produced by a method similar to the production method of compound (II) from compound (XXII).

As the "optionally substituted hydrocarbon group" for $R^{56}$, a group similar to the "optionally substituted hydrocarbon group" for the aforementioned $R^{40}$ can be mentioned.

Compound (XXXVII) can be converted to compound (XXXIX) (wherein each symbol is as defined above) by converting the compound to compound (XXXVIII) wherein $R^{57}$ is an amino-protecting group (e.g., tert-butylcarbamate group [BOC group], benzylcarbamate group (Cbz group) and the like), and other symbols are as defined above by protecting an amino group according to a method known per se, for example, the method described in *Protective Groups in Organic Synthesis*, $3^{rd}$ Ed. (Theodora W. Greene, Peter G. M. Wuts), pages 494-653, Wiley-Interscience, 1999, and the like, and then by a method similar to the production method of compound (XXIX).

Compound (XXXIX) can be converted to compound (XXXX) (wherein each symbol is as defined above) by eliminating the amino-protecting group by a method known per se, for example, the method described in *Protective Groups in Organic Synthesis*, $3^{rd}$ Ed. (Theodora W. Greene, Peter G. M. Wuts), pages 494-653, Wiley-Interscience, 1999, and the like.

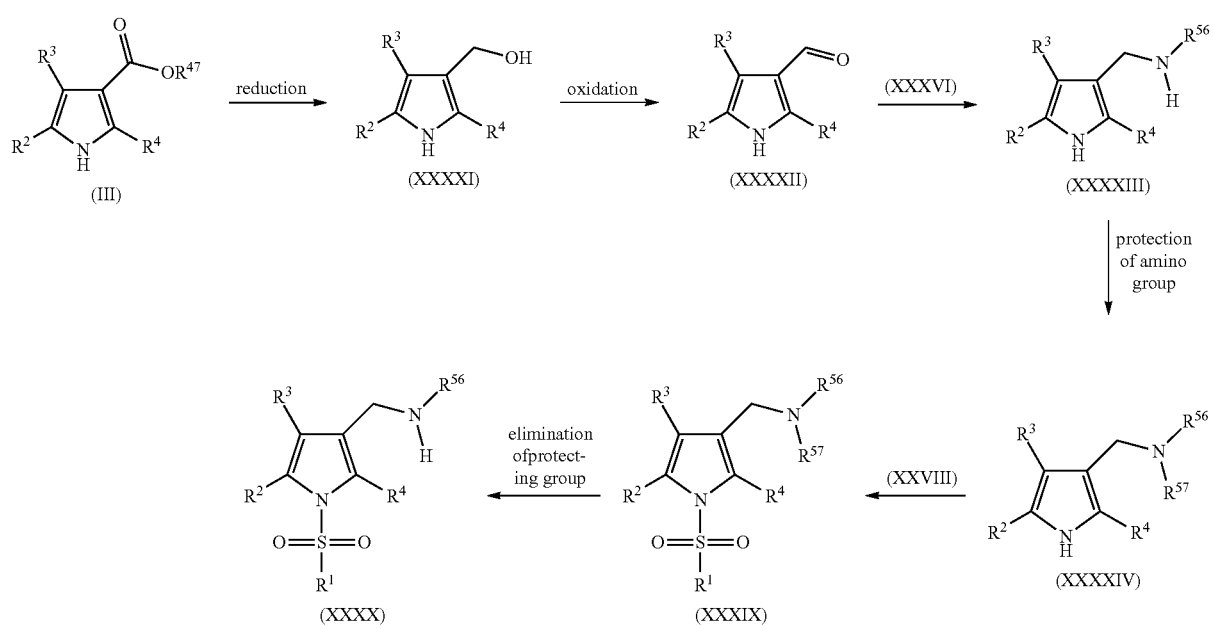

Compound (III) can be converted to compound (XXXXI) (wherein each symbol is as defined above) by a method similar to the production method of compound (XXI).

Compound (XXXXI) can be converted to compound (XXXXII) (wherein each symbol is as defined above) by a method similar to the production method of compound (XXII).

Compound (XXXXII) can be converted to compound (XXXXIII) (wherein each symbol is as defined above) by a method similar to the production method of compound (XXXVII).

Compound (XXXXIII) can be converted to compound (XXXIX) (wherein each symbol is as defined above) by converting the compound to compound (XXXXIV) (wherein each symbol is as defined above) by protecting an amino group according to a method known per se, for example, the method described in *Protective Groups in Organic Synthesis*, $3^{rd}$ Ed. (Theodora W. Greene, Peter G.

M. Wuts), pages 494-653, Wiley-Interscience, 1999, and the like, and then by a method similar to the production method of compound (XXVII).

Compound (XXXIX) can be converted to compound (XXXX) (wherein each symbol is as defined above) by eliminating the amino-protecting group by a method known per se, for example, the method described in *Protective Groups in Organic Synthesis*, 3$^{rd}$ Ed. (Theodora W. Greene, Peter G. M. Wuts), pages 494-653, Wiley-Interscience, 1999, and the like.

In addition, compounds (XXXV), (XXXI) and (XXXIII) can also be produced by the following methods.

Compound (XXXI) wherein each symbol is as defined above can be converted to compound (XXXIII) wherein each symbol is as defined above by the aforementioned method.

In each of the aforementioned reactions, when the starting compound has an amino group, a carboxyl group or a hydroxyl group as a substituent, a protecting group generally used in peptide chemistry and the like may be introduced into these groups. In this case, by eliminating the protecting group as necessary after the reaction, the objective compound can be obtained. Introduction and elimination of these protecting groups can be performed by a method known per

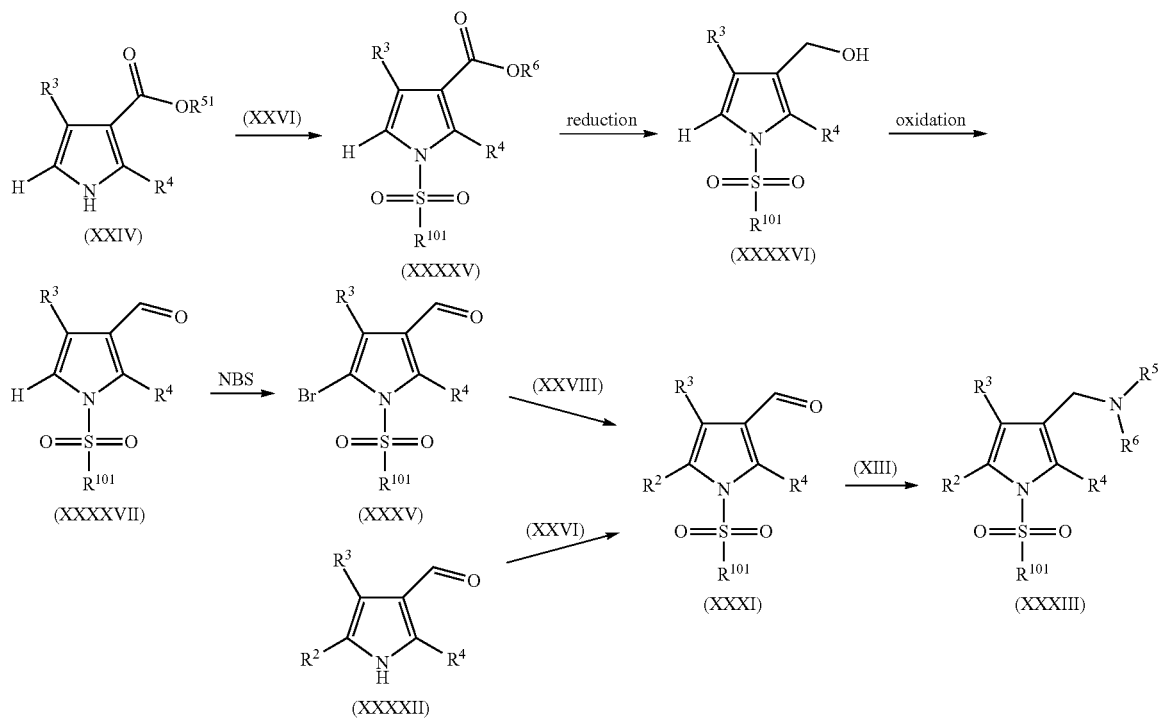

Compound (XXIV) wherein each symbol is as defined above can be converted to compound (XXXXV) wherein each symbol is as defined above by a method similar to the production method of compound (XXVII).

Compound (XXXXV) wherein each symbol is as defined above can be converted to compound (XXXXVI) wherein each symbol is as defined above by a method similar to the production method of compound (XXI).

Compound (XXXXVI) wherein each symbol is as defined above can be converted to compound (XXXXVII) wherein each symbol is as defined above by a method similar to the production method of compound (XXII).

Compound (XXXXVII) wherein each symbol is as defined above can be converted to compound (XXXV) wherein each symbol is as defined above by a method similar to the production method of compound (XXV).

Compound (XXXV) wherein each symbol is as defined above can be converted to compound (XXXI) wherein each symbol is as defined above by a method similar to the production method of compound (XXIX).

Compound (XXXXII) wherein each symbol is as defined above can be converted to compound (XXXI) wherein each symbol is as defined above by a method similar to the production method of compound (XXVII).

se, for example, the method described in *Protective Groups in Organic Synthesis*, 3rd Ed., Theodora W. Greene, Peter G. M. Wuts, Wiley-Interscience (1999) and the like.

Compound (I) can be isolated and purified by a known means such as phase transfer, concentration, solvent extraction, fractionation, liquid conversion, crystallization, recrystallization, chromatography and the like.

When compound (I) is obtained as a free compound, it can be converted to a desired salt by a method known per se or a method analogous thereto; conversely, when compound (I) is obtained as a salt, it can be converted into a free form or another desired salt by a method known per se or a method analogous thereto.

Compound (I) (or compound (II)) may be used as a prodrug. The prodrug of compound (I) means a compound which is converted to compound (I) under the physiological condition in the body by a reaction with an enzyme, gastric acid, or the like, that is, a compound which is converted to compound (I) by enzymatic oxidation, reduction, hydrolysis, and the like; a compound which is converted to compound (I) by hydrolysis with gastric acid, and the like.

The prodrug of compound (I) includes a compound wherein the amino group of compound (I) is modified with acyl, alkyl or phosphoryl (e.g., a compound wherein the amino group of compound (I) is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein the hydroxyl group of compound (I) is modified with acyl, alkyl, phosphoric acid or boric acid (e.g., a compound wherein the hydroxyl group of compound (I) is modified with acetyl, palmitoyl, propanoyl, pivaloyl, succinyl, fumaryl, alanyl or dimethylaminomethylcarbonyl, etc.); a compound wherein a carboxy group of compound (I) is modified to ester or amide (e.g., a compound wherein a carboxy group of compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These compounds can be produced from compound (I) by a method known per se.

In addition, the prodrug of compound (I) may be a compound, which is converted to compound (I) under the physiological conditions, as described in *Pharmaceutical Research and Development*, Vol. 7 (Molecule Design), pp. 163-198 (1990), published by Hirokawa Publishing Co.

When compound (I) contains isomers such as an optical isomer, a stereoisomer, a regioisomer, a rotamer and the like, either isomer and a mixture of these are also encompassed in compound (I). For example, when compound (I) has an optical isomer, an optical isomer resolved from a racemate is also encompassed in compound (I). These isomers can be obtained as single products according to synthesis and separation methods known per se (concentration, solvent extraction, column chromatography, recrystallization, etc.).

The compound (I) may be a crystal, and both a single crystal and crystal mixtures are encompassed in compound (I). Crystals can be produced by crystallization according to crystallization methods known per se.

The compound (I) may be a solvate (e.g., hydrate etc.) or a non-solvate, both of which are encompassed in the compound (I).

A compound labeled with an isotope (e.g., $^3$H, $^{14}$C, $^{35}$S, $^{125}$I and the like) is also encompassed in the compound (I).

Compound (I) (or compound (II)) and a prodrug thereof of the present invention (hereinafter sometimes to be abbreviated as the compound of the present invention) have a proton pump inhibitory effect and effectively suppress gastric acid secretion. In addition, since they show low toxicity (e.g., acute toxicity, chronic toxicity, genetic toxicity, reproductive toxicity, cardiotoxicity, drug interaction, carcinogenicity and the like) and high water-solubility, and are superior in the stability, in vivo kinetics (absorbability, distribution, metabolism, excretion and the like), and efficacy expression, they are useful as pharmaceutical agents.

The compound of the present invention is useful for the prophylaxis or treatment of peptic ulcer (e.g., gastric ulcer, gastric ulcer due to postoperative stress, duodenal ulcer, anastomotic ulcer, ulcer caused by non-steroidal anti-inflammatory agents etc.); gastritis; erosive esophagitis; gastroesophageal reflux disease (Symptomatic Gastroesophageal Reflux Disease (symptomatic GERD)) free of esophagitis and the like; NUD (Non Ulcer Dyspepsia); gastric cancer (including gastric cancer associated with promoted production of interleukin-1β due to gene polymorphism of interleukin-1); stomach MALT lymphoma; Zollinger-Ellison syndrome; gastric hyperacidity (e.g., gastric hyperacidity and ulcer due to postoperative stress); upper gastrointestinal hemorrhage due to peptic ulcer, acute stress ulcer, hemorrhagic gastritis or invasive stress (e.g. stress caused by major surgery requiring postoperative intensive management, and cerebrovascular disorder, head trauma, multiple organ failure and extensive burn, each requiring intensive treatment) and the like; and the like, pre-anesthetic administration, eradication of *Helicobacter pylori* and the like, in mammals (e.g., human, simian, sheep, cattle, horse, dog, cat, rabbit, rat, mouse etc.).

As used herein, the above-mentioned reflux esophagitis and gastroesophageal reflux disease (Symptomatic Gastroesophageal Reflux Disease (symptomatic GERD)) free of esophagitis are sometimes collectively referred to simply as GERD.

The content of a compound of the present invention in the pharmaceutical composition of the present invention is about 0.01 to 100% by weight relative to the entire composition. Though subject to change depending on the administration target, administration route, target disease and the like, its dose is about 0.5 to about 1,500 mg/day, preferably about 5 to about 150 mg/day, based on the active ingredient, when, for example, the compound is orally administered as an anti-ulcer agent to an adult human (60 kg). The compound of the present invention may be administered once daily or in 2 or 3 divided portions per day.

The compound of the present invention shows low toxicity and can be safely administered orally or parenterally (e.g., topical, rectal, intravenous administrations and the like) as it is or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, liquid, injection, suppository, sustained-release preparation, plaster and the like. Particularly, the compound of the present invention is preferably administered as an oral preparation in the form of tablet, granule, capsule and the like.

The pharmacologically acceptable carrier that may be used to produce the pharmaceutical composition of the present invention includes various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonizing agents, buffers and soothing agents for liquid preparations and the like. Other conventional additives such as preservatives, anti-oxidants, coloring agents, sweetening agents, souring agents, bubbling agents and flavorings may also be used as necessary.

Such "excipients" include, for example, lactose, sucrose, D-mannitol, starch, cornstarch, crystalline cellulose, light anhydrous silicic acid, titanium oxide and the like.

Such "lubricants" include, for example, magnesium stearate, sucrose fatty acid esters, polyethylene glycol, talc, stearic acid and the like.

Such "binders" include, for example, hydroxypropyl cellulose, hydroxypropylmethyl cellulose, crystalline cellulose, starch, polyvinylpyrrolidone, gum arabic powder, gelatin, pullulan, low-substituted hydroxypropyl cellulose and the like.

Such "disintegrants" include (1) crosspovidone, (2) what is called super-disintegrants such as crosscarmellose sodium (FMC-Asahi Chemical) and carmellose calcium (Gotoku Yakuhin) etc, (3) carboxymethyl starch sodium (e.g., product of Matsutani Chemical), (4) low-substituted hydroxypropyl cellulose (e.g., product of Shin-Etsu Chemical), (5) corn starch, and so forth. Said "crosspovidone" may be any crosslinked polymer having the chemical name 1-ethenyl- 2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Such "water-soluble polymers" include, for example, ethanol-soluble water-soluble polymers [e.g., cellulose derivatives such as hydroxypropyl cellulose (hereinafter also referred to as HPC) etc, polyvinylpyrrolidone and the like], ethanol-insoluble water-soluble polymers [e.g., cellulose derivatives such as hydroxypropylmethyl cellulose (hereinafter also referred to as HPMC) etc., methyl cellulose, carboxymethyl cellulose sodium and the like, sodium polyacrylate, polyvinyl alcohol, sodium alginate, guar gum and the like] and the like.

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogencarbonate, disodium hydrogenphosphate and the like. Such basic inorganic salts of potassium include, for example, potassium carbonate, potassium hydrogencarbonate and the like. Such basic inorganic salts of magnesium include, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}\cdot CO_3\cdot 4H_2O$], and aluminum magnesium hydroxide. Preferred are heavy magnesium carbonate, magnesium carbonate, magnesium oxide, magnesium hydroxide and the like. Such basic inorganic salts of calcium include, for example, precipitated calcium carbonate, calcium hydroxide, etc.

Such "solvents" include, for example, water for injection, alcohol, propylene glycol, macrogol, sesame oil, corn oil, olive oil and the like.

Such "dissolution aids" include, for example, polyethylene glycol, propylene glycol, D-mannitol, benzyl benzoate, ethanol, trisaminomethane, cholesterol, triethanolamine, sodium carbonate, sodium citrate and the like.

Such "suspending agents" include, for example, surfactants such as stearyltriethanolamine, sodium lauryl sulfate, laurylaminopropionic acid, lecithin, benzalkonium chloride, benzethonium chloride, glyceryl monostearate etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose etc., and the like.

Such "isotonizing agents" include, for example, glucose, D-sorbitol, sodium chloride, glycerol, D-mannitol and the like.

Such "buffers" include, for example, buffer solutions of phosphates, acetates, carbonates, citrates etc, and the like.

Such "soothing agents" include, for example, benzyl alcohol and the like.

Such "preservatives" include, for example, p-oxybenzoic acid esters, chlorobutanol, benzyl alcohol, phenethyl alcohol, dehydroacetic acid, sorbic acid and the like.

Such "antioxidants" include, for example, sulfites, ascorbic acid, α-tocopherol and the like.

Such "coloring agents" include, for example, food colors such as Food Color Yellow No. 5, Food Color Red No. 2, Food Color Blue No. 2 etc.; food lake colors, red ferric oxide and the like.

Such "sweetening agents" include, for example, saccharin sodium, dipotassium glycyrrhizinate, aspartame, stevia, thaumatin and the like.

Such "souring agents" include, for example, citric acid (citric anhydride), tartaric acid, malic acid and the like.

Such "bubbling agents" include, for example, sodium bicarbonate and the like.

Such "flavorings" may be synthetic substances or naturally occurring substances, and include, for example, lemon, lime, orange, menthol, strawberry and the like.

The compound of the present invention may be prepared as a preparation for oral administration in accordance with a commonly-known method, by, for example, compression-shaping with a carrier such as an excipient, a disintegrant, a binder, a lubricant, or the like, and subsequently coating the preparation as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the compound of the present invention as an orally disintegrating tablet, available methods include, for example, a method in which a core containing crystalline cellulose and lactose is coated with the compound of the present invention and, where necessary, a basic inorganic salt, and then further coated with a coating layer containing a water-soluble polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

The above-mentioned "enteric coating layer" includes, for example, a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., Eudragit L30D-55 (trade name; produced by Rohm), Colicoat MAE30DP (trade name; produced by BASF), Polyquid PA30 (trade name; produced by San-yo Chemical) etc.), carboxymethylethyl cellulose, shellac and the like; sustained-release substrates such as methacrylic acid copolymers (e.g., Eudragit NE30D (trade name), Eudragit RL30D (trade name), Eudragit RS30D (trade name), etc.) and the like; water-soluble polymers; plasticizers such as triethyl citrate, polyethylene glycol, acetylated monoglycerides, triacetin, castor oil and the like; and the like, and the like.

The above-mentioned "additive" includes, for example, water-soluble sugar alcohols (e.g., sorbitol, mannitol, maltitol, reduced starch saccharides, xylitol, reduced palatinose, erythritol, etc.), crystalline cellulose (e.g., Ceolas KG 801, Avicel PH 101, Avicel PH 102, Avicel PH 301, Avicel PH 302, Avicel RC-591 (crystalline cellulose carmellose sodium) etc.), low-substituted hydroxypropyl cellulose (e.g., LH-22, LH-32, LH-23, LH-33 (Shin-Etsu Chemical), mixtures thereof etc.) and the like. Furthermore, binders, souring agents, bubbling agents, sweetening agents, flavorings, lubricants, coloring agents, stabilizers, excipients, disintegrants etc. are also used.

The compound of the present invention may be used in combination with 1 to 3 other active ingredients.

Such "other active ingredients" include, for example, anti-*Helicobacter pylori* active substances, imidazole compounds, bismuth salts, quinolone compounds, and so forth.

Such "anti-*Helicobacter pylori* active substances" include, for example, antibiotic penicillins (e.g., amoxicillin, benzylpenicillin, piperacillin, mecillinam, etc.), antibiotic cefems (e.g., cefixime, cefaclor, etc.), antibiotic macrolides (e.g., erythromycin, clarithromycin, etc.), antibiotic tetracyclines (e.g., tetracycline, minocycline, streptomycin, etc.), antibiotic aminoglycosides (e.g., gentamicin, amikacin, etc.), imipenem and so forth. Of these substances, preferred are antibiotic penicillins, antibiotic macrolides and the like.

Such "imidazole compounds" include, for example, metronidazole, miconazole and the like.

Such "bismuth salts" include, for example, bismuth acetate, bismuth citrate and the like.

Such "quinolone compounds" include, for example, ofloxacin, ciploxacin and the like.

For eradication of *Helicobacter pylori*, a compound (I) or a salt thereof of the present invention with antibiotic penicillin (e.g., amoxicillin and the like) and antibiotic erythromycin (e.g., clarithromycin and the like) is preferably used. When the compound of the present invention is used for the purpose of eradication of *Helicobacter pylori*, while the compound of the present invention has an antibacterial activity against *H. pylori*, when co-used with other active ingredient, it can enhance the antibacterial action of other antibiotics based on the pH controlling action in the stomach and the like, in addition to the antibacterial activity of the compound per se of the present invention, and also provides an assistant effect such as an eradication effect based on the action of the antibiotics to be used in combination.

Such "other active ingredients" and the compound (I) or a salt thereof of the present invention may be mixed, prepared as a single pharmaceutical composition [e.g., tablets, powders, granules, capsules (including soft capsules), liquids, injectable preparations, suppositories, sustained-release preparations, etc.], according to a method known per se for combined use, or may also be prepared as separate preparations and administered to the same subject simultaneously or in a staggered manner.

EXAMPLES

The present invention is explained in detail in the following by referring to Reference Examples, Examples and Experimental Examples, which are not to be construed as limitative.

In the following Reference Examples and Examples, the "room temperature" generally means about 10° C. to about 35° C., but it is not particularly strictly limited. The mixing ratio of liquids shows a volume ratio. Unless otherwise specified, "%" means weight %. The yield is in mol/mol %. Silica gel column chromatography was performed using silica gel 60 (0.063-0.200 mm) manufactured by MERCK or Fuji Silysia Chemical Ltd. Chromatorex (trade name) NH (described as basic silica gel column chromatography). For $^1$H-NMR spectrum, tetramethylsilane was used as the internal standard, and Varian Gemini-200 (200 MHz), Mercury-300 (300 MHz) spectrometer, Bruker AVANCE AV300 (300 MHz) spectrometer and JNM-AL400 (400 MHz) nuclear magnetic resonance apparatuses (JEOL DATUM (JEOL DATUM LTD.)) were used for the measurement. The following abbreviations are used for showing the measurement results.

s: singlet, d: doublet, dd: double doublet, ddd: double double doublet, t: triplet, dt: double triplet, t: triplet, q: quartet, m: multiplet, br: broad, brs: broad singlet, brd: broad doublet, brt: broad triplet, J: coupling constant, Hz: Hertz.

Reference Example 1

Ethyl 2-cyano-4-oxo-4-phenylbutanoate

Potassium carbonate (13.82 g) was added to ethyl cyanoacetate (37 mL), and the mixture was stirred at 40-45° C. for 45 min. A solution (100 mL) of phenacyl bromide (10.0 g) in acetone was added dropwise over 30 min. After completion of the dropwise addition, and the mixture was stirred at room temperature for 18 hr. The reaction mixture was filtered, and the filtrate was concentrated under reduced pressure. Water was added to the residue, and the mixture was extracted with ethyl acetate. The extract was washed with saturated brine, dried over anhydrous sodium sulfate, and concentrated under reduced pressure. Excess ethyl cyanoacetate contained in the obtained oil was evaporated under reduced pressure, and the residue was purified by silica gel column chromatography (eluent: hexane-ethyl acetate=8:1→1:1) to give the title compound as a pale-yellow oil (yield 10.41 g, 90%).

$^1$H-NMR (CDCl$_3$) δ: 1.35 (3H, t, J=7.2 Hz), 3.55 (1H, dd, J=16.0 Hz, 5.6 Hz), 3.80 (1H, dd, J=16.0 Hz, 7.0 Hz), 4.16 (1H, dd, J=7.0 Hz, 5.6 Hz), 4.31 (2H, q, J=7.2 Hz), 7.40-7.70 (3H, m), 7.90-8.00 (2H, m).

Reference Example 2

Ethyl 2-chloro-5-phenyl-1H-pyrrole-3-carboxylate

To a solution (60 mL) of ethyl 2-cyano-4-oxo-4-phenylbutanoate (5.0 g) in tetrahydrofuran was blown in hydrogen chloride (28 g) under ice-cooling, and the mixture was stirred at room temperature for 3 hr. Then, nitrogen was blown in to remove hydrogen chloride. The reaction mixture was concentrated under reduced pressure, and the residue was purified by silica gel column chromatography (eluent: hexane-ethyl acetate=6:1) to give the title compound as a pale-yellow solid (yield 4.24 g, 79%).

$^1$H-NMR (CDCl$_3$) δ: 1.37 (3H, t, J=6.8 Hz), 4.33 (2H, q, J=6.8 Hz), 6.87 (1H, d, J=3.2 Hz), 7.20-7.60 (5H, m), 8.79 (1H, br).

Reference Example 3

Ethyl 5-phenyl-1H-pyrrole-3-carboxylate

To a solution (50 mL) of ethyl 2-chloro-5-phenyl-1H-pyrrole-3-carboxylate (8.5 g) in ethanol was added 10% palladium carbon (50% water containing product, 0.5 g), and the mixture was stirred under a hydrogen atmosphere at room temperature for 24 hr. The reaction mixture was filtered, and the filtrate was concentrated under reduced pressure. The residue was purified by silica gel column chromatography (eluent: hexane-ethyl acetate=9:1→1:1) to give the title compound as a colorless solid (yield 4.50 g, 62%).

$^1$H-NMR (CDCl$_3$) δ: 1.36 (3H, t, J=7.2 Hz), 4.31 (2H, q, J=7.2 Hz), 6.91 (1H, m), 7.20-7.70 (6H, m), 8.77 (1H, br).

Reference Example 4

Ethyl 1-[(4-methylphenyl)sulfonyl]-5-phenyl-1H-pyrrole-3-carboxylate

Sodium hydride (60% in oil, 408 mg) was washed with hexane and added to N,N-dimethylformamide (5 mL). The mixture was cooled to 0° C., and a solution (5 mL) of ethyl 5-phenyl-1H-pyrrole-3-carboxylate (2.0 g) in N,N-dimethylformamide was added. After stirring at 0° C. for 30 min, a solution (10 mL) of tosyl chloride (1.94 g) in N,N-dimethylformamide was added, and the reaction mixture was stirred at room temperature for 1 hr. Water was added, and the mixture was extracted with ethyl acetate. The extract was washed with saturated brine, dried over anhydrous sodium sulfate, and concentrated under reduced pressure. The residue was purified by silica gel column chromatography (eluent: hexane-ethylacetate=6:1→1:1) to give the title compound as a colorless oil (yield 2.90 g, 84%).

$^1$H-NMR (CDCl$_3$) δ: 1.36 (3H, t, J=7.2 Hz), 2.36 (3H, s), 4.31 (2H, q, J=7.2 Hz), 6.52 (1H, d, J=1.8 Hz), 7.05-7.40 (9H, m), 8.07 (1H, d, J=1.8 Hz).

Reference Example 5

{1-[(4-Methylphenyl)sulfonyl]-5-phenyl-1H-pyrrol-3-yl}methanol

A solution (30 mL) of ethyl 1-[(4-methylphenyl)sulfonyl]-5-phenyl-1H-pyrrole-3-carboxylate (2.85 g) in tetrahydrofuran was cooled to −78° C., and a 1.5 mol/l toluene solution (12.8 mL) of diisobutylaluminum hydride was added dropwise over 30 min, and the mixture was further stirred at −78° C. for 1 hr. 1 mol/l Hydrochloric acid (20 mL) was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=6:1→1:1) to give the title compound as a brown oil (yield 2.29 g, 91%).

$^1$H-NMR (CDCl$_3$) δ: 2.35 (3H, s), 4.55 (2H, d, J=4.8 Hz), 6.19 (1H, d, J=2.2 Hz), 7.09 (2H, d, J=8.4 Hz), 7.15-7.40 (8H, m).

Reference Example 6

1-[(4-Methylphenyl)sulfonyl]-5-phenyl-1H-pyrrole-3-carbaldehyde

To a solution (10 mL) of {1-[(4-methylphenyl)sulfonyl]-5-phenyl-1H-pyrrol-3-yl}methanol (1.50 g) in acetonitrile were added tetra-n-propylammonium perruthenate (150 mg), N-methylmorpholine N-oxide (932 mg) and molecular sieves 4A powder (1.5 g), and the mixture was stirred at room temperature for 1 hr. The reaction mixture was concentrated under reduced pressure, and the residue was suspended in ethyl acetate and filtered through celite. The filtrate was concentrated under reduced pressure, and the residue was purified by silica gel column chromatography (eluent: hexane-ethyl acetate=6:1→1:1) to give the title compound as a brown oil (yield 1.23 g, 82%).

$^1$H-NMR (CDCl$_3$) δ: 2.37 (3H, s), 6.55 (1H, d, J=2.2 Hz), 7.05-7.50 (9H, m), 8.10 (1H, d, J=2.2 Hz), 9.87 (1H, s).

Reference Example 7

{1-[(4-Fluorophenyl)sulfonyl]-5-phenyl-1H-pyrrol-3-yl}methanol

A solution (5 mL) of ethyl 5-phenyl-1H-pyrrole-3-carboxylate (500 mg) in N,N-dimethylformamide was cooled to 0° C., and sodium hydride (60% in oil, 139 mg) was added after washing with hexane. The mixture was further stirred at 0° C. for 30 min, 4-fluorobenzenesulfonyl chloride (542 mg) was added, and the mixture was stirred at room temperature for 30 min. The reaction mixture was concentrated under reduced pressure, and water was added to the residue, and the mixture was extracted with ethyl acetate. The extract was washed with saturated brine, dried over anhydrous sodium sulfate, and concentrated under reduced pressure. The residue was dissolved in tetrahydrofuran (10 mL) and the mixture was cooled to −78° C. A 1.5 mol/l toluene solution (3.86 mL) of diisobutylaluminum hydride was added dropwise, and the mixture was further stirred at −78° C. for 1 hr. 1 mol/l Hydrochloric acid (20 mL) was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→1:1) to give the title compound as a brown oil (yield 410 mg, 53%).

$^1$H-NMR (CDCl$_3$) δ: 4.57 (2H, d, J=5.0 Hz), 6.21 (1H, d, J=1.8 Hz), 6.97 (2H, t, J=9.2 Hz), 7.15-7.45 (8H, m).

Reference Example 8

1-[(4-Fluorophenyl)sulfonyl]-5-phenyl-1H-pyrrole-3-carbaldehyde

Using {1-[(4-fluorophenyl)sulfonyl]-5-phenyl-1H-pyrrol-3-yl}methanol (405 mg), tetra-n-propylammonium perruthenate (42 mg), N-methylmorpholine N-oxide (247 mg) and molecular sieves 4 A powder (1.0 g), a procedure as in Reference Example 6 was performed to give the title compound as a brown oil (yield 321 mg, 80%).

$^1$H-NMR (CDCl$_3$) δ: 6.57 (1H, d, J=1.8 Hz), 6.98 (2H, t, J=8.8 Hz), 7.10-7.45 (7H, m), 8.10 (1H, d, J=1.8 Hz), 9.89 (1H, s).

Reference Example 9

[1-(Methylsulfonyl)-5-phenyl-1H-pyrrol-3-yl]methanol

A solution (5 mL) of ethyl 5-phenyl-1H-pyrrole-3-carboxylate (500 mg) in N,N-dimethylformamide was cooled to 0° C., sodium hydride (60% in oil, 140 mg) was added after washing with hexane. The mixture was stirred at room temperature for 30 min, cooled to 0° C., and mesyl chloride (0.269 mL) was added. The reaction mixture was stirred at room temperature for 2 hr, and 1 mol/l hydrochloric acid (5 mL) was added. The mixture was neutralized with saturated aqueous sodium hydrogen carbonate, and concentrated under reduced pressure. Water was added to the residue, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=6:1→1:1). The obtained colorless solid was dissolved in tetrahydrofuran (10 mL) and cooled to −78° C. A 1.5 mol/l solution (3.5 mL) of diisobutylaluminum hydride in toluene was added dropwise, and the mixture was further stirred at −78° C. for 1 hr. 1 mol/l Hydrochloric acid (20 mL) was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→1:1) to give the title compound as a colorless solid (yield 230 mg, 39%).
$^1$H-NMR (CDCl$_3$) δ: 2.85 (3H, s), 4.60 (2H, d, J=4.4 Hz), 6.36 (1H, d, J=2.2 Hz), 7.20-7.60 (6H, m).

Reference Example 10

1-(Methylsulfonyl)-5-phenyl-1H-pyrrole-3-carbaldehyde

Using [1-(methylsulfonyl)-5-phenyl-1H-pyrrol-3-yl]methanol (220 mg), tetra-n-propylammonium perruthenate (31 mg), N-methylmorpholine N-oxide (177 mg) and molecular sieves 4 A powder (500 mg), a procedure as in Reference Example 6 was performed to give the title compound as a brown oil (yield 165 mg, 76%).
$^1$H-NMR (CDCl$_3$) δ: 2.88 (3H, s), 6.30 (1H, d, J=1.6 Hz), 7.20-7.60 (6H, m), 9.98 (1H, s).

Reference Example 11

Ethyl 1-[(4-methoxyphenyl)sulfonyl]-5-phenyl-1H-pyrrole-3-carboxylate

Using ethyl 5-phenyl-1H-pyrrole-3-carboxylate (250 mg), sodium hydride (60% in oil, 60 mg) and 4-methoxybenzenesulfonyl chloride (264 mg), a procedure as in Reference Example 4 was performed to give the title compound as a colorless oil (yield 433 mg, 97%).
$^1$H-NMR (CDCl$_3$) δ: 1.37 (3H, t, J=7.4 Hz), 3.82 (3H, s), 4.30 (2H, q, J=7.4 Hz), 6.51 (1H, d, J=1.8 Hz), 6.74 (2H, d, J=9.0 Hz), 7.15-7.40 (7H, m), 8.07 (1H, d, J=1.8 Hz).

Reference Example 12

1-[(4-Methoxyphenyl)sulfonyl]-5-phenyl-1H-pyrrole-3-carbaldehyde

Ethyl 1-[(4-methoxyphenyl)sulfonyl]-5-phenyl-1H-pyrrole-3-carboxylate (430 mg) was dissolved in tetrahydrofuran (10 mL), and the mixture was cooled to −78° C. A 1.5 mol/l solution (3.36 mL) of diisobutylaluminum hydride in toluene was added dropwise, and the mixture was further stirred at −78° C. for 1 hr. 1 mol/l Hydrochloric acid (20 mL) was added to the reaction mixture, and the mixture was extracted with ethyl acetate. The extract washed with saturated brine, dried over anhydrous sodium sulfate, and concentrated under reduced pressure. The residue was dissolved in acetonitrile (10 mL), tetra-n-propylammonium perruthenate (39 mg), N-methylmorpholine N-oxide (227 mg) and molecular sieves 4 A powder (500 mg) were added, and the mixture was stirred at room temperature for 30 min. The reaction mixture was concentrated under reduced pressure, and the residue was suspended in ethyl acetate and filtered through celite. The filtrate was concentrated under reduced pressure, and the residue was purified by silica gel column chromatography (eluent: hexane-ethyl acetate=9:1→1:1) to give the title compound as a brown oil (yield 249 mg, 65%).
$^1$H-NMR (CDCl$_3$) δ: 3.82 (3H, s), 6.55 (1H, d, J=1.8 Hz), 6.74 (2H, d, J=8.8 Hz), 7.15-7.45 (7H, m), 8.10 (1H, d, J=1.8 Hz), 9.87 (1H, s).

Reference Example 13

Ethyl 2-acetyl-4-oxo-4-phenylbutanoate

A solution (20 mL) of ethyl 3-oxobutanoate (6.37 mL) in N,N-dimethylformamide was cooled to 0° C., sodium hydride (60% in oil, 2.4 g) was added after washing with hexane. The reaction mixture was stirred at room temperature for 30 min and cooled to 0° C., and a solution (10 mL) of phenacyl bromide (10.0 g) in N,N-dimethylformamide was added dropwise. The reaction mixture was stirred at room temperature for 30 min and concentrated under reduced pressure. Water was added to the residue, and the mixture was extracted with ethylacetate. The extract was washed with saturated brine, dried over anhydrous sodium sulfate, concentrated under reduced pressure to give the title compound as a pale-yellow oil (yield 11.52 g, 93%).
$^1$H-NMR (CDCl$_3$) δ: 1.20-1.35 (3H, m), 2.45 (3H, s), 3.40-3.80 (2H, m), 3.90-4.10 (1H, m), 4.15-4.30 (2H, m), 7.40-7.60 (3H, m), 7.90-8.00 (2H, m).

Reference Example 14

Ethyl 2-methyl-5-phenyl-1H-pyrrole-3-carboxylate

Ethyl 2-acetyl-4-oxo-4-phenylbutanoate (3.0 g) and ammonium acetate (1.39 g) were added to acetic acid (20 mL), and the mixture was stirred at 80° C. for 18 hr. The reaction mixture was concentrated under reduced pressure, and the residue was purified by silica gel column chromatography (eluent: hexane-ethyl acetate=9:1→1:1) to give the title compound as a brown solid (yield 1.25 g, 45%).
$^1$H-NMR (CDCl$_3$) δ: 1.37 (3, t, J=7.4 Hz), 2.59 (3H, s), 4.30 (2H, q, J=7.4 Hz), 6.83 (1H, d, J=3.0 Hz), 7.20-7.50 (5H, m), 8.40 (1H, br).

Reference Example 15

Ethyl 1-[(4-fluorophenyl)sulfonyl]-2-methyl-5-phenyl-1H-pyrrole-3-carboxylate

Using ethyl 2-methyl-5-phenyl-1H-pyrrole-3-carboxylate (500 mg), sodium hydride (60% in oil, 175 mg) and 4-fluorobenzenesulfonyl chloride (848 mg), a procedure as in Reference Example 4 was performed to give the title compound as a brown oil (yield 270 mg, 32%).
$^1$H-NMR (CDCl$_3$) δ: 1.35 (3H, t, J=8.8 Hz), 2.89 (3H, s), 4.26 (2H, q, J=8.8 Hz), 6.48 (1H, s), 7.05 (2H, t, J=8.0 Hz), 7.20-7.50 (7H, m).

Reference Example 16

1-[(4-Fluorophenyl)sulfonyl]-2-methyl-5-phenyl-1H-pyrrole-3-carbaldehyde

Ethyl 1-[(4-fluorophenyl)sulfonyl]-2-methyl-5-phenyl-1H-pyrrole-3-carboxylate (380 mg) was dissolved in tetrahydrofuran (15 mL), and the mixture was cooled to −78° C. A 1.5 mol/l solution (1.96 mL) of diisobutylaluminum hydride in toluene was added dropwise, and the mixture was further stirred at −78° C. for 1 hr. 1 mol/l Hydrochloric acid (20 mL) was added to the reaction mixture, and the mixture was stirred at room temperature for 15 min and extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→2:1). The obtained brown oil was dissolved in acetonitrile (5 mL), and the mixture was cooled to 0° C. Tetra-n-propylammonium perruthenate (34 mg), N-methylmorpholine N-oxide (172 mg) and molecular sieves 4 A powder (500 mg) were added, and the mixture was stirred at room temperature for 1 hr. The reaction mixture was concentrated under reduced pressure, and the residue was suspended in ethyl acetate, and filtered through celite. The filtrate was concentrated under reduced pressure, and the residue was purified by silica gel column chromatography (eluent: hexane-ethyl acetate=9:1→2:1) to give the title compound as a colorless oil (yield 210 mg, 62%).

$^1$H-NMR (CDCl$_3$) δ: 2.90 (3H, s), 6.48 (1H, s), 7.05 (2H, t, J=9.4 Hz), 7.15-7.45 (7H, m), 10.01 (1H, s).

Reference Example 17

5-(4-Fluorophenyl)-1-[(4-methylphenyl)sulfonyl]-1H-pyrrole-3-carbaldehyde

Using 4-fluorophenacyl bromide instead of phenacyl bromide, a procedure as in Reference Example 1 was performed to synthesize ethyl 2-cyano-4-(4-fluorophenyl)-4-oxobutanoate, and procedures as in Reference Examples 2, 3, 4, 5 and 6 were sequentially performed to give the title compound as a colorless solid.

$^1$H-NMR (CDCl$_3$) δ: 2.39 (3H, s), 6.54 (1H, d, J=2.1 Hz), 7.00 (2H, t, J=8.4 Hz), 7.09-7.27 (6H, m), 8.10 (1H, d, J=1.8 Hz), 9.87 (1H, s).

Reference Example 18

5-(3-Methylphenyl)-1-[(4-methylphenyl)sulfonyl]-1H-pyrrole-3-carbaldehyde

Using 3-methylphenacyl bromide instead of phenacyl bromide, a procedure as in Reference Example 1 was performed to synthesize ethyl 2-cyano-4-(3-methylphenyl)-4-oxobutanoate, and procedures as in Reference Examples 2, 3, 4, 5 and 6 were sequentially performed to give the title compound as a pale-brown oil.

$^1$H-NMR (CDCl$_3$): 2.29 (3H, s), 2.38 (3H, s), 6.52 (1H, d, J=2.1 Hz), 6.85 (1H, s), 6.95-7.00 (1H, m), 7.10-7.22 (6H, m), 8.08 (1H, d, J=2.1 Hz), 9.86 (1H, s).

Reference Example 19

5-(3-Fluorophenyl)-1-[(4-methylphenyl)sulfonyl]-1H-pyrrole-3-carbaldehyde

Using 3-fluorophenacyl bromide instead of phenacyl bromide, a procedure as in Reference Example 1 was performed to synthesize ethyl 2-cyano-4-(3-fluorophenyl)-4-oxobutanoate, and procedures as in Reference Examples 2, 3, 4, 5 and 6 were sequentially performed to give the title compound as a pale-brown oil.

$^1$H-NMR (CDCl$_3$): 2.39 (3H, s), 6.57 (1H, d, J=1.8 Hz), 6.79-6.85 (1H, m), 6.98-7.34 (7H, m), 8.11 (1H, d, J=1.8 Hz), 9.88 (1H, s).

Reference Example 20

1-[(2-Methylphenyl)sulfonyl]-5-phenyl-1H-pyrrole-3-carbaldehyde

Using 2-methylbenzenesulfonyl chloride instead of tosyl chloride, a procedure as in Reference Example 4 was performed to synthesize ethyl 1-[(2-methylphenyl)sulfonyl]-5-phenyl-1H-pyrrole-3-carboxylate, and procedures as in Reference Examples 5 and 6 were sequentially performed to give the title compound as a colorless oil.

$^1$H-NMR (CDCl$_3$): δ2.25 (3H, s), 6.58 (1H, d, J=2.0 Hz), 6.88-6.92 (1H, m), 7.00-7.02 (2H, m), 7.13-7.18 (4H, m), 7.26-7.30 (1H, m), 7.34-7.38 (1H, m), 8.22 (1H, d, J=1.7 Hz), 9.91 (1H, s).

Reference Example 21

5-Phenyl-1-{[4-(trifluoromethyl)phenyl]sulfonyl}-1H-pyrrole-3-carbaldehyde

Using 4-trifluoromethylbenzenesulfonyl chloride instead of tosyl chloride, a procedure as in Reference Example 4 was performed to synthesize ethyl 5-phenyl-1-{[4-(trifluoromethyl)phenyl]sulfonyl}-1H-pyrrole-3-carboxylate, and procedures as in Reference Examples 5 and 6 were sequentially performed to give the title compound as a colorless solid.

$^1$H-NMR (CDCl$_3$): δ6.60 (1H, d, J=1.7 Hz), 7.13-7.16 (2H, m), 7.29-7.33 (2H, m), 7.41-7.45 (3H, m), 7.58 (2H, d, J=8.6 Hz), 8.12 (1H, d, J=2.0 Hz), 9.90 (1H, s).

Reference Example 22

1-[(4-Fluoro-2-methylphenyl)sulfonyl]-5-phenyl-1H-pyrrole-3-carbaldehyde

Using 4-fluoro-2-methylbenzenesulfonyl chloride instead of tosyl chloride, a procedure as in Reference Example 4 was performed to synthesize ethyl 1-[(4-fluoro-2-methylphenyl)sulfonyl]-5-phenyl-1H-pyrrole-3-carboxylate, and procedures as in Reference Examples 5 and 6 were sequentially performed to give the title compound as a pale-yellow oil.

$^1$H-NMR (CDCl$_3$): δ2.24 (3H, s), 6.53-6.59 (2H, m), 6.88 (1H, dd, J=9.2 Hz, 2.6 Hz), 7.03-7.05 (2H, m), 7.16-7.21 (3H, m), 7.27-7.33 (1H, m), 8.20-8.22 (1H, m), 9.91-9.92 (1H, m).

Reference Example 23

Ethyl 2-cyano-4-(2-methylphenyl)-4-oxobutanoate

2'-Methylacetophenone (13.42 g) was dissolved in diethyl ether (100 mL), and bromine (16.0 g) was added dropwise while maintaining the reaction temperature at not higher than 25° C. After dropwise addition, the mixture was stirred at room temperature for 30 min. Water was added to the reaction mixture and the mixture was extracted with diethyl ether. The extract was washed with saturated brine, dried over anhydrous magnesium sulfate, and concentrated under reduced pressure to give crude 1-bromo-1-(2-methylphenyl)ethanone (21.3 g) as an oil. To ethyl cyanoacetate (79.20 g) was added potassium carbonate (27.64 g), and the mixture was stirred at 43-45° C. for 45 min. A solution (150 mL) of crude 1-bromo-1-(2-methylphenyl)ethanone (21.3 g) in acetone was added dropwise over 30 min. After completion of the dropwise addition, the mixture was stirred at room temperature for 16 hr. The reaction mixture was filtrated, and the filtrate was concentrated under reduced pressure. Water was added to the residue, and the mixture was extracted with ethyl acetate. The extract was washed with saturated brine, dried over anhydrous magnesium sulfate, and concentrated under reduced pressure. An excess ethyl cyanoacetate contained in the obtained oil was evaporated under reduced pressure, and the residue was purified by silica gel column chromatography (eluent: hexane-ethyl acetate=10:1→8:1) to give the title compound as a pale-yellow oil (yield 46.44 g, about 100%).

$^1$H-NMR (CDCl$_3$) δ: 1.35 (3H, t, J=7.9 Hz), 2.53 (3H, s), 3.50 (1H, dd, J=5.2, 18.7 Hz), 3.71 (1H, dd, J=7.1, 17.9 Hz), 4.11-4.20 (1H, m), 4.31 (2H, q, J=7.9 Hz), 7.25-7.34 (2H, m), 7.41-7.49 (1H, m), 7.72 (1H, d, J=7.7 Hz).

Reference Example 24

Ethyl 2-cyano-4-(4-methoxyphenyl)-4-oxobutanoate

4'-Methoxyacetophenone (15.0 g) was dissolved in chloroform (70 mL) and diethyl ether (50 mL), and a solution of bromine (16.0 g) in chloroform (20 mL) was added dropwise while maintaining the reaction temperature at not higher than 25° C. After dropwise addition, the mixture was stirred at room temperature for 2 hr. Water was added to the reaction mixture and the mixture was extracted with chloroform. The extract was washed with saturated brine, dried over anhydrous magnesium sulfate, and concentrated under reduced pressure to give crude 1-bromo-1-(4-methoxyphenyl)ethanone (yield 22.05 g) as crystals. To ethyl cyanoacetate (79.20 g) was added potassium carbonate (27.65 g), and the mixture was stirred at 45° C. for 1 hr. A solution (100 mL) of crude 1-bromo-1-(4-methoxyphenyl)ethanone (22.0 g) in acetone was added dropwise over 20 min. After completion of the dropwise addition, the mixture was stirred at room temperature for 18 hr. The reaction mixture was filtered, and the filtrate was concentrated under reduced pressure. Water was added to the residue, and the mixture was extracted with ethyl acetate. The extract was washed with saturated brine, dried over anhydrous magnesium sulfate, and concentrated under reduced pressure. An excess ethyl cyanoacetate contained in the obtained oil was evaporated under reduced pressure, and the residue was purified by silica gel column chromatography (eluent: hexane-ethyl acetate=9:1→3:1) to give the title compound as an oil (yield 30.25 g, about 100%).

$^1$H-NMR (CDCl$_3$) δ: 1.35 (3H, t, J=7.2 Hz), 3.45-3.56 (1H, m), 3.68-3.79 (1H, m), 3.89 (3H, s), 4.08-4.20 (1H, m), 4.31 (2H, q, J=7.2 Hz), 6.96 (2H, d, J=8.9 Hz), 7.95 (2H, d, J=8.9 Hz).

Reference Example 25

Ethyl 2-cyano-4-oxo-4-[(2-trifluoromethylphenyl)butanoate

2'-(Trifluoromethyl)acetophenone (10.0 g) was dissolved in chloroform (30 mL) and diethyl ether (30 mL), a solution of bromine (8.50 g) in chloroform (20 mL) was added dropwise while maintaining the reaction temperature at not higher than 25° C. After the dropwise addition, the mixture was stirred at room temperature for 1 hr, water was added to the reaction mixture and the mixture was extracted with chloroform. The extract was washed with saturated brine, dried over anhydrous magnesium sulfate, concentrated under reduced pressure to give crude 1-bromo-1-(2-trifluoromethylphenyl)ethanone. Potassium carbonate (13.82 g) was added to ethyl cyanoacetate (44.44 g), and the mixture was stirred at 45° C. for 1 hr. A solution (100 mL) of crude 1-bromo-1-(2-trifluoromethylphenyl)ethanone in acetone was added dropwise. After completion of the dropwise addition, the mixture was stirred at the same temperature for 1 hr, and stirred overnight at room temperature. The reaction mixture was filtered, and the filtrate was concentrated under reduced pressure. Water was added to the residue, and the mixture was extracted with ethyl acetate. The extract was washed with saturated brine, dried over anhydrous magnesium sulfate, and concentrated under reduced pressure. Excess ethyl cyanoacetate contained in the obtained oil was evaporated under reduced pressure and the residue was purified by silica gel column chromatography (eluent: hexane-ethyl acetate=9:1→7:1) to give the title compound as an oil (yield 10.43 g, from 2'-(trifluoromethyl)acetophenone, 66%).

$^1$H-NMR (CDCl$_3$) δ: 1.36 (3H, t, J=7.2 Hz), 3.34-3.46 (1H, m), 3.59-3.70 (1H, m), 4.08-4.22 (1H, m), 4.32 (2H, q, J=7.2 Hz), 7.57-7.80 (4H, m).

Reference Example 26

Ethyl 5-(4-methoxyphenyl)-1H-pyrrole-3-carboxylate

Using ethyl 2-cyano-4-(4-methoxyphenyl)-4-oxobutanoate, procedures as in Reference Example 2 and 3 were performed to give the title compound as colorless crystals.

$^1$H-NMR (CDCl$_3$) δ: 1.36 (3H, t, J=7.1 Hz), 3.83 (3H, s), 4.31 (2H, q, J=7.1 Hz), 6.79 (1H, d, J=1.2 Hz), 6.93 (2H, d, J=8.9 Hz), 7.38-7.46 (3H, m), 8.60 (1H, brs).

Reference Example 27

Ethyl 5-(2-trifluoromethylphenyl)-1H-pyrrole-3-carboxylate

Using ethyl 2-cyano-4-oxo-4-(2-trifluoromethylphenyl)butanoate, procedures as in Reference Example 2 and 3 were performed to give the title compound as colorless crystals.

$^1$H-NMR (CDCl$_3$) δ: 1.36 (3H, t, J=7.2 Hz), 4.31 (2H, q, J=7.2 Hz), 6.81 (1H, s), 7.42-7.61 (5H, m), 8.69 (1H, br).

Reference Example 28

Ethyl 5-(4-fluorophenyl)-1-(phenylsulfonyl)-1H-pyrrole-3-carboxylate

Using 4-fluorophenacyl bromide instead of phenacyl bromide, a procedure as in Reference Example 1 was performed to synthesize ethyl 2-cyano-4-(4-fluorophenyl)-4-oxobutanoate, and procedures as in Reference Examples 2 and 3 were performed to synthesize ethyl 5-(4-fluorophenyl)-1H-pyrrole-3-carboxylate. Sodium hydride (60% in oil, 0.32 g) was added to a solution (20 mL) of ethyl 5-(4-fluorophenyl)-1H-pyrrole-3-carboxylate (1.56 g) in N,N-dimethylformamide under ice-cooling. The mixture was stirred at the same temperature for 15 min, added benzenesulfonyl chloride (1.41 g), and the mixture was stirred at room temperature for 18 hr. Water was added to the reaction mixture, and the mixture was extracted with diethyl ether. The extract was washed with saturated brine, dried over anhydrous magnesium sulfate, and concentrated under reduced pressure. The residue was purified by silica gel column chromatography (eluent: hexane-ethyl acetate=4:1→7:2) to give the title compound as crystals (yield 1.70 g, 68%).

$^1$H-NMR (CDCl$_3$) δ: 1.36 (3H, t, J=7.2 Hz), 4.31 (2H, q, J=7.2 Hz), 6.52 (1H, d, J=1.9 Hz), 6.98 (2H, t, J=8.7 Hz), 7.12 (2H, dd, J=5.5 Hz, 8.7 Hz), 7.33-7.35 (4H, m), 7.50-7.60 (1H, m), 8.09 (1H, d, J=1.9 Hz).

Reference Example 29

Ethyl 5-(4-fluorophenyl)-1-[(4-fluorophenyl)sulfonyl]-1H-pyrrole-3-carboxylate

Using 4-fluorophenacyl bromide instead of phenacyl bromide, a procedure as in Reference Example 1 was performed to synthesize ethyl 2-cyano-4-(4-fluorophenyl)-4-oxobutanoate, and procedures as in Reference Examples 2 and 3 were performed to synthesize ethyl 5-(4-fluorophenyl)-1H-pyrrole-3-carboxylate. Sodium hydride (60% in oil, 0.58 g) was added to a solution (20 mL) of ethyl 5-(4-fluorophenyl)-1H-pyrrole-3-carboxylate (2.85 g) in N,N-dimethylformamide under ice-cooling. The mixture was stirred at the same temperature for 15 min, 4-fluorobenzenesulfonyl chloride (2.92 g) was added, and the mixture was stirred at room temperature for 3 hr. Water was added to the reaction mixture, and the mixture was extracted with diethylether. The extract was washed with saturated brine, dried over anhydrous magnesium sulfate, and concentrated under reduced pressure. The residue was purified by silica gel column chromatography (eluent: hexane-ethyl acetate=4:1) to give the title compound as crystals (yield 4.66 g, 97%).
$^1$H-NMR (CDCl$_3$) δ: 1.36 (3H, t, J=7.2 Hz), 4.31 (2H, q, J=7.2 Hz), 6.53 (1H, d, J=1.9 Hz), 6.96-7.06 (4H, m), 7.16-7.24 (2H, m), 7.36-7.45 (2H, m), 8.06 (1H, d, J=1.9 Hz).

Reference Example 30

Ethyl 5-(4-fluorophenyl)-1-{[4-(trifluoromethyl)phenyl]sulfonyl}-1H-pyrrole-3-carboxylate Using 4-fluorophenacyl bromide instead of phenacyl bromide, a procedure as in Reference Example 1 was performed to synthesize ethyl 2-cyano-4-(4-fluorophenyl)-4-oxobutanoate, and procedures as in Reference Examples 2 and 3 were performed to synthesize ethyl 5-(4-fluorophenyl)-1H-pyrrole-3-carboxylate. Sodium hydride (60% in oil, 0.28 g) was added to a solution (20 mL) of ethyl 5-(4-fluorophenyl)-1H-pyrrole-3-carboxylate (1.49 g) in N,N-dimethylformamide under ice-cooling. The mixture was stirred at the same temperature for 15 min, 4-trifluoromethylbenzenesulfonyl chloride (1.85 g) was added, and the mixture was stirred at room temperature for 3 hr. Water was added to the reaction mixture, and the mixture was extracted with diethyl ether. The extract was washed with saturated brine, dried over anhydrous magnesium sulfate, and concentrated under reduced pressure. The residue was purified by silica gel column chromatography (eluent: hexane-ethyl acetate=7:2) to give the title compound as crystals (yield 1.80 g, 64%).
$^1$H-NMR (CDCl$_3$) δ: 1.36 (3H, t, J=7.1 Hz), 4.32 (2H, q, J=7.1 Hz), 6.55 (1H, d, J=1.9 Hz), 7.01 (2H, t, J=8.8 Hz), 7.11-7.18 (2H, m), 7.47 (2H, d, J=8.3 Hz), 7.62 (2H, d, J=8.3 Hz), 8.07 (1H, d, J=1.9 Hz).

Reference Example 31

5-(4-Fluorophenyl)-1-(phenylsulfonyl)-1H-pyrrole-3-carbaldehyde

Using ethyl 5-(4-fluorophenyl)-1-(phenylsulfonyl)-1H-pyrrole-3-carboxylate, procedures as in Reference Examples 5 and 6 were performed to give the title compound as an oil.
$^1$H-NMR (CDCl$_3$) δ: 6.55 (1H, d, J=1.9 Hz), 6.98 (2H, t, J=8.8 Hz), 7.08-7.18 (2H, m), 7.33-7.40 (4H, m), 7.51-7.63 (1H, m), 8.12 (1H, d, J=1.9 Hz), 9.88 (1H, s).

Reference Example 32

5-(2-Methylphenyl)-1-[(4-methylphenyl)sulfonyl]-1H-pyrrole-3-carbaldehyde

Using ethyl 2-cyano-4-(2-methylphenyl)-4-oxobutanoate, a procedure as in Reference Example 2 was performed to synthesize ethyl 2-chloro-5-(2-methylphenyl)-1H-pyrrole-3-carboxylate, and procedures as in Reference Examples 3, 4, 5 and 6 were sequentially performed to give the title compound as crystals.
$^1$H-NMR (CDCl$_3$) δ: 1.80 (3H, s), 2.41 (3H, s), 6.50 (1H, s), 6.90 (1H, d, J=6.2 Hz), 7.07-7.35 (7H, m), 8.12 (1H, s), 9.89 (1H, s).

Reference Example 33

1-[(4-Fluorophenyl)sulfonyl]-5-(4-methoxyphenyl)-1H-pyrrole-3-carbaldehyde

Using ethyl 5-(4-methoxyphenyl)-1H-pyrrole-3-carboxylate and 4-fluorobenzenesulfonyl chloride, a procedure as in Reference Example 4 was performed to synthesize ethyl 1-[(4-fluorophenyl)sulfonyl]-5-(4-methoxyphenyl)-1H-pyrrole-3-carboxylate, and procedures as in Reference Examples 5 and 6 were sequentially performed to give the title compound as an oil.
$^1$H-NMR (CDCl$_3$) δ: 3.86 (3H, s), 6.52 (1H, d, J=1.9 Hz), 6.84 (2H, d, J=8.7 Hz), 7.01 (2H, t, J=8.7 Hz), 7.09 (2H, d, J=8.7 Hz), 7.34 (2H, dd, J=8.9 Hz, 4.9 Hz), 8.08 (1H, d, J=1.9 Hz), 9.87 (1H, s).

Reference Example 34

5-(4-Fluorophenyl)-1-[(4-fluorophenyl)sulfonyl]-1H-pyrrole-3-carbaldehyde

Using ethyl 5-(4-fluorophenyl)-1-[(4-fluorophenyl)sulfonyl]-1H-pyrrole-3-carboxylate, procedures as in Reference Examples 5 and 6 were performed to give the title compound as a solid.
$^1$H-NMR (CDCl$_3$) δ: 6.57 (1H, d, J=1.8 Hz), 6.97-7.08 (4H, m), 7.12-7.18 (2H, m), 7.32-7.39 (2H, m), 8.10 (1H, d, J=1.8 Hz), 9.88 (1H, s).

Reference Example 35

5-(4-Fluorophenyl)-1-{[4-(trifluoromethyl)phenyl]sulfonyl}-1H-pyrrole-3-carbaldehyde Using ethyl 5-(4-fluorophenyl)-1-{[4-(trifluoromethyl)phenyl]sulfonyl}-1H-pyrrole-3-carboxylate, procedures as in Reference Examples 5 and 6 were performed to give the title compound as crystals.
$^1$H-NMR (CDCl$_3$) δ: 6.59 (1H, d, J=1.7 Hz), 7.02 (2H, t, J=8.7 Hz), 7.11-7.17 (2H, m), 7.47 (2H, d, J=8.5 Hz), 7.63 (2H, d, J=8.5 Hz), 8.11 (1H, d, J=1.9 Hz), 9.89 (1H, s).

Reference Example 36

1-[(4-Fluorophenyl)sulfonyl]-5-[2-(trifluoromethyl)phenyl]-1H-pyrrole-3-carbaldehyde Using ethyl 5-(2-trifluoromethylphenyl)-1H-pyrrole-3-carboxylate and 4-fluorobenzenesulfonyl chloride, a procedure as in Reference Example 4 was performed to synthesize ethyl 1-[(4-fluorophenyl)sulfonyl]-5-[2-(trifluoromethyl)phenyl]-1H-pyrrole-3-carboxylate, and procedures as in Reference Examples 5 and 6 were sequentially performed to give the title compound as crystals.

$^1$H-NMR (CDCl$_3$) δ: 6.65 (1H, s), 7.00-7.09 (2H, m), 7.33-7.46 (3H, m), 7.57-7.67 (3H, m), 8.13 (1H, d, J=1.9 Hz), 9.89 (1H, s).

Reference Example 37

1-[(4-Methylphenyl)sulfonyl]-5-[2-(trifluoromethyl)phenyl]-1H-pyrrole-3-carbaldehyde Using ethyl 2-cyano-4-oxo-4-(2-trifluoromethylphenyl)butanoate, a procedure as in Reference Example 2 was performed to synthesize ethyl 2-chloro-5-(2-trifluoromethylphenyl)-1H-pyrrole-3-carboxylate, and procedures as in Reference Examples 3, 4, 5 and 6 were sequentially performed to give the title compound as crystals.

$^1$H-NMR (CDCl$_3$) δ: 2.40 (3H, s), 6.63 (1H, d, J=1.7 Hz), 7.16 (2H, d, J=8.3 Hz), 7.25 (2H, d, J=8.3 Hz), 7.36-7.42 (1H, m), 7.53-7.64 (3H, m), 8.12 (1H, d, J=1.9 Hz), 9.88 (1H, s).

Reference Example 38

2-Methyl-5-phenyl-1-(phenylsulfonyl)-1H-pyrrole-3-carbaldehyde

Using ethyl 2-methyl-5-phenyl-1H-pyrrole-3-carboxylate and benzenesulfonyl chloride, a procedure as in Reference Example 4 was performed to synthesize ethyl 2-methyl-5-phenyl-1-(phenylsulfonyl)-1H-pyrrole-3-carboxylate, and procedures as in Reference Examples 5 and 6 were sequentially performed to give the title compound as a colorless oil.

$^1$H-NMR (CDCl$_3$) δ: 2.88 (3H, s), 6.47 (1H, s), 7.18-7.23 (2H, m), 7.48-7.61 (1H, m), 10.00 (1H, s).

Reference Example 39

Methyl 1H-pyrrole-3-carboxylate

A solution (250 mL) of p-toluenesulfonylmethyl isocyanide (15.0 g) and methyl acrylate (6.92 mL) in tetrahydrofuran was added dropwise to a suspension (100 mL) of potassium tert-butoxide in tetrahydrofuran over 30 min. The reaction mixture was stirred at room temperature for 1 hr, and filtered through a glass filter filled with silica gel (diameter 8 cm, height 4 cm), and the filtrate was concentrated under reduced pressure. The residue was purified by silica gel column chromatography (eluent: hexane-ethyl acetate=9:1→2:1) to give the title compound as a pale-yellow solid (yield 4.69 g, 49%).

$^1$H-NMR (CDCl$_3$) δ: 3.82 (3H, s), 6.15 (1H, m), 6.75 (1H, m), 7.43 (1H, m), 8.50 (1H, brs).

Reference Example 40

Methyl 5-bromo-1H-pyrrole-3-carboxylate

A solution (70 mL) of methyl 1H-pyrrole-3-carboxylate (4.48 g) in tetrahydrofuran was cooled to −78° C., N-bromosuccinimide (6.30 g) was added, pyridine (5 drops) was added, and the mixture was left standing in a freezer (−20° C.) for 3 days. The reaction mixture was concentrated under reduced pressure, water was added to the residue and the mixture was extracted with ethylacetate. The extract was washed with saturated brine, dried over anhydrous sodium sulfate, and concentrated under reduced pressure. The residue was purified by silica gel column chromatography (eluent: hexane-ethyl acetate=9:1→1:1) to give the title compound as a pale-yellow solid (yield 3.59 g, 49%).

$^1$H-NMR (CDCl$_3$) δ: 3.81 (3H, s), 6.58 (1H, m), 7.36 (1H, m), 8.60 (1H, brs).

Reference Example 41

Methyl 5-bromo-1-[(4-methoxyphenyl)sulfonyl]-1H-pyrrole-3-carboxylate

Sodium hydride (60% in oil, 681 mg) was washed with hexane, and added to N,N-dimethylformamide (10 mL). After cooling to −78° C., a solution (10 mL) of methyl 5-bromo-1H-pyrrole-3-carboxylate (2.90 g) in N,N-dimethylformamide was added dropwise over 15 min. The reaction mixture was stirred at 0° C. for 30 min and at 25° C. for 30 min, and again cooled to −78° C. A solution (5 mL) of 4-methoxybenzenesulfonyl chloride (3.23 g) in N,N-dimethylformamide was added dropwise, and the reaction mixture was stirred at 0° C. for 15 min and at 25° C. for 30 min. The reaction mixture was concentrated under reduced pressure, water was added to the residue, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=9:1→1:1) to give the title compound as a colorless solid (yield 3.02 g, 57%).

$^1$H-NMR (CDCl$_3$) δ: 3.82 (3H, s), 3.88 (3H, s), 6.65 (1H, d, J=2.0 Hz), 7.00 (2H, d, J=9.2 Hz), 7.92 (2H, d, J=9.2 Hz), 8.05 (1H, d, J=2.0 Hz).

Reference Example 42

5-Bromo-1-[(4-methoxyphenyl)sulfonyl]-1H-pyrrole-3-carbaldehyde

A solution (30 mL) of methyl 5-bromo-1-[(4-methoxyphenyl)sulfonyl]-1H-pyrrole-3-carboxylate (3.00 g) in tetrahydrofuran was cooled to −78° C., a 1.5 mol/l solution (11.0 mL) of diisobutylaluminum hydride in toluene was added dropwise over 15 min, and the mixture was further stirred at −78° C. for 1 hr. A 1.5 mol/l solution (5.0 mL) of diisobutylaluminum hydride in toluene was added, and the mixture was stirred at −78° C. for 15 min, and at 25° C. for 2 hr. 1 mol/l Hydrochloric acid (40 mL) was added to the reaction mixture, and the mixture was stirred at 25° C. for 15 min and extracted with ethyl acetate. The extract was washed with saturated brine, dried over anhydrous sodium sulfate, and concentrated under reduced pressure. A solution (30 mL) of the residue in acetonitrile was cooled to 0° C., tetra-n-propylammonium perruthenate (281 mg), N-methylmorpholine N-oxide (1.41 g) and molecular sieves 4 A powder (1.5 g) were added, and the mixture was stirred at room temperature for 1.5 hr. The reaction mixture was concentrated under reduced pressure, and the residue was suspended in ethyl acetate and filtered through celite. The filtrate was concentrated under reduced pressure, and the residue was purified by silica gel column chromatography (eluent: hexane-ethyl acetate=9:1→1:1) to give the title compound as a brown oil (yield 2.07 g, 75%).

$^1$H-NMR (CDCl$_3$) δ: 3.90 (3H, s), 6.71 (1H, d, J=2.2 Hz), 7.02 (2H, d, J=9.2 Hz), 7.94 (2H, d, J=9.2 Hz), 8.07 (1H, d, J=2.2 Hz), 9.75 (1H, s).

Reference Example 43 tert-Butyl ({5-bromo-1-[(4-methoxyphenyl)sulfonyl]-1H-pyrrol-3-yl}methyl)methylcarbamate To a solution (90 mL) of 5-bromo-1-[(4-methoxyphenyl)sulfonyl]-1H-pyrrole-3-carbaldehyde (3.0 g) in methanol was added methylammonium chloride (5.88 g), and the mixture was stirred at room temperature for 15 min. Sodium cyanotrihydroborate (1.64 g) was added, and the mixture was further stirred at room temperature for 2 hr. The reaction mixture was concentrated under reduced pressure, saturated aqueous sodium hydrogen carbonate was added to the residue and the mixture was extracted with ethyl acetate. The extract was washed with saturated brine, dried over anhydrous sodium sulfate, and filtered. To the filtrate was added di-tert-butyl bicarbonate (2.28 g), and the mixture was concentrated under reduced pressure. The residue was dissolved in tetrahydrofuran (10 mL), sodium hydrogencarbonate (1.10 g) and water (10 mL) were added, and the mixture was stirred at room temperature for 15 min. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→1:1) to give the title compound as a pale-yellow oil (yield 2.25 g, 56%).
$^1$H-NMR (CDCl$_3$) δ: 1.47 (9H, s), 2.78 (3H, s), 3.87 (3H, s), 4.16 (2H, s), 6.22 (1H, s), 6.97 (2H, d, J=9.2 Hz), 7.33 (1H, s), 7.86 (2H, d, J=9.2 Hz).

Reference Example 44

4-(Azidomethyl)-1-[(4-methylphenyl)sulfonyl]-2-phenyl-1H-pyrrole

A solution (10 mL) of ethyl 1-[(4-methylphenyl)sulfonyl]-5-phenyl-1H-pyrrole-3-carboxylate (500 mg) in tetrahydrofuran was cooled to −78° C., a 1.5 mol/l solution (2.70 mL) of diisobutylaluminum hydride in toluene was added dropwise, and the mixture was stirred at 25° C. for 30 min. 1 mol/l Hydrochloric acid (6 mL) was added to the reaction mixture, and the mixture was stirred at 25° C. for 15 min and extracted with ethyl acetate. The extract was washed with saturated brine, dried over anhydrous sodium sulfate, and concentrated under reduced pressure. A solution (2 mL) of the residue in dichloromethane was added to a solution (5 mL) of 2,3-dichloro-5,6-dicyano-1,4-benzoquinone (612 mg), triphenylphosphine (532 mg) and tetra-n-butylammoniumazide (768 mg) in tetrahydrofuran, and the mixture was stirred at 25° C. for 1 hr. The reaction mixture was concentrated under reduced pressure, and the residue was purified by silica gel column chromatography (eluent: hexane-ethyl acetate=9:1→1:1) to give the title compound as a pale-yellow solid (yield 233 mg, 49%).
$^1$H-NMR (CDCl$_3$) δ: 2.36 (3H, s), 4.48 (2H, s), 6.19 (1H, d, J=2.2 Hz), 7.09 (2H, d, J=8.6 Hz), 7.15-7.40 (8H, m).

Reference Example 45

Ethyl 4-methyl-1H-pyrrole-3-carboxylate

Using p-toluenesulfonylmethyl isocyanide (8.55 g), ethyl crotonate (5.0 g) and potassium tert-butoxide (5.90 g), a procedure as in Reference Example 39 was performed to give the title compound as a pale-yellow solid (yield 4.77 g, 71%).
$^1$H-NMR (CDCl$_3$) δ: 1.34 (3H, t, J=6.8 Hz), 2.29 (3H, s), 4.27 (2H, q, J=6.8 Hz), 6.53 (1H, m), 7.38 (1H, m), 8.30 (1H, brs).

Reference Example 46

Ethyl 5-bromo-4-methyl-1H-pyrrole-3-carboxylate

Using ethyl 4-methyl-1H-pyrrole-3-carboxylate (4.50 g) and N-bromosuccinimide (5.2 g), a procedure as in Reference Example 40 was performed to give the title compound as a pale-yellow solid (yield 5.20 g, 76%).
$^1$H-NMR (CDCl$_3$) δ: 1.34 (3H, t, J=7.4 Hz), 2.23 (3H, s), 4.27 (2H, q, J=7.4 Hz), 7.38 (1H, d, J=3.0 Hz), 8.30 (1H, brs).

Reference Example 47

Ethyl 5-bromo-4-methyl-1-[(4-methylphenyl)sulfonyl]-1H-pyrrole-3-carboxylate

Using sodium hydride (60% in oil, 620 mg), ethyl 5-bromo-4-methyl-1H-pyrrole-3-carboxylate (3.0 g) and tosyl chloride (2.95 g), a procedure as in Reference Example 41 was performed to give the title compound as pale-yellow crystals (yield 4.27 g, 86%).
$^1$H-NMR (CDCl$_3$) δ: 1.35 (3H, t, J=7.0 Hz), 2.15 (3H, s), 2.44 (3H, s), 4.29 (2H, q, J=7.0 Hz), 7.34 (2H, d, J=7.6 Hz), 7.84 (2H, d, J=7.6 Hz), 8.09 (1H, s).

Reference Example 48

Ethyl 4-methyl-1-[(4-methylphenyl)sulfonyl]-5-phenyl-1H-pyrrole-3-carboxylate

Ethyl 5-bromo-4-methyl-1-[(4-methylphenyl)sulfonyl]-1H-pyrrole-3-carboxylate (1.0 g), phenylboronic acid (473 mg), sodium carbonate (823 mg) and tetrakis(triphenylphosphine)palladium (299 mg) were suspended in a mixture of 1,2-dimethoxyethane (10 mL) and distilled water (10 mL), and the mixture was refluxed under a nitrogen atmosphere for 16 hr. The reaction mixture was filtrated, water was added to the filtrate and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→1:1) to give the title compound as a pale-brown oil (yield 430 mg, 42%).
$^1$H-NMR (CDCl$_3$) δ: 1.37 (3H, t, J=7.0 Hz), 1.98 (3H, s), 2.37 (3H, s), 4.31 (2H, q, J=7.0 Hz), 6.95-7.40 (9H, m), 8.06 (1H, s).

Reference Example 49

4-Methyl-1-[(4-methylphenyl)sulfonyl]-5-phenyl-1H-pyrrole-3-carbaldehyde

A solution of (10 mL) ethyl 4-methyl-1-[(4-methylphenyl)sulfonyl]-5-phenyl-1H-pyrrole-3-carboxylate (420 mg) in tetrahydrofuran was cooled to −78° C., a 1.5 mol/l solution (2.1 mL) of diisobutylaluminum hydride in toluene was added dropwise, and the mixture was further stirred at −78° C. for 30 min. 1 mol/l Hydrochloric acid (10 mL) was added to the reaction mixture, and the mixture was stirred at room temperature and extracted with ethyl acetate. The extract was washed with saturated brine, dried over anhydrous sodium sulfate, and concentrated under reduced pressure. A solution (15 mL) of the residue in acetonitrile was cooled to −78° C., tetra-n-propylammonium perruthenate (37 mg), N-methylmorpholine N-oxide (185 mg) and molecular sieves 4 A powder (1.0 g) were added, and the mixture was stirred at room temperature for 1 hr. The reaction mixture was concentrated under reduced pressure, and the residue was suspended in ethyl acetate and filtered through celite. The filtrate was concentrated under reduced pressure, and the residue was purified by silica gel column chromatography (eluent: hexane-ethyl acetate=9:1→1:1) to give the title compound as a brown oil (yield 320 mg, 90%).
$^1$H-NMR (CDCl$_3$) δ: 2.02 (3H, s), 2.38 (3H, s), 6.99-7.40 (9H, m), 8.04 (1H, s), 9.95 (1H, s).

Reference Example 50 tert-Butyl ({5-bromo-1-[(4-methylphenyl)sulfonyl]-1H-pyrrol-3-yl}methyl)methylcarbamate Using methyl 5-bromo-1H-pyrrole-3-carboxylate and tosyl chloride, a procedure as in Reference Example 41 was performed to synthesize methyl 5-bromo-1-[(4-methylphenyl)sulfonyl]-1H-pyrrole-3-carboxylate, and procedures as in Reference Examples 42 and 43 were sequentially performed to give the title compound as a colorless solid.
$^1$H-NMR (CDCl$_3$) δ: 1.47 (9H, s), 2.43 (3H, s), 2.78 (3H, s), 4.17 (2H, s), 6.23 (1H, s), 7.25-7.35 (3H, m), 7.80 (2H, d, J=8.4 Hz).

Reference Example 51

Methyl 5-bromo-1-(phenylsulfonyl)-1H-pyrrole-3-carboxylate

Sodium hydride (60% in oil, 1.1 g) was washed with hexane and added to N,N-dimethylformamide (50 mL). The mixture was cooled to 0° C., and a solution (10 mL) of methyl 5-bromo-1H-pyrrole-3-carboxylate (5.0 g) in N,N-dimethylformamide was added. After stirring at 0° C. for 30 min, a solution (5 mL) of benzenesulfonyl chloride (3.3 mL) in N,N-dimethylformamide was added. The reaction mixture was stirred at room temperature for 1 hr, water was added, and the mixture was extracted with ethyl acetate. The extract was washed with saturated aqueous sodium hydrogen carbonate, water and saturated brine, dried over anhydrous sodium sulfate, and concentrated under reduced pressure. The residue was purified by silica gel column chromatography (eluent: hexane-ethylacetate=5:1) to give the title compound as a colorless solid (yield 8.5 g, 99%).
$^1$H-NMR (CDCl$_3$) δ: 3.83 (3H, s), 6.68 (1H, d, J=2.1 Hz), 7.55-7.60 (2H, m), 7.67-7.72 (1H, m), 7.96-7.99 (2H, m), 8.08 (1H, d, J=2.1 Hz).

Reference Example 52

[5-Bromo-1-(phenylsulfonyl)-1H-pyrrol-3-yl]methanol

A solution (80 mL) of methyl 5-bromo-1-(phenylsulfonyl)-1H-pyrrole-3-carboxylate (7.1 g) in tetrahydrofuran was cooled to −78° C., a 1.5 mol/l solution (42 mL) of diisobutylaluminum hydride in toluene was added dropwise over 30 min, and the mixture was further stirred at −78° C. for 1 hr. 1 mol/l Hydrochloric acid (20 mL) was added to the reaction mixture, and the mixture was extracted with ethyl acetate. The extract was washed with saturated aqueous sodium hydrogen carbonate, water, saturated brine, dried over anhydrous sodium sulfate, and concentrated under reduced pressure to give the title compound as a brown oil (yield 7.1 g, quantitative).
$^1$H-NMR (CDCl$_3$) δ: 1.62 (1H, brs), 4.51 (2H, s), 6.33-6.34 (1H, m), 7.44-7.45 (1H, m), 7.51-7.57 (2H, m), 7.62-7.68 (1H, m), 7.93-7.97 (2H, m).

Reference Example 53

5-Bromo-1-(phenylsulfonyl)-1H-pyrrole-3-carbaldehyde

To a solution (80 mL) of [5-bromo-1-(phenylsulfonyl)-1H-pyrrol-3-yl]methanol (7.1 g) in acetonitrile were added tetra-n-propylammonium perruthenate (0.63 g), N-methylmorpholine N-oxide hydrate (4.2 g) and molecular sieves 4 A powder (3.5 g) and the mixture was stirred at room temperature for 2 hr. The reaction mixture was concentrated under reduced pressure, water was added to the residue, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=4:1) to give the title compound as a colorless solid (yield 4.6 g, 71%).
$^1$H-NMR (CDCl$_3$) δ: 6.73 (1H, d, J=2.1 Hz), 7.57-7.63 (2H, m), 7.70-7.75 (1H, m), 7.98-8.02 (2H, m), 8.10 (1H, d, J=2.1 Hz), 9.77 (1H, s).

Reference Example 54

1-[5-Bromo-1-(phenylsulfonyl)-1H-pyrrol-3-yl]-N-methylmethanamine

To a solution (60 mL) of 5-bromo-1-(phenylsulfonyl)-1H-pyrrole-3-carbaldehyde (3.5 g) in methanol were added methylammonium chloride (7.5 g) and sodium cyanoborohydride (2.4 g), and the mixture was stirred at room temperature for 1 hr. The reaction mixture was concentrated under reduced pressure. Saturated aqueous sodium hydrogen carbonate was added to the residue, and the mixture was extracted with ethyl acetate. The extract was washed with saturated aqueous sodium hydrogen carbonate, water and saturated brine, dried over anhydrous sodium sulfate, and concentrated under reduced pressure to give the title compound as a brown oil (yield 4.4 g, quantitative).
$^1$H-NMR (CDCl$_3$) δ: 2.47 (3H, s), 2.98 (1H, brs), 3.66 (2H, s), 6.35 (1H, d, J=2.4 Hz), 7.51-7.57 (3H, m), 7.61-7.68 (1H, m), 7.93-7.97 (2H, m).

Reference Example 55 tert-Butyl {[5-bromo-1-(phenylsulfonyl)-1H-pyrrol-3-yl]methyl}methylcarbamate

To a solution of 1-[5-bromo-1-(phenylsulfonyl)-1H-pyrrol-3-yl]-N-methylmethanamine (4.4 g) in ethyl acetate (60 mL) was added di-tert-butyl bicarbonate (2.8 mL), and the mixture was stirred at room temperature for 14 hr. Saturated aqueous sodium hydrogen carbonate was added to the reaction mixture, and the mixture was extracted with ethyl acetate. The extract was washed with aqueous sodium hydrogencarbonate solution and saturated brine, dried over anhydrous sodium sulfate, and concentrated under reduced pressure. The residue was purified by silica gel column chromatography (eluent: hexane-ethyl acetate=4:1) to give the title compound as a colorless oil (yield 3.4 g, 73%).

$^1$H-NMR (CDCl$_3$) δ: 1.48 (9H, s), 2.79 (3H, brs), 4.17 (2H, brs), 6.24 (1H, brs), 7.35 (1H, brs), 7.51-7.57 (2H, m), 7.62-7.68 (1H, m), 7.90-7.94 (2H, m).

Reference Example 56 tert-Butyl methyl{[1-(phenylsulfonyl)-5-(3-thienyl)-1H-pyrrol-3-yl]methyl}carbamate A suspension of tert-butyl {[5-bromo-1-(phenylsulfonyl)-1H-pyrrol-3-yl]methyl}methylcarbamate (1.02 g), 3-thienylboronic acid (0.61 g), tetrakis(triphenylphosphine)palladium (0.41 g) and sodium carbonate (0.75 g) in 1,2-dimethoxyethane (25 mL)-water (25 mL) was stirred at 105° C. for 7 hr. After cooling, saturated aqueous sodium hydrogen carbonate was added to the reaction mixture, and the mixture was extracted with ethyl acetate. The extract was washed with saturated aqueous sodium hydrogen carbonate, water and saturated brine, dried over anhydrous magnesium sulfate, and concentrated under reduced pressure. The residue was purified by silica gel column chromatography (eluent: hexane-ethyl acetate=4:1) to give the title compound as a colorless solid (yield 0.90 g, 88%).

$^1$H-NMR (CDCl$_3$) δ: 1.47 (9H, s), 2.81 (3H, brs), 4.21 (2H, brs), 6.13 (1H, brs), 7.04 (1H, dd, J=1.2, 3.0 Hz), 7.11 (1H, dd, J=1.2, 3.0 Hz), 7.24 (1H, dd, J=3.0, 5.1 Hz), 7.30-7.39 (5H, m), 7.48-7.54 (1H, m).

Reference Example 57 tert-Butyl methyl{[5-phenyl-1-(phenylsulfonyl)-1H-pyrrol-3-yl]methyl}carbamate

A suspension of tert-butyl {[5-bromo-1-(phenylsulfonyl)-1H-pyrrol-3-yl]methyl}methylcarbamate (1.04 g), phenylboronic acid (0.45 g), tetrakis(triphenylphosphine)palladium (0.42 g) and sodium carbonate (0.77 g) in 1,2-dimethoxyethane (25 mL)-water (25 mL) was stirred at 105° C. for 12 hr. After cooling, saturated aqueous sodium hydrogen carbonate was added to the reaction mixture, and the mixture was extracted with ethyl acetate. The extract was washed with saturated aqueous sodium hydrogen carbonate, water and saturated brine, dried over anhydrous magnesium sulfate, and concentrated under reduced pressure. The residue was purified by silica gel column chromatography (eluent: hexane-ethyl acetate=4:1) to give the title compound as a colorless solid (yield 0.97 g, 94%).

$^1$H-NMR (CDCl$_3$) δ: 1.46 (9H, s), 2.80 (3H, brs), 4.22 (2H, brs), 6.09 (1H, brs), 7.19-7.23 (2H, m), 7.26-7.38 (8H, m), 7.47-7.53 (1H, m).

Reference Example 58 tert-Butyl {{5-bromo-1-[(4-fluorophenyl)sulfonyl]-1H-pyrrol-3-yl}methyl}methylcarbamate Using methyl 5-bromo-1H-pyrrole-3-carboxylate and 4-fluorobenzenesulfonyl chloride, a procedure as in Reference Example 55 was performed to synthesize methyl 5-bromo-1-[(4-fluorophenyl)sulfonyl]-1H-pyrrole-3-carboxylate, and procedures as in Reference Examples 52, 53, 54 and 55 were sequentially performed to give the title compound as a colorless oil.

$^1$H-NMR (CDCl$_3$) δ: 1.47 (9H, s), 2.79 (3H, brs), 4.17 (2H, brs), 6.25 (1H, brs), 7.19-7.25 (2H, m), 7.33 (1H, brs), 7.93-7.98 (2H, m).

Reference Example 59 tert-Butyl {{1-[(4-fluorophenyl)sulfonyl]-5-(3-thienyl)-1H-pyrrol-3-yl}methyl}methylcarbamate Using tert-butyl {{5-bromo-1-[(4-fluorophenyl)sulfonyl]-1H-pyrrol-3-yl}methyl}methylcarbamate (0.60 g), 3-thienylboronic acid (0.35 g), tetrakis(triphenylphosphine)palladium (0.24 g) and sodium carbonate (0.43 g), a procedure as in Reference Example 56 was performed to give the title compound as a colorless solid (yield 0.42 g, 69%).

$^1$H-NMR (CDCl$_3$) δ: 1.47 (9H, s), 2.81 (3H, brs), 4.22 (2H, brs), 6.14 (1H, brs), 6.97-7.06 (3H, m), 7.14-7.15 (1H, m), 7.25-7.31 (2H, m), 7.34-7.39 (2H, m).

Reference Example 60 tert-Butyl {{5-bromo-1-[(3-chlorophenyl)sulfonyl]-1H-pyrrol-3-yl}methyl}methylcarbamate Using methyl 5-bromo-1H-pyrrole-3-carboxylate and 3-chlorobenzenesulfonyl chloride, a procedure as in Reference Example 55 was performed to synthesize methyl 5-bromo-1-[(3-chlorophenyl)sulfonyl]-1H-pyrrole-3-carboxylate, and procedures as in Reference Examples 52, 53, 54 and 55 were sequentially performed to give the title compound as a pale-yellow oil.

$^1$H-NMR (CDCl$_3$) δ: 1.47 (9H, s), 2.80 (3H, brs), 4.18 (2H, brs), 6.26 (1H, brs), 7.33 (1H, brs), 7.46-7.51 (1H, m), 7.60-7.63 (1H, m), 7.80-7.82 (1H, m), 7.89-7.90 (1H, m).

Reference Example 61 tert-Butyl {{1-[(3-chlorophenyl)sulfonyl]-5-phenyl-1H-pyrrol-3-yl}methyl}methylcarbamate Using tert-butyl {{5-bromo-1-[(3-chlorophenyl)sulfonyl]-1H-pyrrol-3-yl}methyl}methylcarbamate (1 g), phenylboronic acid (526 mg), sodium carbonate (687 mg) and tetrakis(triphenylphosphine)palladium (374 mg), a procedure as in Reference Example 57 was performed to give the title compound as a pale-yellow oil (yield 726 mg, 73%).

$^1$H-NMR (CDCl$_3$) δ: 1.47 (9H, s), 2.81 (3H, brs), 4.81 (2H, brs), 6.11 (1H, brs), 7.19-7.49 (10H, m).

Reference Example 62 tert-Butyl {{1-[(3-chlorophenyl)sulfonyl]-5-(3-thienyl)-1H-pyrrol-3-yl}methyl}methylcarbamate Using tert-butyl ({5-bromo-1-[(3-chlorophenyl)sulfonyl]-1H-pyrrol-3-yl}methyl)methylcarbamate (1 g), 3-thienylboronic acid (553 mg), sodium carbonate (687 mg) and tetrakis(triphenylphosphine)palladium (374 mg) a procedure as in Reference Example 56 was performed to give the title compound as a pale-yellow oil (yield 712 mg, 71%).

$^1$H-NMR (CDCl$_3$) δ: 1.47 (9H, s), 2.82 (3H, brs), 4.22 (2H, brs), 6.16 (1H, brs), 7.03-7.05 (1H, m), 7.14-7.16 (1H, m), 7.23-7.31 (5H, m), 7.45-7.49 (1H, m).

Reference Example 63 tert-Butyl {{1-[(3-chlorophenyl)sulfonyl]-5-(4-fluorophenyl)-1H-pyrrol-3-yl}methyl}methylcarbamate Using tert-butyl {{5-bromo-1-[(3-chlorophenyl)sulfonyl]-1H-pyrrol-3-yl}methyl}methylcarbamate (1 g), (4-fluorophenyl)boronic acid (628 mg), sodium carbonate (708 mg) and tetrakis(triphenylphosphine)palladium (388 mg), a procedure as in Reference Example 56 was performed to give the title compound as a pale-yellow oil (yield 930 mg, 87%).
$^1$H-NMR (CDCl$_3$) δ: 1.47 (9H, s), 2.80 (3H, s), 4.22 (2H, brs), 6.09 (1H, brs), 6.91-7.50 (9H, m).

Reference Example 64

(5-Phenyl-1H-pyrrol-3-yl)methanol

A solution (100 mL) of ethyl 5-phenyl-1H-pyrrole-3-carboxylate (2.16 g) in tetrahydrofuran was cooled to −78° C., and a 1.5 mol/L solution (24 mL) of diisobutylaluminum hydride in toluene was added dropwise over 10 min. The mixture was further stirred at −78° C. for 1 hr, water (2 mL) was added dropwise over 2 min, and the mixture was further stirred at room temperature for 1 hr. To the reaction mixture were added celite and anhydrous magnesium sulfate, the mixture was filtered and the filtrate was concentrated under reduced pressure to give the title compound as a pale-red powder (yield 1.51 g, 87%).
$^1$H-NMR (DMSO-d$_6$) δ: 4.34 (2H, d, J=5.4 Hz), 4.60 (1H, t, J=5.4 Hz), 6.45-6.46 (1H, m), 6.74 (1H, br), 7.11-7.15 (1H, m), 7.31-7.35 (2H, m), 7.57-7.59 (2H, m), 11.05 (1H, s).

Reference Example 65

5-Phenyl-1H-pyrrole-3-carbaldehyde

To a solution (45 mL) of (5-phenyl-1H-pyrrol-3-yl)methanol (1.51 g) in acetonitrile were added tetra-n-propylammonium perruthenate (0.46 g), N-methylmorpholine N-oxide (2.36 g) and molecular sieves 4 A powder (4.5 g), and the mixture was stirred at room temperature for 1.5 hr. The reaction mixture was filtered through celite, and the filtrate was concentrated under reduced pressure. The residue was purified by silica gel column chromatography (eluent: hexane-ethyl acetate=4:1→1:1) to give the title compound as a pale-yellow powder (yield 0.92 g, 62%).
$^1$H-NMR (CDCl$_3$) δ: 6.95 (1H, m), 7.29-7.32 (1H, m), 7.40-7.44 (2H, m), 7.50-7.52 (3H, m), 9.02 (1H, br), 9.84 (1H, s).

Reference Example 66 tert-Butyl methyl[(5-phenyl-1H-pyrrol-3-yl)methyl]carbamate

To a solution (92 mL) of 5-phenyl-1H-pyrrole-3-carbaldehyde (0.92 g) in methanol was added 40% methylamine solution (1.26 g) at room temperature and the mixture was stirred for 30 min. To the reaction mixture was added sodium borohydride (305 mg) at room temperature and the mixture was stirred for 10 min. Water (200 mL) was added and the mixture was further stirred for 1 hr. Saturated brine (50 mL) was added and the mixture was extracted with ethyl acetate. The extract was washed with saturated brine, dried over anhydrous sodium sulfate, and concentrated under reduced pressure. The residue was dissolved in acetonitrile (48 mL), and di-tert-butyl bicarbonate (1.41 g) was added dropwise at room temperature. The mixture was stirred for 1.5 hr and partitioned with water and ethyl acetate. The ethyl acetate layer was washed with saturated brine, dried over anhydrous sodium sulfate, and concentrated under reduced pressure. The residue was purified by silica gel column chromatography (eluent: hexane-ethyl acetate=9:1→4:1) to give the title compound as colorless crystals (yield 0.99 g, 64%).
$^1$H-NMR (CDCl$_3$) δ: 1.50 (9H, s), 2.84 (3H, s), 4.30 (2H, s), 6.45 (1H, s), 6.75 (1H, s), 7.18-7.22 (1H, m), 7.34-7.38 (2H, m), 7.44-7.46 (2H, m), 8.37 (1H, br).

Reference Example 67

2-Bromo-1-(2-fluorophenyl)propan-1-one

To a solution of 2'-fluoropropiophenone (25.0 g) in acetic acid (250 mL) was slowly added bromine (8.4 mL). The mixture was stirred at room temperature for 3 hr, and concentrated under reduced pressure. To the residue was added water (200 mL), and the mixture was extracted with diisopropyl ether. The extract was washed with saturated aqueous sodium hydrogencarbonate solution, water and saturated brine, dried over anhydrous magnesium sulfate, and filtrated. The filtrate was concentrated under reduced pressure to give the title compound as a yellow oil (yield 36.8 g, 97%).
$^1$H-NMR (CDCl$_3$) δ: 1.89-1.91 (3H, m), 5.27-5.34 (1H, m), 7.12-7.19 (1H, m), 7.24-7.30 (1H, m), 7.52-7.59 (1H, m), 7.88-7.93 (1H, m).

Reference Example 68

2-Bromo-1-(3-thienyl)ethanone

To a solution of 3-acetylthiophene (3.73 g) in diethyl ether (60 mL) was added aluminum chloride (386 mg), and the mixture was stirred for 5 min. Bromine (1.55 mL) was slowly added at room temperature to this mixture, and the mixture was further stirred for 2 hr. Aqueous sodium carbonate solution was added to the reaction mixture, and the mixture was extracted with diethylether. The extract was dried over anhydrous sodium sulfate, filtrated, and concentrated under reduced pressure. The residue was recrystallized from diisopropyl ether to give the title compound as white crystals (yield 3.93 g, 65%).
$^1$H-NMR (CDCl$_3$) δ: 4.34 (2H, s), 7.35-7.38 (1H, m), 7.57-7.60 (1H, m), 8.17-8.19 (1H, m).

Reference Example 69

Ethyl 2-cyano-4-(2-fluorophenyl)-4-oxobutanoate

To a solution of 2'-fluoroacetophenone (28.6 g) in ethyl acetate (400 mL), copper (II) bromide (92.6 g) was added, and the mixture was heated under reflux for 4 hr. The reaction mixture was cooled to room temperature and the insoluble material was filtered off. The filtrate was concentrated under reduced pressure to give crude 1-bromo-1-(2-fluorophenyl)ethanone (yield 90.5 g) as an oil. Potassium carbonate (88 g) was added to ethyl cyanoacetate (168 g), and the mixture was stirred at 45° C. for 1 hr. A solution (360 mL) of crude 1-bromo-1-(2-fluorophenyl)ethanone (90.5 g) in acetone was added dropwise over 20 min. After completion of the dropwise addition, the mixture was stirred at the same temperature for 1 hr. To the reaction mixture water (300 mL) and ethyl acetate (300 mL) were added, and the mixture was extracted with ethyl acetate. The extract was washed with 10% aqueous sodium dihydrogenphosphate solution and saturated brine, dried over anhydrous sodium sulfate, and concentrated under reduced pressure. An excess ethyl cyanoacetate contained in the obtained oil was evaporated under reduced pressure, and the residue was purified by silica gel column chromatography (eluent: hexane-ethyl acetate=20:1→4:1) to give the title compound as an oil (yield 64.0 g, about 100%).

$^1$H-NMR (CDCl$_3$) δ: 1.35 (3H, t, J=7.2 Hz), 3.55-3.80 (2H, m), 4.11 (1H, t, J=6.0 Hz), 4.24-4.34 (2H, m), 7.15-7.29 (2H, m), 7.55-7.62 (1H, m), 7.94 (1H, dt, J=1.8, 7.5 Hz).

Reference Example 70

Methyl 2-cyano-4-(2-fluorophenyl)-3-methyl-4-oxobutanoate

To a solution of methyl cyanoacetate (15.5 mL) and diisopropylethylamine (64 mL) in tetrahydrofuran (110 mL) was added a solution of 2-bromo-1-(2-fluorophenyl)propan-1-one (36.8 g) in tetrahydrofuran (160 mL), and the mixture was stirred at 70° C. for 20 hr. The reaction mixture was allowed to cool to room temperature, the insoluble material was filtered off, and the filtrate was concentrated under reduced pressure. The residue was purified by silica gel column chromatography (eluent: hexane-ethyl acetate=5:1) to give the title compound as a brown oil (yield 31.9 g, 80%).

$^1$H-NMR (CDCl$_3$) δ: 1.42-1.46 (3H, m), 3.82-3.85 (4H, m), 3.99-4.17 (1H, m), 7.14-7.22 (1H, m), 7.25-7.31 (1H, m), 7.55-7.63 (1H, m), 7.85-7.91 (1H, m).

Reference Example 71

Ethyl 2-acetyl-3-methyl-4-oxo-4-phenylbutanoate

Using ethyl 3-oxobutanoate (12.2 g), sodium hydride (60% in oil, 4.24 g) and 2-bromopropiophenone (22.0 g), a procedure as in Reference Example 13 was performed to give the title compound as a brown oil (yield 22.1 g, 90%).

$^1$H-NMR (CDCl$_3$) δ: 1.13-1.21 (3H, m), 1.31-1.36 (3H, m), 2.31-2.41 (3H, m), 4.04-4.31 (4H, m), 7.45-7.51 (2H, m), 7.55-7.61 (1H, m), 7.98-8.03 (2H, m).

Reference Example 72

Ethyl 2-acetyl-3-methyl-4-oxo-4-(3-thienyl)butanoate

Using ethyl 3-oxobutanoate (2.40 g), sodium hydride (60% in oil, 803 mg) and 2-bromo-1-(3-thienyl)ethanone (3.80 g), a procedure as in Reference Example 13 was performed to give the title compound as a brown oil (yield 1.87 g, 40%).

$^1$H-NMR (CDCl$_3$) δ: 1.27-1.32 (3H, m), 2.43 (3H, s), 3.39-3.48 (1H, m), 3.59-3.68 (1H, m), 4.18-4.26 (3H, m), 7.31-7.34 (1H, m), 7.53-7.55 (1H, m), 8.12-8.14 (1H, m).

Reference Example 73

Ethyl 2-chloro-5-(2-fluorophenyl)-1H-pyrrole-3-carboxylate

A mixture of ethyl 2-cyano-4-(2-fluorophenyl)-4-oxobutanoate (19.3 g) and 4 mol/L hydrogen chloride-ethyl acetate solution (100 mL) was stirred at room temperature for 18 hr. The reaction mixture was concentrated under reduced pressure, and the residue was purified by silica gel column chromatography (eluent: hexane-ethyl acetate=10:1→3:1) to give the title compound as a brown solid (yield 8.76 g, 53%).

$^1$H-NMR (CDCl$_3$) δ: 1.36-1.41 (3H, m), 4.33 (2H, q, J=7.2 Hz), 6.99-7.00 (1H, m), 7.09-7.26 (3H, m), 7.55-7.61 (1H, m), 9.08 (1H, brs).

Reference Example 74

Methyl 2-chloro-5-(2-fluorophenyl)-4-methyl-1H-pyrrole-3-carboxylate

To a solution of methyl 2-cyano-4-(2-fluorophenyl)-3-methyl-4-oxobutanoate (31.0 g) in ethyl acetate (30 mL) was added 4 mol/L hydrogen chloride-ethyl acetate solution (150 mL), and the mixture was stirred at room temperature for 2 days. To the reaction mixture was added water (200 mL), and the mixture was extracted with ethyl acetate. The extract was washed with water (twice) and saturated aqueous sodium hydrogencarbonate solution, dried over anhydrous sodium sulfate, filtered, and concentrated under reduced pressure. The residue was recrystallized from ethyl acetate to give the title compound as white crystals (yield 19.3 g, 58%).

$^1$H-NMR (CDCl$_3$) δ: 2.33 (3H, s), 3.86 (3H, s), 7.12-7.42 (4H, m), 8.53 (1H, brs).

Reference Example 75

Ethyl 2,4-dimethyl-5-phenyl-1H-pyrrole-3-carboxylate

Using ethyl 2-acetyl-3-methyl-4-oxo-4-phenylbutanoate (20.3 g) and ammonium acetate (6.61 g), a procedure as in Reference Example 14 was performed to give the title compound as a brown oil (yield 17.1 g, 91%).

$^1$H-NMR (CDCl$_3$) δ: 1.36 (3H, t, J=7.2 Hz), 2.38 (3H, s), 2.54 (3H, s), 4.29 (2H, q, J=7.2 Hz), 7.24-7.30 (1H, m), 7.35-7.43 (4H, m), 8.13 (1H, brs).

Reference Example 76

Ethyl 2-methyl-5-(3-thienyl)-1H-pyrrole-3-carboxylate

Using ethyl 2-acetyl-3-methyl-4-oxo-4-(3-thienyl)butanoate (1.86 g) and ammonium acetate (626 mg), a procedure as in Reference Example 14 was performed to give the title compound as a brown oil (yield 1.57 g, 91%).

$^1$H-NMR (CDCl$_3$) δ: 1.36 (3H, t, J=7.2 Hz), 2.57 (3H, s), 4.29 (2H, q, J=7.2 Hz), 6.69-6.70 (1H, m), 7.17-7.18 (1H, m), 7.22-7.24 (1H, m), 7.33-7.36 (1H, m), 8.38 (1H, brs).

Reference Example 77

Ethyl 5-(4-fluorophenyl)-2-methyl-1H-pyrrole-3-carboxylate

4'-Fluoroacetophenone (13.8 g) was dissolved in chloroform (60 mL) and diethyl ether (60 mL), and a solution of bromine (16.0 g) in chloroform (10 mL) was added dropwise while maintaining the reaction temperature at not higher than 25° C. After completion of the dropwise addition, the reaction mixture was stirred at room temperature for 30 min, and extracted with ethyl acetate. The extract was washed with water and dried over anhydrous magnesium sulfate, and the solvent was evaporated under reduced pressure to give crude 2-bromo-1-(4-fluorophenyl)ethanone (23.2 g) as crystals. A solution (20 mL) of ethyl 3-oxobutanoate (11.7 g) in N,N-dimethylformamide was added dropwise to a suspension (50 mL) of sodium hydride (60% in oil, 4.00 g) in N,N-dimethylformamide with stirring under ice-cooling. After stirring at the same temperature for 15 min, a solution (10 mL) of crude 2-bromo-1-(4-fluorophenyl)ethanone (23.2 g) obtained above in N,N-dimethylformamide was added dropwise. The reaction mixture was stirred at room temperature for 2 hr, water was added, and the mixture was extracted with diethyl ether. The extract was washed with saturated brine, dried over anhydrous magnesium sulfate, and concentrated under reduced pressure to give crude ethyl 2-acetyl-4-(4-fluorophenyl)-4-oxobutanoate as an oil (yield 23.20 g). Without further purification, the product was stirred with ammonium acetate (11.56 g, 0.15 mol) and acetic acid (100 mL) with heating at 80° C. for 20 hr. The reaction mixture was concentrated under reduced pressure, dissolved in ethyl acetate, washed with water, and dried over anhydrous magnesium sulfate. The solvent was evaporated under reduced pressure, and the residue was purified by silica gel column chromatography (eluent: hexane-ethyl acetate=7:2). The residue was crystallized from hexane to give the title compound as crystals (yield 13.6 g, from ethyl 3-oxobutanoate, 61%).

$^1$H-NMR (CDCl$_3$) δ: 1.36 (3H, t, J=7.1 Hz), 2.58 (3H, s), 4.29 (2H, q, J=7.1 Hz), 6.76 (1H, s), 7.06 (2H, t, J=8.7 Hz), 7.41 (2H, dd, J=8.9, 5.1 Hz), 8.39 (1H, s).

Reference Example 78

Ethyl 2-chloro-5-(pyridin-2-yl)-1H-pyrrole-3-carboxylate hydrochloride

2-Bromo-1-(pyridin-2-yl)ethanone hydrobromide (20 g) and potassium carbonate (14.8 g) were suspended in acetone (100 mL), and the mixture was stirred at room temperature for 1.5 hr. Ethyl cyanoacetate (60.4 g) was dissolved in acetone (100 mL), potassium carbonate (29.6 g) was added and the mixture was stirred at 45° C. for 1 hr. The suspension obtained earlier was added dropwise by small portions at the same temperature. The reaction mixture was stirred at 45° C. for 3 hr, and the insoluble material was filtered off. The filtrate was concentrated under reduced pressure. The residue was suspended in ethyl acetate, washed with water and saturated brine, dried over anhydrous magnesium sulfate, and concentrated under reduced pressure. A 4 mol/L hydrogen chloride-ethyl acetate solution (250 mL) was added to the obtained oil and the mixture was stirred at 60° C. for 3 hr and concentrated under reduced pressure. A saturated aqueous sodium hydrogencarbonate solution was added and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1). A 4 mol/L hydrogen chloride-ethyl acetate solution (20 mL) was added and the mixture was concentrated under reduced pressure and crystallized from ethyl acetate to give the title compound as colorless crystals (yield 3.08 g, 15%).

$^1$H-NMR (DMSO-d$_6$) δ: 1.30 (3H, t, J=7.0 Hz), 4.25 (2H, q, J=7.0 Hz), 7.48-7.54 (2H, m), 8.13-8.19 (2H, m), 8.61-8.63 (1H, m), 13.47 (1H, br).

Reference Example 79

Ethyl 5-(2-fluorophenyl)-1H-pyrrole-3-carboxylate

To a solution (80 mL) of ethyl 2-chloro-5-(2-fluorophenyl)-1H-pyrrole-3-carboxylate (8.6 g) in ethanol was added 10% palladium carbon (50% containing water, 0.86 g), and the mixture was stirred under a hydrogen atmosphere at room temperature for 36 hr. The reaction mixture was filtrated, and the filtrate was concentrated under reduced pressure. The residue was dissolved in ethanol (70 mL), 10% palladium carbon (50% containing water, 0.90 g) was added, and the mixture was stirred under a hydrogen atmosphere at room temperature for 60 hr. The reaction mixture was filtrated, and the filtrate was concentrated under reduced pressure. The residue was purified by silica gel column chromatography (eluent: hexane-ethyl acetate=10:1→5:1) to give the title compound as a brown solid (yield 1.37 g, 18%).

$^1$H-NMR (CDCl$_3$) δ: 1.67 (3H, t, J=7.2 Hz), 4.31 (2H, q, J=7.2 Hz), 7.03-7.05 (1H, m), 7.08-7.25 (3H, m), 7.49-7.50 (1H, m), 7.58-7.66 (1H, m), 9.22 (1H, brs).

Reference Example 80

Methyl 5-(2-fluorophenyl)-4-methyl-1H-pyrrole-3-carboxylate

To a solution of methyl 2-chloro-5-(2-fluorophenyl)-4-methyl-1H-pyrrole-3-carboxylate (10.2 g) in methanol (200 mL) was added 10% palladium carbon (50% containing water, 1.28 g), and the mixture was stirred under a hydrogen atmosphere at room temperature for 20 hr. The reaction mixture was filtrated, and the filtrate was concentrated under reduced pressure. A saturated aqueous sodium hydrogencarbonate solution (100 mL) was added to the residue, and the mixture was extracted with ethyl acetate. The extract was washed with saturated aqueous sodium hydrogencarbonate solution, water and saturated brine, dried over anhydrous sodium sulfate, filtrated, and concentrated under reduced pressure. The residue was recrystallized from ethyl acetate-hexane to give the title compound as white crystals (yield 6.70 g, 76%).

$^1$H-NMR (CDCl$_3$) δ: 2.40 (3H, s), 3.82 (3H, s), 7.12-7.33 (3H, m), 7.42-7.49 (2H, m), 8.67 (1H, brs).

Reference Example 81

Ethyl 5-(pyridin-2-yl)-1H-pyrrole-3-carboxylate

Ethyl 2-chloro-5-(pyridin-2-yl)-1H-pyrrole-3-carboxylate hydrochloride (2.73 g) was dissolved in ethanol (200 mL), and 10% palladium carbon (50% containing water, 2.73 g) was added under a nitrogen atmosphere. Under a hydrogen atmosphere, the mixture was stirred at 50° C. for 15 hr. The reaction mixture was filtrated, and the filtrate was concentrated under reduced pressure. Saturated aqueous sodium hydrogencarbonate was added to the residue, and the mixture was extracted with ethyl acetate. The extract was washed with saturated brine, dried over anhydrous magnesium sulfate, and concentrated under reduced pressure to give the title compound as colorless crystals (yield 1.73 g, 84%).

$^1$H-NMR (DMSO-d$_6$) δ: 1.28 (3H, t, J=7.2 Hz), 4.20 (2H, q, J=7.2 Hz), 7.13-7.15 (1H, m), 7.19-7.23 (1H, m), 7.43-7.44 (1H, m), 7.75-7.83 (2H, m), 8.51-8.54 (1H, m), 12.11 (1H, brs).

Reference Example 82

Methyl 5-(2-methylphenyl)-1H-pyrrole-3-carboxylate

2'-Methylacetophenone (16.0 g) was dissolved in chloroform (50 mL) and diethyl ether (50 mL), and a solution of bromine (16.0 g) in chloroform (15 mL) was added dropwise while maintaining the reaction temperature at not higher than 25° C. After completion of the dropwise addition, the reaction mixture was stirred at room temperature for 30 min, and extracted with ethyl acetate. The extract was washed with water, dried over anhydrous magnesium sulfate, and the solvent was evaporated under reduced pressure to give crude 2-bromo-1-(2-methylphenyl)ethanone (21.4 g) as an oil. To a solution (700 mL) of methyl cyanoacetate (10.9 g) and diisopropylethylamine (31.0 g) in tetrahydrofuran was added dropwise a solution (100 mL) of crude 2-bromo-1-(2-methylphenyl)ethanone (21.4 g) obtained above in tetrahydrofuran. The reaction mixture was stirred at room temperature for 16 hr, then at 70° C. for 2 hr. The reaction mixture was filtrated, and the filtrate was concentrated under reduced pressure. The residue was purified by silica gel column chromatography (eluent: hexane-ethyl acetate=4:1) to give methyl 2-cyano-4-(2-methylphenyl)-4-oxobutanoate as an oil (yield 16.0 g). This was dissolved in ethyl acetate (16 mL), 4 mol/L hydrogen chloride-ethyl acetate solution (80 mL) was added, and the mixture was stirred at room temperature for 16 hr. The reaction mixture was concentrated under reduced pressure, water was added to the residue, and the mixture was extracted with ethyl acetate. The extract was washed with water, 6% aqueous sodium hydrogencarbonate solution and saturated brine, dried over anhydrous sodium sulfate, and concentrated under reduced pressure. The residue was purified by silica gel column chromatography (eluent: hexane-ethyl acetate=4:1) to give methyl 2-chloro-5-(2-methylphenyl)-1H-pyrrole-3-carboxylate as an oil (yield 2.7 g). This was dissolved in methanol (15 mL), 10% palladium carbon (50% containing water, 1.0 g) was added, and the mixture was stirred under a hydrogen atmosphere at room temperature for 18 hr. The reaction mixture was filtrated, and the filtrate was concentrated under reduced pressure. The residue was purified by silica gel column chromatography (eluent: hexane-ethyl acetate=4:1) to give the title compound as a colorless solid (yield 0.66 g, 3%).

$^1$H-NMR (CDCl$_3$) δ: 2.44 (3H, s), 3.84 (3H, s), 6.72-6.73 (1H, m), 7.22-7.34 (4H, m), 7.42-7.50 (1H, m), 8.50 (1H, brs).

Reference Example 83

Ethyl 4-chloro-2-methyl-5-phenyl-1H-pyrrole-3-carboxylate

To a solution (20 mL) of ethyl 2-methyl-5-phenyl-1H-pyrrole-3-carboxylate (1.0 g) in N,N-dimethylformamide was added N-chlorosuccinimide (874 mg) at 0° C. The reaction mixture was stirred at room temperature for 4 hr, 6% aqueous sodium hydrogencarbonate solution was added, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→4:1) to give the title compound as colorless crystals (yield 509 mg, 44%).

$^1$H-NMR (CDCl$_3$) δ: 1.39 (3H, t, J=7.2 Hz), 2.56 (3H, s), 4.34 (2H, q, J=7.2 Hz), 7.28-7.34 (1H, m), 7.39-7.45 (2H, m), 7.59-7.63 (2H, m), 8.22 (1H, br).

Reference Example 84

Ethyl 2-fluoro-5-phenyl-1H-pyrrole-3-carboxylate

To a solution (70 mL) of ethyl 5-phenyl-1H-pyrrole-3-carboxylate (1.0 g) in tetrahydrofuran was added xenone difluoride (944 mg) under a nitrogen atmosphere, and the mixture was stirred at room temperature for 72 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=9:1→4:1) to give the title compound as pale-red crystals (yield 350 mg, 32%).

$^1$H-NMR (CDCl$_3$) δ: 1.36 (3H, t, J=7.1 Hz), 4.32 (2H, q, J=7.1 Hz), 6.66-6.68 (1H, m), 7.23-7.29 (1H, m), 7.35-7.45 (4H, m), 8.51 (1H, brs).

Reference Example 85

Ethyl 2-chloro-4-fluoro-5-phenyl-1H-pyrrole-3-carboxylate

To a solution (100 mL) of ethyl 2-chloro-5-phenyl-1H-pyrrole-3-carboxylate (2.0 g) in tetrahydrofuran was added xenone difluoride (1.85 g) under a nitrogen atmosphere, and the mixture was stirred at room temperature for 72 hr. The reaction mixture was concentrated under reduced pressure, and residue was purified by silica gel column chromatography (eluent: hexane-ethylacetate=9:1→4:1) to give the title compound as colorless crystals (yield 350 mg, 15%).

$^1$H-NMR (CDCl$_3$) δ: 1.37-1.42 (3H, m), 4.33-4.41 (2H, m), 7.28-7.62 (5H, m).

Reference Example 86

Ethyl 4-fluoro-5-phenyl-1H-pyrrole-3-carboxylate

To a solution (30 mL) of ethyl 2-chloro-4-fluoro-5-phenyl-1H-pyrrole-3-carboxylate (300 mg) in ethanol was added 10% palladium carbon (50% water-containing product, 0.3 g), and the mixture was stirred under a hydrogen atmosphere at room temperature for 24 hr. The reaction mixture was filtrated, and the filtrate was concentrated under reduced pressure. The residue was purified by silica gel column chromatography (eluent: hexane-ethyl acetate=4:1) to give the title compound as a colorless oil (yield 100 mg, 38%).

$^1$H-NMR (CDCl$_3$) δ: 1.37 (3H, t, J=7.2 Hz), 4.34 (2H, q, J=7.2 Hz), 7.22-7.54 (6H, m), 8.42 (1H, br).

Reference Example 87

Methyl (2E)-hex-2-enoate

To a solution (100 mL) of (2E)-hex-2-enoic acid (5.0 g) in tetrahydrofuran were added dropwise under ice-cooling oxalyl chloride (3.76 mL) and N,N-dimethylformamide (1 mL). The mixture was stirred at the same temperature for 30 min, methanol (10 mL) was gradually added to the reaction mixture, and the mixture was stirred at room temperature for 2 hr. The solvent was evaporated under reduced pressure, and the residue was treated with 6% aqueous sodium hydrogencarbonate solution, and extracted with diethyl ether. The extract was washed with saturated brine, dried over anhydrous sodium sulfate, and concentrated under reduced pressure (50 Torr, water bath 10° C.) to give the title compound as a colorless oil (yield 5.67 g, about 100%).

$^1$H-NMR (CDCl$_3$) δ: 0.94 (3H, t, J=7.5 Hz), 1.43-1.53 (2H, m), 2.14-2.21 (2H, m), 3.73 (3H, s), 5.82 (1H, dt, J=1.8, 15.6 Hz), 6.97 (1H, dt, J=6.9, 15.6 Hz).

Reference Example 88

Methyl 4-methyl-1H-pyrrole-3-carboxylate

Using p-toluenesulfonylmethyl isocyanide (94.6 g), methyl crotonate (48.5 g) and potassium tert-butoxide (76.7 g), a procedure as in Reference Example 39 was performed to give the title compound as a pale-yellow solid (yield 16.8 g, 25%).

$^1$H-NMR (CDCl$_3$) δ: 2.29 (3H, s), 3.80 (3H, s), 6.53-6.54 (1H, m), 7.36-7.38 (1H, m), 8.25 (1H, brs).

Reference Example 89

Methyl 4-ethyl-1H-pyrrole-3-carboxylate

Using p-toluenesulfonylmethyl isocyanide (10.1 g), methyl 2-pentenoate (6.01 g) and potassium tert-butoxide (7.01 g), a procedure as in Reference Example 39 was performed to give the title compound as pale-yellow crystals (yield 5.05 g, 64%).

$^1$H-NMR (CDCl$_3$) δ: 1.21 (3H, t, J=7.5 Hz), 2.73-2.81 (2H, m), 3.80 (3H, s), 6.55-6.56 (1H, m), 7.37-7.39 (1H, m), 8.36 (1H, brs).

Reference Example 90

Methyl 4-propyl-1H-pyrrole-3-carboxylate

Using p-toluenesulfonylmethyl isocyanide (8.6 g), methyl (2E)-hex-2-enoate (5.67 g) and potassium tert-butoxide (5.9 g), a procedure as in Reference Example 39 was performed to give the title compound as colorless crystals (yield 2.8 g, 38%).

$^1$H-NMR (CDCl$_3$) δ: 0.96 (3H, t, J=7.5 Hz), 1.57-1.66 (2H, m), 2.68-2.73 (2H, m), 3.79 (3H, m), 6.53-6.55 (1H, m), 7.36-7.38 (1H, m), 8.40 (1H, br).

Reference Example 91

Methyl 4-isopropyl-1H-pyrrole-3-carboxylate

Using p-toluenesulfonylmethyl isocyanide (7.6 g), methyl (2E)-4-methylpent-2-enoate (5.0 g) and potassium tert-butoxide (5.25 g), a procedure as in Reference Example 39 was performed to give the title compound as a pale-yellow oil (yield 3.5 g, 54%).

$^1$H-NMR (CDCl$_3$) δ: 1.22 (6H, d, J=6.9 Hz), 3.35-3.45 (1H, m), 3.79 (3H, s), 6.55-6.57 (1H, m), 7.36-7.38 (1H, m), 8.30 (1H, br).

Reference Example 92

Methyl 4-phenyl-1H-pyrrole-3-carboxylate

Using p-toluenesulfonylmethyl isocyanide (10.1 g), methyl cinnamate (8.33 g) and potassium tert-butoxide (6.97 g), a procedure as in Reference Example 39 was performed to give the title compound as pale-yellow crystals (yield 5.40 g, 52%).

$^1$H-NMR (CDCl$_3$) δ: 3.74 (3H, s), 6.77-6.79 (1H, m), 7.25-7.38 (3H, m), 7.47-7.51 (3H, m), 8.54 (1H, brs).

Reference Example 93

1-[(1-Isocyanopentyl)sulfonyl]-4-methylbenzene

A mixture of p-toluenesulfonylmethyl isocyanide (9.75 g), tetrabutylammonium iodide (3.69 g), 1-butyl iodide (11.3 mL), dichloromethane (100 mL) and 30% aqueous sodium hydroxide solution (100 mL) was stirred at room temperature for 12 hr. The reaction product was diluted with water (200 mL), and extracted with dichloromethane. The extract was washed with saturated brine, dried over anhydrous magnesium sulfate, and concentrated under reduced pressure. The obtained gum-like residue was extracted 3 times with diethyl ether (100 mL). The extract was concentrated under reduced pressure to give the title compound as a colorless oil (yield 10.8 g, 86%).

$^1$H-NMR (CDCl$_3$) δ: 0.92-0.97 (3H, m), 1.40-1.60 (4H, m), 1.80-1.90 (1H, m), 2.10-2.25 (1H, m), 2.49 (3H, s), 4.41-4.48 (1H, m), 7.41-7.51 (2H, m), 7.85-7.89 (2H, m).

Reference Example 94

Ethyl 5-butyl-1H-pyrrole-3-carboxylate

A solution (120 mL) of 1-[(1-isocyanopentyl)sulfonyl]-4-methylbenzene (10.8 g) and ethyl acrylate (4.78 mL) in tetrahydrofuran was added dropwise to a solution (80 mL) of potassium tert-butoxide (5.79 g) in tetrahydrofuran while stirring at room temperature over 1 hr. The mixture was further stirred at the same temperature for 30 min, and the reaction product was diluted with water, and extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→8:2) to give the title compound as a yellow oil (yield 6.56 g, 78%).

$^1$H-NMR (CDCl$_3$) δ: 0.89-0.95 (3H, m), 1.24-1.45 (5H, m), 1.55-1.65 (2H, m), 2.55-2.60 (2H, m), 4.23-4.30 (2H, m), 6.33 (1H, s), 7.30 (1H, s), 8.11 (1H, br).

Reference Example 95

Ethyl 5-cyclohexyl-1H-pyrrole-3-carboxylate

Under an argon atmosphere, to a solution of ethyl 1H-pyrrole-3-carboxylate (2.09 g) and aluminum(III) chloride (4.0 g) in carbon disulfide (30 mL) was added bromocyclohexane (1.84 mL) under ice-cooling with stirring, and the mixture was stirred at room temperature for 30 min. The mixture was heated to 50° C., and stirred for 2 hr. The reaction product was cooled to room temperature, poured into ice water, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→8:2), and recrystallized from hexane to give the title compound as a colorless solid (yield 530 mg, 16%).

Reference Example 96

Ethyl 2-methyl-1H-pyrrole-3-carboxylate

Vinyl acetate (13.4 g) was added dropwise over 2 hr to bromine (25 g) with stirring under ice-cooling. The reaction mixture was further stirred at the same temperature for 1 hr. Ethyl 3-oxobutanoate (18.5 g) was added, and 25% aqueous ammonia solution (44 mL) was added dropwise over 1 hr. The reaction mixture was further stirred at room temperature for 30 min, water was added and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→3:1) and recrystallized from hexane to give the title compound as a colorless solid (yield 7.56 g, 35%).
$^1$H-NMR (CDCl$_3$) δ: 1.32-1.37 (3H, m), 2.53 (3H, s), 4.24-4.31 (2H, m), 6.55-6.58 (2H, m), 8.13 (1H, br).

Reference Example 97

Methyl 5-bromo-4-methyl-1H-pyrrole-3-carboxylate

By a similar operation as in Reference Example 40 and using methyl 4-methyl-1H-pyrrole-3-carboxylate (1.0 g) and N-bromosuccinimide (1.28 g), the title compound was obtained as a pale-yellow solid (yield 489 mg, 31%).
$^1$H-NMR (CDCl$_3$) δ: 2.23 (3H, s), 3.80 (3H, s), 7.37 (1H, d, J=3.0 Hz), 8.40 (1H, brs).

Reference Example 98

Methyl 5-bromo-4-ethyl-1H-pyrrole-3-carboxylate

Using methyl 4-ethyl-1H-pyrrole-3-carboxylate (2.32 g) and N-bromosuccinimide (2.74 g), a procedure as in Reference Example 40 was performed to give the title compound as white crystals (yield 2.96 g, 84%).
$^1$H-NMR (CDCl$_3$) δ: 1.13 (3H, t, J=4.5 Hz), 2.70 (2H, q, J=4.5 Hz), 3.81 (3H, s), 7.37 (1H, d, J=3.0 Hz), 8.30 (1H, brs).

Reference Example 99

Methyl 5-bromo-4-propyl-1H-pyrrole-3-carboxylate

Using methyl 4-propyl-1H-pyrrole-3-carboxylate (2.8 g), N-bromosuccinimide (3.0 g) and pyridine (0.5 mL), a procedure as in Reference Example 40 was performed to give the title compound as colorless crystals (yield 2.96 g, 72%).
$^1$H-NMR (CDCl$_3$) δ: 0.93 (3H, t, J=7.5 Hz), 1.50-1.60 (2H, m), 2.62-2.68 (2H, m), 3.80 (3H, s), 7.38 (1H, d, J=3.0 Hz), 8.41 (1H, br).

Reference Example 100

Methyl 5-bromo-4-isopropyl-1H-pyrrole-3-carboxylate

Using methyl 4-isopropyl-1H-pyrrole-3-carboxylate (3.5 g), N-bromosuccinimide (3.74 g) and pyridine (0.5 mL), a procedure as in Reference Example 40 was performed to give the title compound as colorless crystals (yield 3.29 g, 64%).
$^1$H-NMR (CDCl$_3$) δ: 1.32 (6H, d, J=7.2 Hz), 3.45-3.55 (1H, m), 3.79 (3H, s), 7.36 (1H, d, J=3.3 Hz), 8.27 (1H, br).

Reference Example 101

Methyl 5-bromo-4-phenyl-1H-pyrrole-3-carboxylate

Using methyl 4-phenyl-1H-pyrrole-3-carboxylate (2.01 g) and N-bromosuccinimide (1.85 g), a procedure as in Reference Example 40 was performed to give the title compound as white crystals (yield 1.97 g, 70%).
$^1$H-NMR (CDCl$_3$) δ: 3.69 (3H, s), 7.30-7.43 (5H, m), 7.48 (1H, d, J=3.0 Hz), 8.54 (1H, brs).

Reference Example 102

Ethyl 5-bromo-2-methyl-1H-pyrrole-3-carboxylate

To a solution of ethyl 2-methyl-1H-pyrrole-3-carboxylate (1.53 g) in tetrahydrofuran (20 mL) was added N-bromosuccinimide (1.78 g) at −78° C., and the mixture was stirred at the same temperature for 30 min. Water was added to the reaction mixture, and the mixture was extracted with diethyl ether. The extract was washed with saturated brine, dried over anhydrous magnesium sulfate, and concentrated under reduced pressure at not more than 5° C. The residue washed with hexane to give the title compound as a colorless solid (yield 2.26 g, 97%).
$^1$H-NMR (CDCl$_3$) δ: 1.30-1.35 (3H, m), 2.51 (3H, s), 4.22-4.29 (2H, m), 6.50 (1H, s), 8.01 (1H, br).

Reference Example 103

Methyl 5-bromo-1-(phenylsulfonyl)-4-propyl-1H-pyrrole-3-carboxylate

Using methyl 5-bromo-4-propyl-1H-pyrrole-3-carboxylate (2.96 g), sodium hydride (60% in oil, 634 mg) and benzenesulfonyl chloride (2.33 g), a procedure as in Reference Example 41 was performed to give the title compound as colorless crystals (yield 3.96 g, 85%).
$^1$H-NMR (CDCl$_3$) δ: 0.87 (3H, t, J=7.5 Hz), 1.43-1.60 (2H, m), 2.54-2.60 (2H, m), 3.83 (3H, s), 7.53-7.59 (2H, m), 7.65-7.71 (1H, m), 7.93-7.97 (2H, m), 8.11 (1H, s).

Reference Example 104

Methyl 5-bromo-4-phenyl-1-(phenylsulfonyl)-1H-pyrrole-3-carboxylate

Using sodium hydride (60% in oil, 281 mg), ethyl 5-bromo-4-phenyl-1H-pyrrole-3-carboxylate (1.70 g) and benzenesulfonyl chloride (0.9 mL), a procedure as in Reference Example 41 was performed to give the title compound as white crystals (yield 2.51 g, 93%).
$^1$H-NMR (CDCl$_3$) δ: 3.71 (3H, s), 7.23-7.26 (3H, m), 7.31-7.40 (3H, m), 7.57-7.62 (2H, m), 7.68-7.74 (1H, m), 8.01-8.05 (2H, m), 8.24 (1H, s).

Reference Example 105

Methyl 5-phenyl-4-propyl-1H-pyrrole-3-carboxylate

Using methyl 5-bromo-1-(phenylsulfonyl)-4-propyl-1H-pyrrole-3-carboxylate (3.96 g), phenylboronic acid (2.5 g), tetrakis(triphenylphosphine)palladium (1.79 g) and sodium carbonate (3.28 g), a procedure as in Reference Example 56 was performed to give the title compound as a pale-yellow oil (yield 2.0 g, 80%).

$^1$H-NMR (CDCl$_3$) δ: 0.95 (3H, t, J=7.5 Hz), 1.60-1.68 (2H, m), 2.76-2.81 (2H, m), 3.82 (3H, s), 7.31-7.46 (6H, m), 8.37 (1H, br).

Reference Example 106

Methyl 4,5-diphenyl-1H-pyrrole-3-carboxylate

Using methyl 5-bromo-4-phenyl-1-(phenylsulfonyl)-1H-pyrrole-3-carboxylate (1.01 g), phenylboronic acid (439 mg), sodium carbonate (771 mg) and tetrakis(triphenylphosphine)palladium (420 mg), a procedure as in Reference Example 56 was performed to give the title compound as pale-yellow crystals (yield 506 mg, 76%).

$^1$H-NMR (CDCl$_3$) δ: 3.69 (3H, s), 7.12-7.32 (10H, m), 7.55 (1H, d, J=3.3 Hz), 8.54 (1H, brs).

Reference Example 107

[5-(2-Fluorophenyl)-4-methyl-1H-pyrrol-3-yl]methanol

By a similar operation as in Reference Example 64 and using methyl 5-(2-fluorophenyl)-4-methyl-1H-pyrrole-3-carboxylate (1.63 g) and a 1.5 mol/L solution (15 mL) of diisobutylaluminum hydride in toluene, the title compound was obtained as white crystals (yield 1.18 g, 82%).

$^1$H-NMR (CDCl$_3$) δ: 1.30 (1H, t, J=4.8 Hz), 2.25 (3H, s), 4.61 (2H, d, J=4.8 Hz), 6.87 (1H, d, J=3.3 Hz), 7.10-7.28 (3H, m), 7.44-7.50 (1H, m), 8.40 (1H, brs).

Reference Example 108

[(5-Pyridin-2-yl)-1H-pyrrol-3-yl]methanol

A solution (30 mL) of ethyl 5-(pyridin-2-yl)-1H-pyrrole-3-carboxylate (1.62 g) in tetrahydrofuran was cooled to −50° C., and a 1.5 mol/L solution (15 mL) of diisobutylaluminum hydride in toluene was added dropwise by small portions. The mixture was further stirred at 0° C. for 1 hr, water (3 mL) was added to the reaction mixture and the mixture was stirred at room temperature for 1 hr. Celite and anhydrous magnesium sulfate were added and the mixture was further stirred for 15 min and filtrated. The obtained filtrate was concentrated under reduced pressure. The residue was purified by silica gel column chromatography (eluent: hexane-ethyl acetate=1:1→1:3) to give the title compound as colorless crystals (yield 1.15 g, 88%).

$^1$H-NMR (CDCl$_3$) δ: 4.61 (2H, s), 6.73-6.74 (1H, m), 6.88-6.89 (1H, m), 7.02-7.07 (1H, m), 7.50-7.54 (1H, m), 7.61-7.66 (1H, m), 8.43-8.45 (1H, m), 9.71 (1H, br).

Reference Example 109

5-(2-Fluorophenyl)-4-methyl-1H-pyrrole-3-carbaldehyde

Using [5-(2-fluorophenyl)-4-methyl-1H-pyrrol-3-yl]methanol (1.17 g), tetra-n-propylammonium perruthenate (101 mg), N-methylmorpholine N-oxide (1.01 g) and molecular sieves 4 A powder (572 mg), a procedure as in Reference Example 65 was performed to give the title compound as pale-pink crystals (yield 0.67 g, 58%).

$^1$H-NMR (CDCl$_3$) δ: 2.45 (3H, s), 7.14-7.36 (3H, m), 7.44-7.50 (2H, m), 8.82 (1H, brs), 9.92 (1H, s).

Reference Example 110

5-(Pyridin-2-yl)-1H-pyrrole-3-carbaldehyde

To a solution (50 mL) of [(5-pyridin-2-yl)-1H-pyrrol-3-yl]methanol (0.96 g) in acetonitrile were added tetra-n-propylammonium perruthenate (194 mg), N-methylmorpholine N-oxide (2.98 g) and molecular sieves 4 A powder (5 g), and the mixture was stirred at room temperature for 3 hr. The reaction mixture was diluted with ethyl acetate, filtered through celite, and the filtrate was concentrated under reduced pressure. The residue was purified by silica gel column chromatography (eluent: hexane-ethyl acetate=4:1→1:1) to give the title compound as colorless crystals (yield 270 mg, 29%).

$^1$H-NMR (CDCl$_3$) δ: 7.14-7.18 (2H, m), 7.52 (1H, br), 7.61-7.64 (1H, m), 7.69-7.74 (1H, m), 8.49-8.51 (1H, m), 9.85 (1H, s), 10.28 (1H, br).

Reference Example 111

5-(2-Fluorophenyl)-1H-pyrrole-3-carbaldehyde

A solution (220 mL) of ethyl 5-(2-fluorophenyl)-1H-pyrrole-3-carboxylate (11.6 g) in tetrahydrofuran was cooled to −78° C., and a 1.5 mol/L solution (100 mL) of diisobutylaluminum hydride in toluene was added dropwise over 10 min. The mixture was stirred at −78° C. for 1 hr and water (10 mL) was added dropwise over 2 min. The mixture was allowed to warm to room temperature and stirred for 2 hr. To the reaction mixture were added celite and anhydrous magnesium sulfate and the mixture was filtered. The filtrate was concentrated under reduced pressure to give a pale-yellow oil (yield 8.30 g). To a solution (220 mL) of the obtained pale-yellow oil (8.30 g) in acetonitrile were added tetra-n-propylammonium perruthenate (1.75 g), N-methylmorpholine N-oxide (13.5 g) and molecular sieves 4 A powder (5 g), and the mixture was stirred at room temperature for 1.5 hr. The reaction mixture was filtered through celite, and the filtrate was concentrated under reduced pressure. The residue was purified by silica gel column chromatography (eluent: hexane-ethyl acetate=7:3→1:1) to give the title compound as yellow crystals (yield 5.6 g, 60%).

$^1$H-NMR (CDCl$_3$) δ: 7.07-7.28 (4H, m), 7.52-7.54 (1H, m), 7.61-7.67 (1H, m), 9.49 (1H, brs), 9.86 (1H, s).

Reference Example 112

5-[2-(Trifluoromethyl)phenyl]-1H-pyrrole-3-carbaldehyde

A solution (28 mL) of ethyl 5-[2-(trifluoromethyl)phenyl]-1H-pyrrole-3-carboxylate (1.38 g) in tetrahydrofuran was cooled to −78° C., and a 1.5 mol/L solution (13 mL) of diisobutylaluminum hydride in toluene was added dropwise over 10 min. The mixture was further stirred at −78° C. for 1 hr, and water (3 mL) was added dropwise over 2 min. The mixture was allowed to warm to room temperature and further stirred for 1 hr. To the reaction mixture were added celite and anhydrous magnesium sulfate, and the mixture was filtered. The filtrate was concentrated under reduced pressure to give a pale-yellow oil (yield 1.14 g). The obtained oil (1.14 g) was dissolved in acetonitrile (50 mL), and tetra-n-propylammonium perruthenate (0.26 g), N-methylmorpholine N-oxide (1.32 g) and molecular sieves 4 A powder (5 g) were added to this solution. The mixture was stirred at room temperature for 1.5 hr. The reaction mixture was filtered through celite, and the filtrate was concentrated under reduced pressure. The residue was purified by silica gel column chromatography (eluent: hexane-ethyl acetate=4:1→1:1) to give the title compound as colorless crystals (yield 0.71 g, 61%).

$^1$H-NMR (CDCl$_3$) δ: 6.79-6.81 (1H, m), 7.46-7.78 (5H, m), 9.13 (1H, br), 9.82 (1H, s).

Reference Example 113

5-(2-Methylphenyl)-1H-pyrrole-3-carbaldehyde

Using ethyl 5-(2-methylphenyl)-1H-pyrrole-3-carboxylate (659 mg), a procedure as in Reference Example 111 was performed to give the title compound as yellow crystals (yield 309 mg, 55%)

$^1$H-NMR (CDCl$_3$) δ: 2.44 (3H, s), 6.75-6.76 (1H, m), 7.24-7.35 (4H, m), 7.49-7.51 (1H, m), 8.80 (H, brs), 9.84 (1H, s).

Reference Example 114

4-Amino-2-fluorobenzonitrile

To a solution of 2-fluoro-4-nitrobenzonitrile (2.51 g) in methanol (125 mL) was added 10% palladium carbon (50% containing water, 237 mg), and the mixture was stirred under a hydrogen atmosphere for 3 hr. The reaction mixture was filtrated, and the filtrate was concentrated under reduced pressure. The residue was purified by basic silica gel column chromatography (eluent: hexane-ethyl acetate=1:1) to give the title compound as a pale-yellow solid (yield 1.43 g, 70%).

$^1$H-NMR (CDCl$_3$) δ: 4.31 (2H, brs), 6.37-6.45 (2H, m), 7.31-7.36 (1H, m).

Reference Example 115

(4-Cyano-3-fluorobenzene)sulfonyl chloride

To a mixture of 4-amino-2-fluorobenzonitrile (433 mg) and concentrated hydrochloric acid (4 mL) was slowly added an aqueous solution (2 mL) of sodium nitrite (658 mg) at 0° C. and the mixture was stirred at the same temperature for 15 min. Concentrated hydrochloric acid (2 mL) and copper (II) sulfate (53.1 mg) were added to the reaction mixture, then a solution of sodium bisulfite (3.58 g) in water (6 mL) was added at 0° C., and the mixture was stirred at the same temperature for 30 min. Water (50 mL) was added to the reaction mixture, and the mixture was extracted with ethyl acetate. The extract was washed with water and saturated brine, dried over anhydrous magnesium sulfate, and filtrated. The filtrate was concentrated under reduced pressure to give the title compound as a white solid (yield 713 mg, about 100%).

$^1$H-NMR (CDCl$_3$) δ: 7.91-8.00 (3H, m).

Reference Example 116

(3-Chloro-4-cyanobenzene)sulfonyl chloride

Using 4-amino-2-fluorobenzonitrile (461 mg), sodium nitrite (626 mg), copper (II) sulfate (54.6 mg) and sodium bisulfite (3.41 g), a procedure as in Reference Example 115 was performed to give the title compound as a white solid (yield 679 mg, 95%).

$^1$H-NMR (CDCl$_3$) δ: 7.96 (1H, d, J=8.1 Hz), 8.06 (1H, dd, J=8.1, 2.1 Hz), 8.19 (1H, t, J=2.1 Hz).

Reference Example 117

1-Benzothiophene 1,1-dioxide

To a solution (120 mL) of 1-benzothiophene (11.2 g) in tetrahydrofuran was added m-chloroperbenzoic acid (70% containing, 43.1 g) at 0° C. and the mixture was stirred at the same temperature for 1 hr, further stirred at room temperature for 1 hr. An aqueous sodium thiosulfate solution (50 mL) was added to the reaction mixture, and the mixture was extracted with ethyl acetate. The extract was washed with 1 mol/L aqueous sodium hydroxide solution, saturated aqueous sodium hydrogencarbonate solution, water and saturated brine, dried over anhydrous magnesium sulfate, and concentrated under reduced pressure. The residue was recrystallized from ethyl acetate to give the title compound as a white solid (yield 10.3 g, 74%).

$^1$H-NMR (CDCl$_3$) δ: 6.72 (1H, d, J=7.0 Hz), 7.20-7.24 (1H, m), 7.34-7.38 (1H, m), 7.52-7.60 (2H, m), 7.70-7.74 (1H, m).

Reference Example 118

6-Nitro-1-benzothiophene 1,1-dioxide

Nitric acid (10 mL) was slowly added to sulfuric acid (10 mL) at 0° C., and the mixture was stirred at the same temperature for 10 min. To this solution was slowly added 1-benzothiophene 1,1-dioxide (3.99 g) at 0° C., and the mixture was further stirred at the same temperature for 30 min. The reaction mixture was poured into ice water, and the mixture was extracted with ethyl acetate. The extract was washed twice with water, saturated aqueous sodium hydrogencarbonate solution and saturated brine, dried over anhydrous magnesium sulfate, and concentrated under reduced pressure. The residue was recrystallized from ethyl acetate-hexane to give the title compound as a pale-yellow solid (yield 4.26 g, 84%).

$^1$H-NMR (CDCl$_3$) δ: 7.00 (1H, d, J=6.9 Hz), 7.33 (1H, dd, J=1.2, 6.9 Hz), 7.58 (1H, d, J=8.4 Hz), 8.47 (1H, dd, J=1.8, 8.4 Hz), 8.55-8.57 (1H, m).

Reference Example 119

2,3-Dihydro-1-benzothiophene-6-amine 1,1-dioxide

To a suspension of 6-nitro-1-benzothiophene 1,1-dioxide (2.02 g) in ethanol (200 mL) and methanol (60 mL) was added 10% palladium carbon (50% containing water, 265 mg), and the mixture was stirred under a hydrogen atmosphere for 12 hr. The reaction mixture was filtrated, and the filtrate was concentrated under reduced pressure. The residue was recrystallized from ethyl acetate to give the title compound as a white solid (yield 1.31 g, 75%).

$^1$H-NMR (CDCl$_3$) δ: 3.25 (2H, t, J=6.9 Hz), 3.44-3.49 (2H, m), 3.93 (2H, brs), 6.84-6.87 (1H, m), 6.94-6.95 (1H, m), 7.12 (1H, d, J=8.1 Hz).

Reference Example 120

6-(2,3-Dihydro-1-benzothiophene)sulfonyl chloride 1,1-dioxide

Using 2,3-dihydro-1-benzothiophene-6-amine 1,1-dioxide (1.06 g), sodium nitrite (1.21 g), copper (II) sulfate (96.9 mg) and sodium bisulfite (6.48 g), a procedure as in Reference Example 115 was performed to give the title compound as a white solid (yield 0.92 g, 60%).

$^1$H-NMR (CDCl$_3$) δ: 3.51-3.56 (2H, m), 3.60-3.65 (2H, m), 7.66-7.69 (1H, m), 8.22-8.26 (1H, m), 8.41-8.42 (1H, m).

Reference Example 121

1,3-Benzothiazol-6-ylsulfonyl chloride

Using 6-aminobenzothiazole (1.55 g), sodium nitrite (2.19 g), copper (II) sulfate (173 mg) and sodium bisulfite (10.2 g), a procedure as in Reference Example 115 was performed to give the title compound as a white solid (yield 0.30 g, 12%).

$^1$H-NMR (CDCl$_3$) δ: 8.17-8.21 (1H, m), 8.35-8.38 (1H, m), 8.73-8.74 (1H, m), 9.33 (1H, s).

Reference Example 122

Methyl 3-(chlorosulfonyl)benzoate

A solution (20 mL) of 3-(chlorosulfonyl)benzoyl chloride (2.4 g) in dichloromethane was cooled to 0° C., and pyridine (791 mg) and methanol (320 mg) were added. The reaction mixture was stirred at room temperature for 2 hr, and the solvent was evaporated under reduced pressure. The residue was filtrated, washed with a mixed solvent of ethyl acetate and isopropyl ether, and the filtrate was concentrated under reduced pressure. The residue was purified by silica gel column chromatography (eluent: hexane-ethylacetate=9:1→4:1) to give the title compound as a colorless oil (yield 2.17 g, 92%).

$^1$H-NMR (CDCl$_3$) δ: 3.99 (3H, s), 7.74 (1H, t, J=8.1 Hz), 8.21-8.24 (1H, m), 8.39-8.43 (1H, m), 8.69-8.70 (1H, m).

Reference Example 123

3-(Ethylthio)aniline

Sodium hydride (60% in oil, 2.3 g) was suspended in a mixed solvent of tetrahydrofuran (35 mL) and N,N-dimethylformamide (15 mL), and 3-aminobenzenethiol (5.0 g) was added dropwise at room temperature. The mixture was stirred at the same temperature for 5 min, iodoethane (6.86 g) was added, and the mixture was stirred for 30 min. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→4:1) to give the title compound as a yellow oil (yield 5.0 g, 82%).

$^1$H-NMR (CDCl$_3$) δ: 1.31 (3H, t, J=7.5 Hz), 2.92 (2H, q, J=7.5 Hz), 3.69 (2H, br), 6.47-6.51 (1H, m), 6.65-6.66 (1H, m), 6.70-6.73 (1H, m), 7.04-7.09 (1H, m).

Reference Example 124

3-(Ethylsulfonyl)aniline

To a solution (75 mL) of 3-(ethylthio)aniline (5.0 g) in methanol was added dropwise an aqueous solution (150 mL) of OXONE® (30 g) at 0° C. The mixture was stirred at room temperature for 2 hr, and methanol was evaporated under reduced pressure. The residue was basified with saturated aqueous sodium hydrogencarbonate solution, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→4:1) to give the title compound as a yellow oil (yield 4.6 g, 77%).

$^1$H-NMR (CDCl$_3$) δ: 1.28 (3H, t, J=7.5 Hz), 3.10 (2H, q, J=7.5 Hz), 3.95 (2H, br), 6.88-6.92 (1H, m), 7.16-7.18 (1H, m), 7.22-7.35 (2H, m).

Reference Example 125

3-(Ethylsulfonyl)benzenesulfonyl chloride

Using 3-(ethylsulfonyl)aniline (1.0 g), a procedure as in Reference Example 115 was performed to give the title compound as a colorless oil (yield 594 mg, 41%).

$^1$H-NMR (CDCl$_3$) δ: 1.35 (3H, t, J=7.5 Hz), 3.21 (2H, q, J=7.5 Hz), 7.87-7.92 (1H, m), 8.27-8.35 (2H, m), 8.57-8.58 (1H, m).

Reference Example 126

4-[(Trifluoromethyl)sulfonyl]benzenesulfonyl chloride

Under ice-cooling, thionyl chloride (2.7 mL) was added dropwise to water (16 mL) over 30 min. The mixture was stirred at room temperature for 12 hr to give a sulfur dioxide-containing solution. Under ice-cooling, {4-[(trifluoromethyl)sulfonyl]phenyl}amine (2.0 g) was added to concentrated hydrochloric acid (9 mL) and the mixture was stirred. An aqueous solution (3 mL) of sodium nitrite (0.67 g) was added dropwise while maintaining the inside temperature at not higher than 5° C. and the mixture was further stirred for 15 min. The mixture was gradually added at 5° C. to a mixture of the above-mentioned sulfur dioxide-containing solution added with cuprous chloride (10 mg). Under ice-cooling, the mixture was further stirred for 30 min. After stirring, the precipitated product was collected by filtration, washed with water, and dried in the presence of phosphorus pentoxide under reduced pressure at 50° C. to give the title compound (yield 2.3 g, 84%).

$^1$H-NMR (CDCl$_3$) δ: 8.35 (4H, s).

Reference Example 127

3-[(Trifluoromethyl)sulfonyl]benzenesulfonyl chloride

Under ice-cooling, thionyl chloride (4 mL) was added dropwise to water (24 mL) over 30 min. The mixture was stirred at room temperature for 12 hr to give a sulfur dioxide-containing solution. Under ice-cooling, {3-[(trifluoromethyl)sulfonyl]phenyl}amine (1.0 g) was added to concentrated hydrochloric acid (6 mL) and the mixture was stirred. An aqueous solution (2 mL) of sodium nitrite (0.34 g) was added dropwise while maintaining the inside temperature at not higher than 5° C. and the mixture was further stirred for 15 min. The mixture was gradually added at 5° C. to a mixture of the above-mentioned sulfur dioxide-containing solution added with cuprous chloride (10 mg). Under ice-cooling, the mixture was further stirred for 30 min, and extracted with ethyl acetate. The extract was dried over anhydrous magnesium sulfate, and concentrated under reduced pressure. The residue was purified by silica gel column chromatography (eluent: hexane-ethyl acetate=9:1→7:3) to give the title compound as a pale-yellow oil (yield 1.08 g, 79%).

$^1$H-NMR (CDCl$_3$) δ: 8.02 (1H, t, J=8.1 Hz), 8.40 (1H, d, J=7.8 Hz), 8.50 (1H, d, J=8.1 Hz), 8.69 (1H, s).

Reference Example 128

2-Hydroxy-5-pyrimidinesulfonic acid

Fuming sulfuric acid (containing 25% sulfur dioxide, 100 mL) was cooled to 0° C., and 2-aminopyrimidine (25 g) was gradually added over 1 hr. The mixture was heated to 180° C. and stirred for 40 hr. After cooling to room temperature, the mixture was poured into ice (1 kg). The precipitate was collected by filtration and recrystallized from water to give the title compound (yield 25.6 g, 55%).

$^1$H-NMR (DMSO-d$_6$) δ: 6.20-7.20 (2H, m), 8.71 (2H, s).

Reference Example 129

2-Chloro-5-pyrimidinesulfonyl chloride

A mixture of 2-hydroxy-5-pyrimidinesulfonic acid (12.8 g) and phosphorus pentachloride (37.8 g) was stirred under reflux at 180° C. for 4 hr. After cooling to room temperature, toluene (200 mL) was added, and the insoluble material was filtered off. The filtrate was washed with ice water, dried over anhydrous magnesium sulfate, and the solvent was evaporated under reduced pressure. The residue was stood in a freezer for one day to give the title compound as a pale-yellow solid (yield 14.8 g, 96%).

$^1$H-NMR (CDCl$_3$) δ: 9.19 (2H, s).

Reference Example 130

6-Chloropyridazine-3-thiol

To a suspension (88 mL) of sodium hydrogensulfide (3.78 g) in ethanol was added 3,6-dichloropyridazine (5.0 g), and the mixture was heated under refluxed for 1 hr. The solvent was evaporated under reduced pressure, and water (12.5 mL) was added. The mixture was adjusted to about pH 9 with 2 mol/L aqueous sodium hydroxide solution, and the precipitate was filtered off. The filtrate was adjusted to about pH 2 with 6 mol/L hydrochloric acid and the precipitate was collected by filtration to give the title compound as a yellow solid (yield 4.74 g, 96%).

$^1$H-NMR (CDCl$_3$) δ: 6.99 (1H, d, J=9.6 Hz), 7.60 (1H, d, J=9.6 Hz).

Reference Example 131

6-Chloropyridazine-3-sulfonyl fluoride

To a mixture cooled to −20° C. of methanol (10 mL) and water (10 mL) were added potassium hydrogenfluoride (16 g) and 6-chloropyridazine-3-thiol (2.37 g). After stirring at the same temperature for 20 min, chlorine was blown in for 30 min. Ice water (20 mL) was added and the precipitate was collected by filtration. Water was added to the precipitate and the mixture was extracted with ethyl acetate. The extract was washed with saturated brine, and dried over anhydrous magnesium sulfate. The solvent was evaporated under reduced pressure to allow crystallization, and the crystals were washed with hexane to give the title compound as a gray solid (yield 1.68 g, 53%).

$^1$H-NMR (CDCl$_3$) δ: 7.86-7.89 (1H, m), 8.17-8.19 (1H, m).

Reference Example 132

Pyridin-3-ylsulfonyl chloride hydrochloride

A mixture of 3-pyridinesulfonic acid (50.0 g), phosphorus pentachloride (80.0 g) and phosphorus oxychloride (100 mL) was stirred at 120° C. for 8 hr. Under a nitrogen atmosphere, the mixture was cooled to room temperature, and chloroform (dehydrated, 330 mL) was added. Hydrogen chloride was blown in, and the precipitated crystals were collected by filtration and washed with chloroform (dehydrated) to give the title compound as a white solid (yield 54.7 g, 81%).

$^1$H-NMR (DMSO-d$_6$) δ: 8.03-8.07 (1H, m), 8.68 (1H, d, J=8.1 Hz), 8.87 (1H, d, J=5.7 Hz), 9.01 (1H, s).

Reference Example 133

6-Methoxypyridin-3-ylsulfonyl chloride

5-Amino-2-methoxypyridine (1.24 g) was dissolved in acetic acid (8.3 mL), and the mixture was stirred under ice-cooling. Concentrated hydrochloric acid (8.3 mL) was added, and an aqueous solution (5 mL) of sodium nitrite (689 mg) was added dropwise over 15 min while keeping the inside temperature at not higher than 10° C. The reaction mixture was stirred for 10 min, and gradually added at 5° C. to a mixture of cuprous chloride (280 mg) and acetic acid (17 mL) saturated in advance with sulfur dioxide gas. The mixture was allowed to gradually warm to room temperature until the generation of gas stopped. The reaction mixture was concentrated to about 5 mL under reduced pressure, and the precipitate was collected by filtration to give the title compound (yield 1.0 g, 51%) as crude crystals. This compound was used for the next reaction without purification.

Reference Example 134

6-Chloropyridin-3-ylsulfonyl chloride

Under ice-cooling, thionyl chloride (12 mL) was added dropwise over 1 hr to water (70 mL) and the mixture was stirred at room temperature for 12 hr to give a sulfur dioxide-containing solution. Under ice-cooling, 5-amino-2-chloropyridine (5.0 g) was added to concentrated hydrochloric acid (40 mL) and the mixture was stirred. An aqueous solution (12.5 mL) of sodium nitrite (2.88 g) was added dropwise while keeping the inside temperature at not higher than 5° C., and the mixture was further stirred for 15 min. The reaction mixture was gradually added at 5° C. to the above-mentioned sulfur dioxide-containing solution added with cuprous chloride (70 mg). Under ice-cooling, the mixture was further stirred for 30 min. The precipitate was collected by filtration, and washed with water and ethanol to give the title compound (yield 4.79 g, 58%).

$^1$H-NMR (CDCl$_3$) δ: 7.60-7.63 (1H, m), 8.24-8.27 (1H, m), 9.03-9.04 (1H, m).

Reference Example 135

2-Chloro-3-pyridinesulfonyl chloride

Under ice-cooling, thionyl chloride (24 mL) was added dropwise over 1 hr to water (140 mL) and the mixture was stirred at room temperature for 12 hr to give a sulfur dioxide-containing solution. Under ice-cooling, 5-amino-2-chloropyridine (10 g) was added to concentrated hydrochloric acid (80 mL) and the mixture was stirred. An aqueous solution (25 mL) of sodium nitrite (5.75 g) was added dropwise while keeping the inside temperature at not higher than 5° C., and the mixture was further stirred for 15 min. The reaction mixture was gradually added at 5° C. to the above-mentioned sulfur dioxide-containing solution added with cuprous chloride (140 mg). Under ice-cooling, the mixture was further stirred for 30 min, and the precipitate was collected by filtration and washed with water and ethanol to give the title compound (yield 6.99 g, 42%).

$^1$H-NMR (CDCl$_3$) δ: 7.54-7.56 (1H, m), 8.46-8.48 (1H, m), 8.71-8.73 (1H, m).

Reference Example 136

6-Chloro-5-methylpyridine-3-amine

Reduced iron (793 mg) was added to an aqueous solution (25 mL) of ammonium chloride (1.27 g), and the mixture was stirred at room temperature for 5 min. A solution (10 mL) of 2-chloro-3-methyl-5-nitropyridine (816 mg) in methanol was added dropwise over 10 min. The reaction mixture was stirred at 40° C. for 20 min and at 50° C. for 1.5 hr and further refluxed under heating for 1 hr. The reaction mixture was filtered through celite, and celite was washed with methanol. Methanol was mostly removed by concentrated under reduced pressure, and saturated aqueous sodium hydrogencarbonate solution was added. The mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→7:3) to give the title compound as a solid (yield 280 mg, 42%).

$^1$H-NMR (CDCl$_3$) δ: 2.29 (3H, s), 3.62 (2H, br), 6.88-6.89 (1H, m), 7.70-7.71 (1H, m).

Reference Example 137

6-Chloro-5-methylpyridine-3-sulfonyl chloride

Under ice-cooling, thionyl chloride (0.6 mL) was added dropwise over 30 min to water (3.4 mL). The mixture was stirred at room temperature for 12 hr to give a sulfur dioxide-containing solution. Under ice-cooling, 6-chloro-5-methylpyridine-3-amine (278 mg) was added to concentrated hydrochloric acid (6 mL) and the mixture was stirred. An aqueous solution (2 mL) of sodium nitrite (148 mg) was added dropwise while keeping the inside temperature at not higher than 5° C., and the mixture was further stirred for 15 min. The reaction mixture was gradually added at 5° C. to the above-mentioned sulfur dioxide-containing solution added with cuprous chloride (5 mg). Under ice-cooling, the mixture was further stirred for 30 min, and the precipitate was collected by filtration and washed with water to give the title compound as a pale-yellow solid (yield 271 mg, 62%).

$^1$H-NMR (CDCl$_3$) δ: 2.54 (3H, s), 8.15 (1H, s), 8.86 (1H, s).

Reference Example 138

2-Pyridinesulfonyl chloride

Under ice-cooling, 2-mercaptopyridine (2.0 g) was added to sulfuric acid (50 mL). To the mixture was added dropwise an aqueous sodium hypochlorite solution (chlorine content 5%, 126 mL) over 1.5 hr, and the mixture was further stirred at the same temperature for 30 min. The reaction mixture was diluted with water (100 mL), and extracted with dichloromethane. The extract washed with saturated brine, dried over anhydrous magnesium sulfate, and concentrated under reduced pressure to give the title compound as a colorless oil (yield 2.45 g, 77%).

$^1$H-NMR (CDCl$_3$) δ: 7.69-7.71 (1H, m), 8.06-8.14 (2H, m), 8.83-8.85 (1H, m).

Reference Example 139

Ethyl 2-methyl-1-(phenylsulfonyl)-1H-pyrrole-3-carboxylate

By a similar operation as in Reference Example 41 and using ethyl 2-methyl-1H-pyrrole-3-carboxylate (8.81 g), sodium hydride (60% in oil, 2.58 g) and benzenesulfonyl chloride (7.8 mL), the title compound was obtained as white crystals (yield 14.3 g, 85%).

$^1$H-NMR (CDCl$_3$) δ: 1.31 (3H, t, J=7.2 Hz), 2.62 (3H, s), 4.24 (2H, q, J=7.2 Hz), 6.63 (1H, d, J=3.3 Hz), 7.30 (1H, d, J=3.3 Hz), 7.51-7.57 (2H, m), 7.62-7.68 (1H, m), 7.81-7.84 (2H, m).

Reference Example 140

Methyl 5-bromo-4-methyl-1-(phenylsulfonyl)-1H-pyrrole-3-carboxylate

Sodium hydride (60% in oil, 202 mg) was washed with hexane and suspended in N,N-dimethylformamide (10 mL). A solution (10 mL) of methyl 5-bromo-4-methyl-1H-pyrrole-3-carboxylate (1.0 g) in N,N-dimethylformamide was added dropwise at −78° C. After completion of the dropwise addition, the reaction mixture was stirred at room temperature for 30 min and added dropwise to an ice-cooled solution (10 mL) of benzenesulfonyl chloride (0.71% mL) in N,N-dimethylformamide. After completion of the dropwise addition, the reaction mixture was stirred at room temperature for 1 hr, and concentrated under reduced pressure. The residue was recrystallized from ethyl acetate-hexane to give the title compound as a brown solid (yield 1.13 g, 69%).

$^1$H-NMR (CDCl$_3$) δ: 2.11 (3H, s), 3.79 (3H, s), 7.45-7.70 (3H, m), 7.85-7.95 (2H, m), 8.06 (1H, s).

Reference Example 141

Methyl 5-bromo-1-[(3-chlorophenyl)sulfonyl]-4-methyl-1H-pyrrole-3-carboxylate

Sodium hydride (60% in oil, 202 mg) was washed with hexane, added to N,N-dimethylformamide solution (10 mL), and a solution (10 mL) of methyl 5-bromo-4-methyl-1H- pyrrole-3-carboxylate (1.0 g) in N,N-dimethylformamide was added dropwise at −78° C. After completion of the dropwise addition, the reaction mixture was stirred at room temperature for 30 min, and added dropwise to an ice-cooled solution (10 mL) of 3-chlorobenzenesulfonyl chloride (0.78 mL) in N,N-dimethylformamide. After completion of the dropwise addition, the reaction mixture was stirred at room temperature for 1 hr and concentrated under reduced pressure. The residue was recrystallized from ethyl acetate-hexane to give the title compound as a brown solid (yield 1.00 g, 56%).

$^1$H-NMR (CDCl$_3$) δ: 2.17 (3H, s), 3.84 (3H, s), 7.50 (1H, t, J=8.0 Hz), 7.60-7.70 (1H, m), 7.80-7.90 (1H, m), 7.94 (1H, m), 8.08 (1H, s).

Reference Example 142

Ethyl 5-bromo-4-methyl-1-[(3-methylphenyl)sulfonyl]-1H-pyrrole-3-carboxylate

Under an argon atmosphere, sodium hydride (60% in oil, 452 mg) was suspended in N,N-dimethylformamide (10 mL), and a solution (10 mL) of ethyl 5-bromo-4-methyl-1H-pyrrole-3-carboxylate (2.20 g) in N,N-dimethylformamide was added dropwise at −78° C. over 30 min. The mixture was stirred at room temperature for 30 min, and added dropwise to an ice-cooled solution (10 mL) of (3-methylbenzene)sulfonyl chloride (1.64 mL) in N,N-dimethylformamide over 10 min. The reaction mixture was stirred at room temperature for 1 hr, water was added, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=9:1→1:1), and recrystallized from diethyl ether to give the title compound as a colorless solid (yield 3.02 g, 83%).

$^1$H-NMR (CDCl$_3$) δ: 1.36 (3H, t, J=7.2 Hz), 2.16 (3H, s), 2.44 (3H, s), 4.29 (2H, dd, J=7.2 Hz, 14.4 Hz), 7.43-7.37 (2H, m), 7.57-7.78 (2H, m), 8.10 (1H, s).

Reference Example 143

Methyl 5-bromo-1-[(4-fluorophenyl)sulfonyl]-4-methyl-1H-pyrrole-3-carboxylate

Under an argon atmosphere, to a suspension of sodium hydride (60% in oil, 405 mg) in N,N-dimethylformamide (10 mL) was added dropwise a solution (10 mL) of methyl 5-bromo-4-methyl-1H-pyrrole-3-carboxylate (1.84 g) in N,N-dimethylformamide at −78° C. over 30 min. The mixture was stirred at room temperature for 30 min and added dropwise to an ice-cooled solution (10 mL) of (4-fluorobenzene)sulfonyl chloride (1.97 g) in N,N-dimethylformamide over 10 min. The reaction mixture was stirred at room temperature for 1 hr, water was added, and the mixture was extracted with ethyl acetate. The extract washed with water and saturated brine, dried over anhydrous magnesium sulfate, and concentrated under reduced pressure. The residue was purified by silica gel column chromatography (eluent: hexane-ethyl acetate=9:1→3:2), and the obtained solid was washed with hexane-diethyl ether (1:1) to give the title compound as a colorless solid (yield 2.21 g, 70%).

$^1$H-NMR (CDCl$_3$) δ: 2.16 (3H, s), 3.83 (3H, s), 7.20-7.26 (2H, m), 7.97-8.02 (2H, m), 8.08 (1H, s).

Reference Example 144

Methyl 5-bromo-4-ethyl-1-(phenylsulfonyl)-1H-pyrrole-3-carboxylate

Using sodium hydride (60% in oil, 393 mg), methyl 5-bromo-4-ethyl-1H-pyrrole-3-carboxylate (2.00 g) and benzenesulfonyl chloride (1.25 mL), a procedure as in Reference Example 41 was performed to give the title compound as white crystals (yield 2.93 g, 91%).

$^1$H-NMR (CDCl$_3$) δ: 1.05 (3H, t, J=7.5 Hz), 2.62 (2H, q, J=7.5 Hz), 3.83 (3H, s), 7.54-7.59 (2H, m), 7.65-7.71 (1H, m), 7.95-7.98 (1H, m), 8.11 (1H, s).

Reference Example 145

Methyl 5-bromo-4-isopropyl-1-(phenylsulfonyl)-1H-pyrrole-3-carboxylate

Using methyl 5-bromo-4-isopropyl-1H-pyrrole-3-carboxylate (3.29 g), sodium hydride (60% in oil, 708 mg), and benzenesulfonyl chloride (2.60 g), a procedure as in Reference Example 41 was performed to give the title compound as a pale-yellow oil (yield 4.8 g, 93%).

$^1$H-NMR (CDCl$_3$) δ: 1.25 (6H, d, J=7.2 Hz), 3.26-3.36 (1H, m), 3.82 (3H, s), 7.54-7.60 (2H, m), 7.66-7.72 (1H, m), 7.94-7.98 (2H, m), 8.13 (1H, s).

Reference Example 146

Methyl 5-bromo-1-(pyridin-3-ylsulfonyl)-1H-pyrrole-3-carboxylate

Sodium hydride (60% in oil, 1.60 g) was washed twice with hexane and suspended in tetrahydrofuran (20 mL). Under ice-cooling, a solution (10 mL) of methyl 5-bromo-1H-pyrrole-3-carboxylate (2.67 g) in tetrahydrofuran was added dropwise, and the mixture was stirred at the same temperature for 10 min. 15-Crown-5 (8.83 g) and pyridin-3-ylsulfonyl chloride hydrochloride (4.21 g) were added to the reaction mixture, and the mixture was further stirred at room temperature for 12 hr. Water was added to the reaction mixture, and the mixture was extracted with ethyl acetate. The extract was washed with saturated aqueous sodium hydrogencarbonate solution, water and saturated brine, dried over anhydrous magnesium sulfate, and concentrated under reduced pressure. The residue was recrystallized from ethyl acetate-hexane to give the title compound as white crystals (yield 4.21 g, 93%).

$^1$H-NMR (CDCl$_3$) δ: 3.84 (3H, s), 6.72 (1H, d, J=1.8 Hz), 7.51-7.56 (1H, m), 8.08 (1H, d, J=1.8 Hz), 8.22-8.26 (1H, m), 8.90-8.92 (1H, m), 9.20-9.21 (1H, m).

Reference Example 147

Methyl 5-bromo-1-{[3-(methylsulfonyl)phenyl]sulfonyl}-1H-pyrrole-3-carboxylate

Using methyl 5-bromo-1H-pyrrole-3-carboxylate (2.89 g), sodium hydride (60% in oil, 850 mg), 15-crown-5 (4.69 g) and 3-methylsulfonylbenzenesulfonyl chloride (4.38 g), a procedure as in Reference Example 146 was performed to give the title compound as white crystals (yield 5.50 g, 92%).

$^1$H-NMR (CDCl$_3$) δ: 3.11 (3H, s), 3.84 (3H, s), 6.72 (1H, d, J=2.1 Hz), 7.83 (1H, t, J=7.8 Hz), 8.07 (1H, d, J=2.1 Hz), 8.22-8.28 (2H, m), 8.59 (1H, t, J=1.8 Hz).

Reference Example 148

Ethyl 5-bromo-2-methyl-1-(pyridin-3-ylsulfonyl)-1H-pyrrole-3-carboxylate

Ethyl 5-bromo-2-methyl-1H-pyrrole-3-carboxylate (2.26 g) was dissolved in tetrahydrofuran (100 mL), sodium hydride (60% in oil, 1.16 g) was added and the mixture was stirred at room temperature for 15 min. 15-Crown-5 (5.90 mL) was added and the mixture was further stirred at the same temperature for 15 min, and 3-pyridinesulfonyl chloride hydrochloride (3.13 g) was added. The reaction mixture was stirred at room temperature for 1 hr, saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→7:3) to give the title compound as a yellow oil (yield 2.31 g, 64%).
$^1$H-NMR (CDCl$_3$) δ: 1.24-1.34 (3H, m), 2.94 (3H, s), 4.23-4.30 (2H, m), 6.69 (1H, s), 7.51-7.55 (1H, m), 8.17-8.21 (1H, m), 8.88-8.91 (1H, m), 9.14 (1H, m).

Reference Example 149

Ethyl 1-[(3-chlorophenyl)sulfonyl]-2-methyl-5-phenyl-1H-pyrrole-3-carboxylate Using ethyl 2-methyl-5-phenyl-1H-pyrrole-3-carboxylate (1.53 g), sodium hydride (60% in oil, 303 mg) and 3-chlorobenzenesulfonyl chloride (848 mg), a procedure as in Reference Example 41 was performed to give the title compound as a brown oil (yield 800 mg, 30%).
$^1$H-NMR (CDCl$_3$) δ: 1.32 (3H, t, J=7.2 Hz), 2.90 (3H, s), 4.29 (2H, q, J=7.2 Hz), 6.50 (1H, s), 7.13-7.56 (9H, m).

Reference Example 150

Ethyl 2-methyl-1-[(3-methylphenyl)sulfonyl]-5-phenyl-1H-pyrrole-3-carboxylate To a solution (10 mL) of ethyl 2-methyl-5-phenyl-1H-pyrrole-3-carboxylate (630 mg) in tetrahydrofuran was added sodium hydride (60% in oil, 73 mg) after washing with hexane, and the mixture was stirred at room temperature for 15 min. 3-Methylbenzenesulfonyl chloride (0.479 mL) was added to the reaction mixture, and the mixture was stirred at room temperature for 18 hr. Water was added to the reaction mixture, and the mixture was extracted with ethyl acetate. The extract was washed with saturated brine, dried over anhydrous sodium sulfate, and the solvent was evaporated under reduced pressure. The residue was purified by silica gel column chromatography (eluent: hexane-ethyl acetate=9:1→2:1) to give the title compound as a brown oil (yield 254 mg, 24%).
$^1$H-NMR (CDCl$_3$) δ: 1.20-1.40 (3H, m), 2.31 (3H, s), 2.89 (3H, s), 4.20-4.40 (2H, m), 6.47 (1H, s), 7.10-7.50 (9H, m).

Reference Example 151

Ethyl 5-phenyl-1-{[4-(trifluoromethoxy)phenyl]sulfonyl}-1H-pyrrole-3-carboxylate Sodium hydride (60% in oil, 0.20 g) was added to a solution (20 mL) of ethyl 5-phenyl-1H-pyrrole-3-carboxylate (0.71 g) in tetrahydrofuran under ice-cooling. After stirring at the same temperature for 15 min, [4-(trifluoromethoxy)benzene]sulfonyl chloride (1.00 g) was added, and the mixture was stirred at room temperature for 4 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:2) to give the title compound as an oil (yield 1.36 g, 94%).
$^1$H-NMR (CDCl$_3$) δ: 1.36 (3H, t, J=7.1 Hz), 4.32 (2H, q, J=7.1 Hz), 6.56 (1H, s), 7.13 (4H, dd, J=13.0 Hz), 7.28-7.42 (5H, m), 8.08 (1H, d, J=1.9 Hz).

Reference Example 152

Ethyl 5-phenyl-1-(2-thienylsulfonyl)-1H-pyrrole-3-carboxylate

To a solution (20 mL) of ethyl 5-phenyl-1H-pyrrole-3-carboxylate (440 mg) in tetrahydrofuran was added sodium hydride (60% in oil, 123 mg) at room temperature and the mixture was stirred for 30 min. 15-Crown-5 (675 mg) was added dropwise and the mixture was stirred for 30 min. 2-Thiophenesulfonyl chloride (485 mg) was added, and the mixture was further stirred for 1 hr. Saturated brine was added to the reaction mixture, and the mixture was extracted with ethyl acetate. The extract washed with saturated brine, dried over anhydrous magnesium sulfate, and concentrated under reduced pressure. The residue was purified by silica gel column chromatography (eluent: hexane-ethyl acetate=19:1→7:3), and crystallized from diisopropyl ether-hexane to give the title compound as colorless crystals (yield 710 mg, 96%).
$^1$H-NMR (CDCl$_3$) δ: 1.36 (3H, t, J=7.2 Hz), 4.31 (2H, q, J=7.2 Hz), 6.56 (1H, d, J=1.8 Hz), 6.89 (1H, dd, J=3.9, 4.9 Hz), 7.07 (1H, dd, J=1.3, 3.9 Hz), 7.24-7.43 (5H, m), 7.58 (1H, dd, J=1.3, 4.9 Hz), 8.04 (1H, d, J=1.8 Hz).

Reference Example 153

Ethyl 1-[(2-chloro-5-pyrimidine)sulfonyl]-5-phenyl-1H-pyrrole-3-carboxylate Ethyl 5-phenyl-1H-pyrrole-3-carboxylate (1.60 g) was dissolved in tetrahydrofuran (50 mL), sodium hydride (60% in oil, 446 mg) was added and the mixture was stirred at room temperature for 15 min. 15-Crown-5 (2.24 mL) was added and the mixture was further stirred at the same temperature for 15 min. 2-Chloro-5-pyrimidinesulfonyl chloride (2.06 g) was added and the reaction mixture was stirred at room temperature for 1 hr. Water was added, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=19:1→7:3) to give the title compound as a yellow oil (yield 2.03 g, 70%).
$^1$H-NMR (CDCl$_3$) δ: 1.35-1.39 (3H, m), 4.30-4.37 (2H, m), 6.64 (1H, s), 7.22-7.26 (2H, m), 7.37-7.51 (3H, m), 8.04 (1H, s), 8.37 (2H, s).

Reference Example 154

Ethyl 1-[(2-methyl-5-pyrimidine)sulfonyl]-5-phenyl-1H-pyrrole-3-carboxylate Under a nitrogen atmosphere, tetrakis(triphenylphosphine)palladium (87 mg) and 2 mol/L trimethylaluminum-hexane solution (1.5 mL) were added to a solution of ethyl 1-[(2-chloro-5-pyrimidine)sulfonyl]-5-phenyl-1H-pyrrole-3-carboxylate (588 mg) in tetrahydrofuran (20 mL) with stirring. The mixture was stirred at room temperature for 15 min and 2 mol/L trimethylaluminum-hexane solution (1 mL) was added. After stirring at the same temperature for 20 min, ice water (100 mL) and ammonium chloride (2.0 g) were added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→1:1) to give the title compound as a pale-yellow oil (yield 350 mg, 63%).

$^1$H-NMR (CDCl$_3$) δ: 1.34-1.39 (3H, m), 2.77 (3H, s), 4.29-4.36 (2H, m), 6.61 (1H, s), 7.21-7.26 (2H, m), 7.37-7.49 (3H, m), 8.06 (1H, s), 8.41 (2H, s).

Reference Example 155

Ethyl 1-[(2-amino-5-pyrimidine)sulfonyl]-5-phenyl-1H-pyrrole-3-carboxylate

A 7 mol/L ammonia-methanol solution (1.0 mL) was added to a solution of ethyl 1-[(2-chloro-5-pyrimidine)sulfonyl]-5-phenyl-1H-pyrrole-3-carboxylate (392 mg) in tetrahydrofuran (10 mL) with stirring. The mixture was stirred at room temperature for 20 min, saturated aqueous sodium hydrogencarbonate solution was added, and the mixture was extracted with ethyl acetate. The extract was washed with saturated brine, dried over anhydrous magnesium sulfate, and concentrated under reduced pressure to give the title compound as a colorless solid (yield 373 mg, about 100%).

$^1$H-NMR (CDCl$_3$) δ: 1.34-1.39 (3H, m), 4.28-4.36 (2H, m), 5.60 (2H, br), 6.59 (1H, s), 7.26-7.46 (5H, m), 8.02-8.03 (3H, m).

Reference Example 156

Ethyl 1-(imidazo[1,2-a]pyrimidin-6-ylsulfonyl)-5-phenyl-1H-pyrrole-3-carboxylate A mixture of ethyl 1-[(2-amino-5-pyrimidine)sulfonyl]-5-phenyl-1H-pyrrole-3-carboxylate (373 mg), 2-bromo-1,1-diethoxyethane (394 mg) and acetic acid (20 mL) was stirred in a microwave reaction apparatus at 130° C. for 30 min. After cooling to room temperature, the solvent was evaporated under reduced pressure. Saturated aqueous sodium hydrogencarbonate solution was added to the residue, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→ethyl acetate) to give the title compound as a brown solid (yield 157 mg, 40%).

$^1$H-NMR (CDCl$_3$) δ: 1.35-1.40 (3H, m), 4.30-4.37 (2H, m), 6.61 (1H, s), 7.17-7.49 (2H, m), 7.26-7.49 (4H, m), 7.94 (1H, s), 7.99 (1H, s), 8.11 (1H, s), 8.38 (1H, s).

Reference Example 157

Ethyl 1-(pyridazin-3-ylsulfonyl)-5-phenyl-1H-pyrrole-3-carboxylate

Ethyl 5-phenyl-1H-pyrrole-3-carboxylate (1.06 g) was dissolved in tetrahydrofuran (30 mL), sodium hydride (60% in oil, 300 mg) was added and the mixture was stirred at room temperature for 15 min. 15-Crown-5 (1.52 mL) was added and the mixture was further stirred at the same temperature for 15 min. 6-Chloropyridazine-3-sulfonyl fluoride (1.28 g) was added and the reaction mixture was stirred at room temperature for 30 min. Hydrazine (1.60 g) was added and the reaction mixture was stirred at room temperature for 15 min. Saturated aqueous sodium hydrogencarbonate solution was added, and the mixture was extracted with ethyl acetate. The extract was washed with water and saturated brine, dried over anhydrous magnesium sulfate, and concentrated under reduced pressure. The residue was dissolved in tetrahydrofuran (30 mL), manganese dioxide (75% chemically treated product, 5.0 g) was added, and the mixture was stirred at room temperature for 10 min. The reaction mixture was filtered through celite, and celite was washed with ethyl acetate. The filtrate was concentrated under reduced pressure, and the residue was purified by silica gel column chromatography (eluent: hexane-ethyl acetate=19:1→1:1) to give the title compound (yield 613 mg, 24%).

$^1$H-NMR (CDCl$_3$) δ: 1.34-1.39 (3H, m), 4.29-4.36 (2H, m), 6.61 (1H, s), 7.11-7.22 (2H, m), 7.24-7.51 (5H, m), 8.20 (1H, s), 9.28-9.30 (1H, s).

Reference Example 158

Ethyl 2,4-dimethyl-5-phenyl-1-(phenylsulfonyl)-1H-pyrrole-3-carboxylate

Using ethyl 2,4-dimethyl-5-phenyl-1H-pyrrole-3-carboxylate (3.0 g), sodium hydride (60% in oil, 596 mg) and benzenesulfonyl chloride (1.92 mL), a procedure as in Reference Example 4 was performed to give the title compound as a brown oil (yield 506 mg, 37%).

$^1$H-NMR (CDCl$_3$) δ: 1.35 (3H, t, J=7.2 Hz), 1.89 (3H, s), 2.85 (3H, s), 4.30 (2H, q, J=7.2 Hz), 7.07-7.46 (9H, m), 7.51-7.58 (1H, m).

Reference Example 159

Ethyl 2-methyl-1-(phenylsulfonyl)-5-(3-thienyl)-1H-pyrrole-3-carboxylate

Using ethyl 2-methyl-5-(3-thienyl)-1H-pyrrole-3-carboxylate (1.25 g), sodium hydride (60% in oil, 255 mg) and benzenesulfonyl chloride (1.22 mL), a procedure as in Reference Example 4 was performed to give the title compound as white crystals (yield 0.80 g, 40%).

$^1$H-NMR (CDCl$_3$) δ: 1.29-1.57 (3H, m), 2.87-2.90 (3H, m), 4.22-4.37 (2H, m), 6.50-6.95 (1H, m), 7.06-7.19 (1H, m), 7.24-7.29 (2H, m), 7.36-7.46 (4H, m), 7.52-7.58 (1H, m).

Reference Example 160

Ethyl 5-(4-fluorophenyl)-2-methyl-1-(phenylsulfonyl)-1H-pyrrole-3-carboxylate

Ethyl 5-(4-fluorophenyl)-2-methyl-1H-pyrrole-3-carboxylate (4.95 g) was dissolved in absolute tetrahydrofuran (50 mL), and sodium hydride (60% in oil, 1.20 g) was added under ice-cooling. The mixture was stirred at room temperature for 15 min, and benzenesulfonyl chloride (5.30 g) was added dropwise. The reaction mixture was stirred at room temperature for 18 hr, ice water was added and the mixture was extracted with ethyl acetate. The extract was washed with water, dried over anhydrous magnesium sulfate, and the solvent was evaporated under reduced pressure. The residue was purified by silica gel column chromatography (eluent: hexane-ethyl acetate=7:2) to give the title compound as a solid (yield 2.75 g, 35%).

$^1$H-NMR (CDCl$_3$) δ: 1.34 (3H, t, J=7.1 Hz), 2.88 (3H, s), 4.26 (2H, q, J=7.1 Hz), 6.46 (1H, s), 6.96-7.27 (3H, m), 7.33-7.47 (5H, m), 7.51-7.66 (1H, m).

Reference Example 161

Methyl 5-phenyl-1-(phenylsulfonyl)-4-propyl-1H-pyrrole-3-carboxylate

Using methyl 5-phenyl-4-propyl-1H-pyrrole-3-carboxylate (2.0 g), sodium hydride (60% in oil, 434 mg) and benzenesulfonyl chloride (1.60 g), a procedure as in Reference Example 4 was performed to give the title compound as colorless crystals (yield 2.73 g, 69%).

$^1$H-NMR (CDCl$_3$) δ: 0.72 (3H, t, J=7.5 Hz), 1.32-1.41 (2H, m), 2.31-2.36 (2H, m), 3.85 (3H, s), 6.94-6.97 (2H, m), 7.24-7.40 (7H, m), 7.51-7.56 (1H, m), 8.09 (1H, s).

Reference Example 162

Methyl 4,5-diphenyl-1-(phenylsulfonyl)-1H-pyrrole-3-carboxylate

Using methyl 4,5-diphenyl-1H-pyrrole-3-carboxylate (428 mg), sodium hydride (60% in oil, 74 mg) and benzenesulfonyl chloride (0.24 mL), a procedure as in Reference Example 4 was performed to give the title compound as white crystals (yield 506 mg, 79%).

$^1$H-NMR (CDCl$_3$) δ: 3.74 (3H, s), 6.87-6.92 (2H, m), 7.00-7.15 (7H, m), 7.20-7.36 (5H, m), 7.49-7.58 (1H, m), 8.21 (1H, s).

Reference Example 163

Ethyl 4-chloro-2-methyl-5-phenyl-1-(phenylsulfonyl)-1H-pyrrole-3-carboxylate

Using ethyl 4-chloro-2-methyl-5-phenyl-1H-pyrrole-3-carboxylate (509 mg), sodium hydride (60% in oil, 139 mg) and benzenesulfonyl chloride (511 mg), a procedure as in Reference Example 4 was performed to give the title compound as a pale-yellow oil (yield 610 mg, 78%).

$^1$H-NMR (CDCl$_3$) δ: 1.36 (3H, t, J=7.2 Hz), 2.85 (3H, s), 4.34 (2H, q, J=7.2 Hz), 7.15-7.19 (2H, m), 7.32-7.45 (7H, m), 7.56-7.61 (1H, m).

Reference Example 164

Ethyl 2-chloro-5-phenyl-1-(phenylsulfonyl)-1H-pyrrole-3-carboxylate

To a solution (40 mL) of ethyl 2-chloro-5-phenyl-1H-pyrrole-3-carboxylate (1.0 g) in tetrahydrofuran was added sodium hydride (60% in oil, 488 mg) at room temperature and the mixture was stirred for 30 min. 15-Crown-5 (2.65 g) was added dropwise and the mixture was stirred for 30 min. Benzenesulfonyl chloride (1.84 g) was added, and the mixture was further stirred for 24 hr. Saturated brine was added to the reaction mixture, and the mixture was extracted with ethyl acetate. The extract washed with saturated brine, dried over anhydrous magnesium sulfate, and concentrated under reduced pressure. The residue was purified by silica gel column chromatography (eluent: hexane-ethyl acetate=85:15), and crystallized from diisopropyl ether to give the title compound as colorless crystals (yield 1.27 g, 81%).

$^1$H-NMR (CDCl$_3$) δ: 1.31 (3H, t, J=7.2 Hz), 4.27 (2H, q, J=7.2 Hz), 6.55 (1H, s), 7.38-7.50 (7H, m), 7.60-7.71 (3H, m).

Reference Example 165

Ethyl 2-fluoro-5-phenyl-1-(phenylsulfonyl)-1H-pyrrole-3-carboxylate

To a solution (20 mL) of ethyl 2-fluoro-5-phenyl-1H-pyrrole-3-carboxylate (300 mg) in tetrahydrofuran was added sodium hydride (60% in oil, 155 mg) at room temperature and the mixture was stirred for 30 min. 15-Crown-5 (850 mg) was added dropwise and the mixture was stirred for 30 min. Benzenesulfonyl chloride (591 mg) was added, and the mixture was further stirred for 24 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=85:15) to give the title compound as a colorless oil (yield 390 mg, 81%).

$^1$H-NMR (CDCl$_3$) δ: 1.32 (3H, t, J=7.2 Hz), 4.28 (2H, q, J=7.2 Hz), 6.31 (1H, d, J=5.1 Hz), 7.30-7.51 (7H, m), 7.61-7.67 (3H, m).

Reference Example 166

Ethyl 2-chloro-4-fluoro-5-phenyl-1-(phenylsulfonyl)-1H-pyrrole-3-carboxylate

To a solution (60 mL) of ethyl 2-chloro-4-fluoro-5-phenyl-1H-pyrrole-3-carboxylate (330 mg) in tetrahydrofuran was added sodium hydride (60% in oil, 296 mg) at room temperature and the mixture was stirred for 30 min. 15-Crown-5 (1.63 g) was added dropwise and the mixture was stirred for 30 min. Benzenesulfonyl chloride (1.13 g) was added, and the mixture was further stirred for 120 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=9:1→8:2) to give the title compound as a pale-yellow oil (yield 260 mg, 52%).

$^1$H-NMR (CDCl$_3$) δ: 1.30-1.38 (3H, m), 4.27-4.38 (2H, m), 7.31-7.54 (7H, m), 7.63-7.73 (3H, m).

Reference Example 167

Ethyl 4-fluoro-5-phenyl-1-(phenylsulfonyl)-1H-pyrrole-3-carboxylate

To a solution (10 mL) of ethyl 4-fluoro-5-phenyl-1H-pyrrole-3-carboxylate (100 mg) in tetrahydrofuran was added sodium hydride (60% in oil, 52 mg) at room temperature and the mixture was stirred for 30 min. 15-Crown-5 (284 mg) was added dropwise and the mixture was stirred for 30 min. Benzenesulfonyl chloride (151 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=9:1) to give the title compound as a colorless oil (yield 60 mg, 38%).

$^1$H-NMR (CDCl$_3$) δ: 1.37 (3H, t, J=7.2 Hz), 4.44 (2H, q, J=7.2 Hz), 7.14-7.16 (2H, m), 7.28-7.59 (8H, m), 7.94 (1H, d, J=5.1 Hz).

Reference Example 168

Ethyl 5-butyl-1-(phenylsulfonyl)-1H-pyrrole-3-carboxylate

Under an argon atmosphere, ethyl 5-butyl-1H-pyrrole-3-carboxylate (976 mg) was dissolved in tetrahydrofuran (50 mL), sodium hydride (60% in oil, 240 mg) was added and the mixture was stirred at room temperature for 30 min. Benzenesulfonyl chloride (0.77 mL) was added, and the mixture was stirred at room temperature for 1 hr. Water was added to the reaction mixture, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=19:1→8:2), and the obtained solid was washed with hexane to give the title compound as a colorless solid (yield 780 mg, 47%).

$^1$H-NMR (CDCl$_3$) δ: 0.84-0.89 (3H, m), 1.26-1.37 (5H, m), 1.47-1.55 (2H, m), 2.59-2.64 (2H, m), 4.25-4.32 (2H, m), 6.37 (1H, m), 7.52-7.66 (3H, m), 7.79-7.82 (2H, m), 7.92 (1H, s).

Reference Example 169

Ethyl 5-cyclohexyl-1-(phenylsulfonyl)-1H-pyrrole-3-carboxylate

Using ethyl 5-cyclohexyl-1H-pyrrole-3-carboxylate (530 mg), a procedure as in Reference Example 168 was performed to give the title compound as a colorless oil (yield 651 mg, 75%).

$^1$H-NMR (CDCl$_3$) δ: 1.15-1.76 (13H, m), 2.83 (1H, m), 4.25-4.32 (2H, m), 6.40 (1H, s), 7.52-7.56 (2H, m), 7.60-7.66 (1H, m), 7.77-7.81 (2H, m), 7.88 (1H, s).

Reference Example 170

Methyl 4-methyl-5-phenyl-1-(phenylsulfonyl)-1H-pyrrole-3-carboxylate

Methyl 5-bromo-4-methyl-1-(phenylsulfonyl)-1H-pyrrole-3-carboxylate (1.1 g), phenylboronic acid (487 mg), sodium carbonate (488 mg) and tetrakis(triphenylphosphine)palladium (355 mg) were suspended in a mixture of 1,2-dimethoxyethane (10 mL) and distilled water (10 mL), and the mixture was reacted in a microwave reactor (Emrys Optimizer, Personal Chemistry, 140° C., 4 min). The reaction mixture was filtered through celite, water was added to the filtrate and the mixture was extracted with ethylacetate. The extract was washed with saturated brine, dried over anhydrous sodium sulfate, and concentrated under reduced pressure. The residue was purified by silica gel column chromatography (eluent: hexane-ethyl acetate=9:1→2:1) to give the title compound as a pale-yellow oil (yield 947 mg, 87%).

$^1$H-NMR (CDCl$_3$) δ: 1.98 (3H, s), 3.85 (3H, s), 6.98 (2H, d, J=8.4 Hz), 7.20-7.60 (8H, m), 8.08 (1H, s).

Reference Example 171

Methyl 1-[(3-chlorophenyl)sulfonyl]-4-methyl-5-phenyl-1H-pyrrole-3-carboxylate

Methyl 5-bromo-1-[(3-chlorophenyl)sulfonyl]-4-methyl-1H-pyrrole-3-carboxylate (1.0 g), phenylboronic acid (403 mg), sodium carbonate (405 mg) and tetrakis(triphenylphosphine)palladium (295 mg) were suspended in a mixture of 1,2-dimethoxyethane (10 mL) and distilled water (10 mL), and the mixture was reacted in a microwave reactor (Emrys Optimizer, Personal Chemistry, 140° C., 4 min). The reaction mixture was filtered through celite, water was added to the filtrate, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→2:1) to give the title compound as a pale-brown oil (yield 724 mg, 73%).

$^1$H-NMR (CDCl$_3$) δ: 1.99 (3H, s), 3.86 (3H, s), 7.00 (2H, d, J=8.0 Hz), 7.15-7.60 (7H, m), 8.05 (1H, s).

Reference Example 172

Ethyl 4-methyl-1-[(3-methylphenyl)sulfonyl]-5-phenyl-1H-pyrrole-3-carboxylate

Under an argon atmosphere, a suspension of ethyl 5-bromo-4-methyl-1-[(3-methylphenyl)sulfonyl]-1H-pyrrole-3-carboxylate (2.80 g), phenylboronic acid (1.84 g), tetrakis(triphenylphosphine)palladium (0.84 g), sodium carbonate (2.31 g) in 1,2-dimethoxyethane (12 mL)-water (12 mL) was stirred at 70° C. for 12 hr. After cooling, the reaction mixture was filtered through celite, and celite was washed with ethyl acetate. The organic layer was separated from the filtrate, washed with water and saturated brine, dried over anhydrous magnesium sulfate, and concentrated under reduced pressure. The residue was purified by silica gel column chromatography (eluent: hexane-ethyl acetate=9:1→7:3) to give the title compound as a colorless oil (yield 2.67 g, 96%).

$^1$H-NMR (CDCl$_3$) δ: 1.38 (3H, t, J=7.0 Hz), 1.98 (3H, s), 2.25 (3H, s), 4.31 (2H, dd, J=7.0, 14.0 Hz), 6.99-7.39 (9H, m), 8.07 (1H, s).

Reference Example 173

Methyl 1-[(4-fluorophenyl)sulfonyl]-4-methyl-5-phenyl-1H-pyrrole-3-carboxylate

Under an argon atmosphere, a suspension of methyl 5-bromo-1-[(4-fluorophenyl)sulfonyl]-4-methyl-1H-pyrrole-3-carboxylate (2.10 g), phenylboronic acid (1.42 g), tetrakis(triphenylphosphine)palladium (0.65 g), sodium carbonate (1.77 g) in 1,2-dimethoxyethane (11 mL)-water (11 mL) was stirred at 70° C. for 12 hr. After cooling, the reaction mixture was filtered through celite, and celite was washed with ethyl acetate. The organic layer was separated from the filtrate, washed with water and saturated brine, dried over anhydrous magnesium sulfate, and concentrated under reduced pressure. The residue was purified by silica gel column chromatography (eluent: hexane-ethyl acetate=19:1→7:3) to give the title compound as a colorless oil (yield 1.75 g, 84%).

$^1$H-NMR (CDCl$_3$) δ: 1.99 (3H, s), 3.85 (3H, s), 6.95-7.42 (9H, m), 8.06 (1H, s).

Reference Example 174

Ethyl 2-methyl-5-phenyl-1-(pyridin-3-ylsulfonyl)-1H-pyrrole-3-carboxylate

A suspension of ethyl 5-bromo-2-methyl-1-(pyridin-3-ylsulfonyl)-1H-pyrrole-3-carboxylate (2.26 g), phenylboronic acid (1.54 g), dichloro[bis(triphenylphosphine)]palladium (211 mg) and sodium carbonate (1.91 g) in 1,2-dimethoxyethane (20 mL)-water (10 mL) was stirred at 80° C. for 40 min. After cooling, the reaction mixture was filtered through celite, and celite was washed with ethyl acetate. The organic layer was separated from the filtrate, washed with water and saturated brine, dried over anhydrous magnesium sulfate, and concentrated under reduced pressure. The residue was purified by silica gel column chromatography (eluent: hexane-ethyl acetate=9:1→6:4) to give the title compound as a colorless oil (yield 2.39 g, about 100%).

$^1$H-NMR (CDCl$_3$) δ: 1.30-1.34 (3H, m), 2.92 (3H, s), 4.23-4.30 (2H, m), 6.59 (1H, s), 7.23-7.39 (4H, m), 7.50-7.68 (2H, m), 8.22-8.25 (1H, m), 8.61-8.62 (1H, m), 8.75-8.77 (1H, m).

Reference Example 175

Methyl 5-cyclopropyl-1-(phenylsulfonyl)-1H-pyrrole-3-carboxylate

Under an argon atmosphere, a suspension of methyl 5-bromo-1-(phenylsulfonyl)-1H-pyrrole-3-carboxylate (2.11 g), cyclopropylboronic acid (683 mg), palladium(II) acetate (69 mg), tricyclohexylphosphine (174 mg) and tripotassium phosphate (4.55 g) in toluene (27 mL)-water (1.3 mL) was stirred at 100° C. for 4 hr. After cooling, the reaction mixture was diluted with water (50 mL), and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→8:2) to give the title compound as a yellow oil (yield 406 mg, 22%).

$^1$H-NMR (CDCl$_3$) δ: 0.30-0.36 (2H, m), 0.71-0.77 (2H, m), 2.00-2.08 (1H, m), 3.79 (3H, s), 6.19 (1H, s), 7.51-7.56 (2H, m), 7.63-7.66 (1H, m), 7.85-7.88 (2H, m), 7.94 (1H, s).

Reference Example 176

[2-methyl-1-(phenylsulfonyl)-1H-pyrrol-3-yl]methanol

Using ethyl 2-methyl-1-(phenylsulfonyl)-1H-pyrrole-3-carboxylate (8.05 g) and a 1.5 mol/L solution (55 mL) of diisobutylaluminum hydride in toluene, a procedure as in Reference Example 5 was performed to give the title compound as white crystals (yield 6.61 g, 96%).

$^1$H-NMR (CDCl$_3$) δ: 1.37 (1H, brs), 2.29 (3H, s), 4.42 (2H, brs), 6.29 (1H, d, J=3.6 Hz), 7.30 (1H, d, J=3.6 Hz), 7.49-7.55 (2H, m), 7.58-7.64 (1H, m), 7.78-7.81 (2H, m).

Reference Example 177

(5-Bromo-1-{[3-(methylsulfonyl)phenyl]sulfonyl}-1H-pyrrol-3-yl)methanol

Using methyl 5-bromo-1-{3-(methylsulfonyl)phenyl]sulfonyl}-1H-pyrrole-3-carboxylate (5.41 g) and a 1.5 mol/L solution (26 mL) of diisobutylaluminum hydride in toluene, a procedure as in Reference Example 5 was performed to give the title compound as white crystals (yield 4.83 g, 96%).

$^1$H-NMR (CDCl$_3$) δ: 1.66 (1H, t, J=8.1 Hz), 3.11 (3H, s), 4.52 (2H, d, J=8.1 Hz), 6.38 (1H, d, J=2.1 Hz), 7.33-7.45 (1H, m), 7.79 (1H, t, J=8.1 Hz), 8.20-8.24 (2H, m), 8.53 (1H, t, J=1.8 Hz).

Reference Example 178

[5-Bromo-4-ethyl-1-(phenylsulfonyl)-1H-pyrrol-3-yl]methanol

Using methyl 5-bromo-4-ethyl-1-(phenylsulfonyl)-1H-pyrrole-3-carboxylate (1.35 g) and a 1.5 mol/L solution (7.5 mL) of diisobutylaluminum hydride in toluene, a procedure as in Reference Example 5 was performed to give the title compound as a brown oil (yield 1.10 g, 88%).

$^1$H-NMR (CDCl$_3$) δ: 1.05 (3H, t, J=7.6 Hz), 2.39 (2H, q, J=7.6 Hz), 4.53 (2H, s), 7.47-7.64 (4H, m), 7.90-7.95 (2H, m), 1H not detected.

Reference Example 179

{1-[(3-Chlorophenyl)sulfonyl]-2-methyl-5-phenyl-1H-pyrrol-3-yl}methanol

Using ethyl 1-[(3-chlorophenyl)sulfonyl]-2-methyl-5-phenyl-1H-pyrrole-3-carboxylate (0.80 g) and a 1.5 mol/L solution (4.0 mL) of diisobutylaluminum hydride in toluene, a procedure as in Reference Example 5 was performed to give the title compound as a brown oil (yield 345 mg, 48%).

$^1$H-NMR (CDCl$_3$) δ: 1.36 (1H, t, J=5.4 Hz), 2.53 (3H, s), 4.49 (2H, d, J=5.4 Hz), 6.20 (1H, s), 7.26-7.38 (8H, m), 7.47-7.51 (1H, m).

Reference Example 180

(5-Phenyl-1-{[4-(trifluoromethoxy)phenyl]sulfonyl}-1H-pyrrol-3-yl)methanol

A solution (30 mL) of ethyl 5-phenyl-1-{[4-(trifluoromethoxy)phenyl]sulfonyl}-1H-pyrrole-3-carboxylate (1.33 g) in tetrahydrofuran was cooled to −78° C., a 1.5 mol/L solution (8.0 mL) of diisobutylaluminum hydride in toluene was added dropwise, and the mixture was further stirred at −78° C. for 3 hr. 1 mol/L hydrochloric acid (20 mL) was added to the reaction mixture, and the mixture was diluted with ethyl acetate. Insoluble material was filtered through celite, and the filtrate was extracted with ethyl acetate. The extract was washed with saturated brine, dried over anhydrous magnesium sulfate, and concentrated under reduced pressure. The residue was purified by silica gel column chromatography (eluent: hexane-ethyl acetate=3:2) to give the title compound as an oil (yield 0.71 g, 59%).

$^1$H-NMR (CDCl$_3$) δ: 1.56 (1H, s), 4.58 (2H, s), 6.22 (1H, s), 7.11 (2H, dd, J=0.85, 8.95 Hz), 7.17-7.22 (2H, m), 7.27-7.39 (5H, m), 7.42-7.43 (1H, m).

Reference Example 181

[5-Phenyl-1-(2-thienylsulfonyl)-1H-pyrrol-3-yl]methanol

A solution (20 mL) of ethyl 5-phenyl-1-(2-thienylsulfonyl)-1H-pyrrole-3-carboxylate (650 mg) in tetrahydrofuran was cooled to −70° C., and a 1.5 mol/L solution (5 mL) of diisobutylaluminum hydride in toluene was added dropwise by small portions. The mixture was further stirred at −70° C. for 1 hr, 1 mol/L hydrochloric acid (20 mL) was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as a pale-red oil (yield 480 mg, 84%).

$^1$H-NMR (CDCl$_3$) δ: 4.57 (2H, d, J=5.6 Hz), 6.23 (1H, d, J=1.8 Hz), 6.89 (1H, dd, J=3.9, 4.9 Hz), 7.09 (1H, dd, J=1.4, 3.9 Hz), 7.28-7.41 (6H, m), 7.53 (1H, dd, J=1.4, 4.9 Hz).

Reference Example 182

[2-Methyl-1-(phenylsulfonyl)-5-(3-thienyl)-1H-pyrrol-3-yl]methanol

Using methyl 2-methyl-1-(phenylsulfonyl)-5-(3-thienyl)-1H-pyrrole-3-carboxylate (0.75 g) and a 1.5 mol/L solution (4.0 mL) of diisobutylaluminum hydride in toluene, a procedure as in Reference Example 5 was performed to give the title compound as a brown oil (yield 0.42 g, 63%).

$^1$H-NMR (CDCl$_3$) δ: 1.35 (3H, t, J=5.4 Hz), 2.53 (3H, s), 4.48 (2H, d, J=5.4 Hz), 6.19 (1H, s), 7.06-7.10 (2H, m), 7.22-7.26 (1H, m), 7.35-7.44 (4H, m), 7.49-7.54 (1H, m).

Reference Example 183

[5-(4-Fluorophenyl)-2-methyl-1-(phenylsulfonyl)-1H-pyrrol-3-yl]methanol

Ethyl 5-(4-fluorophenyl)-2-methyl-1-(phenylsulfonyl)-1H-pyrrole-3-carboxylate (2.70 g) was dissolved in tetrahydrofuran (30 mL), and the mixture was cooled to −78° C. A 1.5 mol/L toluene solution (13.1 mL) of diisobutylaluminum hydride was added dropwise, and the mixture was further stirred at −78° C. for 2 hr. 1 mol/L Hydrochloric acid (15 mL) was added to the reaction mixture, and the mixture was diluted with ethyl acetate. The insoluble material was filtered through celite, and the filtrate was extracted with ethyl acetate. The extract was washed with saturated brine, dried over anhydrous magnesium sulfate, and concentrated under reduced pressure. The residue was purified by silica gel column chromatography (eluent: hexane-ethyl acetate=2:3) to give the title compound as an oil (yield 1.09 g, 45%).

$^1$H-NMR (CDCl$_3$) δ: 2.51 (3H, s), 4.47 (2H, s), 6.15 (1H, s), 7.00 (2H, t, J=8.7 Hz), 7.14-7.27 (2H, m), 7.35-7.43 (4H, m), 7.48-7.61 (1H, m).

Reference Example 184

[2,4-Dimethyl-5-phenyl-1-(phenylsulfonyl)-1H-pyrrol-3-yl]methanol

Using ethyl 2,4-dimethyl-5-phenyl-1-(phenylsulfonyl)-1H-pyrrole-3-carboxylate (1.01 g) and a 1.5 mol/L solution (6.0 mL) of diisobutylaluminum hydride in toluene, a procedure as in Reference Example 5 was performed to give the title compound as a brown oil (yield 0.84 g, 94%).

$^1$H-NMR (CDCl$_3$) δ: 1.22 (3H, t, J=4.8 Hz), 1.83 (3H, s), 2.56 (3H, s), 4.49 (2H, d, J=4.8 Hz), 7.11-7.43 (9H, m), 7.49-7.55 (1H, m).

Reference Example 185

[5-Phenyl-1-(phenylsulfonyl)-4-propyl-1H-pyrrol-3-yl]methanol

Using methyl 5-phenyl-1-(phenylsulfonyl)-4-propyl-1H-pyrrole-3-carboxylate (3.0 g), and a 1.5 mol/L solution (16.1 mL) of diisobutylaluminum hydride in toluene, a procedure as in Reference Example 5 was performed to give the title compound as a pale-red oil (yield 2.73 g, 95%).

$^1$H-NMR (CDCl$_3$) δ: 0.71 (3H, t, J=7.5 Hz), 1.26-1.50 (3H, m), 2.05-2.19 (2H, m), 4.59 (2H, d, J=4.8 Hz), 6.99-7.02 (2H, m), 7.24-7.36 (7H, m), 7.43 (1H, s), 7.48-7.52 (1H, m).

Reference Example 186

[4,5-Diphenyl-1-(phenylsulfonyl)-1H-pyrrol-3-yl]methanol

Using methyl 4,5-diphenyl-1-(phenylsulfonyl)-1H-pyrrole-3-carboxylate (439 mg) and a 1.5 mol/L solution (3.2 mL) of diisobutylaluminum hydride in toluene, a procedure as in Reference Example 5 was performed to give the title compound as a brown oil (yield 361 mg, 88%).

$^1$H-NMR (CDCl$_3$) δ: 1.50 (1H, t, J=5.7 Hz), 4.49 (2H, d, J=5.7 Hz), 6.96-6.99 (2H, m), 7.04-7.07 (2H, m), 7.11-7.18 (5H, m), 7.23-7.37 (5H, m), 7.48-7.53 (1H, m), 7.60 (1H, s).

Reference Example 187

[2-Chloro-5-phenyl-1-(phenylsulfonyl)-1H-pyrrol-3-yl]methanol

A solution (30 mL) of ethyl 2-chloro-5-phenyl-1-(phenylsulfonyl)-1H-pyrrole-3-carboxylate (1.27 g) in tetrahydrofuran was cooled to −70° C., a 1.5 mol/L solution (7.6 mL) of diisobutylaluminum hydride in toluene was added dropwise by small portions. The mixture was further stirred at −70° C. for 1 hr, 1 mol/l hydrochloric acid (20 mL) was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as pale-red crystals (yield 882 mg, 78%).

$^1$H-NMR (CDCl$_3$) δ: 4.47 (2H, s), 6.27 (1H, s), 7.39-7.47 (7H, m), 7.57-7.65 (3H, m).

Reference Example 188

[2-Fluoro-5-phenyl-1-(phenylsulfonyl)-1H-pyrrol-3-yl]methanol

A solution (20 mL) of ethyl 2-fluoro-5-phenyl-1-(phenylsulfonyl)-1H-pyrrole-3-carboxylate (390 mg) in tetrahydrofuran was cooled to −70° C., and a 1.5 mol/L solution (3.5 mL) of diisobutylaluminum hydride in toluene was added dropwise by small portions. The mixture was further stirred at −70° C. for 1 hr, 1 mol/L hydrochloric acid (20 mL) was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as a pale-red oil (yield 330 mg, 95%).

$^1$H-NMR (CDCl$_3$) δ: 4.43 (2H, s), 6.06 (1H, d, J=5.5 Hz), 7.31-7.62 (10H, m).

Reference Example 189

[2-Chloro-4-fluoro-5-phenyl-1-(phenylsulfonyl)-1H-pyrrol-3-yl]methanol

A solution (20 mL) of ethyl 2-chloro-4-fluoro-5-phenyl-1-(phenylsulfonyl)-1H-pyrrole-3-carboxylate (250 mg) in tetrahydrofuran was cooled to −70° C., and a 1.5 mol/L solution (6 mL) of diisobutylaluminum hydride in toluene was added dropwise by small portions. The mixture was further stirred at −70° C. for 1 hr, 1 mol/L hydrochloric acid (50 mL) was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as a colorless oil (yield 210 mg, 94%)

$^1$H-NMR (CDCl$_3$) δ: 4.49 (2H, s), 7.31-7.51 (7H, m), 7.60-7.68 (3H, m).

Reference Example 190

[4-Fluoro-5-phenyl-1-(phenylsulfonyl)-1H-pyrrol-3-yl]methanol

A solution (10 mL) of ethyl 4-fluoro-5-phenyl-1-(phenylsulfonyl)-1H-pyrrole-3-carboxylate (60 mg) in tetrahydrofuran was cooled to −70° C., and a 1.5 mol/L solution (0.5 mL) of diisobutylaluminum hydride in toluene was added dropwise by small portions. The mixture was further stirred at −70° C. for 1 hr, 1 mol/L hydrochloric acid (20 mL) was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3) to give the title compound as a colorless oil (yield 40 mg, 75%).

$^1$H-NMR (CDCl$_3$) δ: 4.60 (2H, br), 7.20-7.23 (2H, m), 7.31-7.56 (9H, m).

Reference Example 191

2-Methyl-1-(phenylsulfonyl)-1H-pyrrole-3-carbaldehyde

To a mixture of [2-methyl-1-(phenylsulfonyl)-1H-pyrrol-3-yl]methanol (6.35 g), dimethyl sulfoxide (50 mL) and triethylamine (25 mL) was added sulfur trioxide pyridine complex (4.57 g), and the mixture was stirred at room temperature for 12 hr. Saturated aqueous sodium hydrogencarbonate solution was added to the reaction mixture, and the mixture was extracted with ethyl acetate. The extract was washed with saturated aqueous sodium hydrogencarbonate solution, water and saturated brine, dried over anhydrous sodium sulfate, filtered, and concentrated under reduced pressure. The residue was purified by silica gel column chromatography (eluent: hexane-ethyl acetate=2:1) to give a white title compound (yield 5.27 g, 84%).

$^1$H-NMR (CDCl$_3$) δ: 2.62 (3H, s), 6.65 (1H, d, J=3.6 Hz), 7.35 (1H, d, J=3.6 Hz), 7.55-7.61 (2H, m), 7.66-7.71 (1H, m), 7.85-7.88 (2H, m), 9.89 (1H, s).

Reference Example 192

5-Bromo-4-ethyl-1-(phenylsulfonyl)-1H-pyrrole-3-carbaldehyde

Using [5-bromo-4-ethyl-1-(phenylsulfonyl)-1H-pyrrol-3-yl]methanol (1.05 g), tetra-n-propylammonium perruthenate (54.3 mg), N-methylmorpholine N-oxide (543 mg) and molecular sieves 4 A powder (522 mg), a procedure as in Reference Example 6 was performed to give the title compound as white crystals (yield 0.51 g, 49%).

$^1$H-NMR (CDCl$_3$) δ: 1.06 (3H, t, J=7.8 Hz), 2.62 (2H, q, J=7.8 Hz), 7.55-7.63 (2H, m), 7.67-7.75 (1H, m), 7.96-8.00 (2H, m), 8.09 (1H, s), 9.81 (1H, s).

Reference Example 193

5-Bromo-1-{[3-(methylsulfonyl)phenyl]sulfonyl}-1H-pyrrole-3-carbaldehyde

Using {5-bromo-1-{[3-(methylsulfonyl)phenyl]sulfonyl}-1H-pyrrol-3-yl}methanol (4.88 g) and sulfur trioxide.pyridine complex (2.19 g), a procedure as in Reference Example 191 was performed to give the title compound as a white solid (yield 2.80 g, 58%).

$^1$H-NMR (CDCl$_3$) δ: 3.12 (3H, s), 6.77 (1H, d, J=1.8 Hz), 7.86 (1H, t, J=7.8 Hz), 8.10 (1H, d, J=1.8 Hz), 8.26-8.30 (2H, m), 8.61-8.62 (1H, m), 9.79 (1H, s).

Reference Example 194

2-Chloro-5-phenyl-1-{[4-(trifluoromethyl)phenyl]sulfonyl}-1H-pyrrole-3-carbaldehyde 5-Phenyl-1-{[4-(trifluoromethyl)phenyl]sulfonyl}-1H-pyrrole-3-carbaldehyde (300 mg) was dissolved in N,N-dimethylformamide (6 mL), N-chlorosuccinimide (116 mg) was added at room temperature, and the mixture was stirred for 24 hr. Water was added to the reaction mixture, and the mixture was extracted with ethyl acetate. The extract was washed with 3% potassium hydrogensulfate solution and saturated brine, dried over anhydrous magnesium sulfate, and concentrated under reduced pressure. The residue was purified by silica gel column chromatography (eluent: hexane-ethyl acetate=19:1→4:1) to give the title compound as colorless crystals (yield 200 mg, 61%).

$^1$H-NMR (CDCl$_3$) δ: 6.55 (1H, s), 7.31-7.35 (2H, m), 7.38-7.50 (3H, m), 7.74-7.80 (4H, m), 9.94 (1H, s).

Reference Example 195

1-[(3-Chlorophenyl)sulfonyl]-2-methyl-5-phenyl-1H-pyrrole-3-carbaldehyde

Using {1-[(3-chlorophenyl)sulfonyl]-2-methyl-5-phenyl-1H-pyrrol-3-yl}methanol (340 mg), tetra-n-propylammonium perruthenate (17.7 mg), N-methylmorpholine N-oxide (179 mg) and molecular sieves 4 A powder (189 mg), a procedure as in Reference Example 6 was performed to give the title compound as a brown oil (yield 237 mg, 70%).

¹H-NMR (CDCl₃) δ: 2.90 (3H, s), 6.50 (1H, s), 7.17-7.21 (2H, m), 7.28-7.43 (6H, m), 7.51-7.55 (1H, m), 10.03 (1H, s).

Reference Example 196

5-Phenyl-1-{[4-(trifluoromethoxyphenyl)sulfonyl]-1H-pyrrole-3-carbaldehyde

To a solution (15 mL) of (5-phenyl-1-{[4-(trifluoromethoxy)phenyl]sulfonyl}-1H-pyrrol-3-yl)methanol (0.70 g) in acetonitrile were added tetra-n-propylammonium perruthenate (55 mg), N-methylmorpholine N-oxide (0.69 g) and molecular sieves 4 A powder (0.45 g), and the mixture was stirred at room temperature for 3 hr. The reaction mixture was concentrated under reduced pressure, and to the residue was added ethyl acetate and filtered through celite. The filtrate was concentrated under reduced pressure, and the residue was purified by silica gel column chromatography (eluent: hexane-ethyl acetate=3:1) to give the title compound as crystals (yield 0.42 g, 60%).
¹H-NMR (CDCl₃) δ: 6.59 (1H, s), 7.09-7.17 (4H, m), 7.27-7.44 (5H, m), 8.12 (1H, d, J=1.9 Hz), 9.90 (1H, s).

Reference Example 197

5-Phenyl-1-(2-thienylsulfonyl)-1H-pyrrole-3-carbaldehyde

To a solution (20 mL) of [5-phenyl-1-(2-thienylsulfonyl)-1H-pyrrol-3-yl]methanol (480 mg) in acetonitrile were added tetra-n-propylammonium perruthenate (80 mg), N-methylmorpholine N-oxide (407 mg) and molecular sieves 4 A powder (500 mg), and the mixture was stirred at room temperature for 1.5 hr. The reaction mixture was diluted with ethyl acetate, filtered through celite, and the filtrate was concentrated under reduced pressure. The residue was purified by silica gel column chromatography (eluent: hexane-ethyl acetate=4:1→3:2) to give the title compound as colorless crystals (yield 272 mg, 57%).
¹H-NMR (CDCl₃) δ: 6.59 (1H, d, J=1.8 Hz), 6.90 (1H, dd, J=4.9 Hz, 3.9 Hz), 7.05 (1H, dd, J=3.9 Hz, 1.4 Hz), 7.24-7.45 (5H, m), 7.62 (1H, dd, J=4.9 Hz, 1.4 Hz), 8.07 (1H, d, J=1.8 Hz), 9.88 (1H, s).

Reference Example 198

2-Methyl-1-(phenylsulfonyl)-5-(3-thienyl)-1H-pyrrole-3-carbaldehyde

Using [2-methyl-1-(phenylsulfonyl)-5-(3-thienyl)-1H-pyrrol-3-yl]methanol (307 mg), tetra-n-propylammonium perruthenate (26.4 mg), N-methylmorpholine N-oxide (216 mg) and molecular sieves 4 A powder (215 mg), a procedure as in Reference Example 6 was performed to give the title compound as a brown oil (yield 309 g, 76%).
¹H-NMR (CDCl₃) δ: 2.90 (3H, s), 6.50 (1H, s), 7.02-7.06 (2H, m), 7.23-7.26 (1H, m), 7.37-7.43 (4H, m), 7.54-7.60 (1H, m), 10.01 (1H, s).

Reference Example 199

5-(4-Fluorophenyl)-2-methyl-1-(phenylsulfonyl)-1H-pyrrole-3-carbaldehyde

[5-(4-Fluorophenyl)-2-methyl-1-(phenylsulfonyl)-1H-pyrrol-3-yl]methanol (1.08 g) was dissolved in acetonitrile (20 mL), tetra-n-propylammonium perruthenate (100 mg), N-methylmorpholine N-oxide (0.52 g) and molecular sieves 4 A powder (1.00 g) were added, and the mixture was stirred at room temperature for 2 hr. The reaction mixture was concentrated under reduced pressure, and the residue was suspended in ethyl acetate and filtered through celite. The filtrate was concentrated under reduced pressure, and the residue was purified by silica gel column chromatography (eluent: hexane-ethyl acetate=3:1) to give the title compound as colorless crystals (yield 0.71 g, 66%).
¹H-NMR (CDCl₃) δ: 2.89 (3H, s), 6.46 (1H, s), 6.99 (2H, t, J=8.7 Hz), 7.11-7.21 (2H, m), 7.37-7.46 (4H, m), 7.56-7.62 (1H, m), 10.01 (1H, s).

Reference Example 200

2,4-Dimethyl-5-phenyl-1-(phenylsulfonyl)-1H-pyrrole-3-carbaldehyde

Using [2,4-dimethyl-5-phenyl-1-(phenylsulfonyl)-1H-pyrrol-3-yl]methanol (0.84 g), tetra-n-propylammonium perruthenate (57.3 mg), N-methylmorpholine N-oxide (437 mg) and molecular sieves 4 A powder (422 mg), a procedure as in Reference Example 6 was performed to give the title compound as a brown oil (yield 0.59 g, 71%).
¹H-NMR (CDCl₃) δ: 1.95 (3H, s), 2.88 (3H, s), 7.03-7.06 (2H, m), 7.26-7.42 (7H, m), 7.54-7.60 (1H, m), 10.13 (1H, s).

Reference Example 201

5-Phenyl-1-(phenylsulfonyl)-4-propyl-1H-pyrrole-3-carbaldehyde

Using [5-phenyl-1-(phenylsulfonyl)-4-propyl-1H-pyrrol-3-yl]methanol (2.73 g), tetra-n-propylammonium perruthenate (142 mg), N-methylmorpholine N-oxide (1.04 g) and molecular sieves 4 A powder (1.5 g), a procedure as in Reference Example 6 was performed to give the title compound as a pale-red oil (yield 1.33 g, 47%).
¹H-NMR (CDCl₃) δ: 0.72 (3H, t, J=7.5 Hz), 1.30-1.43 (2H, m), 2.31-2.37 (2H, m), 6.94-6.97 (2H, m), 7.24-7.40 (7H, m), 7.52-7.58 (1H, m), 8.08 (1H, s), 9.94 (1H, s).

Reference Example 202

4,5-Diphenyl-1-(phenylsulfonyl)-1H-pyrrole-3-carbaldehyde

Using [4,5-diphenyl-1-(phenylsulfonyl)-1H-pyrrol-3-yl]methanol (352 mg), tetra-n-propylammonium perruthenate (13.8 mg), N-methylmorpholine N-oxide (159 mg) and molecular sieves 4 A powder (177 mg), a procedure as in Reference Example 6 was performed to give the title compound as white crystals (yield 250 mg, 72%).
¹H-NMR (CDCl₃) δ: 6.93-6.96 (2H, m), 7.04-7.09 (2H, m), 7.13-7.18 (5H, m), 7.26-7.35 (5H, m), 7.52-7.58 (1H, m), 8.25 (1H, s), 9.86 (1H, s).

Reference Example 203

2-Chloro-5-phenyl-1-(phenylsulfonyl)-1H-pyrrole-3-carbaldehyde

To a solution (50 mL) of [2-chloro-5-phenyl-1-(phenylsulfonyl)-1H-pyrrol-3-yl]methanol (830 mg) in acetonitrile were added tetra-n-propylammonium perruthenate (84 mg), N-methylmorpholine N-oxide (484 mg) and molecular sieves 4 A powder (2.0 g), and the mixture was stirred at room temperature for 5 hr. The reaction mixture was diluted with ethyl acetate, filtered through celite, and the filtrate was concentrated under reduced pressure. The residue was purified by silica gel column chromatography (eluent: hexane-ethyl acetate=19:1→4:1) to give the title compound as a colorless oil (yield 440 mg, 53%).

$^1$H-NMR (CDCl$_3$) δ: 6.52 (1H, s), 7.32-7.52 (7H, m), 7.62-7.69 (3H, m), 9.93 (1H, s).

Reference Example 204

2-Fluoro-5-phenyl-1-(phenylsulfonyl)-1H-pyrrole-3-carbaldehyde

To a solution (20 mL) of [2-fluoro-5-phenyl-1-(phenylsulfonyl)-1H-pyrrol-3-yl]methanol (330 mg) in acetonitrile were added tetra-n-propylammonium perruthenate (53 mg), N-methylmorpholine N-oxide (270 mg) and molecular sieves 4 A powder (500 mg), and the mixture was stirred at room temperature for 1.5 hr. The reaction mixture was diluted with ethyl acetate, filtered through celite, and the filtrate was concentrated under reduced pressure. The residue was purified by silica gel column chromatography (eluent: hexane-ethyl acetate=19:1→4:1) to give the title compound as a colorless oil (yield 110 mg, 34%).

$^1$H-NMR (CDCl$_3$) δ: 6.32 (1H, d, J=5.1 Hz), 7.27-7.31 (2H, m), 7.35-7.52 (5H, m), 7.62-7.69 (3H, m), 9.87 (1H, s).

Reference Example 205

2-Chloro-4-fluoro-5-phenyl-1-(phenylsulfonyl)-1H-pyrrole-3-carbaldehyde

To a solution (15 mL) of [2-chloro-4-fluoro-5-phenyl-1-(phenylsulfonyl)-1H-pyrrol-3-yl]methanol (210 mg) in acetonitrile were added tetra-n-propylammonium perruthenate (31 mg), N-methylmorpholine N-oxide (156 mg) and molecular sieves 4 A powder (500 mg), and the mixture was stirred at room temperature for 1.5 hr. The reaction mixture was diluted with ethyl acetate, filtered through celite, and the filtrate was concentrated under reduced pressure. The residue was purified by silica gel column chromatography (eluent: hexane-ethyl acetate=90:10→85:15) to give the title compound as a colorless oil (yield 140 mg, 67%).

$^1$H-NMR (CDCl$_3$) δ: 7.28-7.36 (2H, m), 7.42-7.55 (5H, m), 7.66-7.71 (3H, m), 9.92 (1H, s).

Reference Example 206

4-Fluoro-5-phenyl-1-(phenylsulfonyl)-1H-pyrrole-3-carbaldehyde

To a solution (10 mL) of [4-fluoro-5-phenyl-1-(phenylsulfonyl)-1H-pyrrol-3-yl]methanol (40 mg) in acetonitrile were added tetra-n-propylammonium perruthenate (21 mg), N-methylmorpholine N-oxide (82 mg) and molecular sieves 4 A powder (1.0 g), and the mixture was stirred at room temperature for 1.5 hr. The reaction mixture was diluted with ethyl acetate, filtered through celite, and the filtrate was concentrated under reduced pressure. The residue was purified by silica gel column chromatography (eluent: hexane-ethyl acetate=7:3) to give the title compound as a colorless oil (yield 10 mg, 25%).

$^1$H-NMR (CDCl$_3$) δ: 7.14-7.17 (2H, m), 7.33-7.61 (8H, m), 7.95 (1H, d, J=5.0 Hz), 9.91 (1H, s).

Reference Example 207

5-Bromo-4-methyl-1-(phenylsulfonyl)-1H-pyrrole-3-carbaldehyde

Using methyl 5-bromo-4-methyl-1-(phenylsulfonyl)-1H-pyrrole-3-carboxylate, a procedure as in Reference Example 49 was performed to give the title compound as a colorless solid (1.78 g, yield 54%).

$^1$H-NMR (CDCl$_3$) δ: 2.14 (3H, s), 7.50-7.62 (3H, m), 7.91-7.96 (2H, m), 8.04 (1H, s), 9.77 (1H, s).

Reference Example 208

4-Methyl-5-phenyl-1H-pyrrole-3-carbaldehyde

A suspension of 5-bromo-4-methyl-1-(phenylsulfonyl)-1H-pyrrole-3-carbaldehyde (1.78 g), phenylboronic acid (1.37 g), dichloro[bis(triphenylphosphine)]palladium (0.19 g) and sodium carbonate (1.72 g) in 1,2-dimethoxyethane (30 mL)-water (10 mL) was stirred at 100° C. for 1 hr. 8 mol/L aqueous sodium hydroxide solution (15 mL) was added, and the mixture was stirred at 90° C. for 3 hr. After cooling, the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=9:1→1:1), and the obtained solid was washed with hexane to give the title compound as a pale-yellow solid (yield 815 mg, 69%).

$^1$H-NMR (CDCl$_3$) δ: 2.47 (3H, s), 7.34-7.48 (6H, m), 8.58 (1H, br), 9.91 (1H, s).

Reference Example 209

5-Bromo-1H-pyrrole-3-carbaldehyde

To a solution methyl 5-bromo-1-(pyridin-3-ylsulfonyl)-1H-pyrrole-3-carboxylate (4.16 g) in tetrahydrofuran (40 mL) was added a 1.5 mol/L solution (26 mL) of diisobutylaluminum hydride in toluene at −78° C. and the mixture was stirred at 0° C. for 30 min. Water (100 mL) was added to the reaction mixture, and the mixture was further stirred at 0° C. for 1 hr, and the mixture was extracted with ethyl acetate. The extract was washed with water and saturated brine, dried over anhydrous sodium sulfate, filtrated, and concentrated under reduced pressure. To a mixture of the residue, dimethyl sulfoxide (25 mL) and triethylamine (13 mL) was added sulfur trioxide.pyridine complex (2.20 g), and the mixture was stirred for 1 hr. Water (100 mL) was added to the reaction mixture, and the mixture was extracted with ethyl acetate. The extract was washed with saturated aqueous sodium hydrogencarbonate solution, water and saturated brine, dried over anhydrous sodium sulfate. The mixture was filtrated, and the filtrate was concentrated under reduced pressure. The residue was purified by silica gel column chromatography (eluent: hexane-ethyl acetate=1:1) to give the title compound as a white solid (yield 1.24 g, 59%).

$^1$H-NMR (CDCl$_3$) δ: 6.65-6.67 (1H, m), 7.38-7.40 (1H, m), 8.80 (1H, brs), 9.71 (1H, s).

Reference Example 210

2-Methyl-1-[(3-methylphenyl)sulfonyl]-5-phenyl-1H-pyrrole-3-carbaldehyde

A solution (10 mL) of ethyl 2-methyl-1-[(3-methylphenyl)sulfonyl]-5-phenyl-1H-pyrrole-3-carboxylate (588 mg) in tetrahydrofuran was cooled to −78° C., a 1.5 mol/L toluene solution (3.00 mL) of diisobutylaluminum hydride was added dropwise. After completion of the dropwise addition, the mixture was stirred at −78° C. for 30 min, and at room temperature for 30 min. 1 mol/l Hydrochloric acid (10 mL) was added to the reaction mixture and extracted with ethyl acetate. The extract was washed with saturated brine, dried over anhydrous sodium sulfate, and concentrated under reduced pressure. A solution (10 mL) of the residue in acetonitrile was cooled to 0° C., tetra-n-propylammonium perruthenate (53 mg), N-methylmorpholine N-oxide (358 mg) and molecular sieves 4 A powder (1.0 g) were added, and the mixture was stirred at room temperature for 2.5 hr. The reaction mixture was concentrated under reduced pressure, and the residue was suspended in ethyl acetate (30 mL) and filtered through celite. The filtrate was concentrated under reduced pressure, and the residue was purified by silica gel column chromatography (eluent: hexane-ethyl acetate=9:1→2:1) to give the title compound as a pale-yellow oil (yield 250 mg, 48%).

$^1$H-NMR (CDCl$_3$) δ: 2.30 (3H, s), 2.89 (3H, s), 6.47 (1H, s), 7.10-7.40 (9H, m), 10.01 (1H, s).

Reference Example 211

1-[(2-Methyl-5-pyrimidine)sulfonyl]-5-phenyl-1H-pyrrole-3-carbaldehyde

Under a nitrogen atmosphere, a solution of ethyl 1-[(2-methyl-5-pyrimidine)sulfonyl]-5-phenyl-1H-pyrrole-3-carboxylate (280 mg) in tetrahydrofuran (20 mL) was cooled to −78° C., a 1.5 mol/L solution (3.0 mL) of diisobutylaluminum in toluene was added while stirring. After stirring at the same temperature for 15 min, the mixture was allowed to warm to −40° C. over 30 min. Water (50 mL) was added, and after stirring at the same temperature for 5 min, the mixture was allowed to warm to 0° C. over 10 min. Ethyl acetate (30 mL) was added, and after stirring at the same temperature for 15 min, the mixture was stirred at room temperature for 20 min. A gel-like mixture was filtered through celite, and celite was washed with ethyl acetate. The organic layer was separated from the filtrate, washed with saturated brine, dried over anhydrous magnesium sulfate, and concentrated under reduced pressure. The residue was dissolved in tetrahydrofuran (50 mL), manganese dioxide (75% chemically treated product, 3.0 g) was added, and the mixture was stirred at room temperature for 1 hr. The reaction mixture was filtered through celite, and celite was washed with ethyl acetate. The filtrate was concentrated under reduced pressure and the residue was purified by silica gel column chromatography (eluent: hexane-ethyl acetate=19:1→1:1) to give the title compound as a pale-yellow solid (yield 150 mg, 61%).

$^1$H-NMR (CDCl$_3$) δ: 2.78 (3H, s), 6.64 (1H, s), 7.21-7.26 (2H, m), 7.36-7.51 (3H, m), 8.10 (1H, s), 8.40 (2H, s), 9.90 (1H, s).

Reference Example 212

4-Methyl-1-[(3-methylphenyl)sulfonyl]-5-phenyl-1H-pyrrole-3-carbaldehyde

Under a nitrogen atmosphere, a solution (60 mL) of ethyl 4-methyl-1-[(3-methylphenyl)sulfonyl]-5-phenyl-1H-pyrrole-3-carboxylate (2.48 g) in tetrahydrofuran was cooled to −78° C., and a 1.5 mol/L solution (13 mL) of diisobutylaluminum hydride in toluene was added dropwise over 15 min, and the mixture was further stirred at −78° C. for 30 min. 1 mol/L Hydrochloric acid (60 mL) was added to the reaction mixture, and the mixture was extracted with ethyl acetate. The extract was washed with water and saturated brine, dried over anhydrous magnesium sulfate, and concentrated under reduced pressure. The residue was dissolved in acetonitrile solution (100 mL), tetra-n-propylammonium perruthenate (0.21 g), N-methylmorpholine N-oxide hydrate (1.31 g) and molecular sieves 4 A powder (6.0 g) were added, and the mixture was stirred at room temperature for 2 hr. The reaction mixture was concentrated under reduced pressure, ethyl acetate (300 mL) was added to the residue, the suspension was filtered through celite, and celite was washed with ethyl acetate. The filtrate was concentrated under reduced pressure, and the residue was purified by silica gel column chromatography (eluent: hexane-ethyl acetate=19:1→3:1) to give the title compound as a yellow oil (yield 1.76 g, 80%).

$^1$H-NMR (CDCl$_3$) δ: 2.02 (3H, s), 2.25 (3H, s), 6.99-7.43 (9H, m), 8.05 (1H, s), 9.96 (1H, s).

Reference Example 213

1-[(4-Fluorophenyl)sulfonyl]-4-methyl-5-phenyl-1H-pyrrole-3-carbaldehyde

Under a nitrogen atmosphere, a solution (40 mL) of methyl 1-[(4-fluorophenyl)sulfonyl]-4-methyl-5-phenyl-1H-pyrrole-3-carboxylate (1.48 g) in tetrahydrofuran was cooled to −78° C., and a 1.5 mol/L solution (7.9 mL) of diisobutylaluminum hydride in toluene was added dropwise over 15 min, and the mixture was further stirred at −78° C. for 30 min. 1 mol/L Hydrochloric acid (40 mL) was added to the reaction mixture, and the mixture was extracted with ethylacetate. The extract was washed with water and saturated brine, dried over anhydrous magnesium sulfate, and concentrated under reduced pressure. The residue was dissolved in acetonitrile solution (60 mL), added tetra-n-propylammonium perruthenate (0.14 g), N-methylmorpholine N-oxide hydrate (0.80 g) and molecular sieves 4 A powder (4.0 g), and the mixture was stirred at room temperature for 2 hr. The reaction mixture was concentrated under reduced pressure, ethyl acetate (200 mL) was added to the residue, the suspension was filtered through celite, and celite washed with ethylacetate. The filtrate was concentrated under reduced pressure, and the residue was purified by silica gel column chromatography (eluent: hexane-ethyl acetate=19:1→3:1) to give the title compound as a colorless oil (yield 721 mg, 53%).

$^1$H-NMR (CDCl$_3$) δ: 2.03 (3H, s), 6.96-7.04 (4H, m), 7.26-7.42 (5H, m), 8.04 (1H, s), 9.96 (1H, s).

Reference Example 214

2-Methyl-5-phenyl-1-(pyridin-3-ylsulfonyl)-1H-pyrrole-3-carbaldehyde

A solution (15 mL) of ethyl 2-methyl-5-phenyl-1-(pyridin-3-ylsulfonyl)-1H-pyrrole-3-carboxylate (980 mg) in tetrahydrofuran was cooled to −78° C., a 1.5 mol/L solution (5.3 mL) of diisobutylaluminum hydride in toluene was added dropwise over 10 min, and the mixture was warmed to 0° C. over 2 hr. Water (100 mL) and ethylacetate (20 mL) were added, and the mixture was stirred at room temperature for 30 min. The reaction mixture was filtered through celite, and the organic layer was separated, washed with saturated brine, dried over anhydrous sodium sulfate, and concentrated under reduced pressure. The residue was dissolved in acetonitrile solution (25 mL), tetra-n-propylammonium perruthenate (93 mg), N-methylmorpholine N-oxide hydrate (466 mg) and molecular sieves 4 A powder (500 mg) were added, and the mixture was stirred at room temperature for 2 hr. The reaction mixture was concentrated under reduced pressure, and ethyl acetate (30 mL) was added to the residue. The mixture was filtered through celite, and celite was washed with ethyl acetate. The filtrate was concentrated under reduced pressure, and the residue was purified by silica gel column chromatography (eluent: hexane-ethyl acetate=19:1→1:1) to give the title compound as a yellow oil (yield 235 mg, 27%).

$^1$H-NMR (CDCl$_3$) δ: 2.93 (3H, s), 6.51 (1H, s), 7.18-7.42 (6H, m), 7.59-7.64 (1H, m), 8.60 (1H, s), 8.77-8.79 (1H, m), 10.03 (1H, s).

Reference Example 215

4-Chloro-2-methyl-5-phenyl-1-(phenylsulfonyl)-1H-pyrrole-3-carbaldehyde

Using ethyl 4-chloro-2-methyl-5-phenyl-1-(phenylsulfonyl)-1H-pyrrole-3-carboxylate (610 mg), a 1.5 mol/L solution (6.0 mL) of diisobutylaluminum hydride in toluene, tetra-n-propylammonium perruthenate (53 mg), N-methylmorpholine N-oxide (195 mg) and molecular sieves 4 A powder (300 mg), a procedure as in Reference Example 49 was performed to give the title compound as a pale-yellow solid (yield 301 mg, 55%).

$^1$H-NMR (CDCl$_3$) δ: 2.94 (3H, s), 7.13-7.16 (2H, m), 7.33-7.46 (7H, m), 7.57-7.62 (1H, m), 10.1 (1H, s).

Reference Example 216

5-Butyl-1-(phenylsulfonyl)-1H-pyrrole-3-carbaldehyde

Using ethyl 5-butyl-1-(phenylsulfonyl)-1H-pyrrole-3-carboxylate (780 mg), a procedure as in Reference Example 212 was performed to give the title compound as a colorless solid (yield 553 mg, 82%).

$^1$H-NMR (CDCl$_3$) δ: 0.84-0.89 (3H, m), 1.26-1.50 (2H, m), 1.48-1.57 (2H, m), 2.59-2.65 (2H, m), 6.43 (1H, m), 7.55-7.60 (2H, m), 7.66-7.71 (1H, m), 7.82-7.84 (2H, m), 7.95 (1H, s), 9.81 (1H, s).

Reference Example 217

5-Cyclohexyl-1-(phenylsulfonyl)-1H-pyrrole-3-carbaldehyde

Using ethyl 5-cyclohexyl-1-(phenylsulfonyl)-1H-pyrrole-3-carboxylate (640 mg), a procedure as in Reference Example 212 was performed to give the title compound as a solid (yield 424 mg, 75%).

$^1$H-NMR (CDCl$_3$) δ: 1.14-1.28 (6H, m), 1.60-1.72 (4H, m), 2.82 (1H, m), 6.44 (1H, s), 7.54-7.59 (2H, m), 7.64-7.67 (1H, m), 7.80-7.83 (2H, m), 7.91 (1H, s), 9.81 (1H, s).

Reference Example 218

5-Cyclopropyl-1-(phenylsulfonyl)-1H-pyrrole-3-carbaldehyde

Using methyl 5-cyclopropyl-1-(phenylsulfonyl)-1H-pyrrole-3-carboxylate (406 mg), a procedure as in Reference Example 212 was performed to give the title compound as an oil (yield 247 mg, 68%).

$^1$H-NMR (CDCl$_3$) δ: 0.32-0.38 (2H, m), 0.73-0.79 (2H, m), 2.01-2.06 (1H, m), 6.24 (1H, s), 7.54-7.59 (2H, m), 7.66-7.71 (1H, m), 7.88-7.90 (2H, m), 7.96 (1H, s), 9.79 (1H, s).

Reference Example 219

1-{[3-(Methylsulfonyl)phenyl]sulfonyl}-5-phenyl-1H-pyrrole-3-carbaldehyde

To a solution (10 mL) of 5-phenyl-1H-pyrrole-3-carbaldehyde (100 mg) in tetrahydrofuran was added sodium hydride (60% in oil, 47 mg) at room temperature and the mixture was stirred for 30 min. 15-Crown-5 (257 mg) was added dropwise and the mixture was stirred for 30 min, [3-(methylsulfonyl)benzene]sulfonyl chloride (223 mg) was added, and the mixture was further stirred for 15 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as a pale-yellow oil (yield 160 mg, 70%).

$^1$H-NMR (CDCl$_3$) δ: 2.98 (3H, s), 6.61 (1H, d, J=1.8 Hz), 7.16-7.20 (2H, m), 7.30-7.36 (2H, m), 7.41-7.47 (1H, m), 7.57-7.59 (2H, m), 7.92-7.94 (1H, m), 8.10-8.13 (2H, m), 9.90 (1H, s).

Reference Example 220

1-{[3-(Ethylsulfonyl)phenyl]sulfonyl}-5-phenyl-1H-pyrrole-3-carbaldehyde

Using 5-phenyl-1H-pyrrole-3-carbaldehyde (171 mg), sodium hydride (60% in oil, 58 mg), 15-crown-5 (264 mg) and [3-(ethylsulfonyl)benzene]sulfonyl chloride (322 mg), a procedure as in Reference Example 219 was performed to give the title compound as a pale-yellow oil (yield 348 mg, 86%).

$^1$H-NMR (CDCl$_3$) δ: 1.23 (3H, t, J=7.5 Hz), 3.03 (2H, q, J=7.5 Hz), 6.61 (1H, d, J=2.1 Hz), 7.15-7.18 (2H, m), 7.30-7.36 (2H, m), 7.41-7.44 (1H, m), 7.55-7.57 (2H, m), 7.91-7.92 (1H, m), 8.05-8.09 (1H, m), 8.13 (1H, d, J=2.1 Hz), 9.91 (1H, s).

Reference Example 221

1-(2,3-Dihydro-1,4-benzodioxin-6-ylsulfonyl)-5-phenyl-1H-pyrrole-3-carbaldehyde

Using 5-phenyl-1H-pyrrole-3-carbaldehyde (171 mg), sodium hydride (60% in oil, 72 mg), 15-crown-5 (330 mg) and 2,3-dihydro-1,4-benzodioxine-6-sulfonyl chloride (352 mg), a procedure as in Reference Example 219 was performed to give the title compound as a pale-yellow oil (yield 258 mg, 70%).

¹H-NMR (CDCl₃) δ: 4.22-4.30 (4H, m), 6.56 (1H, d, J=2.1 Hz), 6.71-6.85 (3H, m), 7.18-7.22 (2H, m), 7.30-7.44 (3H, m), 8.06 (1H, d, J=2.1 Hz), 9.87 (1H, s).

Reference Example 222

2-[(4-Formyl-2-phenyl-1H-pyrrol-1-yl)sulfonyl]benzonitrile

Using 5-phenyl-1H-pyrrole-3-carbaldehyde (171 mg), sodium hydride (60% in oil, 72 mg), 15-crown-5 (330 mg) and (2-cyanobenzene)sulfonyl chloride (302 mg), a procedure as in Reference Example 219 was performed to give the title compound as a pale-yellow oil (yield 253 mg, 75%).
¹H-NMR (CDCl₃) δ: 6.62 (1H, d, J=1.8 Hz), 7.04-7.09 (2H, m), 7.18-7.26 (3H, m), 7.32-7.42 (2H, m), 7.60-7.68 (1H, m), 7.75-7.79 (1H, m), 8.35 (1H, d, J=1.8 Hz), 9.93 (1H, s).

Reference Example 223

4-[(4-Formyl-2-phenyl-1H-pyrrol-1-yl)sulfonyl]benzonitrile

Using 5-phenyl-1H-pyrrole-3-carbaldehyde (171 mg), sodium hydride (60% in oil, 72 mg), 15-crown-5 (330 mg) and (4-cyanobenzene)sulfonyl chloride (302 mg), a procedure as in Reference Example 219 was performed to give the title compound as a pale-yellow oil (yield 303 mg, 90%).
¹H-NMR (CDCl₃) δ: 6.60 (1H, d, J=2.1 Hz), 7.13-7.16 (2H, m), 7.30-7.46 (5H, m), 7.58-7.62 (2H, m), 8.10 (1H, d, J=2.1 Hz), 9.90 (1H, s).

Reference Example 224

Methyl 2-[(4-formyl-2-phenyl-1H-pyrrol-1-yl)sulfonyl]benzoate

Using 5-phenyl-1H-pyrrole-3-carbaldehyde (513 mg), sodium hydride (60% in oil, 216 mg), 15-crown-5 (990 mg) and methyl 2-(chlorosulfonyl)benzoate (1.06 g), a procedure as in Reference Example 219 was performed to give the title compound as a pale-yellow oil (yield 664 mg, 60%).
¹H-NMR (CDCl₃) δ: 3.88 (3H, s), 6.59 (1H, d, J=1.8 Hz), 7.07 (1H, d, J=7.2 Hz), 7.14-7.26 (5H, m), 7.33-7.36 (1H, m), 7.56-7.58 (2H, m), 8.11 (1H, d, J=1.8 Hz), 9.92 (1H, s).

Reference Example 225

Methyl 3-[(4-formyl-2-phenyl-1H-pyrrol-1-yl)sulfonyl]benzoate

Using 5-phenyl-1H-pyrrole-3-carbaldehyde (1.32 g), sodium hydride (60% in oil, 444 mg), 15-crown-5 (2.04 g) and methyl 3-(chlorosulfonyl)benzoate (2.17 g), a procedure as in Reference Example 219 was performed to give the title compound as a pale-yellow oil (yield 1.96 g, 69%).
¹H-NMR (CDCl₃) δ: 3.92 (3H, s), 6.57 (1H, d, J=2.1 Hz), 7.12-7.15 (2H, m), 7.26-7.32 (2H, m), 7.37-7.49 (3H, m), 7.96-7.97 (1H, m), 8.13-8.14 (1H, m), 8.18-8.22 (1H, m), 9.90 (1H, s).

Reference Example 226

2-Fluoro-4-[(4-formyl-2-phenyl-1H-pyrrol-1-yl)sulfonyl]benzonitrile

Using 5-phenyl-1H-pyrrole-3-carbaldehyde (172 mg), sodium hydride (60% in oil, 61.4 mg), 15-crown-5 (0.30 mL) and (4-cyano-3-fluorobenzene)sulfonyl chloride (433 mg), a procedure as in Reference Example 219 was performed to give the title compound as white crystals (yield 283 mg, 79%).
¹H-NMR (CDCl₃) δ: 6.35 (d, 1H, J=1.8 Hz), 7.06-7.09 (1H, m), 7.16-7.25 (3H, m), 7.34-7.39 (2H, m), 7.45-7.50 (1H, m), 7.60-7.64 (1H, m), 8.08 (1H, d, J=1.8 Hz), 9.91 (1H, s).

Reference Example 227

2-Chloro-4-[(4-formyl-2-phenyl-1H-pyrrol-1-yl)sulfonyl]benzonitrile

Using 5-phenyl-1H-pyrrole-3-carbaldehyde (175 mg), sodium hydride (60% in oil, 63.6 mg), 15-crown-5 (0.31 mL) and (3-chloro-4-cyanobenzene)sulfonyl chloride (675 mg), a procedure as in Reference Example 219 was performed to give the title compound as white crystals (yield 310 mg, 82%).
¹H-NMR (CDCl₃) δ: 6.63 (1H, d, J=1.8 Hz), 7.16-7.20 (2H, m), 7.30-7.40 (4H, m), 7.46-7.52 (1H, m), 7.63-7.66 (1H, m), 8.08 (1H, d, J=1.8 Hz), 9.91 (1H, s).

Reference Example 228

1-[(1,1-Dioxido-2,3-dihydro-1-benzothien-6-yl)sulfonyl]-5-phenyl-1H-pyrrole-3-carbaldehyde Using 5-phenyl-1H-pyrrole-3-carbaldehyde (172 mg), sodium hydride (60% in oil, 61.6 mg), 15-crown-5 (0.30 mL) and 6-(2,3-dihydro-1-benzothiophene)sulfonyl chloride 1,1-dioxide (394 mg), a procedure as in Reference Example 219 was performed to give the title compound as white crystals (yield 116 mg, 29%).
¹H-NMR (CDCl₃) δ: 3.39-3.44 (2H, m), 3.50-3.55 (2H, m), 6.60 (1H, d, J=1.8 Hz), 7.17-7.20 (2H, m), 7.34-7.39 (3H, m), 7.45-7.54 (2H, m), 7.62 (1H, d, J=2.1 Hz), 8.09 (1H, d, J=1.8 Hz), 9.89 (1H, s).

Reference Example 229

1-(1,3-Benzothiazol-6-ylsulfonyl)-5-phenyl-1H-pyrrole-3-carbaldehyde

Using 5-phenyl-1H-pyrrole-3-carbaldehyde (135 mg), sodium hydride (60% in oil, 38.3 mg), 15-crown-5 (0.18 mL) and 6-benzothiazolesulfonyl chloride (206 mg), a procedure as in Reference Example 219 was performed to give the title compound as white crystal (yield 248 mg, 85%).
¹H-NMR (CDCl₃) δ: 6.56 (1H, d, J=1.8 Hz), 7.08-7.11 (2H, m), 7.23-7.28 (2H, m), 7.38-7.43 (1H, m), 7.49-7.52 (1H, m), 7.80 (1H, d, J=1.8 Hz), 8.08 (1H, d, J=9.0 Hz), 8.17 (1H, d, J=1.8 Hz), 9.23 (1H, s), 9.90 (1H, s).

Reference Example 230

1-(1-Benzothien-2-ylsulfonyl)-5-phenyl-1H-pyrrole-3-carbaldehyde

To a solution (10 mL) of 5-phenyl-1H-pyrrole-3-carbaldehyde (100 mg) in tetrahydrofuran was added sodium hydride (60% in oil, 47 mg) at room temperature and the mixture was stirred for 30 min. 15-Crown-5 (257 mg) was added dropwise and the mixture was stirred for 30 min, 2-benzothiophenesulfonyl chloride (204 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→3:2) to give the title compound as a colorless oil (yield 180 mg, 84%).

$^1$H-NMR (CDCl$_3$) δ: 6.59 (1H, d, J=1.8 Hz), 7.18-7.32 (5H, m), 7.40-7.54 (3H, m), 7.67-7.80 (2H, m), 8.10 (1H, d, J=1.8 Hz), 9.89 (1H, s).

Reference Example 231

1-{[4-(Methylsulfonyl)phenyl]sulfonyl}-5-phenyl-1H-pyrrole-3-carbaldehyde

To a solution (14 mL) of 5-phenyl-1H-pyrrole-3-carbaldehyde (140 mg) in tetrahydrofuran was added sodium hydride (60% in oil, 66 mg) at room temperature and the mixture was stirred for 30 min. 15-Crown-5 (361 mg) was added dropwise and the mixture was stirred for 30 min, [4-(methylsulfonyl)benzene]sulfonyl chloride (313 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1), crystallized from ethyl acetate.diisopropyl ether mixed solvent (1:1) to give the title compound as yellow crystals (yield 67 mg, 21%).

$^1$H-NMR (CDCl$_3$) δ: 3.05 (3H, s), 6.61 (1H, d, J=1.8 Hz), 7.14-7.17 (2H, m), 7.30-7.35 (2H, m), 7.41-7.52 (3H, m), 7.87-7.91 (2H, m), 8.12 (1H, d, J=1.8 Hz), 9.90 (1H, s).

Reference Example 232

1-[(3-Acetylphenyl)sulfonyl]-5-phenyl-1H-pyrrole-3-carbaldehyde

To a solution (20 mL) of 5-phenyl-1H-pyrrole-3-carbaldehyde (200 mg) in tetrahydrofuran was added sodium hydride (60% in oil, 94 mg) at room temperature and the mixture was stirred for 30 min. 15-Crown-5 (514 mg) was added dropwise and the mixture was stirred for 30 min, (3-acetylbenzene)sulfonyl chloride (384 mg) was added, and the mixture was further stirred for 2 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3) to give the title compound as a yellow oil (yield 200 mg, 48%).

$^1$H-NMR (CDCl$_3$) δ: 2.46 (3H, s), 6.58 (1H, d, J=1.8 Hz), 7.14-7.17 (2H, m), 7.26-7.33 (2H, m), 7.38-7.56 (3H, m), 7.78-7.78 (1H, m), 8.11-8.14 (2H, m), 9.90 (1H, s).

Reference Example 233

1-[(3-Nitrophenyl)sulfonyl]-5-phenyl-1H-pyrrole-3-carbaldehyde

To a solution (40 mL) of 5-phenyl-1H-pyrrole-3-carbaldehyde (520 mg) in tetrahydrofuran was added sodium hydride (60% in oil, 364 mg) at room temperature and the mixture was stirred for 30 min. 15-Crown-5 (2.0 g) was added dropwise and the mixture was stirred for 30 min, (3-nitrobenzene)sulfonyl chloride (1.35 g) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→2:3), crystallized from diisopropyl ether to give the title compound as pale-yellow crystals (yield 810 mg, 75%).

$^1$H-NMR (CDCl$_3$) δ: 6.61 (1H, d, J=1.8 Hz), 7.13-7.16 (2H, m), 7.29-7.34 (2H, m), 7.40-7.46 (1H, m), 7.55-7.60 (1H, m), 7.64-7.68 (1H, m), 8.06-8.07 (1H, m), 8.13 (1H, d, J=1.8 Hz), 8.37-8.41 (1H, m), 9.91 (1H, s).

Reference Example 234

5-Phenyl-1-(pyridin-3-ylsulfonyl)-1H-pyrrole-3-carbaldehyde

Under an argon atmosphere, 5-phenyl-1H-pyrrole-3-carbaldehyde (342 mg) was dissolved in absolute tetrahydrofuran (20 mL) and sodium hydride (60% in oil, 240 mg) was added while stirring at room temperature. After stirring at the same temperature for 15 min, 15-crown-5 (1.21 mL) was added, and the mixture was further stirred at the same temperature for 15 min. Pyridin-3-ylsulfonyl chloride hydrochloride (642 mg) was added, and the mixture was further stirred at the same temperature for 30 min. The reaction mixture was diluted with ethyl acetate, washed successively with saturated aqueous sodium hydrogencarbonate solution and saturated brine, and dried over anhydrous magnesium sulfate. The solvent was evaporated under reduced pressure and the residue was purified by silica gel column chromatography (eluent: hexane-ethyl acetate=19:1→1:1) to give the title compound as a brown solid (yield 470 mg, 75%).

$^1$H-NMR (CDCl$_3$) δ: 6.60 (1H, d, J=1.8 Hz), 7.15-7.19 (2H, m), 7.25-7.37 (3H, m), 7.42-7.48 (1H, m), 7.53-7.57 (1H, m), 8.13 (1H, d, J=1.8 Hz), 8.49-8.50 (1H, m), 8.74-8.76 (1H, m), 9.90 (1H, s).

Reference Example 235

1-[(6-Methoxypyridin-3-yl)sulfonyl]-5-phenyl-1H-pyrrole-3-carbaldehyde

Under an argon atmosphere, 5-phenyl-1H-pyrrole-3-carbaldehyde (171 mg) was dissolved in absolute tetrahydrofuran (20 mL), and sodium hydride (60% in oil, 200 mg) was added at room temperature while stirring. After stirring at the same temperature for 15 min, 15-crown-5 (1.01 mL) was added, and the mixture was further stirred at the same temperature for 15 min. 6-Methoxypyridin-3-ylsulfonyl chloride (623 mg) was added, and the mixture was stirred at the same temperature for 1 hr. The reaction mixture was diluted with ethyl acetate, washed successively with saturated aqueous sodium hydrogencarbonate solution and saturated brine, and dried over anhydrous magnesium sulfate. The solvent was evaporated under reduced pressure and the residue was purified by silica gel column chromatography (eluent: hexane-ethyl acetate=19:1→1:1) to give the title compound as an oil (yield 59 mg, 17%).

$^1$H-NMR (CDCl$_3$) δ: 3.95 (3H, s), 6.59-6.62 (2H, m), 7.19-7.44 (6H, m), 8.08-8.10 (2H, m), 9.88 (1H, s).

Reference Example 236

1-(6-Chloropyridin-3-ylsulfonyl)-5-phenyl-1H-pyrrole-3-carbaldehyde

Under an argon atmosphere, 5-phenyl-1H-pyrrole-3-carbaldehyde (514 mg) was dissolved in absolute tetrahydrofuran (15 mL), and sodium hydride (60% in oil, 180 mg) was added at room temperature while stirring. After stirring at the same temperature for 15 min, 15-crown-5 (0.90 mL) was added, and the mixture was further stirred at the same temperature for 15 min. 6-Chloropyridin-3-ylsulfonyl chloride (827 mg) was added, and the mixture was further stirred at the same temperature for 1 hr. The reaction mixture was diluted with ethyl acetate, washed successively with saturated aqueous sodium hydrogencarbonate solution and saturated brine, and dried over anhydrous magnesium sulfate. The solvent was evaporated under reduced pressure and the residue was purified by silica gel column chromatography (eluent: hexane-ethyl acetate=19:1→7:3) to give the title compound as an oil (yield 762 mg, 73%).

$^1$H-NMR (CDCl$_3$) δ: 6.62 (1H, s), 7.19-7.49 (7H, m), 8.09 (1H, s), 8.24-8.26 (1H, m), 8.90 (1H, s).

Reference Example 237

1-(2-Chloropyridin-3-ylsulfonyl)-5-phenyl-1H-pyrrole-3-carbaldehyde

By a reaction under similar conditions as in Reference Example 234 and using 5-phenyl-1H-pyrrole-3-carbaldehyde (514 mg), sodium hydride (60% in oil, 180 mg), 15-crown-5 (0.90 mL) and 2-chloro-3-pyridinesulfonyl chloride (716 mg), the title compound was obtained as an amorphous form (yield 716 mg, 69%).

$^1$H-NMR (CDCl$_3$) δ: 6.64 (1H, s), 6.70-6.90 (1H, m), 7.05-7.08 (2H, m), 7.15-7.18 (2H, m), 7.26-7.32 (1H, m), 7.55-7.59 (1H, m), 8.26 (1H, s), 8.44-8.46 (1H, m), 9.94 (1H, s).

Reference Example 238

1-(2-Chloropyrimidin-5-ylsulfonyl)-5-phenyl-1H-pyrrole-3-carbaldehyde

By a reaction under similar conditions as in Reference Example 234 and using 5-phenyl-1H-pyrrole-3-carbaldehyde (342 mg), sodium hydride (60% in oil, 120 mg), 15-crown-5 (0.60 mL) and 2-chloro-5-pyrimidinesulfonyl chloride (554 mg), the title compound was obtained as a yellow solid (yield 390 mg, 56%).

$^1$H-NMR (CDCl$_3$) δ: 6.68 (1H, s), 7.22-7.26 (2H, m), 7.39-7.52 (3H, m), 8.09 (1H, s), 8.35 (2H, s), 9.91 (1H, s).

Reference Example 239

1-[(6-Chloro-5-methylpyridin-3-yl)sulfonyl]-5-phenyl-1H-pyrrole-3-carbaldehyde By a reaction under similar conditions as in Reference Example 234 and using 5-phenyl-1H-pyrrole-3-carbaldehyde (171 mg), sodium hydride (60% in oil, 60 mg), 15-crown-5 (0.30 mL) and 6-chloro-5-methylpyridine-3-sulfonyl chloride (270 mg), the title compound was obtained as a solid (yield 244 mg, 68%).

$^1$H-NMR (CDCl$_3$) δ: 2.27 (3H, s), 6.62 (1H, s), 7.20-7.26 (3H, m), 7.35-7.49 (3H, m), 8.09 (1H, s), 8.13 (1H, m), 9.90 (1H, s).

Reference Example 240

5-(2-Fluorophenyl)-1-{[3-(methylsulfonyl)phenyl]sulfonyl}-1H-pyrrole-3-carbaldehyde To a solution (48 mL) of 5-(2-fluorophenyl)-1H-pyrrole-3-carbaldehyde (475 mg) in tetrahydrofuran was added sodium hydride (60% in oil, 302 mg) at room temperature and the mixture was stirred for 30 min. 15-Crown-5 (1.66 g) was added dropwise and the mixture was stirred for 30 min, [3-(methylsulfonyl)benzene]sulfonyl chloride (1.28 g) was added, and the mixture was further stirred for 15 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→2:3), and crystallized from diisopropyl ether.ethyl acetate mixed solvent (4:1) to give the title compound as colorless crystals (yield 576 mg, 56%).

$^1$H-NMR (CDCl$_3$) δ:3.03(3H,s),6.69(1H,d,J=1.8Hz), 6.97-7.02(1H,m),7.19-7.22(2H,m),7.43-7.50(1H,m),7.63-7.75(2H,m),7.99-8.00(1H,m),8.14(1H,d,J=1.8Hz),8.16-8.19(1H,m),9.91(1H,s).

Reference Example 241

1-{[3-(Ethylsulfonyl)phenyl]sulfonyl}-5-(2-fluorophenyl)-1H-pyrrole-3-carbaldehyde Using 5-(2-fluorophenyl)-1H-pyrrole-3-carbaldehyde (147 mg), sodium hydride (60% in oil, 45 mg), 15-crown-5 (205 mg) and [3-(ethylsulfonyl)benzene]sulfonyl chloride (250 mg), a procedure as in Reference Example 219 was performed to give the title compound as a pale-yellow oil (yield 181 mg, 55%).

$^1$H-NMR (CDCl$_3$) δ: 1.25 (3H, t, J=7.5 Hz), 3.08 (2H, q, J=7.5 Hz), 6.68 (1H, d, J=2.4 Hz), 6.95-7.02 (1H, m), 7.18-7.21 (2H, m), 7.43-7.50 (1H, m), 7.62-7.72 (2H, m), 7.16-7.97 (1H, m), 8.12-8.15 (2H, m), 9.91 (1H, s).

Reference Example 242

2-{[2-(2-Fluorophenyl)-4-formyl-1H-pyrrol-1-yl]sulfonyl}benzonitrile

To a solution (28 mL) of 5-(2-fluorophenyl)-1H-pyrrole-3-carbaldehyde (284 mg) in tetrahydrofuran was added sodium hydride (60% in oil, 181 mg) at room temperature and the mixture was stirred for 30 min. 15-Crown-5 (992 mg) was added dropwise and the mixture was stirred for 30 min, (2-cyanobenzene)sulfonyl chloride (606 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→2:3) to give the title compound as colorless crystals (yield 410 mg, 77%).

$^1$H-NMR (CDCl$_3$) δ: 6.70 (1H, d, J=1.7 Hz), 6.83-6.89 (1H, m), 7.08-7.18 (2H, m), 7.32-7.52 (3H, m), 7.70-7.75 (1H, m), 7.82-7.85 (1H, m), 8.39 (1H, d, J=1.7 Hz), 9.94 (1H, s).

Reference Example 243

4-{[2-(2-Fluorophenyl)-4-formyl-1H-pyrrol-1-yl]sulfonyl}benzonitrile

To a solution (28 mL) of 5-(2-fluorophenyl)-1H-pyrrole-3-carbaldehyde (284 mg) in tetrahydrofuran was added sodium hydride (60% in oil, 181 mg) at room temperature and the mixture was stirred for 30 min. 15-Crown-5 (992 mg) was added dropwise and the mixture was stirred for 30 min, (4-cyanobenzene)sulfonyl chloride (606 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→2:3) to give the title compound as colorless crystals (yield 420 mg, 79%).
$^1$H-NMR (CDCl$_3$) δ: 6.69 (1H, d, J=1.8 Hz), 6.98-7.04 (1H, m), 7.16-7.18 (2H, m), 7.42-7.49 (1H, m), 7.51-7.54 (2H, m), 7.67-7.71 (2H, m), 8.12 (1H, d, J=1.8 Hz), 9.90 (1H, s).

Reference Example 244

5-(2-Fluorophenyl)-1-[(2-fluorophenyl)sulfonyl]-1H-pyrrole-3-carbaldehyde

To a solution (25 mL) of 5-(2-fluorophenyl)-1H-pyrrole-3-carbaldehyde (250 mg) in tetrahydrofuran was added sodium hydride (60% in oil, 106 mg) at room temperature and the mixture was stirred for 30 min. 15-Crown-5 (583 mg) was added dropwise and the mixture was stirred for 30 min, (2-fluorobenzene)sulfonyl chloride (386 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→3:2) to give the title compound as colorless crystals (yield 360 mg, 78%).
$^1$H-NMR (CDCl$_3$) δ: 6.67 (1H, d, J=1.8 Hz), 6.86-6.92 (1H, m), 7.03-7.23 (5H, m), 7.33-7.41 (1H, m), 7.59-7.66 (1H, m), 8.21-8.22 (1H, m), 9.91 (1H, s).

Reference Example 245

5-(2-Fluorophenyl)-1-(pyridin-3-ylsulfonyl)-1H-pyrrole-3-carbaldehyde

To a solution (96 mL) of 5-(2-fluorophenyl)-1H-pyrrole-3-carbaldehyde (475 mg) in tetrahydrofuran was added sodium hydride (60% in oil, 503 mg) at room temperature and the mixture was stirred for 30 min. 15-Crown-5 (2.77 g) was added dropwise and the mixture was stirred for 30 min, pyridine-3-sulfonyl chloride hydrochloride (1.35 g) was added, and the mixture was further stirred for 3 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→2:3), and crystallized from diisopropyl ether-ethyl acetate (4:1) to give the title compound as colorless crystals (yield 680 mg, 82%).
$^1$H-NMR (CDCl$_3$) δ: 6.68 (1H, d, J=1.8 Hz), 6.99-7.05 (1H, m), 7.16-7.19 (2H, m), 7.35-7.39 (1H, m), 7.45-7.51 (1H, m), 7.69-7.73 (1H, m), 8.14 (1H, d, J=1.8 Hz), 8.58-8.59 (1H, m), 8.81-8.83 (1H, m), 9.91 (1H, s).

Reference Example 246

1-{[3-(Methylsulfonyl)phenyl]sulfonyl}-5-[2-(trifluoromethyl)phenyl]-1H-pyrrole-3-carbaldehyde To a solution (24 mL) of 5-[2-(trifluoromethyl)phenyl]-1H-pyrrole-3-carbaldehyde (240 mg) in tetrahydrofuran was added sodium hydride (60% in oil, 121 mg) at room temperature and the mixture was stirred for 30 min. 15-Crown-5 (663 mg) was added dropwise and the mixture was stirred for 30 min, [3-(methylsulfonyl)benzene]sulfonyl chloride (512 mg) was added, and the mixture was further stirred for 2 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=7:3→1:1) to give the title compound as colorless crystals (yield 340 mg, 74%).
$^1$H-NMR (CDCl$_3$) δ: 3.00 (3H, s), 6.68-6.68 (1H, m), 7.46-7.48 (1H, m), 7.59-7.70 (5H, m), 7.94-7.94 (1H, m), 8.14-8.18 (2H, m), 9.92 (1H, s)

Reference Example 247

1-(Pyridin-3-ylsulfonyl)-5-[2-(trifluoromethyl)phenyl]-1H-pyrrole-3-carbaldehyde To a solution (36 mL) of 5-[2-(trifluoromethyl)phenyl]-1H-pyrrole-3-carbaldehyde (240 mg) in tetrahydrofuran was added sodium hydride (60% in oil, 201 mg) at room temperature and the mixture was stirred for 30 min. 15-Crown-5 (1.11 g) was added dropwise and the mixture was stirred for 30 min. Pyridine-3-sulfonyl chloride hydrochloride (537 mg) was added, and the mixture was further stirred for 3 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→2:3) and crystallized from diisopropyl ether to give the title compound as colorless crystals (yield 380 mg, about 100%).
$^1$H-NMR (CDCl$_3$) δ: 6.69 (1H, d, J=1.8 Hz), 7.34-7.38 (1H, m), 7.44-7.48 (1H, m), 7.61-7.69 (4H, m), 8.16 (1H, d, J=1.8 Hz), 8.45 (1H, d, J=2.4 Hz), 8.81 (1H, m), 9.91 (1H, s).

Reference Example 248

5-(2-Methylphenyl)-1-{[3-(methylsulfonyl)phenyl]sulfonyl}-1H-pyrrole-3-carbaldehyde To a solution (30 mL) of 5-(2-methylphenyl)-1H-pyrrole-3-carbaldehyde (150 mg) in tetrahydrofuran was added sodium hydride (60% in oil, 98 mg) at room temperature and the mixture was stirred for 30 min. 15-Crown-5 (540 mg)

was added dropwise and the mixture was stirred for 30 min, [3-(methylsulfonyl)benzene]sulfonyl chloride (413 mg) was added, and the mixture was further stirred for 1 hr. 1 mol/L Hydrochloric acid was added to the reaction mixture, and the mixture was extracted with ethyl acetate. The extract was washed with saturated brine, dried over anhydrous magnesium sulfate, and concentrated under reduced pressure. The residue was crystallized from ethyl acetate-diisopropyl ether=1:4 to give the title compound as colorless crystals (yield 309 mg, 95%).

$^1$H-NMR (CDCl$_3$) δ:1.85(3H,s),3.03(3H,s),6.56(1H,d,J=1.8Hz),6.85-6.88(1H,m),7.09-7.18(2H,m),7.33-7.38(1H,m),7.57-7.65(2H,m),7.98-7.99(1H,m),8.14-8.18(2H,m),9.92(1H,s).

Reference Example 249

1-(Phenylsulfonyl)-5-(pyridin-2-yl)-1H-pyrrole-3-carbaldehyde

To a solution (16 mL) of 5-(pyridin-2-yl)-1H-pyrrole-3-carbaldehyde (80 mg) in tetrahydrofuran was added sodium hydride (60% in oil, 56 mg) at room temperature and the mixture was stirred for 30 min. 15-Crown-5 (307 mg) was added dropwise and the mixture was stirred for 30 min. Benzenesulfonyl chloride (165 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→1:1), and crystallized from diisopropyl ether to give the title compound as colorless crystals (yield 85 mg, 59%).

$^1$H-NMR (CDCl$_3$) δ:6.86(1H,d,J=1.8Hz),7.25-7.29(1H,m),7.50-7.55(3H,m),7.61-7.67(1H,m),7.70-7.76(1H,m),7.83-7.87(2H,m),8.17(1H,d,J=1.8Hz),8.43-8.46(1H,m),9.90(1H,s).

Reference Example 250

1-[(3,4-Difluorophenyl)sulfonyl]-5-(pyridin-2-yl)-1H-pyrrole-3-carbaldehyde

To a solution (16 mL) of 5-(pyridin-2-yl)-1H-pyrrole-3-carbaldehyde (80 mg) in tetrahydrofuran was added sodium hydride (60% in oil, 56 mg) at room temperature and the mixture was stirred for 30 min. 15-Crown-5 (307 mg) was added dropwise and the mixture was stirred for 30 min, 3,4-difluorobenzenesulfonyl chloride (198 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→1:1), and crystallized from diisopropyl ether to give the title compound as colorless crystals (yield 114 mg, 70%).

$^1$H-NMR (CDCl$_3$) δ:6.88(1H,d,J=1.8Hz),7.29-7.38(2H,m),7.51-7.55(1H,m),7.72-7.80(2H,m),7.85-7.92(1H,m),8.13(1H,d,J=1.8Hz),8.46-8.49(1H,m),9.90(1H,s).

Reference Example 251

1-(2,3-Dihydro-1,4-benzodioxin-5-ylsulfonyl)-4-methyl-5-phenyl-1H-pyrrole-3-carbaldehyde Using 4-methyl-5-phenyl-1H-pyrrole-3-carbaldehyde (185 mg), sodium hydride (60% in oil, 116 mg), 15-crown-5 (881 mg) and 2,3-dihydro-1,4-benzodioxine-5-sulfonyl chloride (516 mg), a procedure as in Reference Example 219 was performed to give the title compound as a pale-yellow amorphous (yield 295 mg, 77%).

$^1$H-NMR (CDCl$_3$) δ: 2.03 (3H, s), 4.22-4.31 (4H, m), 6.75-6.82 (3H, m), 7.04-7.07 (2H, m), 7.30-7.46 (3H, m), 8.00 (1H, s), 9.93 (1H, s).

Reference Example 252

1-[(2,5-Dimethoxyphenyl)sulfonyl]-4-methyl-5-phenyl-1H-pyrrole-3-carbaldehyde

Using 4-methyl-5-phenyl-1H-pyrrole-3-carbaldehyde (185 mg), sodium hydride (60% in oil, 72 mg), 15-crown-5 (330 mg) and 2,5-dimethoxybenzenesulfonyl chloride (355 mg), a procedure as in Reference Example 219 was performed to give the title compound as a pale-yellow powder (yield 330 mg, 86%).

$^1$H-NMR (CDCl$_3$) δ: 2.03 (3H, s), 3.51 (3H, s), 3.73 (3H, s), 6.56 (1H, d, J=3.0 Hz), 6.83-6.89 (3H, m), 7.02-7.06 (1H, m), 7.17-7.32 (3H, m), 8.11 (1H, s), 9.96 (1H, s).

Reference Example 253

1-(2,3-Dihydro-1,4-benzodioxin-6-ylsulfonyl)-4-methyl-5-phenyl-1H-pyrrole-3-carbaldehyde Using 4-methyl-5-phenyl-1H-pyrrole-3-carbaldehyde (185 mg), sodium hydride (60% in oil, 72 mg), 15-crown-5 (330 mg) and 2,3-dihydro-1,4-benzodioxine-6-sulfonyl chloride (352 mg), a procedure as in Reference Example 219 was performed to give the title compound as a pale-yellow oil (yield 391 mg, about 100%).

$^1$H-NMR (CDCl$_3$) δ: 2.03 (3H, s), 4.22-4.31 (4H, s), 6.72-6.82 (3H, m), 7.04-7.07 (2H, s), 7.30-7.43 (3H, s), 8.00 (1H, s), 9.94 (1H, s).

Reference Example 254

4-Methyl-1-{[3-(methylsulfonyl)phenyl]sulfonyl}-5-phenyl-1H-pyrrole-3-carbaldehyde Using 4-methyl-5-phenyl-1H-pyrrole-3-carbaldehyde (185 mg), sodium hydride (60% in oil, 60 mg), 15-crown-5 (0.30 mL) and [3-(methylsulfonyl)benzene]sulfonyl chloride (331 mg), a procedure as in Reference Example 219 was performed to give the title compound as a solid (yield 191 mg, 47%).

$^1$H-NMR (CDCl$_3$) δ: 2.03 (3H, s), 3.01 (3H, s), 7.01-7.04 (2H, m), 7.31-7.60 (5H, m), 7.92 (1H, m), 8.06 (1H, s), 8.12-8.14 (1H, m), 9.98 (1H, s).

Reference Example 255

4-Methyl-5-phenyl-1-(3-thienylsulfonyl)-1H-pyrrole-3-carbaldehyde

Using 4-methyl-5-phenyl-1H-pyrrole-3-carbaldehyde (185 mg), sodium hydride (60% in oil, 60 mg), 15-crown-5 (0.30 mL) and (3-thienyl)sulfonyl chloride (237 mg), a procedure as in Reference Example 219 was performed to give the title compound as a solid (yield 290 mg, 88%).

$^1$H-NMR (CDCl$_3$) δ: 2.04 (3H, s), 6.91-6.93 (1H, s), 7.06-7.09 (2H, m), 7.26-7.41 (5H, m), 8.03 (1H, s), 9.96 (1H, s).

Reference Example 256

4-Methyl-5-phenyl-1-(pyridin-3-ylsulfonyl)-1H-pyrrole-3-carbaldehyde

4-Methyl-5-phenyl-1H-pyrrole-3-carbaldehyde (185 mg) was dissolved in tetrahydrofuran (10 mL), sodium hydride (60% in oil, 60 mg) was added and the mixture was stirred at room temperature for 15 min. 15-Crown-5 (0.30 mL) was added and the mixture was further stirred at the same temperature for 15 min. 3-Pyridinesulfonyl chloride hydrochloride (231 mg) was added and the reaction mixture was stirred at room temperature for 1 hr. Water was added, and the mixture was extracted with ethyl acetate. The extract washed with water and saturated brine, dried over anhydrous magnesium sulfate, and concentrated under reduced pressure. The residue was purified by silica gel column chromatography (eluent: hexane-ethyl acetate=19:1→1:1) to give the title compound as a colorless solid (yield 172 mg, 53%).

$^1$H-NMR (CDCl$_3$) δ: 2.03 (3H, s), 7.01-7.04 (2H, m), 7.26-7.55 (5H, m), 8.07 (1H, s), 8.47 (1H, m), 8.75-8.78 (1H, m), 9.97 (1H, s).

Reference Example 257

4-Methyl-5-phenyl-1-(pyridin-2-ylsulfonyl)-1H-pyrrole-3-carbaldehyde

By a reaction under similar conditions as in Reference Example 256 and using 4-methyl-5-phenyl-1H-pyrrole-3-carbaldehyde (185 mg), sodium hydride (60% in oil, 60 mg), 15-crown-5 (0.30 mL) and 2-pyridinesulfonyl chloride (231 mg), the title compound was obtained as an amorphous form (yield 262 mg, 80%).

$^1$H-NMR (CDCl$_3$) δ: 2.03 (3H, s), 6.92-6.95 (2H, m), 7.21-7.49 (5H, m), 7.65-7.69 (1H, m), 8.14 (1H, s), 8.64-8.65 (1H, m), 9.98 (1H, s).

Reference Example 258

1-[(1,2-Dimethyl-1H-imidazol-4-yl)sulfonyl]-4-methyl-5-phenyl-1H-pyrrole-3-carbaldehyde By a reaction under similar conditions as in Reference Example 256 and using 4-methyl-5-phenyl-1H-pyrrole-3-carbaldehyde (185 mg), sodium hydride (60% in oil, 60 mg), 15-crown-5 (0.30 mL) and (1,2-dimethyl-1H-imidazol-4-yl)sulfonyl chloride (253 mg), the title compound was obtained as a colorless solid (yield 294 mg, 86%).

$^1$H-NMR (CDCl$_3$) δ: 2.05 (3H, s), 2.33 (3H, s), 3.40 (3H, s), 6.48 (1H, s), 7.11-7.14 (2H, m), 7.26-7.41 (3H, m), 8.08 (1H, s), 9.93 (1H, s).

Reference Example 259

1-[(5-Chloro-1,3-dimethyl-1H-pyrazol-4-yl)sulfonyl]-4-methyl-5-phenyl-1H-pyrrole-3-carbaldehyde By a reaction under similar conditions as in Reference Example 256 and using 4-methyl-5-phenyl-1H-pyrrole-3-carbaldehyde (185 mg), sodium hydride (60% in oil, 60 mg), 15-crown-5 (0.30 mL) and (5-chloro-1,3-dimethyl-1H-pyrazol-4-yl)sulfonyl chloride (298 mg), the title compound was obtained as an oil (yield 379 mg, about 100%).

$^1$H-NMR (CDCl$_3$) δ: 1.74 (3H, s), 2.04 (3H, s), 3.69 (3H, s), 7.04-7.07 (2H, m), 7.28-7.38 (3H, m), 8.09 (1H, s), 9.96 (1H, s).

Reference Example 260

1-[(2,4-Dimethyl-1,3-thiazol-5-yl)sulfonyl]-4-methyl-5-phenyl-1H-pyrrole-3-carbaldehyde By a reaction under similar conditions as in Reference Example 256 and using 4-methyl-5-phenyl-1H-pyrrole-3-carbaldehyde (185 mg), sodium hydride (60% in oil, 60 mg), 15-crown-5 (0.30 mL) and (2,4-dimethyl-1,3-thiazol-5-yl)sulfonyl chloride (275 mg), the title compound was obtained as an oil (yield 27.8 mg, 8%).

$^1$H-NMR (CDCl$_3$) δ: 2.05 (3H, s), 2.10 (3H, s), 2.59 (3H, s), 7.07-7.10 (2H, m), 7.31-7.40 (3H, m), 8.02 (1H, s), 9.96 (1H, s).

Reference Example 261

5-(2-Fluorophenyl)-4-methyl-1-(pyridin-3-ylsulfonyl)-1H-pyrrole-3-carbaldehyde

By a similar procedure as in Reference Example 256 and using 5-(2-fluorophenyl)-4-methyl-1H-pyrrole-3-carbaldehyde (301 mg), sodium hydride (60% in oil, 179 mg), 15-crown-5 (0.88 mL) and pyridin-3-ylsulfonyl chloride (476 mg), the title compound was obtained as white crystals (yield 440 mg, 87%).

$^1$H-NMR (CDCl$_3$) δ: 2.02 (3H, s), 6.98-7.04 (1H, m), 7.13-7.24 (2H, m), 7.33-7.38 (1H, m), 7.43-7.51 (1H, m), 7.65-7.69 (1H, m), 8.09 (1H, s), 8.54-8.55 (1H, m), 8.80-8.82 (1H, m), 9.98 (1H, s).

Reference Example 262

2-[(2-Bromo-4-formyl-1H-pyrrol-1-yl)sulfonyl]benzonitrile

Using 5-bromo-1H-pyrrole-3-carbaldehyde (801 mg), sodium hydride (60% in oil, 282 mg), 15-crown-5 (1.57 g) and (2-cyanobenzene)sulfonyl chloride (1.43 g), a procedure as in Reference Example 146 was performed to give the title compound as a white solid (yield 1.09 g, 70%).

$^1$H-NMR (CDCl$_3$) δ: 6.79 (1H, d, J=2.2 Hz), 7.85-7.96 (3H, m), 8.34 (1H, d, J=2.2 Hz), 8.44-8.49 (1H, m), 9.81 (1H, s).

Reference Example 263

2-Methyl-1H-pyrrole-3-carbaldehyde

To a solution of 2-methyl-1-(phenylsulfonyl)-1H-pyrrole-3-carbaldehyde (4.59 g) in tetrahydrofuran (20 mL) and methanol (5 mL) was added 8 mol/L aqueous sodium hydroxide solution (2.5 mL) at 0° C., and the reaction mixture was stirred at the same temperature for 30 min. Water was added to the reaction mixture, and the mixture was extracted with ethyl acetate. The extract was washed with saturated aqueous sodium hydrogencarbonate solution, water and saturated brine, dried over anhydrous sodium sulfate, filtered, and concentrated under reduced pressure. The residue was purified by silica gel column chromatography (eluent: hexane-ethyl acetate=2:1) to give the title compound as a white solid (yield 1.06 g, 54%).

¹H-NMR (CDCl₃) δ: 2.56 (3H, s), 6.58-6.59 (1H, m), 6.65-6.67 (1H, m), 8.52 (1H, brs), 9.89 (1H, s).

Reference Example 264

2-Methyl-1-(pyridin-3-ylsulfonyl)-1H-pyrrole-3-carbaldehyde

By a similar operation as in Reference Example 146 and using 2-methyl-1H-pyrrole-3-carbaldehyde (1.10 g), sodium hydride (60% in oil, 1.20 g), 15-crown-5 (6.0 mL) and pyridin-3-ylsulfonyl chloride (3.22 g), the title compound was obtained as white crystals (yield 1.10 g, 44%).
¹H-NMR (CDCl₃) δ: 2.66 (3H, s), 6.68 (1H, d, J=3.9 Hz), 7.34 (1H, d, J=3.9 Hz), 7.51-7.55 (1H, m), 8.09-8.13 (1H, m), 8.89-8.91 (1H, m), 9.10-9.11 (1H, m), 9.90 (1H, s).

Reference Example 265

5-Bromo-2-methyl-1-(phenylsulfonyl)-1H-pyrrole-3-carbaldehyde

To a solution of 2-methyl-1-(phenylsulfonyl)-1H-pyrrole-3-carbaldehyde (2.00 g) in N,N-dimethylformamide (20 mL) was added N-bromosuccinimide (1.56 g) at 0° C., and the mixture was stirred at room temperature for 1 hr. Water was added to the reaction mixture, and the mixture was extracted with ethyl acetate. The extract was washed with saturated aqueous sodium hydrogencarbonate solution, water and saturated brine, dried over anhydrous sodium sulfate, filtrated, and concentrated under reduced pressure. The residue was purified by silica gel column chromatography (eluent: hexane-ethyl acetate=3:1) to give the title compound as a white solid (yield 2.28 g, 86%).
¹H-NMR (CDCl₃) δ: 2.86 (3H, s), 6.68 (1H, s), 7.57-7.62 (2H, m), 7.68-7.73 (1H, m), 7.94-7.97 (2H, m), 9.90 (1H, s)

Reference Example 266

5-Bromo-2-methyl-1-(pyridin-3-ylsulfonyl)-1H-pyrrole-3-carbaldehyde

To a solution of 2-methyl-1-(pyridin-3-ylsulfonyl)-1H-pyrrole-3-carbaldehyde (974 mg) in N,N-dimethylformamide (10 mL) was added N-bromosuccinimide (1.17 g) at 0° C., and the mixture was stirred at room temperature for 1 hr. Water was added to the reaction mixture, and the mixture was extracted with ethyl acetate. The extract was washed with saturated aqueous sodium hydrogencarbonate solution, water and saturated brine, dried over anhydrous magnesium sulfate, filtered, and concentrated under reduced pressure. The residue was purified by silica gel column chromatography (eluent: hexane-ethyl acetate=2:1) to give the title compound as white crystals (yield 675 mg, 53%).
¹H-NMR (CDCl₃) δ: 2.89 (3H, s), 6.18 (1H, s), 7.53-7.57 (1H, m), 8.21-8.26 (1H, m), 8.91-8.93 (1H, m), 9.17-9.18 (1H, m), 9.92 (1H, s).

Reference Example 267

2-Methyl-1-(phenylsulfonyl)-5-(3-pyridyl)-1H-pyrrole-3-carbaldehyde

Under an argon atmosphere, a suspension of 5-bromo-2-methyl-1-(phenylsulfonyl)-1H-pyrrole-3-carbaldehyde (497 mg), 3-pyridineboronic acid (376 mg), sodium carbonate (481 mg) and tetrakis(triphenylphosphine)palladium (89.2 mg) in 1,2-dimethoxyethane (12 mL) and water (6 mL) was stirred at 80° C. for 1 hr. The reaction mixture was cooled to room temperature, water was added, and the mixture was extracted with ethyl acetate. The extract was washed with saturated aqueous sodium hydrogencarbonate solution, water and saturated brine, dried over anhydrous sodium sulfate, filtrated, and concentrated under reduced pressure. The residue was purified by silica gel column chromatography (eluent: hexane-ethyl acetate=1:4) to give the title compound as a white solid (yield 353 mg, 72%).
¹H-NMR (CDCl₃) δ: 2.89 (3H, s), 6.56 (1H, s), 7.24-7.33 (1H, m), 7.39-7.48 (4H, m), 7.59-7.65 (1H, m), 7.68-7.72 (1H, m), 8.32 (1H, d, J=2.1 Hz), 8.62 (1H, dd, J=1.5, 4.8 Hz), 10.02 (1H, s).

Reference Example 268

2-Methyl-5-(1-methyl-1H-pyrazol-4-yl)-1-(phenylsulfonyl)-1H-pyrrole-3-carbaldehyde Using 5-bromo-2-methyl-1-(phenylsulfonyl)-1H-pyrrole-3-carbaldehyde (497 mg), 1-methyl-4-(4,4,5,5-tetramethyl-1,3,2-dioxoboran-2-yl)-1H-pyrazole (630 mg), sodium carbonate (480 mg) and tetrakis(triphenylphosphine)palladium (88.3 mg), a procedure as in Reference Example 267 was performed to give the title compound as a white solid (yield 466 mg, 94%).
¹H-NMR (CDCl₃) δ: 2.90 (3H, s), 3.91 (3H, s), 6.45 (1H, s), 7.24 (1H, s), 7.35 (1H, s), 7.39-7.46 (4H, m), 7.56-7.61 (1H, m), 10.00 (1H, s).

Reference Example 269

4-Methyl-1-(phenylsulfonyl)-5-(3-thienyl)-1H-pyrrole-3-carbaldehyde

Under an argon atmosphere, a suspension of 5-bromo-4-methyl-1-(phenylsulfonyl)-1H-pyrrole-3-carbaldehyde (656 mg), 3-thiopheneboronic acid (511 mg), dichloro[bis(triphenylphosphine)]palladium (70 mg) and sodium carbonate (636 mg) in 1,2-dimethoxyethane (10 mL)-water (3 mL) was stirred at 100° C. for 2 hr. After cooling, the reaction mixture was filtered through celite, and celite was washed with ethyl acetate. The organic layer was separated from the filtrate, washed with water and saturated brine, dried over anhydrous magnesium sulfate, and concentrated under reduced pressure. The residue was purified by silica gel column chromatography (eluent: hexane-ethyl acetate=19:1→7:3) to give the title compound as a colorless oil (yield 549 mg, 83%).
¹H-NMR (CDCl₃) δ: 2.06 (3H, s), 6.85 (1H, m), 6.97 (1H, m), 7.26-7.37 (5H, m), 7.55-7.59 (1H, m), 8.06 (1H, s), 9.94 (1H, s).

Reference Example 270

1-[5-Bromo-1-(phenylsulfonyl)-1H-pyrrol-3-yl]-N-methylmethanamine

To a solution (60 mL) of 5-bromo-1-(phenylsulfonyl)-1H-pyrrole-3-carbaldehyde (3.5 g) in methanol were added methylammonium chloride (7.5 g) and sodium cyanoborohydride (2.4 g), and the mixture was stirred at room temperature for 1 hr. The reaction mixture was concentrated under reduced pressure, saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and concentrated under reduced pressure to give the title compound as a brown oil (yield 4.4 g, about 100%).

$^1$H-NMR (CDCl$_3$) δ: 2.47 (3H, s), 2.98 (1H, brs), 3.66 (2H, s), 6.35 (1H, d, J=2.4 Hz), 7.51-7.57 (3H, m), 7.61-7.68 (1H, m), 7.93-7.97 (2H, m).

Reference Example 271

1-[5-Bromo-4-isopropyl-1-(phenylsulfonyl)-1H-pyrrol-3-yl]-N-methylmethanamine

Using methyl 5-bromo-4-isopropyl-1-(phenylsulfonyl)-1H-pyrrole-3-carboxylate (4.8 g), and a 1.5 mol/L solution (50 mL) of diisobutylaluminum hydride in toluene, tetra-n-propylammonium perruthenate (218 mg), N-methylmorpholine N-oxide (1.6 g) and molecular sieves 4 A powder (2.5 g), a procedure as in Reference Example 6 was performed to give crude 5-bromo-4-isopropyl-1-(phenylsulfonyl)-1H-pyrrole-3-carbaldehyde (3.83 g) as an oil. Furthermore, using 40% methylamine methanol solution (877 mg), sodium borohydride (474 mg) and crude 5-bromo-4-isopropyl-1-(phenylsulfonyl)-1H-pyrrole-3-carbaldehyde (3.83 g), a procedure as in Reference Example 66 was performed to give the title compound as a colorless oil (yield 502 mg, 11%).

$^1$H-NMR (CDCl$_3$) δ: 1.18 (6H, d, J=7.2 Hz), 1.50 (1H, br), 2.48 (3H, s), 2.87-2.96 (1H, m), 3.62 (2H, s), 7.43 (1H, s), 7.49-7.54 (2H, m), 7.60-7.64 (1H, m), 7.88-7.92 (2H, m).

Reference Example 272 tert-Butyl {[5-bromo-1-(phenylsulfonyl)-1H-pyrrol-3-yl]methyl}methylcarbamate

To a solution of 1-[5-bromo-1-(phenylsulfonyl)-1H-pyrrol-3-yl]-N-methylmethanamine (4.4 g) in ethyl acetate (60 mL) was added di-tert-butyl bicarbonate (2.8 mL), and the mixture was stirred at room temperature for 14 hr. Saturated aqueous sodium hydrogencarbonate solution was added to the reaction mixture, and the mixture was extracted with ethyl acetate. The extract was washed with aqueous sodium hydrogencarbonate solution and saturated brine, dried over anhydrous sodium sulfate, and concentrated under reduced pressure. The residue was purified by silica gel column chromatography (eluent: hexane-ethyl acetate=4:1) to give the title compound as a colorless oil (yield 3.4 g, 73%).

$^1$H-NMR (CDCl$_3$) δ: 1.48 (9H, s), 2.79 (3H, brs), 4.17 (2H, brs), 6.24 (1H, brs), 7.35 (1H, brs), 7.51-7.57 (2H, m), 7.62-7.68 (1H, m), 7.90-7.94 (2H, m).

Reference Example 273 tert-Butyl {[5-bromo-1-(2-cyanophenyl)sulfonyl-1H-pyrrol-3-yl]methyl}methylcarbamate To a solution of 2-[(2-bromo-4-formyl-1H-pyrrol-1-yl)sulfonyl]benzonitrile (1.18 g) in tetrahydrofuran (10 mL) and methanol (10 mL) was added 40% methylamine methanol solution (3 mL), and the reaction mixture was stirred at room temperature for 1 hr. Sodium borohydride (152 mg) was added to the reaction mixture and the mixture was further stirred for 15 min. The mixture was concentrated under reduced pressure. Water (50 mL) was added to the residue, and the mixture was extracted with ethyl acetate. The extract was washed with saturated aqueous sodium hydrogencarbonate solution, water and saturated brine, dried over anhydrous sodium sulfate, filtrated and the filtrate was concentrated under reduced pressure. The residue was dissolved in ethyl acetate (10 mL), di-tert-butyl dicarbonate (0.8 mL) was added, and the mixture was stirred at room temperature for 2 days. Water (100 mL) was added to the reaction mixture, and the mixture was extracted with ethyl acetate. The extract was washed with saturated aqueous sodium hydrogencarbonate solution, water and saturated brine, filtrated, and the filtrate was concentrated under reduced pressure. The residue was purified by silica gel column chromatography (eluent: hexane-ethyl acetate=2:1) to give the title compound as a yellow oil (yield 296 mg, 38%).

$^1$H-NMR (CDCl$_3$) δ: 1.48 (9H, s), 2.81 (3H, brs), 4.21 (2H, brs), 6.32 (1H, brs), 7.62 (1H, s), 7.76-7.89 (3H, m), 8.3-8.39 (1H, m).

Reference Example 274 tert-Butyl [(5-bromo-1-{[3-(methylsulfonyl)phenyl]sulfonyl}-1H-pyrrol-3-yl)methyl]carbamate Using 5-bromo-1-{3-(methylsulfonyl)phenyl]sulfonyl}-1H-pyrrole-3-carbaldehyde (4.88 g), a procedure as in Reference Example 273 was performed to give the title compound as a yellow oil (yield 0.96 g, 27%).

$^1$H-NMR (CDCl$_3$) δ: 1.47 (9H, s), 2.80 (3H, s), 3.10 (3H, s), 4.18 (2H, brs), 6.28 (1H, brs), 7.35 (1H, d, J=1.8 Hz), 7.79 (1H, t, J=7.8 Hz), 8.18-8.24 (2H, m), 8.51-8.52 (1H, m).

Reference Example 275 tert-Butyl {[5-bromo-4-ethyl-1-(phenylsulfonyl)-1H-pyrrol-3-yl]methyl}methylcarbamate Using 5-bromo-4-ethyl-1-(phenylsulfonyl)-1H-pyrrole-3-carbaldehyde (1.91 g), a procedure as in Reference Example 273 was performed to give the title compound as a brown oil (yield 1.13 g, 44%).

$^1$H-NMR (CDCl$_3$) δ: 0.96 (3H, brt, J=7.5 Hz), 1.49 (9H, s), 2.32 (2H, q, J=7.5 Hz), 2.74 (3H, brs), 4.26 (2H, brs), 7.35 (1H, s), 7.50-7.55 (2H, m), 7.61-7.64 (1H, m), 7.88-7.91 (2H, m).

Reference Example 276 tert-Butyl {[5-bromo-4-isopropyl-1-(phenylsulfonyl)-1H-pyrrol-3-yl]methyl}methylcarbamate Using 1-[5-bromo-4-isopropyl-1-(phenylsulfonyl)-1H-pyrrol-3-yl]-N-methylmethanamine (502 mg) and di-tert-butyl bicarbonate (442 mg), a procedure as in Reference Example 55 was performed to give the title compound as a colorless oil (yield 596 mg, 94%).

$^1$H-NMR (CDCl$_3$) δ: 1.15 (6H, d, J=7.2 Hz), 1.47 (9H, brs), 2.80 (3H, brs), 2.88-2.95 (1H, m), 4.30 (2H, brs), 7.30 (1H, s), 7.49-7.56 (2H, m), 7.61-7.66 (1H, m), 7.87-7.90 (2H, m).

Reference Example 277 tert-Butyl {[4-ethyl-5-phenyl-1-(phenylsulfonyl)-1H-pyrrol-3-yl]methyl}methylcarbamate Using tert-butyl {[5-bromo-4-ethyl-1-(phenylsulfonyl)-1H-pyrrol-3-yl]methyl}methylcarbamate (1.13 g), phenylboronic acid (462 mg), sodium carbonate (789 mg) and tetrakis(triphenylphosphine)palladium (431 mg), a procedure as in Reference Example 56 was performed to give the title compound as a brown oil (yield 602 mg, 54%).

$^1$H-NMR (CDCl$_3$) δ: 0.84 (3H, brt, J=7.5 Hz), 1.49 (9H, s), 2.15 (2H, q, J=7.5 Hz), 2.82 (3H, s), 4.32 (2H, brs), 7.01-7.04 (2H, m), 7.26-7.36 (8H, m), 7.48-7.52 (1H, m).

Reference Example 278 tert-Butyl {[4-isopropyl-5-phenyl-1-(phenylsulfonyl)-1H-pyrrol-3-yl]methyl}methylcarbamate Using tert-butyl {[5-bromo-4-isopropyl-1-(phenylsulfonyl)-1H-pyrrol-3-yl]methyl}methylcarbamate (596 mg), phenylboronic acid (307 mg), tetrakis(triphenylphosphine)palladium (218 mg) and sodium carbonate (401 mg), a procedure as in Reference Example 56 was performed to give the title compound as a pale-red oil (yield 218 mg, 37%).

$^1$H-NMR (CDCl$_3$) δ: 0.96 (6H, d, J=7.2 Hz), 1.50 (9H, brs), 2.55-2.65 (1H, m), 2.89 (3H, s), 4.39 (2H, br), 6.90-7.00 (2H, m), 7.19-7.36 (8H, m), 7.49-7.53 (1H, m).

Reference Example 279

Methyl 2-[(4-{[(tert-butoxycarbonyl)(methyl)amino]methyl}-2-phenyl-1H-pyrrol-1-yl)sulfonyl]benzoate Using methyl 2-({4-[(methylamino)methyl]-2-phenyl-1H-pyrrol-1-yl}sulfonyl)benzoate (367 mg) and di-tert-butyl dicarbonate (250 mg), a procedure as in Reference Example 55 was performed to give the title compound as a colorless oil (yield 524 mg, about 100%).

$^1$H-NMR (CDCl$_3$) δ: 1.47 (9H, s), 2.85 (3H, s), 3.88 (3H, s), 4.27 (2H, br), 6.15 (1H, brs), 6.98-7.01 (1H, s), 7.17-7.32 (7H, m), 7.50-7.52 (2H, m).

Reference Example 280

Methyl 3-[(4-{[(tert-butoxycarbonyl)(methyl)amino]methyl}-2-phenyl-1H-pyrrol-1-yl)sulfonyl]benzoate Using methyl 3-({4-[(methylamino)methyl]-2-phenyl-1H-pyrrol-1-yl}sulfonyl)benzoate (577 mg) and di-tert-butyl dicarbonate (393 mg), a procedure as in Reference Example 55 was performed to give the title compound as a colorless oil (yield 710 mg, 98%).

$^1$H-NMR (CDCl$_3$) δ: 1.46 (9H, s), 2.80 (3H, s), 3.91 (3H, s), 4.22 (2H, brs), 6.10 (1H, brs), 7.19-7.23 (2H, m), 7.27-7.50 (6H, m), 7.97-7.98 (1H, m), 8.15-8.18 (1H, m).

Reference Example 281

2-[(4-{[(tert-Butoxycarbonyl)(methyl)amino]methyl}-2-phenyl-1H-pyrrol-1-yl)sulfonyl]benzoic acid Methyl 2-[(4-{[(tert-butoxycarbonyl)(methyl)amino]methyl}-2-phenyl-1H-pyrrol-1-yl)sulfonyl]benzoate (524 mg) was dissolved in tetrahydrofuran (5 mL) and methanol (3 mL), and 1 mol/L aqueous sodium hydroxide solution (3 mL) was added at 0° C. The mixture was stirred at 0° C. for 1 hr, and at room temperature for 16 hr, cooled again to 0° C., acidified with 1 mol/L hydrochloric acid, and the mixture was extracted with ethyl acetate. The extract was washed with water and saturated brine, dried over anhydrous magnesium sulfate and the solvent was evaporated under reduced pressure. The residue was purified by silica gel column chromatography (eluent: hexane-ethyl acetate=1:1→0:1) to give the title compound as a colorless amorphous (yield 256 mg, 50%).

$^1$H-NMR (CDCl$_3$) δ: 1.53 (9H, brs), 3.08 (3H, brs), 4.27 (2H, brs), 6.06 (1H, br), 7.00-7.52 (10H, m), 1H not detected.

Reference Example 282

3-[(4-{[(tert-Butoxycarbonyl)(methyl)amino]methyl}-2-phenyl-1H-pyrrol-1-yl)sulfonyl]benzoic acid Methyl 3-[(4-{[(tert-butoxycarbonyl)(methyl)amino]methyl}-2-phenyl-1H-pyrrol-1-yl)sulfonyl]benzoate (710 mg) was dissolved in tetrahydrofuran (5 mL) and methanol (3 mL), and 1 mol/L aqueous sodium hydroxide solution (3 mL) was added at 0° C. The mixture was stirred at 0° C. for 1 hr, and at room temperature for 2 hr, cooled again to 0° C., acidified with 1 mol/L hydrochloric acid, and the mixture was extracted with ethyl acetate. The extract was washed with water and saturated brine, dried over anhydrous magnesium sulfate and the solvent was evaporated under reduced pressure. The residual crystals were washed with a mixed solvent of isopropyl ether and hexane to give the title compound as colorless crystals (yield 577 mg, 83%).

$^1$H-NMR (CDCl$_3$) δ: 1.46 (9H, s), 2.81 (3H, brs), 4.22 (2H, br), 6.11 (1H, br), 7.16-7.52 (8H, m), 8.03 (1H, br), 8.19-8.22 (1H, m), 1H not detected.

Reference Example 283 tert-Butyl [(1-{[3-(aminocarbonyl)phenyl]sulfonyl}-5-phenyl-1H-pyrrol-3-yl)methyl]methylcarbamate To a solution (5 mL) of 3-[(4-{[(tert-butoxycarbonyl)(methyl)amino]methyl}-2-phenyl-1H-pyrrol-1-yl)sulfonyl]benzoic acid (205 mg) in N,N-dimethylformamide were added 1-ethyl-3-(3-dimethylaminopropyl)-carbodiimide hydrochloride (125 mg) and 1-hydroxy-1H-benzotriazole ammonium salt (100 mg) at room temperature. The mixture was stirred at the same temperature for 1 hr, water was added and the mixture was extracted with ethyl acetate. The extract was washed with water and saturated brine, dried over anhydrous sodium sulfate, and the solvent was evaporated under reduced pressure. The residue was purified by silica gel column chromatography (eluent: hexane-ethyl acetate=4:1→1:1→1:4) to give the title compound as a colorless oil (yield 193 mg, 94%).

$^1$H-NMR (CDCl$_3$) δ: 1.47 (9H, s), 2.85 (3H, brs), 4.23 (2H, brs), 5.61 (1H, br), 6.10 (1H, d, J=1.8 Hz), 7.21-7.51 (9H, m), 8.07 (1H, d, J=7.5 Hz), 1H not detected.

Reference Example 284 tert-Butyl {[1-({3-[(cyclopropylamino)carbonyl]phenyl}sulfonyl)-5-phenyl-1H-pyrrol-3-yl]methyl}methylcarbamate To a solution (5 mL) of 3-[(4-{[(tert-butoxycarbonyl)(methyl)amino]methyl}-2-phenyl-1H-pyrrol-1-yl)sulfonyl]benzoic acid (150 mg) in N,N-dimethylformamide were added 1-ethyl-3-(3-dimethylaminopropyl)-carbodiimide hydrochloride (92 mg), 1-hydroxy-1H-benzotriazole (73 mg) and cyclopropylamine (27 mg) at room temperature.

After stirring at the same temperature for 30 min, water was added and the mixture was extracted with ethyl acetate. The extract was washed with water and saturated brine, dried over anhydrous sodium sulfate, and the solvent was evaporated under reduced pressure. The residue was purified by silica gel column chromatography (eluent: hexane-ethyl acetate=9:1→4:1) to give the title compound as a colorless amorphous (yield 162 mg, quantitative).

$^1$H-NMR (CDCl$_3$) δ: 0.60-0.64 (2H, m), 0.86-0.95 (2H, m), 1.46 (9H, s), 2.81 (3H, s), 2.80-2.90 (1H, m), 4.22 (2H, m), 5.90 (1H, br), 6.09 (1H, d, J=1.5 Hz), 7.21-7.52 (9H, m), 8.03 (1H, d, J=7.2 Hz).

Reference Example 285 tert-Butyl methyl{[1-({3-[(methylamino)carbonyl]phenyl}sulfonyl)-5-phenyl-1H-pyrrol-3-yl]methyl}carbamate Using 3-[(4-{[(tert-butoxycarbonyl)(methyl)amino]methyl}-2-phenyl-1H-pyrrol-1-yl)sulfonyl]benzoic acid (150 mg) and 2 mol/L methylamine-tetrahydrofuran solution (5 mL), a procedure as in Reference Example 284 was performed to give the title compound as a colorless oil (yield 99 mg, 64%).

$^1$H-NMR (CDCl$_3$) δ: 1.47 (9H, brs), 2.84 (3H, brs), 2.97 (3H, d, J=4.5 Hz), 4.22 (2H, brs), 6.09 (1H, d, J=1.8 Hz), 7.21-7.44 (10H, m), 8.03 (1H, br).

Reference Example 286 tert-Butyl {[1-({3-[(dimethylamino)carbonyl]phenyl}sulfonyl)-5-phenyl-1H-pyrrol-3-yl]methyl}methylcarbamate To a suspension (3 mL) of sodium hydride (60% in oil, 36 mg) in tetrahydrofuran was added a solution (2 mL) of tert-butyl methyl{[1-({3-[(methylamino)carbonyl]phenyl}sulfonyl)-5-phenyl-1H-pyrrol-3-yl]methyl}carbamate (240 mg) in N,N-dimethylformamide at room temperature. After stirring at the same temperature for 15 min, iodomethane (106 mg) was added, and the mixture was stirred for 30 min. Water was added to the reaction mixture, and the mixture was extracted with ethyl acetate. The extract washed with saturated brine, dried over anhydrous sodium sulfate, and concentrated under reduced pressure. The residue was purified by silica gel column chromatography (eluent: hexane-ethyl acetate=4:1→1:1) to give the title compound as a colorless oil (yield 168 mg, 68%).

$^1$H-NMR (CDCl$_3$) δ: 1.47 (9H, s), 2.81 (6H, brs), 3.08 (3H, brs), 4.22 (2H, brs), 6.11 (1H, br), 7.22-7.39 (9H, m), 7.58-7.61 (1H, m).

Reference Example 287 tert-Butyl methyl[(1-{[3-(morpholin-4-ylcarbonyl)phenyl]sulfonyl}-5-phenyl-1H-pyrrol-3-yl)methyl]carbamate Using 3-[(4-{[(tert-butoxycarbonyl)(methyl)amino]methyl}-2-phenyl-1H-pyrrol-1-yl)sulfonyl]benzoic acid (150 mg) and morpholine (42 mg), a procedure as in Reference Example 284 was performed to give the title compound as a colorless oil (yield 164 mg, 95%).

$^1$H-NMR (CDCl$_3$) δ: 1.47 (9H, s), 2.81 (3H, brs), 3.21 (2H, br), 3.57 (2H, br), 3.73 (4H, br), 4.22 (2H, br), 6.12 (1H, br), 7.23-7.43 (9H, m), 7.58-7.61 (1H, m).

Reference Example 288 tert-Butyl [(1-{[3-(1-hydroxy-1-methylethyl)phenyl]sulfonyl}-5-phenyl-1H-pyrrol-3-yl)methyl]carbamate To a solution of methyl 3-[(4-{[(tert-butoxycarbonyl)(methyl)amino]methyl}-2-phenyl-1H-pyrrol-1-yl)sulfonyl]benzoate (513 mg) in tetrahydrofuran (5 mL) was added an about 1 mol/L solution (4.5 mL) of methyllithium in diethyl ether at −78° C., and the mixture was stirred at the same temperature for 1 hr. Water (20 mL) was added to the reaction mixture, and the mixture was extracted with ethyl acetate. The extract was washed with water and saturated brine, and dried over anhydrous magnesium sulfate. The mixture was filtrated, and the filtrate was concentrated under reduced pressure. The residue was purified by silica gel column chromatography (eluent: hexane-ethyl acetate=2:1) to give the title compound as a yellow oil (yield 337 mg, 66%).

$^1$H-NMR (CDCl$_3$) δ: 1.46 (9H, s), 1.58 (6H, s), 1.89 (1H, brs), 2.80 (3H, s), 4.23 (2H, brs), 6.09 (1H, d, J=2.1 Hz), 7.22-7.38 (8H, m), 7.42-7.43 (1H, m), 7.60-7.63 (1H, m).

Reference Example 289 tert-Butyl ({1-[(4-cyano-3-fluorophenyl)sulfonyl]-5-phenyl-1H-pyrrol-3-yl}methyl)carbamate Using 2-fluoro-4-[(4-formyl-2-phenyl-1H-pyrrol-1-yl)sulfonyl]benzonitrile (223 mg), a procedure as in Reference Example 273 was performed to give the title compound as a yellow oil (yield 57.3 mg, 24%).

$^1$H-NMR (CDCl$_3$) δ: 1.47 (9H, s), 2.83 (3H, s), 4.23 (2H, brs), 6.17 (1H, s), 7.08-7.11 (1H, m), 7.19-7.23 (3H, m), 7.26-7.27 (1H, m), 7.32-7.42 (3H, m), 7.57-7.61 (1H, m).

Reference Example 290 tert-Butyl ({1-[(3-cyanophenyl)sulfonyl]-5-phenyl-1H-pyrrol-3-yl}methyl)methylcarbamate To a solution (16 mL) of 3-([(methylamino)methyl-2-phenyl-1H-pyrrol-1-yl]sulfonyl)benzonitrile (0.23 g) in ethyl acetate was added di-tert-butyl bicarbonate (0.19 g), and the mixture was stirred at room temperature for 16 hr. The reaction mixture was diluted with ethyl acetate, washed successively with saturated aqueous sodium hydrogencarbonate solution and saturated brine, dried over anhydrous magnesium sulfate, and concentrated under reduced pressure. The residue was purified by silica gel column chromatography (eluent: hexane-ethyl acetate=4:1→2:1) to give the title compound as an oil (yield 0.30 g, about 100%).

$^1$H-NMR (CDCl$_3$) δ: 1.47 (9H, s), 2.83 (3H, s), 4.23 (2H, brs), 6.14 (1H, s), 7.16-7.22 (2H, m), 7.29-7.38 (3H, m), 7.40-7.49 (3H, m), 7.55 (1H, ddd, J=1.41, 1.55, 8.15 Hz), 7.77 (1H, dt, J=1.37, 7.63 Hz).

Reference Example 291 tert-Butyl methyl[(5-phenyl-1-{[3-(1H-tetrazol-5-yl)phenyl]sulfonyl}-1H-pyrrol-3-yl)methyl]carbamate A mixture of tert-butyl ({1-[(3-Cyanophenyl)sulfonyl]-5-phenyl-1H-pyrrol-3-yl}methyl)methylcarbamate (0.29 g), sodium azide (70 mg), triethylamine hydrochloride (0.19 g) and toluene (10 ml) was heated under reflux for 7 days. After cooling the reaction mixture, ethyl acetate was added to the mixture, and the mixture washed with saturated brine, dried over anhydrous magnesium sulfate, and concentrated under reduced pressure. The residue was purified by silica gel column chromatography (eluent: ethyl acetate-methanol=10:1) to give the title compound as an oil (yield 0.052 g, 16%).

$^1$H-NMR (CDCl$_3$) δ: 1.55 (9H, s), 3.04 (3H, s), 4.28 (2H, s), 6.04 (1H, s), 7.14 (2H, s), 7.23-7.35 (6H, m), 7.44 (1H, t, J=7.9 Hz), 7.85 (1H, s), 8.39 (1H, s).

Reference Example 292 tert-Butyl [(5-bromo-1H-pyrrol-3-yl)methyl]methylcarbamate tert-Butyl {[5-bromo-1-(phenylsulfonyl)-1H-pyrrol-3-yl]methyl}methylcarbamate (1.0 g) was dissolved in a mixed solvent of tetrahydrofuran (15 mL) and methanol (5 mL), and 8 mol/L aqueous sodium hydroxide solution (1.5 mL) was added dropwise at not more than 10° C. After stirring at the same temperature for 4 hr, water was added to the residue and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=9:1→4:1) to give the title compound as a pale-yellow oil (yield 410 mg, 61%).

$^1$H-NMR (CDCl$_3$) δ: 1.48 (9H, s), 2.79 (3H, s), 4.17 (2H, s), 6.09 (1H, brs), 6.64 (1H, brs), 8.07 (1H, br).

Reference Example 293 tert-Butyl {[5-bromo-1-(pyridin-3-ylsulfonyl)-1H-pyrrol-3-yl]methyl}methylcarbamate A solution (3 mL) of tert-butyl [(5-bromo-1H-pyrrol-3-yl)methyl]methylcarbamate (410 mg) in N,N-dimethylformamide was added to a suspension (10 mL) of sodium hydride (60% in oil, 204 mg) in tetrahydrofuran at 0° C., 15-crown-5 (938 mg) and pyridin-3-ylsulfonyl chloride hydrochloride (456 mg) were added at the same temperature. After stirring at room temperature for 2 hr, water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent: hexane-ethyl acetate=8:1→3:1) to give the title compound as a pale-yellow powder (yield 522 mg, 85%).

$^1$H-NMR (CDCl$_3$) δ: 1.47 (9H, s), 2.80 (3H, brs), 4.18 (2H, brs), 6.28 (1H, brs), 7.35 (1H, brs), 7.48-7.52 (1H, m), 8.18-8.22 (1H, m), 8.85-8.88 (1H, m), 9.12-9.13 (1H, m).

Reference Example 294 tert-Butyl {[(2-cyanophenyl)sulfonyl-5-(3-pyridyl)-1H-pyrrol-3-yl]methyl}methylcarbamate Using tert-butyl {[5-bromo-1-(2-cyanophenyl)sulfonyl-1H-pyrrol-3-yl]methyl}methylcarbamate (296 mg), 3-pyridineboronic acid (162 mg), sodium carbonate (208 mg) and tetrakis(triphenylphosphine)palladium (38.2 mg), a procedure as in Reference Example 267 was performed to give the title compound as a white solid (yield 187 mg, 63%).

$^1$H-NMR (CDCl$_3$) δ: 1.47 (9H, s), 2.86 (3H, s), 4.28 (2H, brs), 6.25 (1H, brs), 7.24-7.31 (2H, m), 7.45-7.51 (1H, m), 7.62-7.79 (4H, m), 8.15 (1H, d, J=1.8 hz), 8.57-8.59 (1H, m).

Reference Example 295 tert-Butyl methyl[(1-{[3-(methylsulfonyl)phenyl]sulfonyl}-5-(3-thienyl)-1H-pyrrol-3-yl)methyl]carbamate Using tert-butyl [(5-bromo-1-{[3-(methylsulfonyl)phenyl]sulfonyl}-1H-pyrrol-3-yl)methyl]methylcarbamate (437 mg), 3-thiopheneboronic acid (223 mg), sodium carbonate (275 mg) and tetrakis(triphenylphosphine)palladium (50.8 mg), a procedure as in Reference Example 267 was performed to give the title compound as a white solid (yield 305 mg, 69%).

$^1$H-NMR (CDCl$_3$) δ: 1.47 (9H, s), 2.82 (3H, s), 3.00 (3H, s), 4.22 (2H, brs), 6.18 (1H, brs), 7.05-7.07 (1H, m), 7.19-7.20 (1H, m), 7.26-7.31 (2H, m), 7.55-7.61 (2H, m), 7.95-7.96 (1H, m), 8.06-8.09 (1H, m).

Reference Example 296 tert-Butyl [(1-{[3-(methylsulfonyl)phenyl]sulfonyl}-5-(3-pyridyl)-1H-pyrrol-3-yl)methyl]methylcarbamate Using tert-butyl [(5-bromo-1-{[3-(methylsulfonyl)phenyl]sulfonyl}-1H-pyrrol-3-yl)methyl]methylcarbamate (459 mg), 3-pyridineboronic acid (222 mg), sodium carbonate (287 mg) and tetrakis(triphenylphosphine)palladium (53.1 mg), a procedure as in Reference Example 267 was performed to give the title compound as a white solid (yield 305 mg, 67%).

$^1$H-NMR (CDCl$_3$) δ: 1.47 (9H, s), 2.82 (3H, s), 3.04 (3H, s), 4.24 (2H, brs), 6.22 (1H, brs), 7.36-7.39 (2H, m), 7.61-7.64 (2H, m), 7.75-7.79 (1H, m), 7.86 (1H, s), 8.09-8.13 (1H, m), 8.26-8.27 (1H, m), 8.62-8.64 (1H, m).

Reference Example 297 tert-Butyl {[1-(2-chloro-3-pyridinesulfonyl)-5-phenyl-1H-pyrrol-3-yl]methyl}methylcarbamate 1-(2-Chloro-3-pyridinesulfonyl)-5-phenyl-1H-pyrrole-3-carbaldehyde (443 mg) was dissolved in absolute tetrahydrofuran (5 mL), a 2 mol/L solution (0.74 mL) of methylamine in tetrahydrofuran was added, and the mixture was stirred at room temperature for 30 min. The reaction mixture was added to a solution of sodium borohydride (97 mg) in methanol (2.5 mL), and the mixture was stirred at the same temperature for 20 min. The reaction mixture was diluted with ethyl acetate, washed successively with saturated aqueous sodium hydrogencarbonate solution, water and saturated brine and dried over anhydrous magnesium sulfate, and the solvent was evaporated under reduced pressure. The residue was dissolved in tetrahydrofuran (20 mL), di-tert-butyl bicarbonate (1.40 g), sodium hydrogencarbonate (0.54 g) and water (13 mL) were added, and the mixture was stirred at room temperature for 20 min. The reaction mixture was diluted with ethyl acetate, washed successively with saturated aqueous sodium hydrogencarbonate solution, water and saturated brine and dried over anhydrous magnesium sulfate, and the solvent was evaporated under reduced pressure. The residue was purified by silica gel column chromatography (eluent: hexane-ethyl acetate=19:1→3:1) to give the title compound as a solid (yield 361 mg, 61%).

¹H-NMR (CDCl₃) δ: 1.47 (9H, s), 2.87 (3H, s), 4.29 (2H, s), 6.30-6.32 (1H, m), 6.95-7.00 (1H, m), 7.06-7.33 (5H, m), 7.51-7.56 (2H, m), 8.38-8.41 (1H, m).

Reference Example 298 tert-Butyl {[1-(6-chloro-5-methyl-3-pyridinesulfonyl)-5-phenyl-1H-pyrrol-3-yl]methyl}methylcarbamate 1-[(6-Chloro-5-methylpyridin-3-yl)sulfonyl]-5-phenyl-1H-pyrrole-3-carbaldehyde (244 mg) was dissolved in absolute tetrahydrofuran (6.8 mL), a 2 mol/L solution (0.34 mL) of methylamine in tetrahydrofuran was added, and the mixture was stirred at room temperature for 4 hr. The reaction mixture was added to a solution of sodium borohydride (51 mg) in methanol (3 mL), and the mixture was stirred at the same temperature for 3 min. di-tert-Butyl bicarbonate (654 mg) was added, and water (5 mL) and sodium hydrogencarbonate (420 mg) were added 3 min later. The mixture was further stirred at room temperature for 30 min, water was added to the reaction mixture, and the mixture was extracted with ethyl acetate. The extract was washed with saturated brine, dried over anhydrous magnesium sulfate, and the solvent was evaporated under reduced pressure. The residue was purified by silica gel column chromatography (eluent: hexane-ethyl acetate=19:1→3:1) to give the title compound as an oil (yield 247 mg, 77%).

¹H-NMR (CDCl₃) δ: 1.47 (9H, s), 2.28 (3H, s), 2.82 (3H, s), 4.24-4.28 (2H, m), 6.15 (1H, s), 7.23-7.42 (7H, m), 8.15 (1H, s).

Reference Example 299 tert-Butyl ({[1-(6-chloropyridin-3-yl)sulfonyl]-5-phenyl-1H-pyrrol-3-yl}methyl)methylcarbamate 1-[(6-Chloropyridin-3-yl)sulfonyl]-5-phenyl-1H-pyrrole-3-carbaldehyde (1.27 g) was dissolved in absolute tetrahydrofuran (20 mL), a 2 mol/L solution (2.1 mL) of methylamine in tetrahydrofuran was added, and the mixture was stirred at room temperature for 30 min. The reaction mixture was added to a solution of sodium borohydride (277 mg) in methanol (10 mL), and the mixture was stirred at the same temperature for 20 min. The reaction mixture was diluted with ethyl acetate, washed successively with saturated aqueous sodium hydrogencarbonate solution, water and saturated brine and dried over anhydrous magnesium sulfate. di-tert-Butyl bicarbonate (3.99 g) was added, and the solvent was evaporated under reduced pressure. The residue was dissolved in tetrahydrofuran (30 mL), sodium hydrogencarbonate (1.53 g) and water (36 mL) was added, and the mixture was stirred at room temperature for 30 min. The reaction mixture was diluted with ethyl acetate, washed successively with saturated aqueous sodium hydrogencarbonate solution, water and saturated brine, and dried over anhydrous magnesium sulfate. The solvent was evaporated under reduced pressure and the residue was purified by silica gel column chromatography (eluent: hexane-ethyl acetate=19:1→3:1) to give the title compound as a solid (yield 544 mg, 32%).

¹H-NMR (CDCl₃) δ: 1.47 (9H, s), 2.82 (3H, s), 4.23 (2H, s), 6.16 (1H, s), 7.23-7.49 (8H, m), 8.28 (1H, s).

Reference Example 300 tert-Butyl methyl({[1-(6-methylpyridin-3-yl)sulfonyl]-5-phenyl-1H-pyrrol-3-yl}methyl)carbamate Under an argon atmosphere, a mixture of tert-butyl ({[1-(6-chloropyridin-3-yl)sulfonyl]-5-phenyl-1H-pyrrol-3-yl}methyl)methylcarbamate (100 mg), methylboronic acid (14 mg), tetrakis(triphenylphosphine)palladium (25 mg), potassium carbonate (90 mg) and dioxane (3 mL) was stirred at 80° C. for 24 hr. Methylboronic acid (14 mg) and tetrakis(triphenylphosphine)palladium (25 mg) were added, and the mixture was stirred at 90° C. for 24 hr. Methylboronic acid (14 mg), tetrakis(triphenylphosphine)palladium (25 mg), potassium carbonate (90 mg) and dioxane (2 mL) were added, and the mixture was stirred at 90° C. for 24 hr. The reaction mixture was diluted with ethylacetate, washed successively with saturated aqueous sodium hydrogencarbonate solution, water and saturated brine, and dried over anhydrous magnesium sulfate. The solvent was evaporated under reduced pressure and the residue was purified by silica gel column chromatography (eluent: hexane-ethyl acetate=19:1→1:1) to give the title compound as an oil (yield 85.8 mg, 36%).

¹H-NMR (CDCl₃) δ: 1.46 (9H, s), 2.58 (3H, s), 2.81 (3H, s), 4.20-4.23 (2H, m), 6.13 (1H, s), 7.07-7.10 (1H, m), 7.24-7.42 (7H, m), 8.39 (1H, s).

Reference Example 301 tert-Butyl methyl{[1-(pyridin-3-ylsulfonyl)-5-(3-thienyl)-1H-pyrrol-3-yl]methyl}carbamate Under an argon atmosphere, a suspension of tert-butyl {[5-bromo-1-(pyridin-3-ylsulfonyl)-1H-pyrrol-3-yl]methyl}methylcarbamate (232 mg), 3-thienylboronic acid (138 mg), tetrakis(triphenylphosphine)palladium (31.3 mg) and sodium carbonate (175 mg) in 1,2-dimethoxyethane (10 mL) and water (5 mL) was stirred at 105° C. for 1 hr. The reaction mixture was allowed to cool to room temperature, water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent: hexane-ethylacetate=1:1) to give the title compound as a pale-yellow oil (yield 189 mg, 81%).

¹H-NMR (CDCl₃) δ: 1.47 (9H, s), 2.82 (3H, brs), 4.22 (2H, brs), 6.17 (1H, brs), 7.04-7.06 (1H, m), 7.16-7.17 (1H, m), 7.25-7.32 (3H, m), 7.57-7.61 (1H, m), 8.56 (1H, d, J=2.4 Hz), 8.71-8.73 (1H, m)

Reference Example 302 tert-Butyl {[5-(4-fluorophenyl)-1-(pyridin-3-ylsulfonyl)-1H-pyrrol-3-yl]methyl}methylcarbamate By a similar operation as in Reference Example 301 and using tert-butyl {[5-bromo-1-(pyridin-3-ylsulfonyl)-1H-pyrrol-3-yl]methyl}methylcarbamate (300 mg), (4-fluorophenyl)boronic acid (195 mg), tetrakis(triphenylphosphine)palladium (40 mg) and sodium carbonate (222 mg), the title compound was obtained as a pale-yellow oil (yield 293 mg, 94%).

¹H-NMR (CDCl₃) δ: 1.47 (9H, s), 2.81 (3H, brs), 4.22 (2H, brs), 6.12 (1H, brs), 7.00-7.06 (2H, m), 7.18-7.31 (4H, m), 7.56-7.60 (1H, m), 8.54-8.55 (1H, m), 8.73-8.75 (1H, m).

Reference Example 303 tert-Butyl methyl{[5-(2-methylphenyl)-1-(pyridin-3-ylsulfonyl)-1H-pyrrol-3-yl]methyl}carbamate By a similar operation as in Reference Example 301 and using tert-butyl {[5-bromo-1-(pyridin-3-ylsulfonyl)-1H-pyrrol-3-yl]methyl}methylcarbamate (300 mg), (2-methylphenyl)boronic acid (190 mg), tetrakis(triphenylphosphine) palladium (40 mg) and sodium carbonate (222 mg), the title compound was obtained as a pale-yellow oil (yield 210 mg, 68%).
¹H-NMR (CDCl₃) δ: 1.47 (9H, s), 1.92 (3H, s), 2.84 (3H, brs), 4.26 (2H, brs), 6.07 (1H, d, J=1.2 Hz), 6.87-6.89 (1H, m), 7.09-7.19 (2H, m), 7.26-7.35 (3H, m), 7.58-7.62 (1H, m), 8.54-8.55 (1H, m), 8.75-8.77 (1H, m).

Reference Example 304 tert-Butyl {[5-(4-fluoro-2-methylphenyl)-1-(pyridin-3-ylsulfonyl)-1H-pyrrol-3-yl]methyl}methylcarbamate Using tert-butyl {[5-bromo-1-(pyridin-3-ylsulfonyl)-1H-pyrrol-3-yl]methyl}methylcarbamate (300 mg), (4-fluoro-2-methylphenyl)boronic acid (215 mg), tetrakis(triphenylphosphine)palladium (40 mg) and sodium carbonate (222 mg), a procedure as in Reference Example 301 was performed to give the title compound as a pale-yellow oil (yield 216 mg, 67%).
¹H-NMR (CDCl₃) δ: 1.47 (9H, s), 1.92 (3H, s), 2.84 (3H, brs), 4.25 (2H, brs), 6.05 (1H, br), 6.79-6.91 (3H, m), 7.30-7.35 (2H, m), 7.61-7.65 (1H, m), 8.58-8.59 (1H, m), 8.77-8.79 (1H, m).

Reference Example 305 tert-Butyl methyl{[5-(4-methyl-3-thienyl)-1-(pyridin-3-ylsulfonyl)-1H-pyrrol-3-yl]methyl}carbamate Using tert-butyl {[5-bromo-1-(pyridin-3-ylsulfonyl)-1H-pyrrol-3-yl]methyl}methylcarbamate (300 mg), (4-methyl-3-thienyl)boronic acid (198 mg), tetrakis(triphenylphosphine)palladium (40 mg) and sodium carbonate (222 mg), a procedure as in Reference Example 301 was performed to give the title compound as a pale-yellow oil (yield 200 mg, 64%).
¹H-NMR (CDCl₃) δ: 1.47 (9H, s), 1.81 (3H, s), 2.83 (3H, brs), 4.26 (2H, brs), 6.10 (1H, br), 6.90 (1H, br), 7.02-7.03 (1H, m), 7.26-7.35 (2H, m), 7.61-7.65 (1H, m), 8.58-8.59 (1H, m), 8.75-8.77 (1H, m).

Reference Example 306 tert-Butyl {[5-(3-cyanophenyl)-1-(pyridin-3-ylsulfonyl)-1H-pyrrol-3-yl]methyl}methylcarbamate By a similar operation as in Reference Example 301 and using tert-butyl {[5-bromo-1-(pyridin-3-ylsulfonyl)-1H-pyrrol-3-yl]methyl}methylcarbamate (300 mg), (3-cyanophenyl)boronic acid (205 mg), tetrakis(triphenylphosphine) palladium (40 mg) and sodium carbonate (222 mg), the title compound was obtained as a pale-yellow oil (yield 298 mg, 94%).
¹H-NMR (CDCl₃) δ: 1.47 (9H, s), 2.81 (3H, brs), 4.22 (2H, brs), 6.21 (1H, br), 7.31-7.35 (2H, m), 7.46-7.69 (6H, m), 8.56 (1H, d, J=1.8 Hz), 8.76-8.78 (1H, m)

Reference Example 307 tert-Butyl {[5-(2-chlorophenyl)-1-(pyridin-3-ylsulfonyl)-1H-pyrrol-3-yl]methyl}methylcarbamate By a similar operation as in Reference Example 301 and using tert-butyl {[5-bromo-1-(pyridin-3-ylsulfonyl)-1H-pyrrol-3-yl]methyl}methylcarbamate (300 mg), (2-chlorophenyl)boronic acid (218 mg), tetrakis(triphenylphosphine) palladium (40 mg) and sodium carbonate (222 mg), the title compound was obtained as a pale-blue oil (yield 171 mg, 53%).
¹H-NMR (CDCl₃) δ: 1.47 (9H, s), 2.84 (3H, brs), 4.26 (2H, brs), 6.20 (1H, d, J=1.8 Hz), 7.26-7.36 (6H, m), 7.65-7.71 (1H, m), 8.58-8.59 (1H, m), 8.75-8.79 (1H, m).

Reference Example 308 tert-Butyl {[5-(2,4-difluorophenyl)-1H-pyrrol-3-yl]methyl}methylcarbamate

By a similar operation as in Reference Example 301 and using tert-butyl {[5-bromo-1-(pyridin-3-ylsulfonyl)-1H-pyrrol-3-yl]methyl}methylcarbamate (300 mg), (2,4-difluorophenyl)boronic acid (198 mg), tetrakis(triphenylphosphine)palladium (40 mg) and sodium carbonate (220 mg), the title compound was obtained as a colorless oil (yield 113 mg, 50%).
¹H-NMR (CDCl₃) δ: 1.50 (9H, s), 2.84 (3H, brs), 4.30 (2H, brs), 6.49 (1H, br), 6.78-6.92 (3H, m), 7.48-7.58 (1H, m), 8.78 (1H, br).

Reference Example 309 tert-Butyl {[5-(2,5-difluorophenyl)-1H-pyrrol-3-yl]methyl}methylcarbamate

By a similar operation as in Reference Example 301 and using tert-butyl {[5-bromo-1-(pyridin-3-ylsulfonyl)-1H-pyrrol-3-yl]methyl}methylcarbamate (300 mg), (2,5-difluorophenyl)boronic acid (220 mg), tetrakis(triphenylphosphine)palladium (40 mg) and sodium carbonate (220 mg), the title compound was obtained as a colorless oil (yield 135 mg, 60%).
¹H-NMR (CDCl₃) δ: 1.50 (9H, s), 2.84 (3H, brs), 4.30 (2H, brs), 6.56 (1H, br), 6.77-6.85 (2H, m), 7.00-7.08 (1H, m), 7.20-7.26 (1H, m), 8.90 (1H, br).

Reference Example 310 tert-Butyl {[5-(4-chloro-2-fluorophenyl)-1H-pyrrol-3-yl]methyl}methylcarbamate

By a similar operation as in Reference Example 301 and using tert-butyl {[5-bromo-1-(pyridin-3-ylsulfonyl)-1H-pyrrol-3-yl]methyl}methylcarbamate (300 mg), (4-chloro-2-fluorophenyl)boronic acid (243 mg), tetrakis(triphenylphosphine)palladium (40 mg) and sodium carbonate (220 mg), the title compound was obtained as a colorless oil (yield 127 mg, 54%).

¹H-NMR (CDCl₃) δ: 1.50 (9H, s), 2.84 (3H, s), 4.30 (2H, s), 6.55 (1H, br), 6.80 (1H, br), 7.11-7.15 (2H, m), 7.46-7.52 (1H, m), 8.82 (1H, br).

Reference Example 311 tert-Butyl {[5-(2,4-difluorophenyl)-1-(pyridin-3-ylsulfonyl)-1H-pyrrol-3-yl]methyl}methylcarbamate By a similar operation as in Reference Example 146 and using tert-butyl {[5-(2,4-difluorophenyl)-1H-pyrrol-3-yl]methyl}methylcarbamate (113 mg), sodium hydride (60% in oil, 51 mg), 15-crown-5 (0.21 mL) and pyridin-3-ylsulfonyl chloride hydrochloride (113 mg), the title compound was obtained as a pale-yellow oil (yield 110 mg, 68%).
¹H-NMR (CDCl₃) δ: 1.46 (9H, s), 2.82 (3H, brs), 4.24 (2H, brs), 6.19 (1H, br), 6.77-6.92 (2H, m), 7.11-7.19 (1H, m), 7.33-7.37 (2H, m), 7.68-7.72 (1H, m), 8.62 (1H, d, J=2.4 Hz), 8.77-8.79 (1H, m).

Reference Example 312 tert-Butyl {[5-(2,5-difluorophenyl)-1-(pyridin-3-ylsulfonyl)-1H-pyrrol-3-yl]methyl}methylcarbamate By a similar operation as in Reference Example 146 and using tert-butyl {[5-(2,5-difluorophenyl)-1H-pyrrol-3-yl]methyl}methylcarbamate (135 mg), sodium hydride (60% in oil, 60 mg), 15-crown-5 (0.25 mL) and pyridin-3-ylsulfonyl chloride hydrochloride (135 mg), the title compound was obtained as a colorless oil (yield 105 mg, 54%).
¹H-NMR (CDCl₃) δ: 1.50 (9H, s), 2.82 (3H, s), 4.23 (2H, brs), 6.24 (1H, br), 6.89-7.13 (4H, m), 7.33-7.39 (2H, m), 7.71-7.75 (1H, m), 8.67 (1H, d, J=2.4 Hz), 8.78-8.80 (1H, m).

Reference Example 313 tert-Butyl {[5-(4-chloro-2-fluorophenyl)-1-(pyridin-3-ylsulfonyl)-1H-pyrrol-3-yl]methyl}methylcarbamate By a similar operation as in Reference Example 146 and using tert-butyl {[5-(4-chloro-2-fluorophenyl)-1H-pyrrol-3-yl]methyl}methylcarbamate (127 mg), sodium hydride (60% in oil, 54 mg), 15-crown-5 (0.22 mL) and pyridin-3-ylsulfonyl chloride hydrochloride (120 mg), the title compound was obtained as a colorless oil (yield 103 mg, 57%).
¹H-NMR (CDCl₃) δ: 1.46 (9H, s), 2.81 (3H, s), 4.23 (2H, brs), 6.21 (1H, brs), 7.08-7.15 (4H, m), 7.32-7.38 (2H, m), 7.69-7.73 (1H, m), 8.64 (1H, d, J=2.4 Hz), 8.77-8.79 (1H, m).

Reference Example 314 tert-Butyl {[5-(3-fluorophenyl)-1-(pyridin-3-ylsulfonyl)-1H-pyrrol-3-yl]methyl}methylcarbamate By a similar operation as in Reference Example 301 and using tert-butyl {[5-bromo-1-(pyridin-3-ylsulfonyl)-1H-pyrrol-3-yl]methyl}methylcarbamate (300 mg), (3-fluorophenyl)boronic acid (195 mg), tetrakis(triphenylphosphine)palladium (40 mg) and sodium carbonate (222 mg), the title compound was obtained as a pale-yellow oil (yield 280 mg, 90%).

¹H-NMR (CDCl₃) δ: 1.47 (9H, s), 2.81 (3H, brs), 4.22 (2H, brs), 6.16 (1H, brs), 6.93-7.11 (3H, m), 7.27-7.32 (3H, m), 7.59-7.63 (1H, m), 8.58 (1H, d, J=2.1 Hz), 8.73-8.75 (1H, m).

Reference Example 315 tert-Butyl {1-[5-bromo-2-methyl-1-(pyridin-3-ylsulfonyl)-1H-pyrrol-3-yl]methyl}methylcarbamate 5-Bromo-2-methyl-1-(pyridin-3-ylsulfonyl)-1H-pyrrole-3-carbaldehyde (565 mg) was dissolved in tetrahydrofuran (2 mL) and methanol (2 mL), a 40% solution (1.5 mL) of methylamine in methanol was added at room temperature and the mixture was stirred for 30 min. Sodium borohydride (130 mg) was added to the reaction mixture at room temperature and the mixture was stirred for 15 min. The reaction mixture was concentrated under reduced pressure, a saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was dissolved in ethyl acetate (6 mL), di-tert-butyl bicarbonate (0.45 mL) was added, and the mixture was stirred at room temperature for 1 hr. To the reaction mixture was added 1 mol/L hydrochloric acid (10 mL), and the mixture was further stirred for 15 min. The reaction mixture was neutralized with saturated aqueous sodium hydrogencarbonate solution, and extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by silica gel column chromatography (eluent: hexane-ethyl acetate=4:1→1:1) to give a mixture of the title compound and 5-bromo-2-methyl-1-(pyridin-3-ylsulfonyl)-1H-pyrrole-3-carbaldehyde. The mixture was dissolved in tetrahydrofuran (5 mL), a 2 mol/L solution (4 mL) of methylamine in tetrahydrofuran was added, and the mixture was stirred at room temperature for 12 hr. To the reaction mixture was added a solution of sodium borohydride (131 mg) in methanol (1 mL), and the mixture was stirred for 1 hr. The reaction mixture was concentrated under reduced pressure, a saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was dissolved in ethyl acetate (6 mL), di-tert-butyl bicarbonate (0.45 mL) was added, and the mixture was stirred at room temperature for 1 hr. Saturated aqueous sodium hydrogencarbonate solution was added to the reaction mixture, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by silica gel column chromatography (developing solution: hexane-ethyl acetate=2:1) to give the title compound as a yellow oil (yield 384 mg, 50%).
¹H-NMR (CDCl₃) δ: 1.46 (9H, s), 2.49 (3H, s), 2.71 (3H, brs), 4.15 (2H, brs), 6.24 (1H, brs), 7.47-7.52 (1H, m), 8.13-8.17 (1H, m), 8.84-8.86 (1H, m), 9.07-9.08 (1H, m).

Reference Example 316

N-({1-[(4-Methylphenyl)sulfonyl]-5-phenyl-1H-pyrrol-3-yl}methyl)-1,1-diphenylmethanamine A suspension (12 mL) of 1-[(4-methylphenyl)sulfonyl]-5-phenyl-1H-pyrrole-3-carbaldehyde (1.2 g), diphenylmethylamine (1.35 g) and powder molecular sieves 4 A (5.0 g) in dichloromethane was stirred at room temperature for 6 hr, sodium triacetoxyborohydride (1.56 g) was added, and the mixture was further stirred at room temperature for 3 hr. The reaction mixture was filtered through celite, and the filtrate was partitioned using an ethyl acetate-saturated aqueous sodium hydrogencarbonate solution. The organic layer was washed with saturated brine, dried over anhydrous sodium sulfate, and concentrated under reduced pressure. The residue was purified by silica gel column chromatography (eluent: hexane-ethyl acetate=9:1→1:1). The obtained oil was left standing in a freezer (temperature: −20° C.) to give the title compound as a colorless solid (yield 1.61 g, 89%).

$^1$H-NMR (CDCl$_3$) δ: 2.34 (3H, s), 3.58 (2H, s), 4.82 (1H, s), 6.15 (1H, d, J=1.8 Hz), 7.09 (2H, d, J=8.8 Hz), 7.15-7.45 (18H, m).

Reference Example 317

2,2,2-Trifluoro-N-({1-[(4-methylphenyl)sulfonyl]-5-phenyl-1H-pyrrol-3-yl}methyl)acetamide N-({1-[(4-Methylphenyl)sulfonyl]-5-phenyl-1H-pyrrol-3-yl}methyl)-1,1-diphenylmethanamine (362 mg) was dissolved in ethyl acetate (3 mL), and methanol (5 mL) was added. 10% palladium carbon (50% water-containing product, 200 mg) and 1 mol/L hydrochloric acid (0.73 mL) were added, and the mixture was stirred under a hydrogen atmosphere at room temperature for 3 hr. The reaction mixture was filtrated, and the filtrate was concentrated under reduced pressure. Saturated aqueous sodium hydrogencarbonate solution was added to the residue, and the mixture was extracted with ethyl acetate. The extract was washed with saturated brine, dried over anhydrous sodium sulfate, and concentrated under reduced pressure. The residue was dissolved in tetrahydrofuran (3 mL) and, after cooling to 0° C., triethylamine (0.203 mL) and trifluoroacetic anhydride (0.159 mL) were added. The reaction mixture was stirred at room temperature for 30 min, concentrated under reduced pressure. Water was added to the residue, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→2:1) to give the title compound as a colorless oil (yield 321 mg, 100%).

$^1$H-NMR (CDCl$_3$) δ: 2.36 (3H, s), 4.39 (2H, d, J=5.6 Hz), 6.10 (1H, d, J=2.2 Hz), 6.45 (1H, br), 7.05-7.45 (10H, m).

Example 1

N-Methyl-1-{1-[(4-methylphenyl)sulfonyl]-5-phenyl-1H-pyrrol-3-yl}methanamine

To a solution (10 mL) of 1-[(4-methylphenyl)sulfonyl]-5-phenyl-1H-pyrrole-3-carbaldehyde (200 mg) in methanol were added methylammonium chloride (207 mg) and sodium cyanoborohydride (39 mg), and the mixture was stirred at room temperature for 1 hr. Saturated aqueous sodium hydrogen carbonate was added to the reaction mixture, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=6:1→1:1) to give the title compound as a brown oil (yield 15 mg, 7%).

$^1$H-NMR (CDCl$_3$) δ: 2.35 (3H, s), 2.44 (3H, s), 3.59 (2H, s), 6.13 (1H, d, J=1.8 Hz), 7.08 (2H, d, J=8.0 Hz), 7.20-7.40 (9H, m).

Example 2

1-{1-[(4-Fluorophenyl)sulfonyl]-5-phenyl-1H-pyrrol-3-yl}-N-methylmethanamine

To a solution (5 mL) of 1-[(4-fluorophenyl)sulfonyl]-5-phenyl-1H-pyrrole-3-carbaldehyde (160 mg) in tetrahydrofuran was added benzylmethylamine (88 mg), and the mixture was stirred at room temperature for 30 min. Sodium triacetoxyborohydride (329 mg) was added to the reaction mixture, and the mixture was stirred at room temperature for 1 hr. Saturated aqueous sodium hydrogen carbonate was added, and the mixture was extracted with ethyl acetate. The extract was washed with saturated brine, dried over anhydrous sodium sulfate, and concentrated under reduced pressure. The residue was dissolved in methanol (5 mL), 10% palladium carbon (50% water-containing product, 180 mg) and formic acid (0.027 mL) were added, and the mixture was stirred under a hydrogen atmosphere at room temperature for 10 hr. The reaction mixture was filtrated, and the filtrate was concentrated under reduced pressure. To the residue was added saturated aqueous sodium hydrogen carbonate, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=6:1→2:1) to give the title compound as a colorless oil (yield 55 mg, 33%).

$^1$H-NMR (CDCl$_3$) δ: 2.45 (3H, s), 3.60 (2H, s), 6.16 (1H, d, J=1.8 Hz), 6.96 (2H, t, J=8.8 Hz), 7.20-7.40 (9H, m).

Example 3

1-[1-(Methylsulfonyl)-5-phenyl-1H-pyrrol-3-yl]-N-methylmethanamine

To a solution (5 mL) of 1-(methylsulfonyl)-5-phenyl-1H-pyrrole-3-carbaldehyde (160 mg) in tetrahydrofuran was added benzylmethylamine (117 mg), and the mixture was stirred at room temperature for 30 min. Sodium triacetoxyborohydride (435 mg) was added to the reaction mixture, and the mixture was stirred at room temperature for 1 hr. Saturated aqueous sodium hydrogen carbonate was added, and the mixture was extracted with ethyl acetate. The extract was washed with saturated brine, dried over anhydrous sodium sulfate, and concentrated under reduced pressure. The residue was dissolved in methanol (10 mL), 10% palladium carbon (50% water-containing product, 200 mg) and 1 mol/l hydrochloric acid (1 mL) were added, and the mixture was stirred under a hydrogen atmosphere at room temperature for 18 hr. The reaction mixture was filtrated, and the filtrate was concentrated under reduced pressure. Saturated aqueous sodium hydrogen carbonate was added to the residue, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=6:1→ethyl acetate) to give the title compound as a colorless oil (yield 62 mg, 37%).

$^1$H-NMR (CDCl$_3$) δ: 2.50 (3H, s), 2.82 (3H, s), 3.64 (2H, s), 6.31 (1H, d, J=1.8 Hz), 7.21 (1H, d, J=1.8 Hz), 7.38-7.40 (3H, m), 7.45-7.55 (2H, m).

Example 4

1-{1-[(4-Methoxyphenyl)sulfonyl]-5-phenyl-1H-pyrrol-3-yl}-N-methylmethanamine hydrochloride 1-[(4-Methoxyphenyl)sulfonyl]-5-phenyl-1H-pyrrole-3-carbaldehyde (240 mg) was dissolved in methanol (5 mL), methylammonium chloride (856 mg) and sodium cyanoborohydride (131 mg) were added, and the mixture was stirred at room temperature for 18 hr. The reaction mixture was concentrated under reduced pressure, saturated aqueous sodium hydrogen carbonate was added to the residue, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=6:1→ethyl acetate). The obtained oil was dissolved in ethylacetate (5 mL), 4 mol/L hydrogen chloride-ethyl acetate solution (0.5 mL) was added, and the mixture was concentrated under reduced pressure. The residue was recrystallized from ethyl acetate to give the title compound as colorless crystals (yield 148 mg, 54%).

$^1$H-NMR (CDCl$_3$) δ: 2.56 (3H, s), 3.80 (3H, s), 3.98 (2H, s), 6.45 (1H, d, J=2.2 Hz), 6.74 (2H, d, J=7.0 Hz), 7.10-7.40 (7H, m), 7.64 (1H, d, J=2.2 Hz), 9.82 (2H, br).

Example 5

1-{1-[(4-Fluorophenyl)sulfonyl]-2-methyl-5-phenyl-1H-pyrrol-3-yl}-N-methylmethanamine hydrochloride To a solution (5 mL) of 1-[(4-fluorophenyl)sulfonyl]-2-methyl-5-phenyl-1H-pyrrole-3-carbaldehyde (205 mg) in tetrahydrofuran was added benzylmethylamine (108 mg), and the mixture was stirred at room temperature for 30 min. To the reaction mixture was added sodium triacetoxyborohydride (303 mg), and the mixture was stirred at room temperature for 1 hr. Saturated aqueous sodium hydrogen carbonate was added, and the mixture was extracted with ethyl acetate. The extract was washed with saturated brine, dried over anhydrous sodium sulfate, and concentrated under reduced pressure. The residue was dissolved in methanol (10 mL), 10% palladium carbon (50% water-containing product, 100 mg) and 1 mol/l hydrochloric acid (0.60 mL) were added, and the mixture was stirred under a hydrogen atmosphere at room temperature for 2 hr. 10% palladium carbon (50% water-containing product, 200 mg) was added, and the mixture was stirred under a hydrogen atmosphere at room temperature for 18 hr. The reaction mixture was filtrated, and the filtrate was concentrated under reduced pressure. Saturated aqueous sodium hydrogen carbonate was added to the residue, and the mixture was extracted with ethyl acetate. The extract was washed with saturated brine, dried over anhydrous sodium sulfate, and concentrated under reduced pressure. The residue was dissolved in ethyl acetate (5 mL), 4 mol/L hydrogen chloride-ethyl acetate (0.5 mL) was added, and the mixture was concentrated under reduced pressure to give the title compound as a colorless amorphous solid (yield 100 mg, 42%).

$^1$H-NMR (CDCl$_3$) δ: 2.45 (3H, s), 2.56 (3H, s), 3.89 (2H, s), 6.42 (1H, s), 7.03 (2H, t, J=8.1 Hz), 7.15-7.45 (7H, m), 9.00-10.00 (2H, br).

Example 6

1-{5-(4-Fluorophenyl)-1-[(4-methylphenyl)sulfonyl]-1H-pyrrol-3-yl}-N-methylmethanamine 5-(4-Fluorophenyl)-1-[(4-methylphenyl)sulfonyl]-1H-pyrrole-3-carbaldehyde (0.49 g) was dissolved in methanol (12 mL), and methylammonium chloride (1.17 g) and sodium cyanoborohydride (0.27 g) were added. After stirring at room temperature for 18 hr, the mixture was concentrated under reduced pressure. The residue was dissolved in water, and the solution was alkalized with a saturated aqueous sodium hydrogencarbonate solution and extracted with ethyl acetate. The extract was washed with saturated brine, dried over anhydrous magnesium sulfate, and the solvent was evaporated under reduced pressure. The residue was purified by silica gel column chromatography (eluent: ethylacetate-methanol=5:1) to give the title compound as a colorless solid (yield 0.42 g, 82%).

$^1$H-NMR (CDCl$_3$) δ: 2.36 (3H, s), 2.45 (3H, s), 3.60 (2H, s), 6.13 (1H, d, J=2.1 Hz), 6.98 (2H, t, J=8.8 Hz), 7.09-7.13 (2H, m), 7.17-7.27 (5H, m), 7.33 (1H, s).

Example 7

N-Methyl-1-{5-(3-methylphenyl)-1-[(4-methylphenyl)sulfonyl]-1H-pyrrol-3-yl}methanamine hydrochloride Using 5-(3-methylphenyl)-1-[(4-methylphenyl)sulfonyl]-1H-pyrrole-3-carbaldehyde (0.36 g), methylammonium chloride (0.89 g) and sodium cyanoborohydride (0.21 g), a procedure as in Example 4 was performed to give the title compound as white crystals (yield 0.22 g, 52%).

$^1$H-NMR (DMSO-d$_6$) δ: 2.26 (3H, s), 2.36 (3H, s), 3.33 (3H, s), 3.96 (2H, s), 6.38 (1H, d, J=1.8 Hz), 6.79 (1H, s), 6.84-6.99 (1H, m), 7.22-7.34 (6H, m), 7.69 (1H, d, J=2.1 Hz), 8.98 (2H, brs).

Example 8

N-Methyl-1-{5-(3-fluorophenyl)-1-[(4-methylphenyl)sulfonyl]-1H-pyrrol-3-yl}methanamine hydrochloride Using 5-(3-fluorophenyl)-1-[(4-methylphenyl)sulfonyl]-1H-pyrrole-3-carbaldehyde (0.57 g), methylammonium chloride (1.38 g) and sodium cyanoborohydride (0.32 g), a procedure as in Example 4 was performed to give the title compound as white crystals (yield 0.45 g, 69%).

$^1$H-NMR (DMSO-d$_6$) δ: 2.36 (3H, s), 3.32 (3H, s), 3.98 (2H, s), 6.48 (1H, d, J=1.8 Hz), 6.94-7.00 (2H, m), 7.25-7.45 (6H, m), 7.73 (1H, d, J=1.8 Hz), 8.94 (2H, brs).

Example 9

N-Methyl-1-{1-[(2-methylphenyl)sulfonyl]-5-phenyl-1H-pyrrol-3-yl}methanamine hydrochloride 1-[(2-Methylphenyl)sulfonyl]-5-phenyl-1H-pyrrole-3-carbaldehyde (390 mg) was dissolved in methanol (10 mL), 40% methylamine methanol solution (280 mg) was added at room temperature and the mixture was stirred for 15 min. To the reaction mixture was added sodium borohydride (70 mg) at room temperature and the mixture was stirred for 10 min. Thereto was added 1 mol/l hydrochloric acid (10 mL), and the mixture was stirred for 5 min. The mixture was alkalized with a saturated aqueous sodium hydrogen carbonate and extracted with ethyl acetate. The extract was washed with saturated brine, dried over anhydrous sodium sulfate, and the solvent was evaporated under reduced pressure. The residue was purified by basic silica gel column chromatography (eluent: hexane-ethyl acetate=50:50→0:100), and the obtained oil was dissolved in ethyl acetate (5 mL). 4 mol/l Hydrochloric acid-ethyl acetate (1 mL) was added and the mixture was concentrated under reduced pressure. The residue was crystallized from ethyl acetate to give the title compound as colorless crystals (yield 342 mg, 76%).

$^1$H-NMR (DMSO-d$_6$) δ: 2.21 (3H, s), 2.52-2.54 (3H, m), 4.02 (2H, s), 6.48-6.50 (1H, m), 6.99-7.01 (2H, m), 7.07-7.13 (2H, m), 7.20-7.23 (2H, m), 7.30-7.37 (2H, m), 7.50-7.54 (1H, m), 7.79 (1H, br), 9.13 (2H, br).

Example 10

N-Methyl-1-(5-phenyl-1-{[4-(trifluoromethyl)phenyl]sulfonyl}-1H-pyrrol-3-yl)methanamine hydrochloride Using 5-phenyl-1-{[4-(trifluoromethyl)phenyl]sulfonyl}-1H-pyrrole-3-carbaldehyde (65 mg), 40% methylamine methanol solution (50 mg) and sodium borohydride (24 mg), a procedure as in Example 9 was performed to give the title compound as colorless crystals (yield 50 mg, 68%).

$^1$H-NMR (DMSO-d$_6$) δ: 2.50-2.51 (3H, m), 3.99 (2H, s), 6.48 (1H, s), 7.13-7.15 (2H, m), 7.35-7.38 (2H, m), 7.42-7.46 (1H, m), 7.61 (2H, d, J=8.3 Hz), 7.78-7.78 (1H, m), 7.92 (2H, d, J=8.5 Hz), 9.03 (2H, br).

Example 11

1-{1-[(4-Fluoro-2-methylphenyl)sulfonyl]-5-phenyl-1H-pyrrol-3-yl}-N-methylmethanamine hydrochloride Using 1-[(4-fluoro-2-methylphenyl)sulfonyl]-5-phenyl-1H-pyrrole-3-carbaldehyde (165 mg), 40% methylamine methanol solution (112 mg) and sodium borohydride (28 mg), a procedure as in Example 9 was performed to give the title compound as colorless crystals (yield 106 mg, 56%).

$^1$H-NMR (DMSO-d$_6$) δ: 2.19 (3H, s), 2.53 (3H, s), 4.02 (2H, s), 6.49 (1H, d, J=1.7 Hz), 6.90-6.95 (1H, m), 7.00-7.02 (2H, m), 7.18 (1H, dd, J=9.0 Hz, 5.6 Hz), 7.23-7.26 (2H, m), 7.30 (1H, dd, J=9.9 Hz, 2.6 Hz), 7.32-7.36 (1H, m), 7.79 (1H, s), 9.15 (2H, br).

Example 12

N,N-Dimethyl-1-(5-phenyl-1-{[4-(trifluoromethyl)phenyl]sulfonyl}-1H-pyrrol-3-yl)methanamine hydrochloride Using 5-phenyl-1-{[4-(trifluoromethyl)phenyl]sulfonyl}-1H-pyrrole-3-carbaldehyde (80 mg), 2 mol/l dimethylamine-tetrahydrofuran solution (1 mL) and sodium borohydride (24 mg), a procedure as in Example 9 was performed to give the title compound as colorless crystals (yield 59 mg, 63%).

$^1$H-NMR (DMSO-d$_6$) δ: 2.67 (6H, s), 4.12 (2H, s), 6.56-6.56 (1H, m), 7.15-7.17 (2H, m), 7.34-7.38 (2H, m), 7.42-7.46 (1H, m), 7.63 (2H, d, J=8.3 Hz), 7.85 (1H, d, J=1.7 Hz), 7.92 (2H, d, J=8.3 Hz), 10.68 (1H, br).

Example 13

1-[5-(4-Fluorophenyl)-1-(phenylsulfonyl)-1H-pyrrol-3-yl]-N-methylmethanamine hydrochloride Using 1-(4-phenylsulfonyl)-5-(4-fluorophenyl)-1H-pyrrole-3-carbaldehyde (0.60 g), methylammonium chloride (1.48 g) and sodium cyanoborohydride (0.33 g), a procedure as in Example 4 was performed to give the title compound as colorless crystals (yield 0.35 g, 51%).

$^1$H-NMR (DMSO-d$_6$) δ: 2.52 (3H, s), 3.98 (2H, t, J=8.7 Hz), 6.43 (1H, s), 7.12-7.23 (4H, m), 7.40 (2H, d, J=7.35 Hz), 7.53 (2H, t, J=7.9 Hz), 7.68-7.74 (2H, m), 8.96 (2H, br).

Example 14

N-Methyl-1-[5-(2-methylphenyl)-1-(4-methylphenylsulfonyl)-1H-pyrrol-3-yl]methanamine hydrochloride Using 5-(2-methylphenyl)-1-[(4-methylphenyl)sulfonyl]-1H-pyrrole-3-carbaldehyde (0.46 g), methylammonium chloride (1.11 g) and sodium cyanoborohydride (0.26 g), a procedure as in Example 4 was performed to give the title compound as colorless crystals (yield 0.37 g, 80%).

$^1$H-NMR (DMSO-d$_6$) δ: 1.79 (3H, s), 2.38 (3H, s), 3.32 (3H, s), 4.00 (2H, s), 6.34 (1H, d, J=1.8 Hz), 6.84 (1H, d, J=6.2 Hz), 7.11-7.21 (2H, m), 7.25-7.36 (6H, m), 7.72 (1H, s), 9.02 (1H, brs).

Example 15

1-{5-(4-Fluorophenyl)-1-[(4-fluorophenyl)sulfonyl]-1H-pyrrol-3-yl}-N-methylmethanamine Using 5-(4-fluorophenyl)-1-[(4-fluorophenyl)sulfonyl]-1H-pyrrole-3-carbaldehyde (0.52 g), methylammonium chloride (1.20 g) and sodium cyanoborohydride (0.28 g), a procedure as in Example 6 was performed to give the title compound as a colorless oil (yield 0.39 g, 72%).

$^1$H-NMR (CDCl$_3$) δ: 1.55 (1H, brs), 2.45 (3H, s), 3.59 (2H, s), 6.14 (1H, d, J=1.9 Hz), 6.96-7.04 (4H, m), 7.17-7.23 (2H, m), 7.31-7.38 (3H, m).

Example 16

1-(5-(4-Fluorophenyl)-1-{[4-(trifluoromethyl)phenyl]sulfonyl}-1H-pyrrol-3-yl)-N-methylmethanamine To a solution (12 mL) of 5-(4-fluorophenyl)-1-{[4-(trifluoromethyl)phenyl]sulfonyl}-1H-pyrrole-3-carbaldehyde (0.55 g) in methanol were added methylammonium chloride (1.11 g) and sodium cyanoborohydride (0.26 g), and the mixture was stirred at room temperature for 18 hr. The reaction mixture was concentrated under reduced pressure, saturated aqueous sodium hydrogen carbonate was added, and the mixture was extracted with ethyl acetate. The extract was washed with saturated brine, dried over anhydrous magnesium sulfate, and concentrated under reduced pressure. The residue was purified by basic silica gel column chromatography (eluent: hexane-ethyl acetate=1:1) to give the title compound as colorless crystals (yield 0.39 g, 68%).

$^1$H-NMR (CDCl$_3$) δ: 1.49 (1H, brs), 2.44 (3H, s), 3.60 (2H, s), 6.17 (1H, d, J=1.7 Hz), 7.01 (2H, t, J=8.7 Hz), 7.20 (2H, dd, J=8.8 Hz, 5.4 Hz), 7.34 (1H, d, J=0.94 Hz), 7.47 (2H, d, J=8.3 Hz), 7.60 (2H, d, J=8.3 Hz).

Example 17

1-[1-[(4-Fluorophenyl)sulfonyl]-5-(4-methoxyphenyl)-1H-pyrrol-3-yl]-N-methylmethanamine Using 1-(4-fluorophenylsulfonyl)-5-(4-methoxyphenyl)-1H-pyrrole-3-carbaldehyde (0.28 g), methylammonium chloride (0.62 g) and sodium cyanoborohydride (0.15 g), a procedure as in Example 6 was performed to give the title compound as a colorless oil (yield 0.13 g, 44%).

$^1$H-NMR (CDCl$_3$) δ: 1.52 (1H, brs), 2.45 (3H, s), 3.59 (2H, s), 3.85 (3H, s), 6.10 (1H, s), 6.84 (2H, d, J=8.9 Hz), 6.92-7.02 (2H, m), 7.14 (2H, d, J=8.9 Hz), 7.29-7.38 (3H, m).

Example 18

1-{1-[(4-Fluorophenyl)sulfonyl]-5-[2-(trifluoromethyl)phenyl]-1H-pyrrol-3-yl}-N-methylmethanamine hydrochloride Using 1-[(4-fluorophenyl)sulfonyl]-5-[2-(trifluoromethyl)phenyl]-1H-pyrrole-3-carbaldehyde (0.55 g), methylammonium chloride (1.17 g) and sodium cyanoborohydride (0.27 g), a procedure as in Example 4 was performed to give the title compound as a colorless crystal (yield 0.33 g, 53%).

$^1$H-NMR (DMSO-d$_6$) δ: 2.50 (3H, s), 3.33 (2H, s), 6.48 (1H, s), 7.17 (1H, d, J=8.3 Hz), 7.43 (2H, d, J=8.9 Hz), 7.51-7.59 (2H, m), 7.65-7.74 (2H, m), 7.76-7.81 (2H, m), 9.04 (2H, brs).

Example 19

N-Methyl-1-{1-(4-methylphenyl)sulfonyl}-5-[2-(trifluoromethyl)phenyl]-1H-pyrrol-3-yl}methanamine hydrochloride Using 1-[(4-methylphenyl)sulfonyl]-5-[2-(trifluoromethyl)phenyl]-1H-pyrrole-3-carbaldehyde (0.28 g), methylammonium chloride (0.58 g) and sodium cyanoborohydride (0.14 g), a procedure as in Example 4 was performed to give the title compound as colorless crystals (yield 0.11 g, 35%).

$^1$H-NMR (DMSO-d$_6$) δ: 2.39 (3H, s), 2.50 (3H, s), 3.32 (2H, s), 6.43 (1H, s), 7.12 (1H, d, J=6.8 Hz), 7.37 (4H, s), 7.63-7.79 (4H, m), 8.92 (2H, brs).

Example 20

N-Methyl-1-[2-methyl-5-phenyl-1-(phenylsulfonyl)-1H-pyrrol-3-yl]methanamine hydrochloride Using 2-methyl-5-phenyl-1-phenylsulfonyl-1H-pyrrole-3-carbaldehyde (0.27 g), methylammonium chloride (0.68 g) and sodium cyanoborohydride (0.28 g), a procedure as in Example 4 was performed to give the title compound as colorless crystals (yield 0.11 g, 35%).

$^1$H-NMR (DMSO-d$_6$) δ: 2.44 (3H, s), 2.50 (3H, s), 3.91 (2H, s), 6.40 (1H, s), 7.22-7.28 (2H, m), 7.34-7.49 (5H, m), 7.57 (2H, t, J=7.8 Hz), 7.72 (1H, t, J=6.8 Hz), 8.84 (2H, brs).

Example 21

1-{5-(2,4-Difluorophenyl)-1-[(4-methoxyphenyl)sulfonyl]-1H-pyrrol-3-yl}-N-methylmethanamine hydrochloride tert-Butyl ({5-bromo-1-[(4-methoxyphenyl)sulfonyl]-1H-pyrrol-3-yl}methyl)methylcarbamate (150 mg) was dissolved in a mixture of 1,2-dimethoxyethane (5 mL) and distilled water (5 mL), and (2,4-difluorophenyl)boronic acid (103 mg) and sodium carbonate (104 mg) were added. After nitrogen substitution, tetrakis(triphenylphosphine)palladium (57 mg) was added, and the mixture was stirred under a nitrogen atmosphere at 105° C. for 5 hr. The reaction mixture was filtrated, water was added to the filtrate and the mixture was extracted with ethyl acetate. The extract was washed with saturated brine, dried over anhydrous sodium sulfate, and concentrated under reduced pressure. The residue was dissolved in trifluoroacetic acid (5 mL), and the mixture was stirred at room temperature for 10 min, and concentrated under reduced pressure. Saturated aqueous sodium hydrogen carbonate was added to the residue, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=9:1→1:1), and the obtained oil was dissolved in ethylacetate (5 mL), 4 mol/L hydrogen chloride-ethyl acetate solution (0.5 mL) was added, and the mixture was concentrated under reduced pressure. The residue was recrystallized from ethyl acetate to give the title compound as pale-red crystals (yield 58 mg, 41%).

$^1$H-NMR (CDCl$_3$) δ: 2.56 (3H, t, J=5.2 Hz), 3.83 (3H, s), 3.98 (2H, brs), 6.54 (1H, d, J=1.6 Hz), 6.70-6.90 (4H, m), 7.00-7.20 (1H, m), 7.38 (2H, d, J=9.0 Hz), 6.78 (1H, d, J=1.6 Hz), 9.85 (2H, br).

Example 22

1-[1-[(4-Methoxyphenyl)sulfonyl]-5-(4-phenoxyphenyl)-1H-pyrrol-3-yl]-N-methylmethanamine hydrochloride Using tert-butyl ({5-bromo-1-[(4-methoxyphenyl)sulfonyl]-1H-pyrrol-3-yl}methyl)methylcarbamate (150 mg), (4-phenoxyphenyl)boronic acid (140 mg), sodium carbonate (104 mg) and tetrakis(triphenylphosphine)palladium (57 mg), a procedure as in Example 21 was performed to give the title compound as pale-yellow crystals (yield 88 mg, 55%).

$^1$H-NMR (CDCl$_3$) δ: 2.57 (3H, s), 3.80 (3H, s), 3.98 (2H, s), 6.46 (1H, d, J=2.2 Hz), 6.77 (2H, d, J=9.2 Hz), 6.88 (2H, d, J=8.8 Hz), 7.00-7.20 (5H, m), 7.25-7.45 (4H, m), 7.62 (1H, d, J=2.2 Hz), 9.85 (2H, br).

Example 23

1-[1-[(4-Methoxyphenyl)sulfonyl]-5-(2-naphthyl)-1H-pyrrol-3-yl]-N-methylmethanamine hydrochloride Using tert-butyl ({5-bromo-1-[(4-methoxyphenyl)sulfonyl]-1H-pyrrol-3-yl}methyl)methylcarbamate (150 mg), 2-naphthylboronic acid (112 mg), sodium carbonate (104 mg) and tetrakis(triphenylphosphine)palladium (57 mg), a procedure as in Example 21 was performed to give the title compound as pale-blue crystals (yield 64 mg, 44%).

$^1$H-NMR (DMSO-d$_6$) δ: 3.33 (3H, s), 3.79 (3H, s), 4.00 (2H, s), 6.52 (1H, s), 6.95 (2H, d, J=8.8 Hz), 7.30-7.40 (3H, m), 7.50-7.70 (3H, m), 7.75 (1H, s), 7.80-8.00 (3H, m), 9.02 (2H, br).

Example 24

3-{1-[(4-methoxyphenyl)sulfonyl]-4-[(methylamino)methyl]-1H-pyrrol-2-yl}aniline dihydrochloride Using tert-butyl ({5-bromo-1-[(4-methoxyphenyl)sulfonyl]-1H-pyrrol-3-yl}methyl)methylcarbamate (150 mg), (3-aminophenyl)boronic acid (122 mg), sodium carbonate (104 mg) and tetrakis(triphenylphosphine)palladium (57 mg), a procedure as in Example 21 was performed to give the title compound as colorless crystals (yield 45 mg, 31%).
$^1$H-NMR (DMSO-d$_6$) δ: 2.51 (3H, s), 3.83 (3H, s), 3.96 (2H, s), 6.46 (1H, s), 6.90-7.15 (4H, m), 7.20-7.30 (1H, m), 7.30-7.45 (3H, m), 7.71 (1H, s), 9.11 (2H, br).

Example 25

1-{1-[(4-Methoxyphenyl)sulfonyl]-5-pyridin-3-yl-1H-pyrrol-3-yl}-N-methylmethanamine dihydrochloride Using tert-butyl ({5-bromo-1-[(4-methoxyphenyl)sulfonyl]-1H-pyrrol-3-yl}methyl)methylcarbamate (150 mg), pyridin-3-ylboronic acid (96 mg), sodium carbonate (104 mg) and tetrakis(triphenylphosphine)palladium (57 mg), a procedure as in Example 21 was performed to give the title compound as pale-yellow crystals (yield 16 mg, 11%).
$^1$H-NMR (DMSO-d$_6$) δ: 2.51 (3H, s), 3.82 (3H, s), 3.98 (2H, s), 6.65 (1H, d, J=1.4 Hz), 7.03 (2H, d, J=8.8 Hz), 7.38 (2H, d, J=8.8 Hz), 7.68 (1H, m), 7.82 (1H, d, J=1.4 Hz), 7.92 (1H, d, J=9.2 Hz), 8.50 (1H, s), 8.73 (1H, d, J=4.8 Hz), 9.21 (2H, br).

Example 26

1-{1-[(4-Methylphenyl)sulfonyl]-5-phenyl-1H-pyrrol-3-yl}methanamine hydrochloride To a solution (10 mL) of 4-(azidomethyl)-1-[(4-methylphenyl)sulfonyl]-2-phenyl-1H-pyrrole (230 mg) in methanol was added 10% palladium carbon (50% water-containing product, 150 mg), and the mixture was stirred under a hydrogen atmosphere at room temperature for 18 hr. To the reaction mixture was added acetic acid (1 mL), and the mixture was stirred under a hydrogen atmosphere at room temperature for 18 hr. The reaction mixture was filtrated, saturated aqueous sodium hydrogen carbonate was added to the filtrate, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=9:1→ethyl acetate), and the obtained oil was dissolved in ethyl acetate (5 mL), 4 mol/L hydrogen chloride-ethyl acetate solution (0.5 mL) was added, and the mixture was concentrated under reduced pressure. The residue was recrystallized from ethyl acetate to give the title compound as colorless crystals (yield 10 mg, 4%).
$^1$H-NMR (DMSO-d$_6$) δ: 2.35 (3H, s), 3.89 (2H, s), 6.39 (1H, d, J=1.8 Hz), 7.10-7.20 (2H, m), 7.22-7.50 (7H, m), 7.66 (1H, d, J=1.8 Hz), 8.20 (3H, br).

Example 27

N-Methyl-1-{4-methyl-1-[(4-methylphenyl)sulfonyl]-5-phenyl-1H-pyrrol-3-yl}methanamine hydrochloride Using 4-methyl-1-[(4-methylphenyl)sulfonyl]-5-phenyl-1H-pyrrole-3-carbaldehyde (310 mg), methylammonium chloride (617 mg) and sodium cyanoborohydride (172 mg), a procedure as in Example 4 was performed to give the title compound as colorless crystals (yield 179 mg, 50%).
$^1$H-NMR (DMSO-d$_6$) δ: 1.77 (3H, s), 2.36 (3H, s), 2.55 (3H, s), 3.96 (2H, s), 7.00 (2H, dd, J=1.8 Hz, 8.0 Hz), 7.20-7.50 (7H, m), 7.73 (1H, s), 9.06 (2H, br).

Example 28

3-{4-[(Methylamino)methyl]-1-[(4-methylphenyl)sulfonyl]-1H-pyrrol-2-yl}benzonitrile hydrochloride Using tert-butyl ({5-bromo-1-[(4-methylphenyl)sulfonyl]-1H-pyrrol-3-yl}methyl)methylcarbamate (250 mg), (3-cyanophenyl)boronic acid (103 mg), sodium carbonate (83 mg) and tetrakis(triphenylphosphine)palladium (65 mg), a procedure as in Example 21 was performed to give the title compound as pale-blue crystals (yield 96 mg, 43%).
$^1$H-NMR (DMSO-d$_6$) δ: 2.37 (3H, s), 2.51 (3H, s), 3.98 (2H, s), 6.56 (1H, d, J=1.8 Hz), 7.20-7.40 (4H, m), 7.50-7.65 (3H, m), 7.77 (1H, d, J=1.8 Hz), 7.90 (1H, d, J=7.6 Hz), 9.11 (2H, br).

Example 29

4-{4-[(Methylamino)methyl]-1-[(4-methylphenyl)sulfonyl]-1H-pyrrol-2-yl}benzonitrile hydrochloride Using tert-butyl ({5-bromo-1-[(4-methylphenyl)sulfonyl]-1H-pyrrol-3-yl}methyl)methylcarbamate (250 mg), (4-cyanophenyl)boronic acid (103 mg), sodium carbonate (83 mg) and tetrakis(triphenylphosphine)palladium (65 mg), a procedure as in Example 21 was performed to give the title compound as pale-blue crystals (yield 75 mg, 33%).
$^1$H-NMR (DMSO-d$_6$) δ: 2.36 (3H, s), 2.51 (3H, s), 3.97 (2H, s), 6.59 (1H, d, J=1.8 Hz), 7.34 (4H, m), 7.38 (2H, d, J=8.4 Hz), 7.79 (1H, d, J=1.8 Hz), 7.86 (2H, d, J=8.4 Hz), 9.11 (2H, br).

Example 30

N-methyl-1-[1-(phenylsulfonyl)-5-(3-thienyl)-1H-pyrrol-3-yl]methanamine hydrochloride To a solution of tert-butyl methyl{[1-(phenylsulfonyl)-5-(3-thienyl)-1H-pyrrol-3-yl]methyl}carbamate (0.62 g) in methanol (10 mL) was added 4 mol/L hydrogen chloride-ethyl acetate solution (6 mL), and the mixture was stirred at room temperature for 3 hr. Activated carbon was added to the reaction mixture, the mixture was filtrated, and the filtrate was concentrated under reduced pressure. The residue was recrystallized from ethanol to give the title compound as a colorless solid (yield 0.38 g, 71%).
$^1$H-NMR (CDCl$_3$) δ: 2.55 (3H, s), 3.96 (2H, s), 6.54 (1H, d, J=1.8 Hz), 6.98 (1H, dd, J=1.2, 5.1 Hz), 7.09 (1H, dd, J=1.2, 3.0 Hz), 7.21 (1H, dd, J=3.0, 5.1 Hz), 7.31-7.42 (4H, m), 7.48-7.54 (1H, m), 7.65 (1H, d, J=1.8 Hz), 9.84 (2H, brs).

Example 31

N-Methyl-1-[5-phenyl-1-(phenylsulfonyl)-1H-pyrrol-3-yl]methanamine hydrochloride Using tert-butyl methyl{[5-phenyl-1-(phenylsulfonyl)-1H-pyrrol-3-yl]methyl}carbamate (0.64 g), a procedure as in Example 30 was performed to give the title compound as a colorless solid (yield 0.39 g, 73%).

$^1$H-NMR (CDCl$_3$) δ: 2.55 (3H, s), 3.98 (2H, s), 6.47 (1H, d, J=1.8 Hz), 7.12-7.15 (2H, m), 7.23-7.37 (7H, m), 7.47-7.53 (1H, m), 7.65 (1H, d, J=1.8 Hz), 9.83 (2H, brs).

Example 32

1-{1-[(4-Fluorophenyl)sulfonyl]-5-(3-thienyl)-1H-pyrrol-3-yl}-N-methylmethanamine hydrochloride Using tert-butyl {{1-[(4-fluorophenyl)sulfonyl]-5-(3-thienyl)-1H-pyrrol-3-yl}methyl}methylcarbamate (0.44 g), a procedure as in Example 30 was performed to give the title compound as a colorless solid (yield 92 mg, 32%).

$^1$H-NMR (CDCl$_3$) δ: 2.56-2.60 (3H, m), 3.96-3.98 (2H, m), 6.53 (1H, d, J=2.1 Hz), 6.98-7.04 (3H, m), 7.12-7.14 (1H, m), 7.23-7.26 (1H, m), 7.38-7.44 (2H, m), 7.66 (1H, d, J=2.1 Hz), 9.85 (2H, brs).

Example 33

1-{1-[(3-Chlorophenyl)sulfonyl]-5-phenyl-1H-pyrrol-3-yl}-N-methylmethanamine hydrochloride tert-Butyl {{1-[(3-chlorophenyl)sulfonyl]-5-phenyl-1H-pyrrol-3-yl}methyl}methylcarbamate (726 mg) was dissolved in dichloromethane (3 ml), trifluoroacetic acid (2 ml) was added at 0° C., and the mixture was stirred at room temperature for 15 min. The reaction solution was basified by the dropwise addition to 6% aqueous sodium hydrogencarbonate solution, and the mixture was extracted with ethyl acetate. The organic layer was washed with saturated brine, dried over anhydrous sodium sulfate, and concentrated under reduced pressure. The residue was subjected to basic silica gel column chromatography, and eluted with ethyl acetate-methanol (19:1). The obtained pale-yellow oil was dissolved in ethyl acetate, 4 mol/L hydrogen chloride-ethyl acetate solution was added, activated carbon was added and the mixture was filtered through celite. The celite was washed sufficiently with methanol and the filtrate was concentrated under reduced pressure. The residue was crystallized from ethyl acetate and hexane, and recrystallized from ethyl acetate-ethanol to give the title compound as colorless crystals (yield 324 mg, 52%).

$^1$H-NMR (CDCl$_3$) δ: 1.64 (1H, br), 2.57 (3H, s), 3.99 (1H, s), 6.50 (1H, s), 7.12-7.49 (9H, m), 7.64 (1H, s), 9.85 (1H, br).

Example 34

1-[1-[(3-Chlorophenyl)sulfonyl]-5-(3-thienyl)-1H-pyrrol-3-yl]-N-methylmethanamine hydrochloride Using tert-butyl {[1-[(3-chlorophenyl)sulfonyl]-5-(3-thienyl)-1H-pyrrol-3-yl]methyl}methylcarbamate (712 mg), a procedure as in Example 33 was performed to give the title compound as colorless crystals (yield 388 mg, 63%).

$^1$H-NMR (CDCl$_3$) δ: 1.75 (1H, br), 2.58 (3H, s), 3.97 (2H, s), 6.56 (1H, d, J=2.1 Hz), 6.97-6.99 (1H, m), 7.12-7.14 (1H, m), 7.24-7.31 (4H, m), 7.45-7.49 (1H, m), 7.64 (1H, d, J=2.1 Hz), 9.80 (1H, br).

Example 35

1-[1-[(3-Chlorophenyl)sulfonyl]-5-(4-fluorophenyl)-1H-pyrrol-3-yl]-N-methylmethanamine hydrochloride Using tert-butyl {[1-[(3-chlorophenyl)sulfonyl]-5-(4-fluorophenyl)-1H-pyrrol-3-yl]methyl}methylcarbamate (930 mg), a procedure as in Example 33 was performed to give the title compound as colorless crystals (yield 50 mg, 6%).

$^1$H-NMR (CDCl$_3$) δ: 2.58 (3H, s), 3.98 (2H, s), 6.50 (1H, d, J=1.8 Hz), 6.96-7.02 (2H, m), 7.10-7.15 (2H, m), 7.22-7.24 (1H, m), 7.29-7.31 (2H, m), 7.47-7.51 (1H, m), 7.63-7.64 (1H, m), 9.80 (2H, br).

Example 36

1-{1-[(4-Chlorophenyl)sulfonyl]-5-phenyl-1H-pyrrol-3-yl}-N-methylmethanamine hydrochloride To a solution (7 mL) of tert-butyl methyl[(5-phenyl-1H-pyrrol-3-yl)methyl]carbamate (70 mg) in N,N-dimethylformamide was added sodium hydride (60% in oil, 13 mg) and the mixture was stirred for 30 min. 4-Chlorobenzenesulfonyl chloride (62 mg) was added at room temperature and the mixture was stirred for 1 hr. To the reaction mixture was added ice water, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=19:1→4:1), and dissolved in methanol (10 mL). 4 mol/L Hydrogen chloride-ethyl acetate solution (1.5 mL) was added and the mixture was stirred at 65° C. for 30 min. The reaction mixture was concentrated under reduced pressure, and crystallized from ethyl acetate to give the title compound as pale-red crystals (yield 39 mg, 40%).

$^1$H-NMR (DMSO-d$_6$) δ: 2.51 (3H, s), 3.98 (2H, s), 6.47 (1H, d, J=1.8 Hz), 7.14-7.16 (2H, m), 7.36-7.46 (5H, m), 7.59-7.63 (2H, m), 7.74 (1H, d, J=1.8 Hz), 9.03 (2H, br).

Example 37

1-{1-[(3,4-Difluorophenyl)sulfonyl]-5-phenyl-1H-pyrrol-3-yl}-N-methylmethanamine hydrochloride To a solution (7 mL) of tert-butyl methyl[(5-phenyl-1H-pyrrol-3-yl)methyl]carbamate (70 mg) in tetrahydrofuran was added tert-butoxy potassium (42 mg) at room temperature and the mixture was stirred for 30 min. 3,4-Difluorobenzenesulfonyl chloride (68 mg) was added at room temperature and the mixture was stirred for 1.5 hr. To the reaction mixture was added ice water, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=19:1→4:1), and dissolved in methanol (15 mL). 4 mol/l Hydrogen chloride-ethyl acetate solution (1.5 mL) was added and the mixture was stirred at 65° C. for 30 min. The reaction mixture was concentrated under reduced pressure, and crystallized from ethyl acetate to give the title compound as pale-brown crystals (yield 32 mg, 33%).

$^1$H-NMR (DMSO-d$_6$) δ: 2.53 (3H, s), 3.99 (2H, s), 6.47 (1H, d, J=1.8 Hz), 7.14-7.17 (2H, m), 7.25-7.30 (1H, m), 7.36-7.48 (4H, m), 7.60-7.69 (1H, m), 7.74 (1H, d, J=1.8 Hz), 8.98 (2H, br).

Example 38

1-[1-(2,3-Dihydro-1-benzofuran-5-ylsulfonyl)-5-phenyl-1H-pyrrol-3-yl]-N-methylmethanamine 0.5 oxalic acid salt To a solution (5 mL) of tert-butyl methyl[(5-phenyl-1H-pyrrol-3-yl)methyl]carbamate (28 mg) in N,N-dimethylformamide was added sodium hydride (60% in oil, 40 mg) at room temperature and the mixture was stirred for 30 min. 2,3-Dihydro-1-benzofuran-5-sulfonyl chloride (65 mg) was added at room temperature and the mixture was stirred for 1 hr. To the reaction mixture was added ice water, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→4:1), and dissolved in methanol (10 mL). 4 mol/l Hydrogen chloride-ethyl acetate solution (1.5 mL) was added and the mixture was stirred at 65° C. for 30 min. The reaction mixture was concentrated under reduced pressure to give a free form, which was crystallized from ethyl acetate as a 0.5 oxalic acid salt to give the title compound as pale-red crystals (yield 26 mg, 63%).

$^1$H-NMR (DMSO-d$_6$) δ: 2.53 (3H, s), 3.11 (2H, d, J=8.8 Hz), 3.98 (2H, s), 4.64 (2H, d, J=8.8 Hz), 6.34 (1H, d, J=1.7 Hz), 6.80-6.83 (1H, m), 7.12-7.15 (4H, m), 7.34-7.46 (3H, m), 7.64 (1H, d, J=1.7 Hz).

Example 39

1-[1-(Butylsulfonyl)-5-phenyl-1H-pyrrol-3-yl]-N-methylmethanamine 0.5 oxalic acid salt Using tert-butyl methyl[(5-phenyl-1H-pyrrol-3-yl)methyl]carbamate (70 mg), sodium hydride (60% in oil, 98 mg) and butane-1-sulfonyl chloride (230 mg), a procedure as in Example 38 was performed to give the title compound as pale-purplish red crystals (yield 18 mg, 21%).

$^1$H-NMR (DMSO-d$_6$) δ: 0.75 (3H, t, J=7.2 Hz), 1.14-1.38 (4H, m), 2.56 (3H, s), 3.21 (2H, t, J=7.2 Hz), 4.01 (2H, s), 6.48 (1H, s), 7.44 (5H, br), 7.48 (1H, s).

Example 40

1-{1-[(4-Isopropoxyphenyl)sulfonyl]-5-phenyl-1H-pyrrol-3-yl}-N-methylmethanamine 0.5 oxalic acid salt Using tert-butyl methyl[(5-phenyl-1H-pyrrol-3-yl)methyl]carbamate (70 mg), sodium hydride (60% in oil, 98 mg) and 4-isopropoxybenzenesulfonyl chloride (201 mg), a procedure as in Example 38 was performed to give the title compound as pale-red crystals (yield 47 mg, 45%).

$^1$H-NMR (DMSO-d$_6$) δ: 1.26 (6H, d, J=6.0 Hz), 2.52 (3H, s), 3.98 (2H, s), 4.66-4.74 (1H, m), 6.35 (1H, d, J=1.7 Hz), 6.96 (2H, d, J=9.0 Hz), 7.14-7.16 (2H, m), 7.27 (2H, d, J=9.0 Hz), 7.32-7.45 (3H, m), 7.66 (1H, d, J=1.7 Hz).

Example 41

1-{1-[(3-Methoxyphenyl)sulfonyl]-5-phenyl-1H-pyrrol-3-yl}-N-methylmethanamine hydrochloride Using tert-butyl methyl[(5-phenyl-1H-pyrrol-3-yl)methyl]carbamate (200 mg), sodium hydride (60% in oil, 140 mg) and 3-methoxybenzenesulfonyl chloride (433 mg), a procedure as in Example 36 was performed to give the title compound as pale-purple crystals (yield 186 mg, 68%).

$^1$H-NMR (DMSO-d$_6$) δ: 2.50 (3H, s), 3.68 (3H, s), 3.97 (2H, s), 6.44 (1H, d, J=1.9 Hz), 6.76-6.77 (1H, m), 7.00-7.04 (1H, m), 7.15-7.18 (2H, m), 7.24-7.28 (1H, m), 7.34-7.47 (4H, m), 7.73 (1H, d, J=1.9 Hz).

Example 42

3-({4-[(Methylamino)methyl]-2-phenyl-1H-pyrrol-1-yl}sulfonyl)benzonitrile hydrochloride Using tert-butyl methyl[(5-phenyl-1H-pyrrol-3-yl)methyl]carbamate (250 mg), sodium hydride (60% in oil, 175 mg) and 3-cyanobenzenesulfonyl chloride (528 mg), a procedure as in Example 36 was performed to give the title compound as pale-purple crystals (yield 195 mg, 58%).

$^1$H-NMR (DMSO-d$_6$) δ: 2.52 (3H, s), 3.98 (2H, s), 6.50 (1H, s), 7.11-7.13 (2H, m), 7.35-7.49 (3H, m), 7.68-7.78 (4H, m), 8.17-8.21 (1H, m), 9.16 (2H, br).

Example 43

N-Methyl-1-[5-phenyl-1-(3-thienylsulfonyl)-1H-pyrrol-3-yl]methanamine hydrochloride Using tert-butyl methyl[(5-phenyl-1H-pyrrol-3-yl)methyl]carbamate (250 mg), sodium hydride (60% in oil, 140 mg) and thiophene-3-sulfonyl chloride (340 mg), a procedure as in Example 36 was performed to give the title compound as pale-purple crystals (yield 114 mg, 35%).

$^1$H-NMR (DMSO-d$_6$) δ: 2.52 (3H, s), 3.98 (2H, s), 6.45 (1H, d, J=1.8 Hz), 6.99 (1H, dd, J=5.2 Hz, 1.4 Hz), 7.16-7.19 (2H, m), 7.34-7.45 (3H, m), 7.69 (1H, d, J=1.8 Hz), 7.74 (1H, dd, J=5.2 Hz, 3.0 Hz), 7.98 (1H, dd, J=3.0 Hz, 1.4 Hz).

The structures of the compounds described in Reference Examples are shown in Table 1-Table 17.

TABLE 1

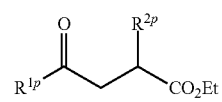

| No. | $R^{1p}$ | $R^{2p}$ |
|---|---|---|
| 1 | phenyl | CN |
| 13 | phenyl | acetyl |

TABLE 1-continued

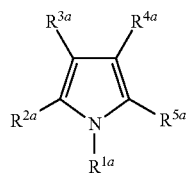

| No. | $R^{1p}$ | $R^{2p}$ |
|---|---|---|
| 23 | 2-methylphenyl | CN |
| 24 | 4-methoxyphenyl | CN |
| 25 | 2-trifluoromethylphenyl | CN | continued on Table 2

TABLE 2

| No. | $R^{1a}$ | $R^{2a}$ | $R^{3a}$ | $R^{4a}$ | $R^{5a}$ |
|---|---|---|---|---|---|
| 2 | H | phenyl | H | $CO_2Et$ | Cl |
| 3 | H | phenyl | H | $CO_2Et$ | H |
| 4 | tosyl | phenyl | H | $CO_2Et$ | H |
| 5 | tosyl | phenyl | H | $CO_2Et$ | H |
| 6 | tosyl | phenyl | H | CHO | H |
| 7 | 4-fluorobenzenesulfonyl | phenyl | H | $CO_2Et$ | H |
| 8 | 4-fluorobenzenesulfonyl | phenyl | H | CHO | H |
| 9 | mesyl | phenyl | H | $CO_2Et$ | H |
| 10 | mesyl | phenyl | H | CHO | H |
| 11 | 4-methoxybenzenesulfonyl | phenyl | H | $CO_2Et$ | H |
| 12 | 4-methoxybenzenesulfonyl | phenyl | H | CHO | H |
| 14 | H | phenyl | H | $CO_2Et$ | Me |
| 15 | 4-fluorobenzenesulfonyl | phenyl | H | $CO_2Et$ | Me |
| 16 | 4-fluorobenzenesulfonyl | phenyl | H | CHO | Me |
| 17 | tosyl | 4-fluorophenyl | H | CHO | H |
| 18 | tosyl | 3-methylphenyl | H | CHO | H |
| 19 | tosyl | 3-fluorophenyl | H | CHO | H |
| 20 | 2-methylbenzenesulfonyl | phenyl | H | CHO | H |
| 21 | 4-trifluoromethylbenzenesulfonyl | phenyl | H | CHO | H |
| 22 | 4-fluoro-2-methylbenzenesulfonyl | phenyl | H | CHO | H |
| 26 | H | 4-methoxyphenyl | H | $CO_2Et$ | H |
| 27 | H | 2-trifluoromethylphenyl | H | $CO_2Et$ | H |
| 28 | benzenesulfonyl | 4-fluorophenyl | H | $CO_2Et$ | H |
| 29 | 4-fluorobenzenesulfonyl | 4-fluorophenyl | H | $CO_2Et$ | H |
| 30 | 4-trifluoromethylbenzenesulfonyl | 4-fluorophenyl | H | $CO_2Et$ | H |
| 31 | benzenesulfonyl | 4-fluorophenyl | H | CHO | H |
| 32 | tosyl | 2-methylphenyl | H | CHO | H |
| 33 | 4-fluorobenzenesulfonyl | 4-methoxyphenyl | H | CHO | H |
| 34 | 4-fluorobenzenesulfonyl | 4-fluorophenyl | H | CHO | H |
| 35 | 4-trifluoromethylbenzenesulfonyl | 4-fluorophenyl | H | CHO | H |
| 36 | 4-fluorobenzenesulfonyl | 2-trifluoromethylphenyl | H | CHO | H |
| 37 | tosyl | 2-trifluoromethylphenyl | H | CHO | H |
| 38 | benzenesulfonyl | phenyl | H | CHO | Me |
| 39 | H | H | H | $CO_2Et$ | H | continued on Table 3

TABLE 3

| | | | | | |
|---|---|---|---|---|---|
| 40 | H | Br | H | $Co_2Me$ | H |
| 41 | 4-methoxybenzenesulfonyl | Br | H | $Co_2Me$ | H |
| 42 | 4-methoxybenzenesulfonyl | Br | H | CHO | H |
| 43 | 4-methoxybenzenesulfonyl | Br | H | $CH_2NCH_3Boc$ | H |
| 44 | tosyl | phenyl | H | $CH_2N_3$ | H |
| 45 | H | H | methyl | $CO_2Et$ | H |
| 46 | H | Br | methyl | $CO_2Et$ | H |
| 47 | tosyl | Br | methyl | $CO_2Et$ | H |
| 48 | tosyl | phenyl | methyl | $CO_2Et$ | H |
| 49 | tosyl | phenyl | methyl | CHO | H |
| 50 | tosyl | Br | H | $CH_2NCH_3Boc$ | H |
| 51 | benzenesulfonyl | Br | H | $Co_2Me$ | H |
| 52 | benzenesulfonyl | Br | H | $CH_2OH$ | H |
| 53 | benzenesulfonyl | Br | H | CHO | H |
| 54 | benzenesulfonyl | Br | H | $CH_2NCH_3$ | H |
| 55 | benzenesulfonyl | Br | H | $CH_2NCH_3Boc$ | H |
| 56 | benzenesulfonyl | 3-thienyl | H | $CH_2NCH_3Boc$ | H |
| 57 | benzenesulfonyl | phenyl | H | $CH_2NCH_3Boc$ | H |
| 58 | 4-fluorobenzenesulfonyl | Br | H | $CH_2NCH_3Boc$ | H |
| 59 | 4-fluorobenzenesulfonyl | 3-thienyl | H | $CH_2NCH_3Boc$ | H |
| 60 | 3-chlorobenzenesulfonyl | Br | H | $CH_2NCH_3Boc$ | H |
| 61 | 3-chlorobenzenesulfonyl | Ph | H | $CH_2NCH_3Boc$ | H |
| 62 | 3-chlorobenzenesulfonyl | 3-thienyl | H | $CH_2NCH_3Boc$ | H |
| 63 | 3-chlorobenzenesulfonyl | 4-fluorophenyl | H | $CH_2NCH_3Boc$ | H |
| 64 | H | phenyl | H | $CH_2OH$ | H |
| 65 | H | phenyl | H | CHO | H |
| 66 | H | phenyl | H | $CH_2NCH_3Boc$ | H | continued on Table 4

TABLE 4

| Ref. Ex. No. | $R^{1a}$ | $R^{2a}$ | $R^{3a}$ | $R^{4a}$ | $R^{5a}$ |
|---|---|---|---|---|---|
| 73 | H | 2-fluorophenyl | H | $CO_2Et$ | Cl |
| 74 | H | 2-fluorophenyl | Me | $CO_2Me$ | Cl |
| 75 | H | phenyl | Me | $CO_2Et$ | Me |
| 76 | H | 3-thienyl | H | $CO_2Et$ | Me |
| 77 | H | 4-fluorophenyl | H | $CO_2Et$ | Me |

TABLE 4-continued

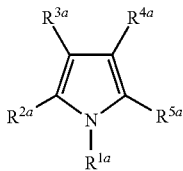

| Ref. Ex. No. | $R^{1a}$ | $R^{2a}$ | $R^{3a}$ | $R^{4a}$ | $R^{5a}$ |
|---|---|---|---|---|---|
| 78 | H | 2-pyridyl | H | CO₂Et | Cl |
| 79 | H | 2-fluorophenyl | H | CO₂Et | H |
| 80 | H | 2-fluorophenyl | Me | CO₂Me | H |
| 81 | H | 2-pyridyl | H | CO₂Et | H |
| 82 | H | 2-methylphenyl | H | CO₂Me | H |
| 83 | H | phenyl | Cl | CO₂Et | Me |

TABLE 4-continued

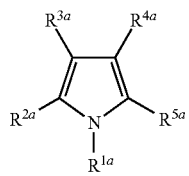

| Ref. Ex. No. | $R^{1a}$ | $R^{2a}$ | $R^{3a}$ | $R^{4a}$ | $R^{5a}$ |
|---|---|---|---|---|---|
| 84 | H | phenyl | H | CO₂Et | F |
| 85 | H | phenyl | F | CO₂Et | Cl |
| 86 | H | phenyl | F | CO₂Et | H |
| 88 | H | H | Me | CO₂Me | H |
| 89 | H | H | Et | CO₂Me | H |
| 90 | H | H | n-Pr | CO₂Me | H |
| 91 | H | H | i-Pr | CO₂Me | H |
| 92 | H | H | phenyl | CO₂Me | H |
| 94 | H | n-Bu | H | CO₂Et | H | continued on Table 5

TABLE 5

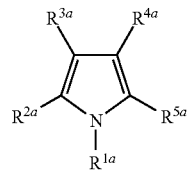

| Ref. Ex. No. | $R^{1a}$ | $R^{2a}$ | $R^{3a}$ | $R^{4a}$ | $R^{5a}$ |
|---|---|---|---|---|---|
| 95 | H | cyclohexyl | H | CO₂Et | H |
| 96 | H | H | H | CO₂Et | Me |
| 97 | H | Br | Me | CO₂Me | H |
| 98 | H | Br | Et | CO₂Me | H |
| 99 | H | Br | n-Pr | CO₂Me | H |
| 100 | H | Br | i-Pr | CO₂Me | H |
| 101 | H | Br | phenyl | CO₂Me | H |

TABLE 5-continued
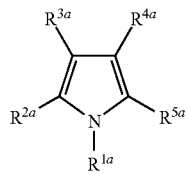
| Ref. Ex. No. | R$^{1a}$ | R$^{2a}$ | R$^{3a}$ | R$^{4a}$ | R$^{5a}$ |
|---|---|---|---|---|---|
| 102 | H | Br | H | CO$_2$Et | Me |
| 103 | PhSO$_2$ | Br | n-Pr | CO$_2$Me | H |
| 104 | PhSO$_2$ | Br | Ph | CO$_2$Me | H |
| 105 | H | Ph | n-Pr | CO$_2$Me | H |
| 106 | H | Ph | Ph | CO$_2$Me | H |
| 107 | H | 2-F-C$_6$H$_4$ | Me | CH$_2$OH | H |
| 108 | H | 2-pyridyl | H | CH$_2$OH | H |
| 109 | H | 2-F-C$_6$H$_4$ | Me | CHO | H |
| 110 | H | 2-pyridyl | H | CHO | H |
| 111 | H | 2-F-C$_6$H$_4$ | H | CHO | H |
| 112 | H | 2-CF$_3$-C$_6$H$_4$ | H | CHO | H |
| 113 | H | 2-Me-C$_6$H$_4$ | H | CHO | H | continued on Table 6

TABLE 6

[Pyrrole structure with substituents R¹ᵃ on N, R²ᵃ and R⁵ᵃ at 2,5-positions, R³ᵃ and R⁴ᵃ at 3,4-positions]

| Ref. Ex. No. | R¹ᵃ | R²ᵃ | R³ᵃ | R⁴ᵃ | R⁵ᵃ |
|---|---|---|---|---|---|
| 139 | PhSO₂– | H | H | CO₂Et | Me |
| 140 | PhSO₂– | Br | Me | CO₂Me | H |
| 141 | 3-Cl-C₆H₄-SO₂– | Br | Me | CO₂Me | H |
| 142 | 3-Me-C₆H₄-SO₂– | Br | Me | CO₂Et | H |
| 143 | 4-F-C₆H₄-SO₂– | Br | Me | CO₂Me | H |
| 144 | PhSO₂– | Br | Et | CO₂Me | H |
| 145 | PhSO₂– | Br | i-Pr | CO₂Me | H |
| 146 | 3-pyridyl-SO₂– | Br | H | CO₂Me | H |
| 147 | 3-Me-C₆H₄-SO₂– | Br | H | CO₂Me | H |
| 148 | 3-pyridyl-SO₂– | Br | H | CO₂Et | Me |
| 149 | 3-Cl-C₆H₄-SO₂– | Ph | H | CO₂Et | Me |

TABLE 6-continued
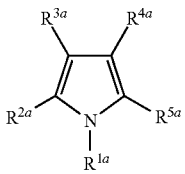
| Ref. Ex. No. | $R^{1a}$ | $R^{2a}$ | $R^{3a}$ | $R^{4a}$ | $R^{5a}$ |
|---|---|---|---|---|---|
| 150 | 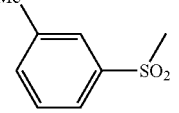 | 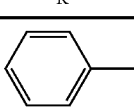 | H | $CO_2Et$ | Me |
| 151 | 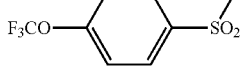 | 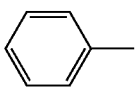 | H | $CO_2Et$ | H |
| 152 | 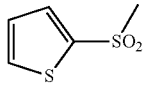 | 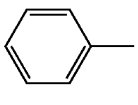 | H | $CO_2Et$ | H |
| 153 | 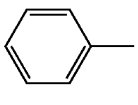 | 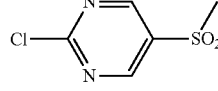 | H | $CO_2Et$ | H |
| 154 | 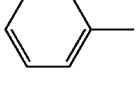 | 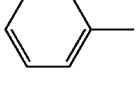 | H | $CO_2Et$ | H |
| 155 | 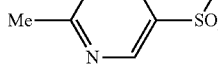 | 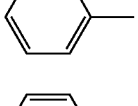 | H | $CO_2Et$ | H |
continued on Table 7
TABLE 7
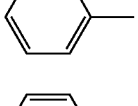
| Ref. Ex. No. | $R^{1a}$ | $R^{2a}$ | $R^{3a}$ | $R^{4a}$ | $R^{5a}$ |
|---|---|---|---|---|---|
| 156 | 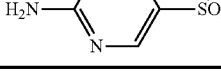 | 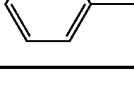 | H | $CO_2Et$ | H |
| 157 | 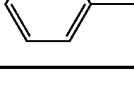 | 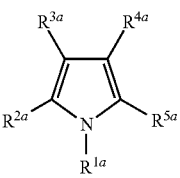 | H | $CO_2Et$ | H |

TABLE 7-continued

Structure: pyrrole with R2a, R3a, R4a, R5a on ring carbons and R1a on N

| Ref. Ex. No. | R1a | R2a | R3a | R4a | R5a |
|---|---|---|---|---|---|
| 158 | phenyl-SO2 | phenyl | Me | CO2Et | Me |
| 159 | phenyl-SO2 | 3-thienyl | H | CO2Et | Me |
| 160 | phenyl-SO2 | 4-F-phenyl | H | CO2Et | Me |
| 161 | phenyl-SO2 | phenyl | n-Pr | CO2Me | H |
| 162 | phenyl-SO2 | phenyl | phenyl | CO2Me | H |
| 163 | phenyl-SO2 | phenyl | Cl | CO2Et | Me |
| 164 | phenyl-SO2 | phenyl | H | CO2Et | Cl |
| 165 | phenyl-SO2 | phenyl | H | CO2Et | F |
| 166 | phenyl-SO2 | phenyl | F | CO2Et | Cl |
| 167 | phenyl-SO2 | phenyl | F | CO2Et | H |
| 168 | phenyl-SO2 | n-Bu | H | CO2Et | H |
| 169 | phenyl-SO2 | cyclohexyl | H | CO2Et | H |
| 170 | phenyl-SO2 | phenyl | Me | CO2Me | H |

TABLE 7-continued
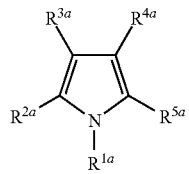
| Ref. Ex. No. | $R^{1a}$ | $R^{2a}$ | $R^{3a}$ | $R^{4a}$ | $R^{5a}$ |
|---|---|---|---|---|---|
| 171 | 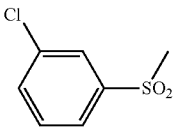 | 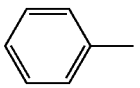 | Me | CO$_2$Me | H |
| 172 | 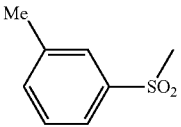 | 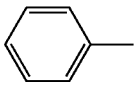 | Me | CO$_2$Et | H |
continued on Table 8
TABLE 8
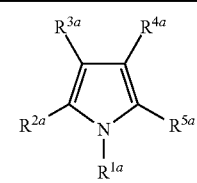
| Ref. Ex. No. | $R^{1a}$ | $R^{2a}$ | $R^{3a}$ | $R^{4a}$ | $R^{5a}$ |
|---|---|---|---|---|---|
| 173 | 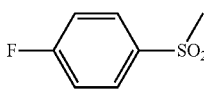 | 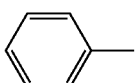 | Me | CO$_2$Me | H |
| 174 | 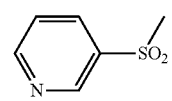 | 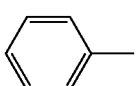 | H | CO$_2$Et | Me |
| 175 | 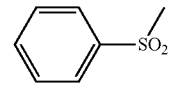 |  | H | CO$_2$Me | H |
| 176 | 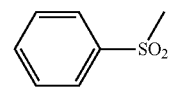 | H | H | CH$_2$OH | Me |
| 177 | 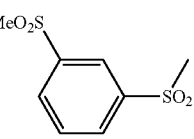 | Br | H | CH$_2$OH | H |
| 178 | 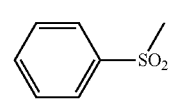 | Br | Et | CH$_2$OH | H |

TABLE 8-continued
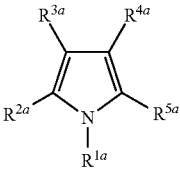
| Ref. Ex. No. | $R^{1a}$ | $R^{2a}$ | $R^{3a}$ | $R^{4a}$ | $R^{5a}$ |
|---|---|---|---|---|---|
| 179 | 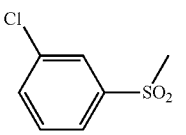 | 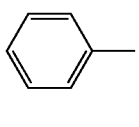 | H | CH$_2$OH | Me |
| 180 | 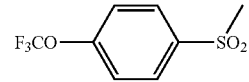 | 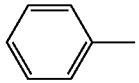 | H | CH$_2$OH | H |
| 181 | 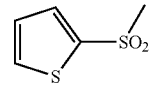 | 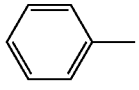 | H | CH$_2$OH | H |
| 182 | 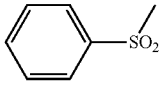 | 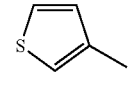 | H | CH$_2$OH | Me |
| 183 | 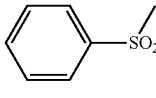 | 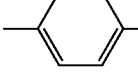 | H | CH$_2$OH | Me |
| 184 | 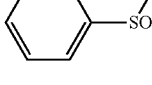 | 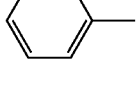 | Me | CH$_2$OH | Me |
| 185 | 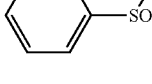 | 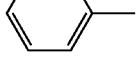 | n-Pr | CH$_2$OH | H |
| 186 | 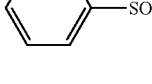 | 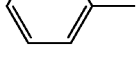 | 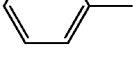 | CH$_2$OH | H |
| 187 | 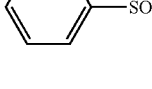 | 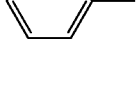 | H | CH$_2$OH | Cl |
| 188 | 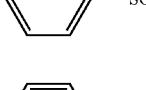 | 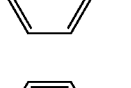 | H | CH$_2$OH | F |
| 189 | 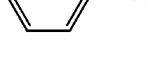 | 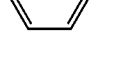 | F | CH$_2$OH | Cl |

TABLE 8-continued

[Pyrrole core structure with substituents $R^{1a}$, $R^{2a}$, $R^{3a}$, $R^{4a}$, $R^{5a}$]

| Ref. Ex. No. | $R^{1a}$ | $R^{2a}$ | $R^{3a}$ | $R^{4a}$ | $R^{5a}$ |
|---|---|---|---|---|---|
| 190 | phenyl-SO$_2$- | phenyl- | F | CH$_2$OH | H | continued on Table 9

TABLE 9

[Pyrrole core structure with substituents $R^{1a}$, $R^{2a}$, $R^{3a}$, $R^{4a}$, $R^{5a}$]

| Ref. Ex. No. | $R^{1a}$ | $R^{2a}$ | $R^{3a}$ | $R^{4a}$ | $R^{5a}$ |
|---|---|---|---|---|---|
| 191 | phenyl-SO$_2$- | H | H | CHO | Me |
| 192 | phenyl-SO$_2$- | Br | Et | CHO | H |
| 193 | 3-(MeO$_2$S)-phenyl-SO$_2$- | Br | H | CHO | H |
| 194 | 4-(F$_3$C)-phenyl-SO$_2$- | phenyl- | H | CHO | Cl |
| 195 | 3-Cl-phenyl-SO$_2$- | phenyl- | H | CHO | Me |
| 196 | 4-(F$_3$CO)-phenyl-SO$_2$- | phenyl- | H | CHO | H |
| 197 | thiophen-2-yl-SO$_2$- | phenyl- | H | CHO | H |
| 198 | phenyl-SO$_2$- | thiophen-3-yl- | H | CHO | Me |

TABLE 9-continued
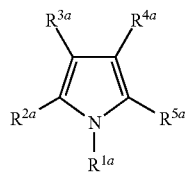
| Ref. Ex. No. | R$^{1a}$ | R$^{2a}$ | R$^{3a}$ | R$^{4a}$ | R$^{5a}$ |
|---|---|---|---|---|---|
| 199 | 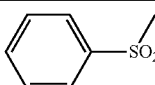 | 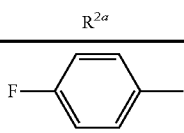 | H | CHO | Me |
| 200 | 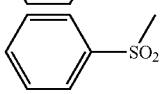 |  | Me | CHO | Me |
| 201 | 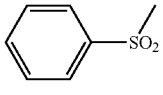 |  | n-Pr | CHO | Me |
| 202 | 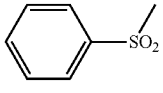 | 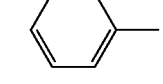 | 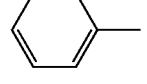 | CHO | H |
| 203 | 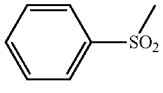 |  | H | CHO | Cl |
| 204 | 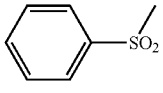 |  | H | CHO | F |
| 205 | 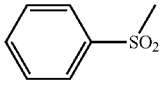 |  | F | CHO | Cl |
| 206 | 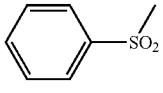 |  | F | CHO | H |
| 207 | 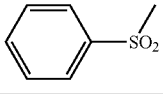 | Br | Me | CHO | H |
continued on Table 10
TABLE 10
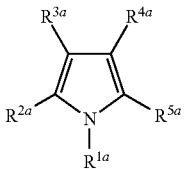
| Ref. Ex. No. | R$^{1a}$ | R$^{2a}$ | R$^{3a}$ | R$^{4a}$ | R$^{5a}$ |
|---|---|---|---|---|---|
| 208 | H | 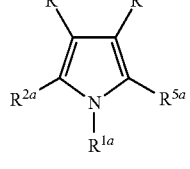 | Me | CHO | H |
TABLE 10-continued
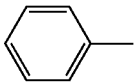
| Ref. Ex. No. | R$^{1a}$ | R$^{2a}$ | R$^{3a}$ | R$^{4a}$ | R$^{5a}$ |
|---|---|---|---|---|---|
| 209 | H | Br | H | CHO | H |

TABLE 10-continued

Structure: pyrrole with R$^{2a}$, R$^{3a}$, R$^{4a}$, R$^{5a}$ substituents and N-R$^{1a}$

| Ref. Ex. No. | R$^{1a}$ | R$^{2a}$ | R$^{3a}$ | R$^{4a}$ | R$^{5a}$ |
|---|---|---|---|---|---|
| 210 | 3-(methylsulfonyl)phenyl-methyl | phenyl | H | CHO | Me |
| 211 | (2-methylpyrimidin-5-yl)sulfonylmethyl | phenyl | H | CHO | H |
| 212 | 3-(methylsulfonyl)phenyl-methyl | phenyl | Me | CHO | H |
| 213 | (4-fluorophenyl)sulfonylmethyl | phenyl | Me | CHO | H |
| 214 | (pyridin-3-yl)sulfonylmethyl | phenyl | H | CHO | Me |
| 215 | phenylsulfonylmethyl | phenyl | Cl | CHO | Me |
| 216 | phenylsulfonylmethyl | n-Bu | H | CHO | H |
| 217 | phenylsulfonylmethyl | cyclohexyl | H | CHO | H |
| 218 | phenylsulfonylmethyl | cyclopropyl | H | CHO | H |
| 219 | 3-(methylsulfonyl)phenyl (MeO$_2$S-) sulfonylmethyl | phenyl | H | CHO | H |
| 220 | 3-(ethylsulfonyl)phenyl (EtO$_2$S-) sulfonylmethyl | phenyl | H | CHO | H |
| 221 | (2,3-dihydrobenzo[b][1,4]dioxin-6-yl)sulfonylmethyl | phenyl | H | CHO | H |
| 222 | (2-cyanophenyl)sulfonylmethyl | phenyl | H | CHO | H | continued on Table 11

TABLE 11

Structure: pyrrole with R$^{2a}$, R$^{3a}$, R$^{4a}$, R$^{5a}$ substituents and N-R$^{1a}$

| Ref. Ex. No. | R$^{1a}$ | R$^{2a}$ | R$^{3a}$ | R$^{4a}$ | R$^{5a}$ |
|---|---|---|---|---|---|
| 223 | (4-cyanophenyl)sulfonylmethyl | phenyl | H | CHO | H |
| 224 | (2-(methoxycarbonyl)phenyl)sulfonylmethyl | phenyl | H | CHO | H |

TABLE 11-continued

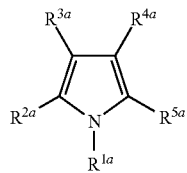

| Ref. Ex. No. | R¹ᵃ | R²ᵃ | R³ᵃ | R⁴ᵃ | R⁵ᵃ |
| --- | --- | --- | --- | --- | --- |
| 225 | 3-(MeO₂C)-phenyl-SO₂- (MeO₂C at meta, SO₂ linker) | phenyl | H | CHO | H |
| 226 | 2-F-4-(SO₂-)-benzonitrile (F ortho to CN, SO₂ para to CN) | phenyl | H | CHO | H |
| 227 | 2-Cl-4-(SO₂-)-benzonitrile | phenyl | H | CHO | H |
| 228 | 2,3-dihydrobenzothiophene-1,1-dioxide-6-SO₂- | phenyl | H | CHO | H |
| 229 | benzothiazol-6-yl-SO₂- | phenyl | H | CHO | H |
| 230 | benzo[b]thiophen-2-yl-SO₂- | phenyl | H | CHO | H |
| 231 | 4-(MeO₂S)-phenyl-SO₂- | phenyl | H | CHO | H |
| 232 | 3-(MeC(O))-phenyl-SO₂- | phenyl | H | CHO | H |
| 233 | 3-(O₂N)-phenyl-SO₂- | phenyl | H | CHO | H |
| 234 | pyridin-3-yl-SO₂- | phenyl | H | CHO | H |

TABLE 11-continued
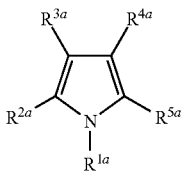
| Ref. Ex. No. | R1a | R2a | R3a | R4a | R5a |
|---|---|---|---|---|---|
| 235 | 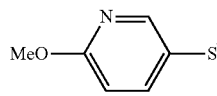 | 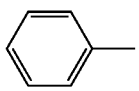 | H | CHO | H |
| 236 | 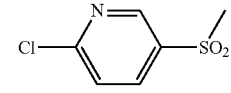 | 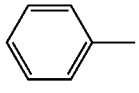 | H | CHO | H |
continued on Table 12
TABLE 12
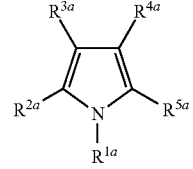
| Ref. Ex. No. | R1a | R2a | R3a | R4a | R5a |
|---|---|---|---|---|---|
| 237 | 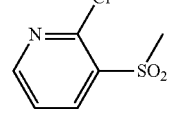 | 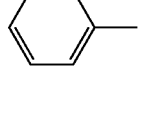 | H | CHO | H |
| 238 | 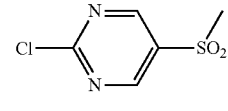 | 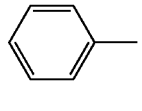 | H | CHO | H |
| 239 | 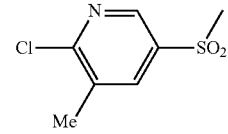 | 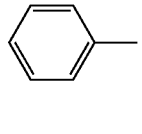 | H | CHO | H |
| 240 | 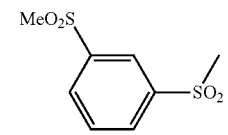 | 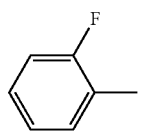 | H | CHO | H |
| 241 | 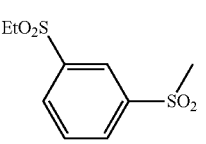 | 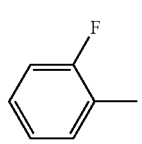 | H | CHO | H |
TABLE 12-continued
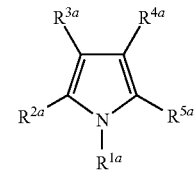
| Ref. Ex. No. | R1a | R2a | R3a | R4a | R5a |
|---|---|---|---|---|---|
| 242 | 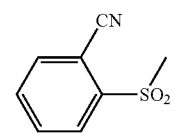 | 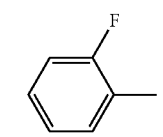 | H | CHO | H |
| 243 | 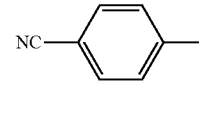 | 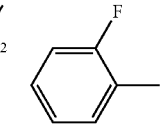 | H | CHO | H |
| 244 | 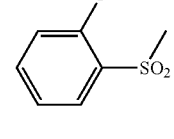 | 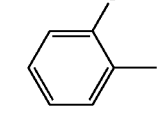 | H | CHO | H |
| 245 | 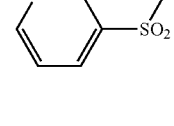 | 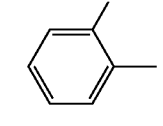 | H | CHO | H |
| 246 | 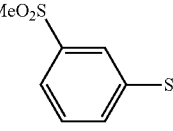 | 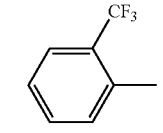 | H | CHO | H |

TABLE 12-continued

| Ref. Ex. No. | R$^{1a}$ | R$^{2a}$ | R$^{3a}$ | R$^{4a}$ | R$^{5a}$ |
|---|---|---|---|---|---|
| 247 | 3-pyridyl-SO$_2$-CH$_2$- | 2-CF$_3$-phenyl | H | CHO | H |
| 248 | 3-(MeO$_2$S)-phenyl-SO$_2$-CH$_2$- | 2-Me-phenyl | H | CHO | H |
| 249 | phenyl-SO$_2$-CH$_2$- | 2-pyridyl | H | CHO | H |
| 250 | 3,4-difluorophenyl-SO$_2$-CH$_2$- | 2-pyridyl | H | CHO | H | continued on Table 13

TABLE 13

| Ref. Ex. No. | R$^{1a}$ | R$^{2a}$ | R$^{3a}$ | R$^{4a}$ | R$^{5a}$ |
|---|---|---|---|---|---|
| 251 | 2,3-dihydro-1,4-benzodioxin-5-yl-SO$_2$-CH$_2$- | phenyl | Me | CHO | H |
| 252 | 2,5-dimethoxyphenyl-SO$_2$-CH$_2$- | phenyl | Me | CHO | H |
| 253 | 2,3-dihydro-1,4-benzodioxin-6-yl-SO$_2$-CH$_2$- | phenyl | Me | CHO | H |
| 254 | 3-(MeO$_2$S)-phenyl-SO$_2$-CH$_2$- | phenyl | Me | CHO | H |
| 255 | thiophen-3-yl-SO$_2$-CH$_2$- | phenyl | Me | CHO | H |
| 256 | 3-pyridyl-SO$_2$-CH$_2$- | phenyl | Me | CHO | H |
| 257 | 2-pyridyl-SO$_2$-CH$_2$- | phenyl | Me | CHO | H |
| 258 | 1,2-dimethylimidazol-4-yl-SO$_2$-CH$_2$- | phenyl | Me | CHO | H |
| 259 | 5-chloro-1,3-dimethylpyrazol-4-yl-SO$_2$-CH$_2$- | phenyl | Me | CHO | H |
| 260 | 2,4-dimethylthiazol-5-yl-SO$_2$-CH$_2$- | phenyl | Me | CHO | H |
| 261 | 3-pyridyl-SO$_2$-CH$_2$- | 2-F-phenyl | Me | CHO | H |
| 262 | 2-CN-phenyl-SO$_2$-CH$_2$- | Br | H | CHO | H |

TABLE 14
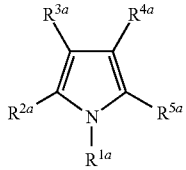
| Ref. Ex. No. | R$^{1a}$ | R$^{2a}$ | R$^{3a}$ | R$^{4a}$ | R$^{5a}$ |
|---|---|---|---|---|---|
| 263 | H | H | H | CHO | Me |
| 264 | 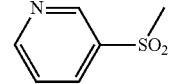 | H | H | CHO | Me |
| 265 | 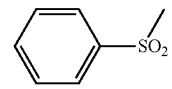 | Br | H | CHO | Me |
| 266 | 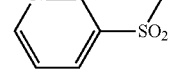 | Br | H | CHO | Me |
| 267 | 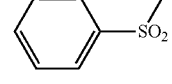 | 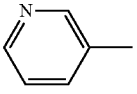 | H | CHO | Me |
| 268 | 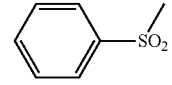 | 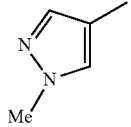 | H | CHO | Me |
| 269 | 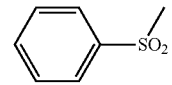 | 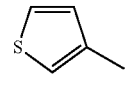 | Me | CHO | H |
| 270 | 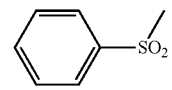 | Br | H | CH$_2$NHMe | H |
| 271 | 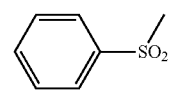 | Br | i-Pr | CH$_2$NHMe | H |
| 272 | 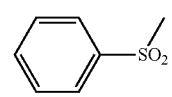 | Br | H | 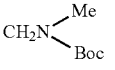 | H |
| 273 | 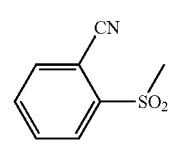 | Br | H | 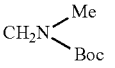 | H |
| 274 | 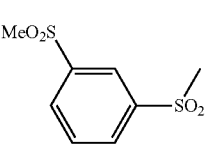 | Br | H | 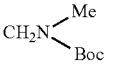 | H |
continued on Table 14

TABLE 14-continued
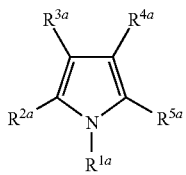
| Ref. Ex. No. | R¹ᵃ | R²ᵃ | R³ᵃ | R⁴ᵃ | R⁵ᵃ |
|---|---|---|---|---|---|
| 275 | Ph-SO₂- | Br | Et | CH₂N(Me)(Boc) | H |
| 276 | Ph-SO₂- | Br | i-Pr | CH₂N(Me)(Boc) | H |
| 277 | Ph-SO₂- | Ph | Et | CH₂N(Me)(Boc) | H |
continued on Table 15
TABLE 15
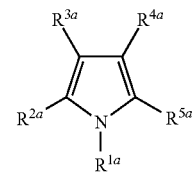
| Ref. Ex. No. | R¹ᵃ | R²ᵃ | R³ᵃ | R⁴ᵃ | R⁵ᵃ |
|---|---|---|---|---|---|
| 278 | Ph-SO₂- | Ph | i-Pr | CH₂N(Me)(Boc) | H |
| 279 | 2-(CO₂Me)C₆H₄-SO₂- | Ph | H | CH₂N(Me)(Boc) | H |
| 280 | 3-(MeO₂C)C₆H₄-SO₂- | Ph | H | CH₂N(Me)(Boc) | H |
| 281 | 2-(CO₂H)C₆H₄-SO₂- | Ph | H | CH₂N(Me)(Boc) | H |
| 282 | 3-(HO₂C)C₆H₄-SO₂- | Ph | H | CH₂N(Me)(Boc) | H |

TABLE 15-continued

| Ref. Ex. No. | R$^{1a}$ | R$^{2a}$ | R$^{3a}$ | R$^{4a}$ | R$^{5a}$ |
|---|---|---|---|---|---|
| 283 | H$_2$NOC-C$_6$H$_4$-SO$_2$- | Ph | H | CH$_2$N(Me)(Boc) | H |
| 284 | cyclopropyl-HNOC-C$_6$H$_4$-SO$_2$- | Ph | H | CH$_2$N(Me)(Boc) | H |
| 285 | MeHNOC-C$_6$H$_4$-SO$_2$- | Ph | H | CH$_2$N(Me)(Boc) | H |
| 286 | Me$_2$NOC-C$_6$H$_4$-SO$_2$- | Ph | H | CH$_2$N(Me)(Boc) | H |
| 287 | morpholino-CO-C$_6$H$_4$-SO$_2$- | Ph | H | CH$_2$N(Me)(Boc) | H |
| 288 | HO-C(Me)$_2$-C$_6$H$_4$-SO$_2$- | Ph | H | CH$_2$N(Me)(Boc) | H |
| 289 | 2-F-4-(SO$_2$-)-C$_6$H$_3$-CN | Ph | H | CH$_2$N(Me)(Boc) | H |
| 290 | 3-CN-C$_6$H$_4$-SO$_2$- | Ph | H | CH$_2$N(Me)(Boc) | H | continued on Table 16

TABLE 16

[Pyrrole core structure with R¹ᵃ on N, R²ᵃ, R³ᵃ, R⁴ᵃ, R⁵ᵃ substituents]

| Ref. Ex. No. | R¹ᵃ | R²ᵃ | R³ᵃ | R⁴ᵃ | R⁵ᵃ |
|---|---|---|---|---|---|
| 291 | 5-(1H-tetrazol-5-yl)-3-(methylsulfonyl)phenyl | phenyl | H | CH₂N(Me)(Boc) | H |
| 292 | H | Br | H | CH₂N(Me)(Boc) | H |
| 293 | 3-(methylsulfonyl)pyridin-2-yl | Br | H | CH₂N(Me)(Boc) | H |
| 294 | 2-cyano-6-(methylsulfonyl)phenyl | pyridin-3-yl | H | CH₂N(Me)(Boc) | H |
| 295 | 3-(methylsulfonyl)-5-(MeO₂S)phenyl | thiophen-3-yl | H | CH₂N(Me)(Boc) | H |
| 296 | 3-(methylsulfonyl)-5-(MeO₂S)phenyl | pyridin-3-yl | H | CH₂N(Me)(Boc) | H |
| 297 | 2-chloro-3-(methylsulfonyl)pyridin-4-yl | phenyl | H | CH₂N(Me)(Boc) | H |
| 298 | 2-chloro-3-methyl-5-(methylsulfonyl)pyridin-4-yl | phenyl | H | CH₂N(Me)(Boc) | H |
| 299 | 6-chloro-3-(methylsulfonyl)pyridin-2-yl | phenyl | H | CH₂N(Me)(Boc) | H |
| 300 | 6-methyl-3-(methylsulfonyl)pyridin-2-yl | phenyl | H | CH₂N(Me)(Boc) | H |

TABLE 16-continued
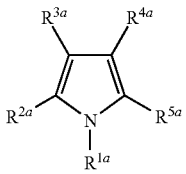
| Ref. Ex. No. | R$^{1a}$ | R$^{2a}$ | R$^{3a}$ | R$^{4a}$ | R$^{5a}$ |
|---|---|---|---|---|---|
| 301 | 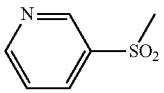 | 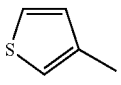 | H | CH$_2$N(Me)(Boc) | H |
| 302 |  | 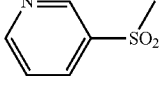 | H | CH$_2$N(Me)(Boc) | H |
| 303 | 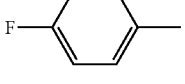 |  | H | CH$_2$N(Me)(Boc) | H |
| 304 | 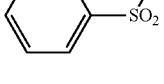 | 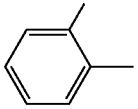 | H | CH$_2$N(Me)(Boc) | H |
| 305 |  | 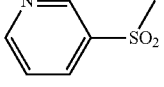 | H | CH$_2$N(Me)(Boc) | H |
continued on Table 17
TABLE 17
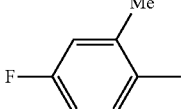
| Ref. Ex. No. | R$^{1a}$ | R$^{2a}$ | R$^{3a}$ | R$^{4a}$ | R$^{5a}$ |
|---|---|---|---|---|---|
| 306 |  | 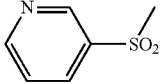 | H | CH$_2$N(Me)(Boc) | H |
| 307 | 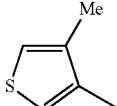 |  | H | CH$_2$N(Me)(Boc) | H |

TABLE 17-continued
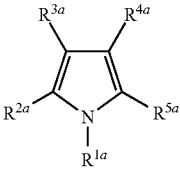
| Ref. Ex. No. | R¹ᵃ | R²ᵃ | R³ᵃ | R⁴ᵃ | R⁵ᵃ |
|---|---|---|---|---|---|
| 308 | H | 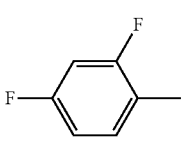 | H | 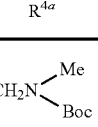 CH₂N(Me)(Boc) | H |
| 309 | H | 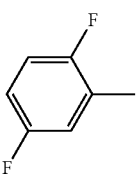 | H |  CH₂N(Me)(Boc) | H |
| 310 | H | 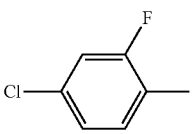 | H |  CH₂N(Me)(Boc) | H |
| 311 | 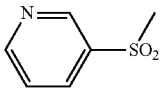 pyridin-3-yl-SO₂ | 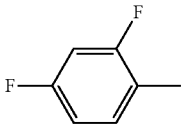 | H |  CH₂N(Me)(Boc) | H |
| 312 | 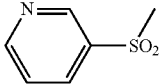 pyridin-3-yl-SO₂ | 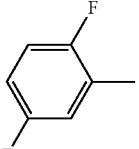 | H |  CH₂N(Me)(Boc) | H |
| 313 | 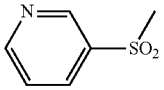 pyridin-3-yl-SO₂ | 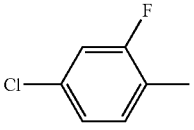 | H |  CH₂N(Me)(Boc) | H |
| 314 | 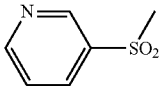 pyridin-3-yl-SO₂ | 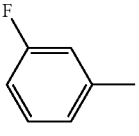 | H |  CH₂N(Me)(Boc) | H |
| 315 | 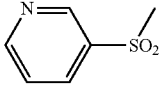 pyridin-3-yl-SO₂ | Br | H |  CH₂N(Me)(Boc) | Me |

TABLE 17-continued

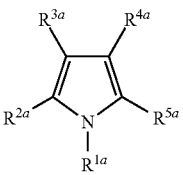

| Ref. Ex. No. | R$^{1a}$ | R$^{2a}$ | R$^{3a}$ | R$^{4a}$ | R$^{5a}$ |
|---|---|---|---|---|---|
| 316 | 4-Me-C$_6$H$_4$-SO$_2$- | phenyl | H | CH$_2$NH-CH(C$_6$H$_5$)$_2$ | H |
| 317 | 4-Me-C$_6$H$_4$-SO$_2$- | phenyl | H | CF$_3$C(O)NH-CH$_2$- | H |

The structures of the compounds described in Examples are shown in Table 18-Table 19.

TABLE 18

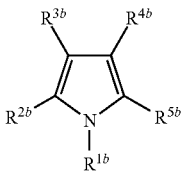

| No. | R$^{1b}$ | R$^{2b}$ | R$^{3b}$ R$^{4b}$ | R$^{5b}$ |
|---|---|---|---|---|
| 1 | tosyl | phenyl | H CH$_2$NHCH$_3$ (hydrochloride) | H |
| 2 | 4-phenylbenzene-sulfonyl | phenyl | H CH$_2$NHCH$_3$ | H |
| 3 | mesyl | phenyl | H CH$_2$NHCH$_3$ | H |
| 4 | 4-methoxybenzene-sulfonyl | phenyl | H CH$_2$NHCH$_3$ (hydrochloride) | H |
| 5 | 4-fluorobenzene-sulfonyl | phenyl | H CH$_2$NHCH$_3$ (hydrochloride) | Me |
| 6 | tosyl | 4-fluoro-phenyl | H CH$_2$NHCH$_3$ | H |
| 7 | tosyl | 3-methyl-phenyl | H CH$_2$NHCH$_3$ (hydrochloride) | H |
| 8 | tosyl | 3-fluoro-phenyl | H CH$_2$NHCH$_3$ (hydrochloride) | H |
| 9 | 2-methylbenzene-sulfonyl | phenyl | H CH$_2$NHCH$_3$ (hydrochloride) | H |
| 10 | 4-trifluoromethyl-benzenesulfonyl | phenyl | H CH$_2$NHCH$_3$ (hydrochloride) | H |
| 11 | 4-fluoro-2-methylbenzene-sulfonyl | phenyl | H CH$_2$NHCH$_3$ (hydrochloride) | H |
| 12 | 4-trifluoromethyl-benzenesulfonyl | phenyl | H CH$_2$N(CH$_3$)$_2$ (hydrochloride) | H |
| 13 | benzenesulfonyl | 4-fluoro-phenyl | H CH$_2$NHCH$_3$ (hydrochloride) | H |
| 14 | tosyl | 2-methylphenyl | H CH$_2$NHCH$_3$ (hydrochloride) | H |
| 15 | 4-fluorobenzene-sulfonyl | 4-fluoro-phenyl | H CH$_2$NHCH$_3$ | H |

TABLE 18-continued

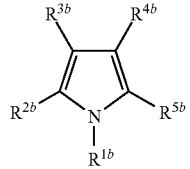

| No. | R$^{1b}$ | R$^{2b}$ | R$^{3b}$ R$^{4b}$ | R$^{5b}$ |
|---|---|---|---|---|
| 16 | 4-trifluoromethyl-benzenesulfonyl | 4-fluoro-phenyl | H CH$_2$NHCH$_3$ | H |
| 17 | 4-fluorobenzene-sulfonyl | 4-methoxy-phenyl | H CH$_2$NHCH$_3$ | H |
| 18 | 4-fluorobenzene-sulfonyl | 2-trifluoro-methylphenyl | H CH$_2$NHCH$_3$ (hydrochloride) | H |
| 19 | tosyl | 2-trifluoro-methylphenyl | H CH$_2$NHCH$_3$ (hydrochloride) | H |
| 20 | benzenesulfonyl | phenyl | H CH$_2$NHCH$_3$ (hydrochloride) | Me |
| 21 | 4-methoxybenzene-sulfonyl | 2,4-difluoro-phenyl | H CH$_2$NHCH$_3$ (hydrochloride) | H | continued on Table 19

TABLE 19

| | | | | | |
|---|---|---|---|---|---|
| 22 | 4-methoxybenzene-sulfonyl | 4-phenoxy-phenyl | H | CH$_2$NHCH$_3$ (hydrochloride) | H |
| 23 | 4-methoxybenzene-sulfonyl | 2-naphthyl | H | CH$_2$NHCH$_3$ (hydrochloride) | H |
| 24 | 4-methoxybenzene-sulfonyl | 3-aminophenyl | H | CH$_2$NHCH$_3$ (dihydrochloride) | H |
| 25 | 4-methoxybenzene-sulfonyl | 5-pyridyl | H | CH$_2$NHCH$_3$ (dihydrochloride) | H |
| 26 | tosyl | phenyl | H | CH$_2$NH$_2$ (hydrochloride) | H |
| 27 | tosyl | phenyl | methyl | CH$_2$NHCH$_3$ (hydrochloride) | H |
| 28 | tosyl | 3-cyanophenyl | H | CH$_2$NHCH$_3$ (hydrochloride) | H |
| 29 | tosyl | 4-cyanophenyl | H | CH$_2$NHCH$_3$ (hydrochloride) | H |

TABLE 19-continued

| | | | | | |
|---|---|---|---|---|---|
| 30 | benzenesulfonyl | 3-thienyl | H | CH$_2$NHCH$_3$ (hydrochloride) | H |
| 31 | benzenesulfonyl | phenyl | H | CH$_2$NHCH$_3$ (hydrochloride) | H |
| 32 | 4-fluorobenzene-sulfonyl | 3-thienyl | H | CH$_2$NHCH$_3$ (hydrochloride) | H |
| 33 | 3-chlorobenzene-sulfonyl | phenyl | H | CH$_2$NHCH$_3$ (hydrochloride) | H |
| 34 | 3-chlorobenzene-sulfonyl | 3-thienyl | H | CH$_2$NHCH$_3$ (hydrochloride) | H |
| 35 | 3-chlorobenzene-sulfonyl | 4-fluoro phenyl | H | CH$_2$NHCH$_3$ (hydrochloride) | H |
| 36 | 4-chlorobenzene-sulfonyl | phenyl | H | CH$_2$NHCH$_3$ (hydrochloride) | H |
| 37 | 3, 4-difluoro-benzenesulfonyl | phenyl | H | CH$_2$NHCH$_3$ (hydrochloride) | H |
| 38 | 2, 3-dihydro-1-benzofuran-5-ylsulfonyl | phenyl | H | CH$_2$NHCH$_3$ (0.5 oxalate) | H |
| 39 | butylsulfonyl | phenyl | H | CH$_2$NHCH$_3$ (0.5 oxalate) | H |
| 40 | 4-isopropoxy-benzenesulfonyl | phenyl | H | CH$_2$NHCH$_3$ (0.5 oxalate) | H |
| 41 | 3-methoxybenzene-sulfonyl | phenyl | H | CH$_2$NHCH$_3$ (hydrochloride) | H |
| 42 | 3-cyanobenzene-sulfonyl | phenyl | H | CH$_2$NHCH$_3$ (hydrochloride) | H |
| 43 | 3-thienylsulfonyl | phenyl | H | CH$_2$NHCH$_3$ (hydrochloride) | H |

The compounds of Examples 44-116 were synthesized by the following methods.

LC-MS measurement condition: in the following Examples, HPLC-mass spectrum (LC-MS) was measured under the following conditions.

Measurement device: ZMD Micromass, and HP1100 Agilent Technologies

Column: CAPCELL PAK C18UG120, S-3 μm, 1.5×35 mm

Solvent: SOLUTION A; 0.05% trifluoroacetic acid containing water, SOLUTION B; 0.04% trifluoroacetic acid containing acetonitrile Gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.45 min (SOLUTION A/SOLUTION B=90/10)

Injection volume: 2 μl

Flow rate: 0.5 mL/min, detection: UV 220 nm

Ionization method: electron impact ionization method (Electron Spray Ionization: ESI)

Preparative HPLC conditions: in the following Reference Examples and Examples, purification by preparative HPLC was conducted under the following conditions.

Equipment: high throughput purified system Gilson

Column: YMC CombiPrep ODS-A, S-5 μm, 50×20 mm

Solvent: SOLUTION A; 0.1% trifluoroacetic acid containing water, SOLUTION B; 0.1% trifluoroacetic acid containing acetonitrile Gradient cycle: 0.00 min (SOLUTION A/SOLUTION B=90/10), 1.00 min (SOLUTION A/SOLUTION B=90/10), 4.00 min (SOLUTION A/SOLUTION B=10/95), 8.50 min (SOLUTION A/SOLUTION B=10/95), 8.60 min (SOLUTION A/SOLUTION B=90/10), 8.70 min (SOLUTION A/SOLUTION B=90/10)

Flow rate: 20 mL/min, detection: UV 220 nm

Other Conditions:

$^1$H-NMR spectrum was measured by Mercury 300 (300 MHz) using tetramethylsilane as the internal standard, and all δ values are shown in ppm. Unless otherwise specified, the numerical values shown for mixed solvents are volume mixing ratios of respective solvents. Unless otherwise specified, % means weight %. The room temperature (ambient temperature) in the present specification shows a temperature from about 10° C. to about 35° C. In addition, as a microwave reactor, Emrys Optimizer of Personal Chemistry was used.

Example 44

1-[5-(3-Furyl)-1-[(4-methoxyphenyl)sulfonyl]-1H-pyrrol-3-yl]-N-methylmethanamine trifluoroacetate tert-Butyl ({5-bromo-1-[(4-methoxyphenyl)sulfonyl]-1H-pyrrol-3-yl}methyl)methylcarbamate (0.053 mmol), furan-3-boronic acid (0.100 mmol), tetrakis(triphenylphosphine)palladium (0.0025 mmol) were dissolved in a mixed solvent of dimethoxyethane (1.0 mL), ethanol (0.3 mL) and acetonitrile (0.2 mL), 0.5 mol/l aqueous sodium carbonate solution (0.3 mL) was added, and the mixture was subjected to microwave irradiation in a sealed reaction container and stirred at 150° C. for 4 min. After completion of the reaction, water (2 mL) and ethyl acetate (2 mL) were added to the reaction mixture and the mixture was stirred for a while. The organic layer was passed through a PTFE tube (polytetrafluoroethylene membrane processed tube) to give a solution containing the object compound. The solvent was evaporated under reduced pressure, a 10% solution (0.5 mL) of tetrafluoroacetic acid in dichloromethane was added to the residue and the mixture was stood at 50° C. for 3 hr. After concentration, the residue was purified by preparative HPLC to give the title compound (13.5 mg, LC-MS purity 97%).

Examples 45-86

The compounds of Example 45 to Example 86 were obtained by reaction with various boronic acids in the same manner as in Example 44 (Tables 20 and 21). The proton NMR data of the representative compounds are shown in the following Table 22.

TABLE 20

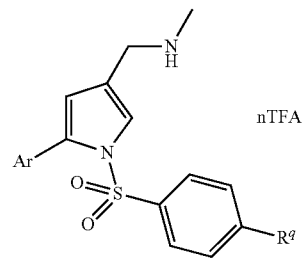

| | | | | LC/MS | |
|---|---|---|---|---|---|
| Ex. | N | Ar | R$^q$ | HPLC purity (%) | m/e (M$^+$ + 1) |
| 45 | 2 | 3-pyridyl | methoxy | 97 | 358 |
| 46 | 1 | 3-thienyl | methoxy | 96 | 363 |
| 47 | 1 | p-tolyl | methoxy | 96 | 371 |
| 48 | 1 | 4-cyanophenyl | methoxy | 100 | 382 |
| 49 | 1 | 3,5-dimethylphenyl | methoxy | 96 | 385 |
| 50 | 1 | 4-methoxyphenyl | methoxy | 97 | 387 |
| 51 | 1 | 4-chlorophenyl | methoxy | 91 | 391 |
| 52 | 1 | 4-acetylphenyl | methoxy | 98 | 399 |
| 53 | 1 | 3-acetylphenyl | methoxy | 97 | 399 |
| 54 | 1 | 4-aminocarbonyl-phenyl | methoxy | 98 | 400 |

TABLE 20-continued

Structure: Ar-[pyrrole with CH2-NH-Me]-N-SO2-C6H4-R^q · nTFA

| Ex. | N | Ar | R^q | HPLC purity (%) | LC/MS m/e (M⁺ + 1) |
|---|---|---|---|---|---|
| 55 | 2 | 4-(N,N-dimethylamino)phenyl | methoxy | 98 | 400 |
| 56 | 1 | 4-(methylthio)phenyl | methoxy | 81 | 403 |
| 57 | 1 | benzo[b]thiophen-2-yl | methoxy | 99 | 413 |
| 58 | 1 | 3-(acetylamino)phenyl | methoxy | 93 | 414 |
| 59 | 1 | 2,4-dimethoxyphenyl | methoxy | 97 | 417 |
| 60 | 1 | 3-(trifluoromethyl)phenyl | methoxy | 94 | 425 |
| 61 | 1 | 4-(trifluoromethoxy)phenyl | methoxy | 87 | 441 |
| 62 | 1 | 2-isopropoxyphenyl | methoxy | 99 | 415 |
| 63 | 1 | 3-(6-methoxy)pyridyl | methoxy | 93 | 388 |
| 64 | 1 | 3-cyanophenyl | methoxy | 98 | 382 |
| 65 | 1 | 3-furyl | methyl | 98 | 331 |
| 66 | 2 | 3-pyridyl | methyl | 100 | 342 |
| 67 | 1 | 3-thienyl | methyl | 99 | 347 |
| 68 | 1 | p-tolyl | methyl | 96 | 355 |
| 69 | 1 | 4-cyanophenyl | methyl | 98 | 366 |
| 70 | 1 | 3,5-dimethylphenyl | methyl | 93 | 369 |
| 71 | 1 | 4-methoxyphenyl | methyl | 99 | 371 |
| 72 | 1 | 4-chlorophenyl | methyl | 93 | 375 |
| 73 | 1 | 4-acetylphenyl | methyl | 98 | 383 |
| 74 | 1 | 3-acetylphenyl | methyl | 98 | 383 |
| 75 | 1 | 4-aminocarbonylphenyl | methyl | 98 | 384 | continued on Table 21

TABLE 21

| 76 | 2 | 4-(N,N-dimethylamino)phenyl | methyl | 99 | 384 |
|---|---|---|---|---|---|
| 77 | 1 | 4-(methylthio)phenyl | methyl | 96 | 387 |
| 78 | 1 | benzo[b]thiophen-2-yl | methyl | 99 | 397 |
| 79 | 1 | 3-(acetylamino)phenyl | methyl | 89 | 398 |
| 80 | 1 | 2,4-dimethoxyphenyl | methyl | 99 | 401 |
| 81 | 1 | 3-(trifluoromethyl)phenyl | methyl | 81 | 409 |
| 82 | 1 | 4-(trifluoromethoxy)phenyl | methyl | 89 | 425 |
| 83 | 1 | 2-isopropoxyphenyl | methyl | 92 | 399 |
| 84 | 1 | 3-(hydroxymethyl)phenyl | methyl | 91 | 371 |
| 85 | 1 | 3-(6-methoxy)pyridyl | methyl | 99 | 372 |
| 86 | 1 | 3-cyanophenyl | methyl | 98 | 366 |

TABLE 22

| compound | ¹H-NMR (DMSO-d₆, 300 MHz); δ |
|---|---|
| Ex. 48 (TFA salt) | 2.50 (3H, s), 3.82 (3H, s), 3.99 (2H, s), 6.49 (1H, s), 7.03 (2H, d, J = 9.0 Hz) 7.30-7.46 (4H, m), 7.74 (1H, s), 7.87 (2H, d, J = 6.0 Hz), 8.65 (2H, brs) |
| Ex. 77 (TFA salt) | 2.36 (3H, s), 2.50 (3H, s), 3.36 (3H, s), 3.98 (2H, s), 6.33 (1H, s), 7.09 (2H, d, J = 6.0 Hz), 7.20-7.40 (6H, m), 7.66 (1H, s), 8.69 (2H, s) |

Example 87

1-{1-[(2,5-Dichloro-3-thienyl)sulfonyl]-5-phenyl-1H-pyrrol-3-yl}-N-methylmethanamine trifluoroacetate A solution of tert-butyl methyl[(5-phenyl-1H-pyrrol-3-yl)methyl]carbamate (0.06 mmol) in DMF (1.8 mL) was added to sodium hydride (60% in oil, 0.6 mmol), and the mixture was stirred at room temperature for 10 min. 2,5-Dichlorothiophene-3-sulfonyl chloride (0.18 mmol) was added and the mixture was stirred at room temperature for 30 min. Water (2 mL) was added and the mixture was stirred and extracted with dichloromethane (3 mL). The extract was washed twice with water (2 mL) and aminomethyl scavenger Lantern (trade name) resin (Mimotopes Pty Ltd., 0.25 mmol) was added to the obtained solution. The mixture was stirred at room temperature for 1 hr and Lantern was removed. trifluoroacetic acid (0.4 mL) was added to the obtained solution, and the mixture was stood at room temperature for 3 days. The solvent was evaporated, and the obtained residue was purified by preparative HPLC to give the title compound (8.1 mg, LC-MS purity 100%).

Examples 88-116

The compounds of Example 88 to Example 116 were obtained by reaction with various sulfonyl chlorides in the same manner as in Example 87 (Table 23). The proton NMR data of the representative compounds are shown in the following Table 24.

TABLE 23

Structure: phenyl-pyrrole with CH2-NH-Me, N-SO2-R^r · TFA

| Ex. | R^r | HPLC purity (%) | LC/MS m/e (M⁺ + 1) |
|---|---|---|---|
| 88 | 4-biphenyl | 100 | 403 |
| 89 | m-toluyl | 100 | 341 |
| 90 | 2,4-dichlorophenyl | 100 | 395 |
| 91 | 2-methoxy-4-methylphenyl | 100 | 371 |
| 92 | 2-chlorophenyl | 100 | 361 |
| 93 | 4-carboxyphenyl | 99 | 371 |
| 94 | 3,5-dimethylphenyl | 100 | 355 |
| 95 | 3,5-dichlorophenyl | 93 | 395 |
| 96 | 4-tert-butylphenyl | 99 | 383 |
| 97 | n-propyl | 99 | 293 |
| 98 | ethyl | 100 | 279 |
| 99 | 3,4-dimethoxyphenyl | 95 | 387 |
| 100 | 3-chlorophenyl | 100 | 361 |
| 101 | 4-cyanophenyl | 98 | 352 |
| 102 | 3-cyanophenyl | 98 | 352 |
| 103 | 2-cyanophenyl | 99 | 352 |

TABLE 23-continued

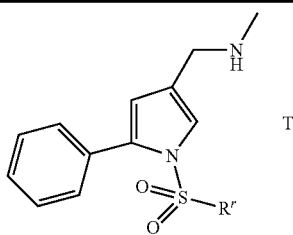

| Ex. | R$^r$ | HPLC purity (%) | LC/MS m/e (M$^+$ + 1) |
|---|---|---|---|
| 104 | 2,1,3-benzothiadiazol-4-yl | 96 | 385 |
| 105 | 3,4-dichlorophenyl | 99 | 395 |
| 106 | 3-thienyl | 96 | 333 |
| 107 | phenyl | 100 | 327 |
| 108 | 1-naphthyl | 97 | 377 |
| 109 | p-styryl | 99 | 353 |
| 110 | 4-ethylphenyl | 100 | 355 |
| 111 | 2,5-dichlorophenyl | 99 | 395 |
| 112 | isopropyl | 100 | 293 |
| 113 | 2-(1-naphthyl)ethyl | 99 | 405 |
| 114 | 2-naphthyl | 99 | 377 |
| 115 | 2,4,6-trimethylphenyl | 100 | 369 |
| 116 | 4-bromophenyl | 99 | 405 |

TABLE 24

| compound | $^1$H-NMR (DMSO-d$_6$, 300 MHz); δ |
|---|---|
| Ex. 91 (TFA salt) | 2.33 (3H, s), 2.63 (3H, s), 3.71 (3H, s), 4.02 (2H, s), 6.20 (1H, s), 6.51 (1H, d, J = 8.1 Hz), 6.66 (1H, s), 6.99 (2H, d, J = 7.5 Hz), 7.07 (1H, d, J = 8.3 Hz), 7.14 (2H, t, J = 7.6 Hz), 7.23 (1H, d, J = 7.3 Hz), 7.61 (1H, s), 9.42 (1H, s) |
| Ex. 98 (TFA salt) | 1.05 (3H, t, J = 7.3 Hz), 2.63 (3H, s), 2.93 (2H, q, J = 7.5 Hz), 3.98 (2H, s), 6.40 (1H, d, J = 1.9 Hz), 7.31-7.55 (6H, m), 9.68 (1H, s) |
| Ex. 106 (TFA salt) | 2.60 (3H, s), 3.97 (2H, s), 6.26 (1H, s), 6.90 (1H, d, J = 5.3 Hz), 7.18 (2H, d, J = 7.3 Hz), 7.21-7.49 (5H, m), 7.56 (1H, s), 9.61 (1H, s) |
| Ex. 112 (TFA salt) | 1.09 (6H, d, J = 6.8 Hz), 2.63 (3H, s), 2.88-3.04 (1H, m), 3.99 (2H, s), 6.40 (1H, d, J = 1.9 Hz), 7.32-7.51 (6H, m), 9.65 (1H, s) |

Example 117

1-(2-Chloro-5-phenyl-1-{[4-(trifluoromethyl)phenyl]sulfonyl}-1H-pyrrol-3-yl)-N-methylmethanamine hydrochloride 2-Chloro-5-phenyl-1-{[4-(trifluoromethyl)phenyl]sulfonyl}-1H-pyrrole-3-carbaldehyde (160 mg) was dissolved in methanol (20 mL), 40% methylamine methanol solution (150 mg) was added at room temperature, and the mixture was stirred for 30 min. Sodium borohydride (44 mg) was added at room temperature, and the mixture was stirred for 10 min. 1 mol/L Hydrochloric acid (10 mL) was added, and the mixture was stirred for 5 min. The reaction mixture was alkalized with a saturated aqueous sodium hydrogencarbonate solution, and extracted with ethyl acetate. The extract was washed with saturated brine, dried over anhydrous sodium sulfate, and concentrated under reduced pressure. The residue was purified by basic silica gel column chromatography (eluent: hexane-ethyl acetate=1:4→0:1), and dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 98 mg, 55%).

$^1$H-NMR (DMSO-d$_6$) δ: 2.43 (3H, s), 3.89 (2H, s), 6.65 (1H, s), 7.38-7.48 (5H, m), 7.85 (2H, d, J=8.4 Hz), 8.05 (2H, d, J=8.4 Hz).

Example 118

1-{1-[(3-Chlorophenyl)sulfonyl]-2-methyl-5-phenyl-1H-pyrrol-3-yl}-N-methylmethanamine hydrochloride Using 1-[(3-chlorophenyl)sulfonyl]-2-methyl-5-phenyl-1H-pyrrole-3-carbaldehyde (171 mg), methylammonium chloride (311 mg) and sodium cyanoborohydride (103 mg), a procedure as in Example 4 was performed to give the title compound as a colorless oil (yield 64 mg, 34%).

$^1$H-NMR (CDCl$_3$) δ: 2.44 (3H, brs), 2.56 (3H, s), 3.87 (2H, brs), 6.47 (1H, s), 7.18-7.22 (2H, m), 7.26-7.36 (6H, m), 7.47-7.50 (1H, m), 9.78 (2H, brs).

Example 119

N-Methyl-1-(5-phenyl-1-{[4-(trifluoromethoxy)phenyl]sulfonyl}-1H-pyrrol-3-yl)methanamine hydrochloride To a solution (12 mL) of 5-phenyl-1-{[4-(trifluoromethoxy)phenyl]sulfonyl}-1H-pyrrole-3-carbaldehyde (0.41 g) in methanol were added methylammonium chloride (0.86 g) and sodium cyanoborohydride (0.27 g), and the mixture was stirred at room temperature for 24 hr. The reaction mixture was concentrated under reduced pressure, saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by basic silica gel column chromatography (eluent: hexane-ethyl acetate=2:1→1:1) to give free base of the title compound as an oil (0.32 g). The obtained oil (0.32 g) was dissolved in ethyl acetate (5 mL). A 4 mol/L hydrogen chloride-ethyl acetate solution (4 mL) was added, and the mixture was concentrated under reduced pressure. The residue was crystallized from ethyl acetate to give the title compound as white crystals (yield 0.29 g, 63%).

$^1$H-NMR (DMSO-d$_6$) δ: 2.50 (3H, s), 3.99 (2H, s), 6.47 (1H, d, J=1.9 Hz), 7.10-7.15 (2H, m), 7.32-7.43 (3H, m), 7.45-7.54 (4H, m), 7.75 (1H, d, J=1.7 Hz), 9.04 (2H, s).

Example 120

N-Methyl-1-[5-phenyl-1-(2-thienylsulfonyl)-1H-pyrrol-3-yl]methanamine hydrochloride 5-Phenyl-1-(2-thienylsulfonyl)-1H-pyrrole-3-carbaldehyde (180 mg) was dissolved in methanol (20 mL), a 40% methylamine methanol solution (220 mg) was added at room temperature, and the mixture was stirred for 30 min. Sodium borohydride (64 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: hexane-ethyl acetate=1:4→0:1), and dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 171 mg, 82%).

$^1$H-NMR (DMSO-$d_6$) δ: 2.50 (3H, s), 3.98 (2H, s), 6.49 (1H, d, J=1.8 Hz), 7.12 (1H, dd, J=3.9, 5.0 Hz), 7.22-7.25 (2H, m), 7.32 (1H, dd, J=1.4, 3.9 Hz), 7.36-7.46 (3H, m), 7.69 (1H, d, J=1.8 Hz), 8.08 (1H, dd, J=1.4, 5.0 Hz), 9.10 (2H, br).

Example 121

N-Methyl-1-[2-methyl-1-(phenylsulfonyl)-5-(3-thienyl)-1H-pyrrol-3-yl]methanamine hydrochloride To a solution of 2-methyl-1-(phenylsulfonyl)-5-(3-thienyl)-1H-pyrrole-3-carbaldehyde (307 mg) in tetrahydrofuran (5 mL) were added 40% methylamine methanol solution (0.4 mL), and anhydrous magnesium sulfate (268 mg), and the mixture was stirred at room temperature for 14 hr. To the reaction mixture was added sodium borohydride (45 mg) at room temperature, and the mixture was stirred for 30 min, and concentrated under reduced pressure. Saturated aqueous sodium hydrogencarbonate solution was added to the residue, and the mixture was extracted with ethyl acetate. The extract was washed with saturated aqueous sodium hydrogencarbonate solution, water and saturated brine, and dried over anhydrous sodium sulfate, and the solvent was evaporated under reduced pressure. The residue was purified by basic silica gel column chromatography (eluent: ethyl acetate) to give free base of the title compound as a yellow oil. To solution (5 mL) of the obtained free base in methanol was added 4 mol/L hydrogen chloride-ethyl acetate solution (2.0 mL), and the mixture was stirred for 2 hr. The reaction mixture was concentrated under reduced pressure, and the residue was recrystallized from ethanol to give the title compound as white crystals (yield 85 mg, 23%).

$^1$H-NMR (CDCl$_3$) δ: 2.43 (3H, brt, J=5.1 Hz), 2.55 (3H, s), 3.86 (2H, brs), 6.48 (1H, s), 7.00-7.02 (1H, m), 7.05-7.06 (1H, m), 7.18-7.20 (1H, m), 7.35-7.44 (4H, m), 7.50-7.55 (1H, m), 9.72 (2H, brs).

Example 122

1-[5-(4-Fluorophenyl)-2-methyl-1-(phenylsulfonyl)-1H-pyrrol-3-yl]-N-methylmethanamine hydrochloride To a solution (20 mL) of 5-(4-fluorophenyl)-2-methyl-1-(phenylsulfonyl)-1H-pyrrole-3-carbaldehyde (0.40 g) in methanol were added methylammonium chloride (0.95 g) and sodium cyanoborohydride (0.30 g), and the mixture was stirred at room temperature for 20 hr. The reaction mixture was concentrated under reduced pressure, saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by basic silica gel column chromatography (eluent: hexane-ethyl acetate=1:0→1:2) to give free base of the title compound as an oil (0.30 g). The obtained oil (0.30 g) was dissolved in ethyl acetate (6 mL), and a 4 mol/L hydrogen chloride-ethyl acetate solution (3 mL) was added. The mixture was concentrated under reduced pressure, and the residue was crystallized from ethyl acetate to give the title compound as colorless crystals (yield 0.31 g, 92%).

$^1$H-NMR (DMSO-$d_6$) δ: 2.44 (3H, s), 2.50 (3H, s), 3.91 (2H, s), 6.43 (1H, s), 7.16-7.30 (4H, m), 7.44-7.49 (2H, m), 7.57 (2H, t, J=7.8 Hz), 7.69-7.75 (1H, m), 8.97 (2H, brs).

Example 123

N-Ethyl-1-[5-(4-fluorophenyl)-2-methyl-1-(phenylsulfonyl)-1H-pyrrol-3-yl]methylamine hydrochloride To a solution (15 mL) of 5-(4-fluorophenyl)-2-methyl-1-(phenylsulfonyl)-1H-pyrrole-3-carbaldehyde (0.30 g) in methanol were added ethylamine (content about 70%, 0.17 g) and sodium cyanoborohydride (0.16 g, 2.6 mmol), and the mixture was stirred at room temperature for 24 hr. The reaction mixture was concentrated under reduced pressure, water was added, and the mixture was extracted with ethyl acetate. The extract was washed with saturated brine, dried over anhydrous magnesium sulfate, and concentrated under reduced pressure. The residue was purified by basic silica gel column chromatography (eluent: hexane-ethyl acetate=1:0→1:2) to give free base of the title compound as an oil (0.095 g). The obtained oil (0.095 g) was dissolved in ethyl acetate (3 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 0.082 g, 23%).

$^1$H-NMR (DMSO-$d_6$) δ: 1.17 (3H, t, J=7.2 Hz), 2.48 (3H, s), 3.90 (2H, s), 6.47 (1H, s), 7.16-7.31 (4H, m), 7.44-7.50 (2H, m), 7.58 (2H, t, J=7.8 Hz), 7.72 (1H, t, J=7.4 Hz), 8.94 (2H, brs).

Example 124

1-[2,4-Dimethyl-5-phenyl-1-(phenylsulfonyl)-1H-pyrrol-3-yl]-N-methylmethanamine hydrochloride Using 2,4-dimethyl-5-phenyl-1-(phenylsulfonyl)-1H-pyrrole-3-carbaldehyde (585 mg), a procedure as in Example 121 was performed to give the title compound as white crystals (yield 140 mg, 22%).

$^1$H-NMR (CDCl$_3$) δ: 1.90 (3H, s), 2.41 (3H, brs), 2.64 (3H, s), 3.92 (2H, brs), 7.07-7.10 (2H, m), 7.26-7.45 (7H, m), 7.51-7.56 (1H, m), 9.62 (2H, brs).

Example 125

N-Methyl-1-[5-phenyl-1-(phenylsulfonyl)-4-propyl-1H-pyrrol-3-yl]methanamine hydrochloride Using 5-phenyl-1-(phenylsulfonyl)-4-propyl-1H-pyrrole-3-carbaldehyde (1.33 g), 40% methylamine methanol solution (877 mg) and sodium borohydride (474 mg), a procedure as in Example 9 was performed. Recrystallization from a mixed solvent of ethyl acetate and ethanol gave the title compound as colorless crystals (yield 515 mg, 34%).

$^1$H-NMR (CDCl$_3$) δ: 0.70 (3H, t, J=7.5 Hz), 1.20-1.29 (2H, m), 2.16-2.21 (2H, m), 2.71 (3H, s), 4.08 (2H, s), 6.95-6.99 (2H, m), 7.25-7.54 (8H, m), 7.96 (1H, s), 9.83 (2H, br).

Example 126

1-[4,5-Diphenyl-1-(phenylsulfonyl)-1H-pyrrol-3-yl]-N-methylmethanamine 4,5-Diphenyl-1-(phenylsulfonyl)-1H-pyrrole-3-carbaldehyde (202 mg) was dissolved in methanol (2 mL) and tetrahydrofuran (2 mL), 40% methylamine methanol solution (0.5 mL) was added at room temperature, and the mixture was stirred for 15 min. To the reaction mixture was added sodium borohydride (22 mg) at room temperature, and the mixture stirred for 1 hr. The reaction mixture was concentrated under reduced pressure, to the residue was added saturated aqueous sodium hydrogencarbonate solution, and the mixture was extracted with ethyl acetate. The extract was washed with saturated aqueous sodium hydrogencarbonate solution, water and saturated brine, and dried over anhydrous sodium sulfate, and the solvent was evaporated under reduced pressure. The residue was purified by basic silica gel column chromatography (eluent: ethyl acetate) to give the title compound as white crystals (yield 181 mg, 87%).

$^1$H-NMR (CDCl$_3$) δ: 1.39 (1H, brs), 2.40 (3H, s), 3.61 (2H, s), 6.95-7.02 (4H, m), 7.08-7.19 (5H, m), 7.21-7.37 (5H, m), 7.46-7.52 (2H, m).

Example 127

1-[2-Chloro-5-phenyl-1-(phenylsulfonyl)-1H-pyrrol-3-yl]-N-methylmethanamine hydrochloride 2-Chloro-5-phenyl-1-(phenylsulfonyl)-1H-pyrrole-3-carbaldehyde (440 mg) was dissolved in methanol (20 mL), 40% methylamine methanol solution (494 mg) was added at room temperature, and the mixture was stirred for 30 min. Sodium borohydride (144 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: hexane-ethyl acetate=3:7→0:1), and dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 308 mg, 61%).

$^1$H-NMR (DMSO-d$_6$) δ: 2.43 (3H, s), 3.89 (2H, s), 6.61 (1H, s), 7.36-7.46 (5H, m), 7.62-7.69 (4H, m), 7.75-7.82 (1H, m), 8.97 (2H, br).

Example 128

1-[2-Fluoro-5-phenyl-1-(phenylsulfonyl)-1H-pyrrol-3-yl]-N-methylmethanamine hydrochloride 2-Fluoro-5-phenyl-1-(phenylsulfonyl)-1H-pyrrole-3-carbaldehyde (110 mg) was dissolved in methanol (20 mL), 40% methylamine methanol solution (130 mg) was added at room temperature, and the mixture was stirred for 30 min. Sodium borohydride (38 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: hexane-ethyl acetate=3:7→0:1), and dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as pale-yellow crystals (yield 32 mg, 25%).

$^1$H-NMR (DMSO-d$_6$) δ: 2.43 (3H, br), 3.88 (2H, br), 6.38 (1H, d, J=5.5 Hz), 7.28-7.31 (2H, m), 7.40-7.44 (3H, m), 7.58-7.67 (4H, m), 7.78-7.84 (1H, m), 9.00 (2H, br).

Example 129

1-[2-Chloro-4-fluoro-5-phenyl-1-(phenylsulfonyl)-1H-pyrrol-3-yl]-N-methylmethanamine hydrochloride 2-Chloro-4-fluoro-5-phenyl-1-(phenylsulfonyl)-1H-pyrrole-3-carbaldehyde (140 mg) was dissolved in methanol (10 mL), 40% methylamine methanol solution (150 mg) was added at room temperature, and the mixture was stirred for 30 min. Sodium borohydride (44 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: hexane-ethyl acetate=3:7→0:10), and dissolved in ethyl acetate (5 mL). A 4 mol/L hydrogen chloride-ethyl acetate solution (1 mL) was added, and the mixture was concentrated under reduced pressure. The residue was crystallized from ethyl acetate-diisopropyl ether to give the title compound as colorless crystals (yield 19 mg, 12%).

$^1$H-NMR (DMSO-d$_6$) δ: 2.44 (3H, s), 3.97 (2H, s), 7.33-7.42 (2H, m), 7.48-7.51 (3H, m), 7.67-7.70 (4H, m), 7.80-7.86 (1H, m), 8.94 (2H, br).

Example 130

1-[4-Fluoro-5-phenyl-1-(phenylsulfonyl)-1H-pyrrol-3-yl]-N-methylmethanamine hydrochloride 4-Fluoro-5-phenyl-1-(phenylsulfonyl)-1H-pyrrole-3-carbaldehyde (10 mg) was dissolved in methanol (5 mL), 40% methylamine methanol solution (236 mg) was added at room temperature, and the mixture was stirred for 30 min. Sodium borohydride (12 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 1 mg, 9%). MS (ESI+): 345 (M+H)

Example 131

N-Methyl-1-{2-methyl-1-[(3-methylphenyl)sulfonyl]-5-phenyl-1H-pyrrol-3-yl}methanamine hydrochloride To a solution (5 mL) of 2-methyl-1-[(3-methylphenyl)sulfonyl]-5-phenyl-1H-pyrrole-3-carbaldehyde (245 mg) in methanol was added 40% methylamine-methanol solution (0.17 mL), and the mixture was stirred at room temperature for 30 min. To the reaction mixture was added sodium tetrahydroborate (82 mg), and the mixture was stirred at room temperature for 3 hr. The reaction mixture was concentrated under reduced pressure, water was added to the residue, and the mixture was extracted with ethyl acetate. The extract was washed with saturated brine, and dried over anhydrous sodium sulfate, and the solvent was evaporated under reduced pressure. The residue was purified by basic silica gel column chromatography (eluent: hexane-ethyl acetate=9:1→ethyl acetate). The obtained colorless oil was dissolved in ethyl acetate (5 mL), a 4 mol/L hydrogen chloride-ethyl acetate solution (0.5 mL) was added, and the mixture was left standing in a freezer at −20° C. for 18 hr. The precipitated crystals were collected by filtration, and vacuum-dried to give the title compound as a colorless solid (yield 42 mg, 15%).

$^1$H-NMR (DMSO-$d_6$) δ: 2.31 (3H, s), 2.43 (3H, s), 2.48 (3H, s), 3.90 (2H, s), 6.41 (1H, s), 7.15-7.60 (9H, m), 8.92 (2H, br).

Example 132

N-Methyl-1-[1-(2-methylpyrimidin-5-ylsulfonyl)-5-phenyl-1H-pyrrol-3-yl]methanamine dihydrochloride 1-[(2-Methyl-5-pyrimidine)sulfonyl]-5-phenyl-1H-pyrrole-3-carbaldehyde (148 mg) was dissolved in absolute tetrahydrofuran (10 mL), 2 mol/L methylamine-tetrahydrofuran solution (1.25 mL) was added, and the mixture was stirred overnight at room temperature. The reaction mixture was added to a solution of sodium borohydride (95 mg) in methanol (3.0 mL), and the mixture was stirred at the same temperature for 20 min. The reaction mixture was diluted with ethyl acetate, washed with saturated brine, and dried over anhydrous magnesium sulfate, and the solvent was evaporated under reduced pressure. The residue was dissolved in tetrahydrofuran (20 mL), di-tert-butyl bicarbonate (0.55 g), sodium hydrogencarbonate (0.25 g) and water (10 mL) were added, and the mixture was stirred at room temperature for 30 min. The reaction mixture was diluted with ethyl acetate, washed successively with saturated aqueous sodium hydrogencarbonate solution and saturated brine, and dried over anhydrous magnesium sulfate, and the solvent was evaporated under reduced pressure. The residue was dissolved in tetrahydrofuran (20 mL), manganese dioxide (75% chemical-treated product, 1.5 g) was added, and the mixture was stirred at room temperature for 1 hr. The reaction product was filtered through celite, and the celite washed with ethylacetate. The filtrate was concentrated under reduced pressure, and the residue was purified by silica gel column chromatography (eluent: hexane-ethyl acetate=19:1→1:1) to give N-Boc compound of the title compound. The obtained N-Boc compound was dissolved in ethanol (1 mL) and added a 4 mol/L hydrogen chloride-ethyl acetate solution (1 mL). The mixture was stirred at room temperature for 3 hr, and the solvent was evaporated under reduced pressure to give a solid (67 mg). The solid was recrystallized from ethanol to give the title compound as a colorless solid (yield 34 mg, 18%).

$^1$H-NMR (DMSO-$d_6$) δ: 2.53 (3H, s), 2.70 (3H, s), 3.98 (2H, s), 6.50 (1H, s), 7.18-7.20 (2H, m), 7.38-7.47 (3H, m), 7.76-7.77 (1H, m), 8.59 (2H, s), 8.88 (2H, br), 1H not detected.

Example 133

N-Methyl-1-{4-methyl-[1-(3-methylphenyl)sulfonyl]-5-phenyl-1H-pyrrol-3-yl}methanamine hydrochloride To a solution (15 mL) of 4-methyl-1-[(3-methylphenyl)sulfonyl]-5-phenyl-1H-pyrrole-3-carbaldehyde (0.50 g) in methanol were added methylammonium chloride (1.0 g) and sodium cyanoborohydride (0.28 g), and the mixture was stirred at room temperature for 2 hr. To the reaction mixture was added saturated aqueous sodium hydrogencarbonate solution, and the mixture was extracted with ethyl acetate. The extract was washed with saturated aqueous sodium hydrogencarbonate solution, water and saturated brine, dried over anhydrous magnesium sulfate, and concentrated under reduced pressure. The residue was purified by silica gel column chromatography (eluent: hexane-ethyl acetate=9:1→0:1) to give free base of the title compound. To a solution (10 mL) of the obtained free base in ethyl acetate was added a 4 mol/L hydrogen chloride-ethyl acetate solution (1 mL). The solution was concentrated under reduced pressure, and the residue was recrystallized from ethanol-ethyl acetate to give the title compound as a colorless solid (yield 208 mg, 36%).

$^1$H-NMR (DMSO-$d_6$) δ: 1.77 (3H, s), 2.26 (3H, s), 2.55 (3H, s), 3.96 (2H, s), 6.96-6.99 (2H, m), 7.08 (1H, s), 7.20-7.21 (1H, m), 7.35-7.52 (5H, m), 7.73 (1H, s), 9.07 (2H, br).

Example 134

1-{[1-(4-Fluorophenyl)sulfonyl]-4-methyl-5-phenyl-1H-pyrrol-3-yl}-N-methylmethanamine hydrochloride To a solution (3 mL) of 1-[(4-fluorophenyl)sulfonyl]-4-methyl-5-phenyl-1H-pyrrole-3-carbaldehyde (0.23 g) in tetrahydrofuran was added 2 mol/L methylamine-tetrahydrofuran solution (0.9 mL), and the mixture was stirred at room temperature for 12 hr. The reaction mixture was added to a solution (5 mL) of sodium borohydride (68 mg) in methanol, and the mixture was stirred at room temperature for 30 min. Water was added to the reaction mixture, and the mixture was extracted with ethyl acetate. The extract was washed with saturated aqueous sodium hydrogencarbonate solution, water and saturated brine, dried over anhydrous magnesium sulfate, and concentrated under reduced pressure. The residue was purified by basic silica gel column chromatography (eluent: hexane-ethyl acetate=9:1→0:1) to give free base of the title compound. To a solution (3 mL) of the obtained free base in ethyl acetate was added a 4 mol/L hydrogen chloride-ethyl acetate solution (0.5 mL). The mixture was left standing at room temperature for 30 min, and the precipitated crystals were collected by filtration to give the title compound as a colorless solid (yield 172 mg, 48%).

$^1$H-NMR (DMSO-$d_6$) δ: 1.78 (3H, s), 2.57 (3H, s), 3.98 (2H, s), 6.98-7.01 (2H, m), 7.35-7.45 (7H, m), 7.74 (1H, s), 9.01 (2H, br).

Example 135

N-Methyl-1-[2-methyl-1-(pyridin-3-ylsulfonyl)-5-phenyl-1H-pyrrol-3-yl]methanamine dihydrochloride Using 2-methyl-5-phenyl-1-(pyridin-3-ylsulfonyl)-1H-pyrrole-3-carbaldehyde (235 mg), a procedure as in Example 9 was performed to give 1 equivalent of ethanolate of the title compound as a solid (yield 110 mg, 39%).
$^1$H-NMR (DMSO-$d_6$) δ: 1.06 (3H, t, J=7.2 Hz), 2.43-2.50 (6H, m), 3.44 (2H, dd, J=7.2, 14.1 Hz), 3.91-3.94 (2H, m), 6.47 (1H, s), 7.21-7.43 (2H, m), 7.36-7.41 (3H, m), 7.56-7.63 (1H, m), 7.82-7.88 (1H, m), 8.53 (1H, s), 8.87-8.93 (3H, m), 2H not detected.

Example 136

1-[4-Chloro-2-methyl-5-phenyl-1-(phenylsulfonyl)-1H-pyrrol-3-yl]-N-methylmethanamine hydrochloride Using 4-chloro-2-methyl-5-phenyl-1-(phenylsulfonyl)-1H-pyrrole-3-carbaldehyde (301 mg), 40% methylamine methanol solution (195 mg) and sodium borohydride (106 mg), a procedure as in Example 9 was performed. Recrystallization from a mixed solvent of ethyl acetate and ethanol gave the title compound as colorless crystals (yield 146 mg, 42%).
$^1$H-NMR (CDCl$_3$) δ: 2.55 (3H, s), 2.77 (3H, s), 4.05 (2H, s), 7.13-7.16 (2H, m), 7.32-7.45 (7H, m), 7.47-7.59 (1H, m), 9.73 (1H, br), 1H not detected.

Example 137

1-[5-Butyl-1-(phenylsulfonyl)-1H-pyrrol-3-yl]-N-methylmethanamine hydrochloride

Using 5-butyl-1-(phenylsulfonyl)-1H-pyrrole-3-carbaldehyde (553 mg), a procedure as in Example 134 was performed to give the title compound as a colorless solid (yield 425 mg, 65%).
$^1$H-NMR (DMSO-$d_6$) δ: 0.79-0.85 (3H, m), 1.24-1.48 (4H, m), 2.48 (3H, s), 2.58-2.63 (2H, m), 3.91 (2H, s), 6.25 (1H, s), 7.54 (1H, s), 7.66-7.88 (5H, m), 8.91 (2H, br).

Example 138

1-[5-Cyclohexyl-1-(phenylsulfonyl)-1H-pyrrol-3-yl]-N-methylmethanamine hydrochloride Using 5-cyclohexyl-1-(phenylsulfonyl)-1H-pyrrole-3-carbaldehyde (424 mg), a procedure as in Example 134 was performed to give the title compound as a colorless solid (yield 321 mg, 49%).
$^1$H-NMR (DMSO-$d_6$) δ: 1.10-1.35 (5H, m), 1.53-1.67 (5H, m), 2.48 (3H, s), 2.80-2.84 (1H, m), 3.90 (2H, s), 6.29 (1H, s), 7.51 (1H, s), 7.65-7.70 (2H, m), 7.76-7.87 (3H, m), 9.00 (2H, br).

Example 139

1-[5-Cyclopropyl-1-(phenylsulfonyl)-1H-pyrrol-3-yl]-N-methylmethanamine hydrochloride Using 5-cyclopropyl-1-(phenylsulfonyl)-1H-pyrrole-3-carbaldehyde (247 mg), a procedure as in Example 134 was performed to give the title compound as a colorless solid. (yield 175 mg, 59%)
$^1$H-NMR (DMSO-$d_6$) δ: 0.22-0.27 (2H, m), 0.75-0.81 (2H, m), 1.97-2.05 (1H, m), 2.47 (3H, s), 3.87 (2H, s), 6.09 (1H, s), 7.55 (1H, s), 7.66-7.91 (5H, m), 8.92 (2H, br).

Example 140

N-Methyl-1-(1-{[3-(methylsulfonyl)phenyl]sulfonyl}-5-phenyl-1H-pyrrol-3-yl)methanamine hydrochloride 1-{[3-(Methylsulfonyl)phenyl]sulfonyl}-5-phenyl-1H-pyrrole-3-carbaldehyde (160 mg) was dissolved in methanol (20 mL), 40% methylamine methanol solution (160 mg) was added at room temperature, and the mixture was stirred for 30 min. Sodium borohydride (32 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was dissolved in methanol (5 mL), a 4 mol/L hydrogen chloride-ethyl acetate solution (1 mL) was added, and the mixture was concentrated under reduced pressure. The residue was crystallized from tetrahydrofuran to give the title compound as colorless crystals (yield 150 mg, 83%).
$^1$H-NMR (DMSO-$d_6$) δ: 2.49 (3H, s), 3.26 (3H, s), 3.98 (2H, s), 6.49 (1H, d, J=1.8 Hz), 7.13-7.17 (2H, m), 7.34-7.46 (3H, m), 7.77-7.87 (4H, m), 8.25-8.29 (1H, m), 9.08 (2H, br).

Example 141

1-(1-{[3-(Ethylsulfonyl)phenyl]sulfonyl}-5-phenyl-1H-pyrrol-3-yl)-N-methylmethanamine hydrochloride Using 1-{[3-(ethylsulfonyl)phenyl]sulfonyl}-5-phenyl-1H-pyrrole-3-carbaldehyde (348 mg), 40% methylamine methanol solution (201 mg) and sodium borohydride (109 mg), a procedure as in Example 9 was performed. Recrystallization from a mixed solvent of ethyl acetate and ethanol gave the title compound as colorless crystals (yield 250 mg, 64%).
$^1$H-NMR (CDCl$_3$) δ: 1.22 (3H, t, J=7.5 Hz), 2.61 (3H, s), 3.06 (2H, q, J=7.5 Hz), 4.00 (2H, s), 6.50 (1H, d, J=2.1 Hz), 7.13-7.16 (2H, m), 7.29-7.41 (3H, m), 7.54-7.59 (1H, m), 7.65-7.68 (1H, m), 7.74 (1H, d, J=2.1 Hz), 7.87-7.89 (1H, m), 8.01-8.05 (1H, m), 9.80 (2H, br).

Example 142

1-[1-(2,3-Dihydro-1,4-benzodioxin-6-ylsulfonyl)-5-phenyl-1H-pyrrol-3-yl]-N-methylmethanamine hydrochloride Using 1-(2,3-dihydro-1,4-benzodioxin-6-ylsulfonyl)-5-phenyl-1H-pyrrole-3-carbaldehyde (258 mg), 40% methylamine methanol solution (163 mg) and sodium borohydride (87 mg), a procedure as in Example 9 was performed. Recrystallization from a mixed solvent of ethylacetate and ethanol gave the title compound as colorless crystals (yield 130 mg, 44%).

¹H-NMR (CDCl₃) δ: 2.55 (3H, s), 3.97 (2H, s), 4.19-4.28 (4H, m), 6.50 (1H, d, J=1.8 Hz), 6.71-6.85 (3H, m), 7.17-7.35 (4H, m), 7.57 (1H, d, J=1.8 Hz), 9.82 (1H, br), 1H not detected.

Example 143

2-({4-[(Methylamino)methyl]-2-phenyl-1H-pyrrol-1-yl}sulfonyl)benzonitrile hydrochloride Using 2-[(4-formyl-2-phenyl-1H-pyrrol-1-yl)sulfonyl]benzonitrile (253 mg), 40% methylamine methanol solution (175 mg) and sodium borohydride (95 mg), a procedure as in Example 9 was performed. Recrystallization from a mixed solvent of ethyl acetate and ethanol gave the title compound as colorless crystals (yield 112 mg, 38%).
¹H-NMR (CDCl₃) δ: 2.64 (3H, s), 4.04 (2H, s), 6.67 (1H, d, J=1.8 Hz), 7.03-7.06 (2H, m), 7.13-7.18 (2H, m), 7.25-7.37 (3H, m), 7.56-7.60 (1H, m), 7.70-7.73 (1H, m), 7.80 (1H, d, J=1.8 Hz), 9.84 (1H, br), 1H not detected.

Example 144

4-({4-[(Methylamino)methyl]-2-phenyl-1H-pyrrol-1-yl}sulfonyl)benzonitrile hydrochloride Using 4-[(4-formyl-2-phenyl-1H-pyrrol-1-yl)sulfonyl]benzonitrile (303 mg), 40% methylamine methanol solution (210 mg) and sodium borohydride (113 mg), a procedure as in Example 9 was performed. Recrystallization from a mixed solvent of ethyl acetate and ethanol gave the title compound as colorless crystals (yield 36 mg, 10%).
¹H-NMR (CDCl₃) δ: 2.62 (3H, s), 4.01 (2H, s), 6.46 (1H, d, J=2.1 Hz), 7.11-7.14 (2H, m), 7.27-7.32 (2H, m), 7.37-7.41 (1H, m), 7.47-7.50 (2H, m), 7.59-7.62 (2H, m), 7.73 (1H, d, J=2.1 Hz), 9.90 (1H, br), 1H not detected.

Example 145

Methyl 2-({4-[(methylamino)methyl]-2-phenyl-1H-pyrrol-1-yl}sulfonyl)benzoate

Methyl 2-[(4-formyl-2-phenyl-1H-pyrrol-1-yl)sulfonyl]benzoate (664 mg) was dissolved in methanol (10 mL), 40% methylamine methanol solution (419 mg) was added at room temperature, and the mixture was stirred for 30 min. To the reaction mixture was added sodium borohydride (227 mg) at 0° C., the mixture was stirred for 1 hr. Water was added, and the mixture was extracted with ethylacetate. The extract was washed with saturated brine, and dried over anhydrous sodium sulfate, and the solvent was evaporated under reduced pressure. The residue was purified by basic silica gel column chromatography (eluent: hexane-ethyl acetate=1:1→0:1) to give the title compound as a pale-yellow oil (yield 472 mg, 68%).
¹H-NMR (CDCl₃) δ: 2.48 (3H, s), 3.64 (2H, s), 3.89 (3H, s), 6.22 (1H, d, J=1.8 Hz), 7.00 (1H, d, J=8.1 Hz), 7.18-7.35 (7H, m), 7.50-7.52 (2H, m).

Example 146

Methyl 2-({4-[(methylamino)methyl]-2-phenyl-1H-pyrrol-1-yl}sulfonyl)benzoate hydrochloride To a solution (1 mL) of methyl 2-({4-[(methylamino)methyl]-2-phenyl-1H-pyrrol-1-yl}sulfonyl)benzoate (105 mg) in ethyl acetate was added 4 mol/L hydrogen chloride-ethyl acetate solution (0.5 mL) at room temperature. The solvent was evaporated under reduced pressure, and the residue was crystallized from 2-propanol and isopropyl ether. The obtained crystals were recrystallized from a mixed solvent of ethyl acetate and ethanol to give the title compound as colorless crystals (yield 68 mg, 60%).
¹H-NMR (CDCl₃) δ: 2.62 (3H, s), 3.87 (3H, s), 4.03 (2H, s), 6.56 (1H, d, J=2.1 Hz), 7.04 (1H, d, J=7.8 Hz), 7.11-7.33 (6H, m), 7.50-7.52 (2H, m), 7.57 (1H, d, J=2.1 Hz), 9.82 (1H, br), 1H not detected.

Example 147

Methyl 3-({4-[(methylamino)methyl]-2-phenyl-1H-pyrrol-1-yl}sulfonyl)benzoate

Using methyl 3-[(4-formyl-2-phenyl-1H-pyrrol-1-yl)sulfonyl]benzoate (1.32 g), 40% methylamine methanol solution (416 mg) and sodium borohydride (100 mg), a procedure as in Reference Example 145 was performed to give the title compound as a pale-yellow oil (yield 668 mg, 49%).
¹H-NMR (CDCl₃) δ: 2.43 (3H, s), 3.59 (2H, s), 3.91 (3H, s), 6.15 (1H, d, J=1.8 Hz), 7.20-7.41 (7H, m), 7.48-7.52 (1H, m), 7.97-7.98 (1H, m), 8.13-8.16 (1H, m), 1H not detected.

Example 148

Methyl 3-({4-[(methylamino)methyl]-2-phenyl-1H-pyrrol-1-yl}sulfonyl)benzoate hydrochloride Using methyl 3-({4-[(methylamino)methyl]-2-phenyl-1H-pyrrol-1-yl}sulfonyl)benzoate (91 mg), a procedure as in Example 146 was performed to give the title compound as colorless crystals (yield 58 mg, 58%).
¹H-NMR (CDCl₃) δ: 2.56 (3H, s), 3.90 (3H, s), 3.98 (2H, s), 6.50 (1H, d, J=1.8 Hz), 7.11-7.14 (2H, m), 7.22-7.28 (2H, m), 7.32-7.43 (2H, m), 7.51-7.55 (1H, m), 7.66 (1H, d, J=1.8 Hz), 7.92-7.93 (1H, m), 8.13-8.17 (1H, m), 2H not detected.

Example 149

2-Chloro-4-({4-[(methylamino)methyl]-2-phenyl-1H-pyrrol-1-yl}sulfonyl)benzonitrile hydrochloride Using 2-chloro-4-[(4-formyl-2-phenyl-1H-pyrrol-1-yl)sulfonyl]benzonitrile (248 mg), 40% methylamine methanol solution (1.4 mL) and sodium borohydride (28.9 mg), a procedure as in Example 9 was performed to give the title compound as white crystals (yield 67.8 mg, 24%).
¹H-NMR (CDCl₃) δ: 2.64 (3H, brs), 4.01 (2H, brs), 6.49 (1H, d, J=1.8 Hz), 7.14-7.16 (2H, m), 7.31-7.36 (3H, m), 7.41-7.47 (2H, m), 7.64-7.67 (1H, m), 7.72 (1H, brs), 9.95 (2H, brs).

Example 150

[1-(1,3-Benzothiazol-6-ylsulfonyl)-5-phenyl-1H-pyrrol-3-yl]-N-methylmethanamine oxalic acid salt Using 1-(1,3-benzothiazol-6-ylsulfonyl)-5-phenyl-1H-pyrrole-3-carbaldehyde (247 mg), 40% methylamine methanol solution (0.7 mL) and sodium borohydride (31.3 mg), a procedure as in Example 126 was performed to give free base of the title compound as a yellow oil. To a solution (3 mL) of the obtained free base in ethanol was added oxalic acid (10 mg), and the reaction mixture was heated until it became uniform. The reaction mixture was cooled to room temperature, and concentrated under reduced pressure. The residue was recrystallized from ethanol to give the title compound as white crystals (yield 20.3 mg, 11%).

$^1$H-NMR (DMSO-d$_6$) δ: 2.53 (3H, s), 3.99 (2H, s), 6.36 (1H, d, J=2.1 Hz), 7.08-8.10 (2H, m), 7.29-7.34 (2H, m), 7.39-7.41 (2H, m), 7.45-7.48 (1H, m), 7.74 (1H, s), 8.18 (1H, d, J=8.4 Hz), 8.30 (1H, d, J=2.1 Hz), 9.69 (1H, s), 3H not detected.

Example 151

1-{1-[(1,1-Dioxido-2,3-dihydro-1-benzothien-6-yl) sulfonyl]-5-phenyl-1H-pyrrol-3-yl}-N-methylmethanamine Using 1-[(1,1-dioxido-2,3-dihydro-1-benzothiophen-6-yl)sulfonyl]-5-phenyl-1H-pyrrole-3-carbaldehyde (114 mg), 40% methylamine methanol solution (0.3 mL) and sodium borohydride (10.8 mg), a procedure as in Example 126 was performed to give the title compound as a white solid (yield 76.3 mg, 65%).

$^1$H-NMR (CDCl$_3$) δ: 2.45 (3H, s), 3.36-3.40 (2H, m), 3.48-3.53 (2H, m), 3.59 (2H, s), 6.18 (1H, d, J=1.8 Hz), 7.24-7.41 (7H, m), 7.50-7.53 (1H, m), 7.66-7.67 (1H, m), 1H not detected.

Example 152

1-[1-(1-Benzothien-2-ylsulfonyl)-5-phenyl-1H-pyrrol-3-yl]-N-methylmethanamine hydrochloride 1-(1-Benzothien-2-ylsulfonyl)-5-phenyl-1H-pyrrole-3-carbaldehyde (180 mg) was dissolved in methanol (20 mL), 40% methylamine methanol solution (190 mg) was added at room temperature, and the mixture was stirred for 30 min. Sodium borohydride (56 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract washed with saturated brine, dried over anhydrous sodium sulfate, and concentrated under reduced pressure. The residue was purified by basic silica gel column chromatography (eluent: hexane-ethyl acetate=3:7→0:1), and dissolved in ethyl acetate (5 mL). A 4 mol/L hydrogen chloride-ethylacetate solution (1 mL) was added, and the mixture was concentrated under reduced pressure. The residue was crystallized from ethyl acetate to give the title compound as colorless crystals (yield 126 mg, 61%).

$^1$H-NMR (DMSO-d$_6$) δ: 2.49 (3H, s), 3.99 (2H, s), 6.54 (1H, d, J=1.8 Hz), 7.23-7.26 (2H, m), 7.34-7.62 (5H, m), 7.75 (1H, d, J=1.8 Hz), 7.77-7.78 (1H, m), 7.96-7.98 (1H, m), 8.08-8.11 (1H, m), 9.23 (2H, br).

Example 153

N-Methyl-1-(1-{[4-(methylsulfonyl)phenyl]sulfonyl}-5-phenyl-1H-pyrrol-3-yl)methanamine hydrochloride 1-{[4-(Methylsulfonyl)phenyl]sulfonyl}-5-phenyl-1H-pyrrole-3-carbaldehyde (60 mg) was dissolved in methanol (20 mL), 40% methylamine methanol solution (120 mg) was added at room temperature, and the mixture was stirred for 30 min. Sodium borohydride (30 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3), and dissolved in methanol (5 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 42 mg, 62%).

$^1$H-NMR (DMSO-d$_6$) δ: 2.50 (3H, s), 3.30 (3H, s), 3.99 (2H, s), 6.50 (1H, d, J=1.8 Hz), 7.13-7.16 (2H, m), 7.34-7.47 (3H, m), 7.63-7.68 (2H, m), 7.78 (1H, d, J=1.8 Hz), 8.03-8.08 (2H, m), 9.11 (2H, br).

Example 154

1-[3-({4-[(Methylamino)methyl]-2-phenyl-1H-pyrrol-1-yl}sulfonyl)phenyl]ethanone 0.5 oxalic acid salt 1-[(3-Acetylphenyl)sulfonyl]-5-phenyl-1H-pyrrole-3-carbaldehyde (200 mg) was dissolved in methanol (30 mL), methylamine hydrochloride (192 mg) was added at room temperature and the mixture was stirred for 30 min. Sodium triacetoxyborohydride (360 mg) was added at room temperature and the mixture was stirred for 2 hr. Saturated aqueous sodium hydrogencarbonate solution was added to the reaction mixture and the mixture was extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3), and dissolved in ethyl acetate (10 mL). Oxalic acid (50 mg) was added and the mixture was stirred for 15 min. The crystallized crystals were collected by filtration to give the title compound as colorless crystals (yield 6.7 mg, 3%).

MS (ESI+): 369 (M+H)

Example 155

N-Methyl-1-{1-[(3-nitrophenyl)sulfonyl]-5-phenyl-1H-pyrrol-3-yl}methanamine hydrochloride 1-[(3-Nitrophenyl)sulfonyl]-5-phenyl-1H-pyrrole-3-carbaldehyde (750 mg) was dissolved in methanol (50 mL), 40% methylamine methanol solution (1.64 g) was added at room temperature, and the mixture was stirred for 30 min. Sodium borohydride (240 mg) was added at room temperature, and the mixture was stirred for 10 min. 1 mol/L Hydrochloric acid (100 mL) was added, and the mixture was stirred for 5 min. The reaction mixture was alkalized with a saturated aqueous sodium hydrogencarbonate solution and extracted with ethyl acetate. The extract washed with saturated brine, dried over anhydrous sodium sulfate. The mixture was concentrated under reduced pressure to give a free base of the title compound as a crude product. A part (50 mg) of the obtained crude free base was dissolved in methanol (10 mL), a 4 mol/L hydrogen chloride-ethylacetate solution (1 mL) was added, and the mixture was concentrated under reduced pressure. The residue was crystallized from ethyl acetate to give the title compound as colorless crystals (yield 43 mg, 5%).

$^1$H-NMR (DMSO-d$_6$) δ: 2.50 (3H, t, J=5.1 Hz), 3.98 (2H, t, J=5.1 Hz), 6.52 (1H, d, J=1.8 Hz), 7.12-7.16 (2H, m), 7.33-7.46 (3H, m), 7.80-8.01 (4H, m), 8.51-8.55 (1H, m), 9.21 (2H, br).

Example 156

N-Methyl-1-[5-phenyl-1-(pyridin-3-ylsulfonyl)-1H-pyrrol-3-yl]methanamine dihydrochloride 5-Phenyl-1-(pyridin-3-ylsulfonyl)-1H-pyrrole-3-carbaldehyde (230 mg) was dissolved in absolute tetrahydrofuran (10 mL), a 2 mol/L solution (1 mL) of methylamine in tetrahydrofuran was added, and the mixture was stirred at room temperature for 2 hr. The reaction mixture was added to a solution of sodium borohydride (76 mg) in methanol (5 mL), and the mixture was stirred at the same temperature for 20 min. The reaction mixture was diluted with ethyl acetate, washed successively with saturated aqueous sodium hydrogencarbonate solution, water and saturated brine, and dried over anhydrous magnesium sulfate. The solvent was evaporated under reduced pressure. The residue was purified by silica gel column chromatography (eluent: ethyl acetate-methanol=1:0→1:1), and further purified by HPLC (ODS, 0.1% trifluoroacetic acid containing water-0.1% trifluoroacetic acid containing acetonitrile=97:3→0.1% trifluoroacetic acid containing acetonitrile) to give trifluoroacetate of the title compound. The obtained trifluoroacetate was neutralized with saturated aqueous sodium hydrogencarbonate solution, extracted with ethyl acetate, washed successively with saturated aqueous sodium hydrogencarbonate solution, water and saturated brine, and dried over anhydrous magnesium sulfate. The solvent was evaporated under reduced pressure. The residue was dissolved in ethyl acetate (5 mL). A 4 mol/L hydrogen chloride-ethyl acetate solution (1 mL) and ethanol (5 mL) were added, and the mixture was concentrated under reduced pressure. The residue was crystallized from ethyl acetate-ethanol to give the title compound (yield 85 mg, 29%).

$^1$H-NMR (DMSO-d$_6$) δ: 2.50 (3H, s), 3.97-4.00 (2H, s), 6.50 (1H, s), 7.14-7.16 (2H, m), 7.35-7.45 (3H, m), 7.62-7.70 (1H, m), 7.78-7.83 (2H, m), 8.47-8.48 (1H, m), 8.84-8.86 (1H, m), 9.08 (2H, br), 1H not detected.

Example 157

1-{1-[(6-Methoxypyridin-3-yl)sulfonyl]-5-phenyl-1H-pyrrol-3-yl}-N-methylmethanamine hydrochloride 1-[(6-Methoxypyridin-3-yl)sulfonyl]-5-phenyl-1H-pyrrole-3-carbaldehyde (59 mg) was dissolved in absolute tetrahydrofuran (5 mL), a 2 mol/L solution (0.25 mL) of methylamine in tetrahydrofuran was added, and the mixture was stirred at room temperature for 3 hr. The reaction mixture was added to a solution of sodium borohydride (19 mg) in methanol (2 mL), and the mixture was stirred at the same temperature for 20 min. The reaction mixture was diluted with ethyl acetate, washed successively with water and saturated brine, and dried over anhydrous magnesium sulfate. The solvent was evaporated under reduced pressure. The residue was purified by silica gel column chromatography (eluent: ethyl acetate-methanol=1:0→1:1) to give a free base (48 mg) of the title compound. The obtained free base was dissolved in ethyl acetate (2 mL), a 4 mol/L hydrogen chloride-ethyl acetate solution (3 mL) was added, and the mixture was stood at room temperature for 30 min. The precipitated crystals were collected by filtration, and washed with ethyl acetate to give the title compound (yield 39 mg, 58%).

$^1$H-NMR (DMSO-d$_6$) δ: 2.50 (3H, s), 3.90 (3H, s), 3.98 (2H, s), 6.45 (1H, s), 6.91-6.94 (1H, m), 7.16-7.18 (2H, m), 7.36-7.45 (3H, m), 7.59-7.63 (1H, m), 7.72 (1H, s), 8.09-8.10 (1H, m), 8.91 (2H, br).

Example 158

N-Methyl-1-[1-(4-methylaminopyridin-3-ylsulfonyl)-5-phenyl-1H-pyrrol-3-yl]methanamine dihydrochloride Using 1-(6-chloro-3-pyridinesulfonyl)-5-phenyl-1H-pyrrole-3-carbaldehyde (100 mg), a procedure as in Example 157 was performed to give the title compound (yield 58 mg, 47%).

$^1$H-NMR (DMSO-d$_6$) δ: 2.50 (3H, s), 2.78 (3H, s), 3.95-3.99 (2H, m), 6.39-6.42 (2H, m), 7.20-7.23 (3H, m), 7.35-7.43 (3H, m), 7.63 (1H, s), 7.82-7.85 (2H, m), 9.00 (2H, br), 1H not detected.

Example 159

N-Methyl-1-[1-(2-methylaminopyridin-3-ylsulfonyl)-5-phenyl-1H-pyrrol-3-yl]methanamine dihydrochloride 1-(2-Chloropyridin-3-ylsulfonyl)-5-phenyl-1H-pyrrole-3-carbaldehyde (173 mg) was dissolved in tetrahydrofuran (10 mL), a 2 mol/L solution (1.25 mL) of methylamine in tetrahydrofuran was added, and the mixture was stirred at room temperature for 12 hr. The reaction mixture was added to a solution (2 mL) of sodium borohydride (76 mg) in methanol, and the mixture was stirred at room temperature for 20 min. Saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent: ethyl acetate→ethyl acetate-methanol=1:4) to give a free base of the title compound. A 4 mol/L hydrogen chloride-ethyl acetate solution (1 mL) was added to a solution (3 mL) of the obtained free base in ethanol. The solvent was evaporated under reduced pressure, and the residue was recrystallized from ethanol to give the title compound (yield 126 mg, 59%).

$^1$H-NMR (DMSO-d$_6$) δ: 2.50 (3H, s), 2.77 (3H, d, J=4.5 Hz), 3.95-3.99 (2H, m), 4.80 (1H, br), 6.28-6.30 (1H, m), 6.41-6.47 (2H, m), 7.10-7.19 (3H, m), 7.32-7.44 (3H, m), 7.88 (1H, s), 8.25-8.27 (1H, m), 9.19 (2H, br).

Example 160

N-Methyl-1-[1-(2-methylaminopyrimidin-5-ylsulfonyl)-5-phenyl-1H-pyrrol-3-yl]methanamine hydrochloride Using 1-(2-chloropyrimidin-5-ylsulfonyl)-5-phenyl-1H-pyrrole-3-carbaldehyde (100 mg), a procedure as in Example 157 was performed to give the title compound (yield 64 mg, 57%).

$^1$H-NMR (DMSO-d$_6$) δ: 2.50 (3H, s), 2.80-2.82 (3H, s), 3.98 (2H, s), 6.47 (1H, s), 7.23-7.26 (2H, m), 7.39-7.43 (3H, m), 7.66-7.67 (1H, m), 7.96-7.97 (1H, m), 8.11-8.12 (1H, m), 8.48-8.52 (1H, m), 8.97 (2H, br).

Example 161

1-[5-(2-Fluorophenyl)-1-{[3-(methylsulfonyl)phenyl]sulfonyl}-1H-pyrrol-3-yl]-N-methylmethanamine hydrochloride 5-(2-Fluorophenyl)-1-{[3-(methylsulfonyl)phenyl]sulfonyl}-1H-pyrrole-3-carbaldehyde (550 mg) was dissolved in methanol (55 mL), 40% methylamine methanol solution (1.05 g) was added at room temperature, and the mixture was stirred for 30 min. Sodium borohydride (154 mg) was added at room temperature, and the mixture was stirred for 10 min. 1 mol/L Hydrochloric acid (100 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was dissolved in methanol (10 mL). A 4 mol/L hydrogen chloride-ethyl acetate solution (2 mL) was added, and the mixture was concentrated under reduced pressure. The residue was crystallized from ethyl acetate to give the title compound as colorless crystals (yield 400 mg, 65%).
$^1$H-NMR (DMSO-d$_6$) δ: 2.48 (3H, t, J=5.5 Hz), 3.30 (3H, s), 3.98 (2H, t, J=5.5 Hz), 6.61 (1H, d, J=1.7 Hz), 7.07-7.12 (1H, m), 7.20-7.26 (2H, m), 7.50-7.57 (1H, m), 7.86-7.90 (4H, m), 8.29-8.33 (1H, m), 9.31 (2H, br).

Example 162

1-[1-{[3-(Ethylsulfonyl)phenyl]sulfonyl}-5-(2-fluorophenyl)-1H-pyrrol-3-yl]-N-methylmethanamine hydrochloride Using 1-{[3-(ethylsulfonyl)phenyl]sulfonyl}-5-(2-fluorophenyl)-1H-pyrrole-3-carbaldehyde (181 mg), 40% methylamine methanol solution (100 mg) and sodium borohydride (54 mg), a procedure as in Example 9 was performed. Recrystallization from a mixed solvent of ethyl acetate and ethanol gave the title compound as colorless crystals (yield 107 mg, 53%).
$^1$H-NMR (DMSO-d$_6$) δ: 1.08 (3H, t, J=7.5 Hz), 2.49-2.51 (3H, m), 3.37 (2H, q, J=7.5 Hz), 3.98 (2H, brs), 6.57 (1H, d, J=2.1 Hz), 7.07-7.12 (1H, m), 7.19-7.25 (2H, m), 7.50-7.55 (1H, m), 7.81-7.90 (4H, m), 8.24-8.28 (1H, m), 9.06 (2H, br).

Example 163

2-{[2-(2-Fluorophenyl)-4-[(methylamino)methyl]-1H-pyrrol-1-yl]sulfonyl}benzonitrile hydrochloride 2-{[2-(2-Fluorophenyl)-4-formyl-1H-pyrrol-1-yl]sulfonyl}benzonitrile (370 mg) was dissolved in methanol (20 mL), 40% methylamine methanol solution (811 mg) was added at room temperature, and the mixture was stirred for 30 min. Sodium borohydride (120 mg) was added at room temperature, and the mixture was stirred for 10 min. 1 mol/L Hydrochloric acid (50 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3), and dissolved in methanol (10 mL). A 4 mol/L hydrogen chloride-ethyl acetate solution (2 mL) was added, and the mixture was concentrated under reduced pressure. The residue was crystallized from ethyl acetate to give the title compound as colorless crystals (yield 280 mg, 66%).
$^1$H-NMR (DMSO-d$_6$) δ: 2.52 (3H, s), 4.04 (2H, s), 6.65 (1H, d, J=1.8 Hz), 7.03-7.18 (3H, m), 7.35-7.38 (1H, m), 7.45-7.53 (1H, m), 7.74-7.80 (1H, m), 7.87 (1H, d, J=1.8 Hz), 7.90-7.95 (1H, m), 8.14-8.17 (1H, m), 9.28 (2H, br).

Example 164

4-{[2-(2-Fluorophenyl)-4-[(methylamino)methyl]-1H-pyrrol-1-yl]sulfonyl}benzonitrile hydrochloride 4-{[2-(2-Fluorophenyl)-4-formyl-1H-pyrrol-1-yl]sulfonyl}benzonitrile (385 mg) was dissolved in methanol (20 mL), 40% methylamine methanol solution (844 mg) was added at room temperature, and the mixture was stirred for 30 min. Sodium borohydride (124 mg) was added at room temperature, and the mixture was stirred for 10 min. 1 mol/L Hydrochloric acid (50 mL) was added, and the mixture was stirred for 5 min. The reaction mixture was alkalized with a saturated aqueous sodium hydrogencarbonate solution and extracted with ethyl acetate. The extract was purified with saturated brine, dried over anhydrous sodium sulfate, and concentrated under reduced pressure. The residue washed with basic silica gel column chromatography (eluent: ethyl acetate-methanol=1:0→7:3), and dissolved in methanol (10 mL). A 4 mol/L hydrogen chloride-ethyl acetate solution (2 mL) was added, and the mixture was concentrated under reduced pressure. The residue was crystallized from ethyl acetate to give the title compound as colorless crystals (yield 274 mg, 62%).
$^1$H-NMR (DMSO-d$_6$) δ: 2.50 (3H, s), 3.99 (2H, s), 6.60 (1H, d, J=1.7 Hz), 7.04-7.10 (1H, m), 7.20-7.27 (2H, m), 7.50-7.57 (1H, m), 7.62-7.66 (2H, m), 7.84 (1H, d, J=1.7 Hz), 8.05-8.09 (2H, m), 9.25 (2H, br).

Example 165

1-{5-(2-Fluorophenyl)-1-[(2-fluorophenyl)sulfonyl]-1H-pyrrol-3-yl}-N-methylmethanamine hydrochloride 5-(2-Fluorophenyl)-1-[(2-fluorophenyl)sulfonyl]-1H-pyrrole-3-carbaldehyde (330 mg) was dissolved in methanol (33 mL), 40% methylamine methanol solution (370 mg) was added at room temperature, and the mixture was stirred for 30 min. Sodium borohydride (108 mg) was added at room temperature, and the mixture was stirred for 10 min. 1 mol/L Hydrochloric acid (50 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3), and dissolved in methanol (5 mL). A 4 mol/L hydrogen chloride-ethyl acetate solution (2 mL) was added, and the mixture was concentrated under reduced pressure. The residue was crystallized from ethyl acetate to give the title compound as colorless crystals (yield 266 mg, 70%).

$^1$H-NMR (DMSO-d$_6$) δ: 2.51 (3H, s), 4.02 (2H, s), 6.61 (1H, d, J=1.8 Hz), 7.01-7.30 (5H, m), 7.44-7.52 (2H, m), 7.79-7.85 (2H, m), 9.28 (2H, br).

Example 166

1-[5-(2-Fluorophenyl)-1-(pyridin-3-ylsulfonyl)-1H-pyrrol-3-yl]-N-methylmethanamine fumarate 5-(2-Fluorophenyl)-1-(pyridin-3-ylsulfonyl)-1H-pyrrole-3-carbaldehyde (1.52 g) was dissolved in methanol (30 mL), 40% methylamine methanol solution (3.57 g) was added at room temperature and the mixture was stirred for 30 min. Sodium borohydride (523 mg) was added at room temperature and the mixture was stirred for 10 min. 1 mol/L Hydrochloric acid (50 mL) was added and the mixture was stirred for 5 min. The reaction mixture was basified with saturated aqueous sodium hydrogencarbonate solution, and the mixture was extracted with ethyl acetate. The extract was washed with saturated brine, dried over anhydrous sodium sulfate, and concentrated under reduced pressure. The residue was purified by basic silica gel column chromatography (eluent: ethylacetate-methanol=1:0→7:3) to give a free base of the title compound as a pale-yellow oil (yield 1.30 g). The obtained free base (750 mg) was dissolved in ethyl acetate (30 mL), and a solution of fumaric acid (278 mg) in methanol (3 mL) was added dropwise at room temperature. After stirring for 30 min, the obtained crystals were collected by filtration, and washed with ethyl acetate to give the title compound as colorless crystals (yield 912 mg, 74%).

$^1$H-NMR (DMSO-d$_6$) δ: 2.43 (3H, s), 3.87 (2H, s), 6.47 (2H, s), 6.49 (1H, d, J=1.8 Hz), 7.07-7.13 (1H, m), 7.19-7.26 (2H, m), 7.49-7.56 (1H, m), 7.59-7.64 (1H, m), 7.74 (1H, d, J=1.8 Hz), 7.86-7.90 (1H, m), 8.56-8.57 (1H, m), 8.87-8.89 (1H, m), 3H not detected.

Example 167

N-Methyl-1-(1-{[3-(methylsulfonyl)phenyl]sulfonyl}-5-[2-(trifluoromethyl)phenyl]-1H-pyrrol-3-yl)methanamine hydrochloride 1-{[3-(Methylsulfonyl)phenyl]sulfonyl}-5-[2-(trifluoromethyl)phenyl]-1H-pyrrole-3-carbaldehyde (300 mg) was dissolved in methanol (30 mL), 40% methylamine methanol solution (510 mg) was added at room temperature, and the mixture was stirred for 30 min. Sodium borohydride (75 mg) was added at room temperature, and the mixture was stirred for 10 min. 1 mol/L Hydrochloric acid (30 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: ethylacetate-methanol=1:0→7:3), and dissolved in methanol (5 mL). A 4 mol/L hydrogen chloride-ethyl acetate solution (2 mL) was added, and the mixture was concentrated under reduced pressure. The residue was crystallized from ethyl acetate to give the title compound as colorless crystals (yield 214 mg, 64%).

$^1$H-NMR (DMSO-d$_6$) δ: 2.46-2.50 (3H, m), 3.30 (3H, s), 3.99-4.03 (2H, m), 6.54 (1H, d, J=1.7 Hz), 7.16-7.18 (1H, m), 7.64-7.96 (7H, m), 8.32-8.35 (1H, m), 9.20 (2H, br).

Example 168

N-Methyl-1-{1-(pyridin-3-ylsulfonyl)-5-[2-(trifluoromethyl)phenyl]-1H-pyrrol-3-yl}methanamine dihydrochloride 1-(Pyridin-3-ylsulfonyl)-5-[2-(trifluoromethyl)phenyl]-1H-pyrrole-3-carbaldehyde (340 mg) was dissolved in methanol (34 mL), 40% methylamine methanol solution (695 mg) was added at room temperature and the mixture was stirred for 30 min. sodium borohydride (102 mg) was added at room temperature and the mixture was stirred for 10 min. 1 mol/L Hydrochloric acid (10 mL) was added and the mixture was stirred for 5 min. The reaction mixture was basified with saturated aqueous sodium hydrogencarbonate solution, and the mixture was extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3), and dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as pale-red crystals (yield 288 mg, 69%).

$^1$H-NMR (DMSO-d$_6$) δ: 2.47 (3H, t, J=5.5 Hz), 4.00 (2H, t, J=5.5 Hz), 6.60 (1H, d, J=1.8 Hz), 7.18-7.21 (1H, m), 7.63-7.81 (4H, m), 7.91-8.00 (2H, m), 8.58 (1H, d, J=1.8 Hz), 8.90-8.92 (1H, m), 9.48-9.57 (2H, m), 1H not detected.

Example 169

N-Methyl-1-[5-(2-methylphenyl)-1-{[3-(methylsulfonyl)phenyl]sulfonyl}-1H-pyrrol-3-yl]methanamine hydrochloride 5-(2-Methylphenyl)-1-{[3-(methylsulfonyl)phenyl]sulfonyl}-1H-pyrrole-3-carbaldehyde (250 mg) was dissolved in methanol (25 mL), 40% methylamine methanol solution (482 mg) was added at room temperature, and the mixture was stirred for 30 min. Sodium borohydride (71 mg) was added at room temperature, and the mixture was stirred for 10 min. 1 mol/L Hydrochloric acid (30 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3), and dissolved in methanol (5 mL). To the solution was added a 4 mol/L hydrogen chloride-ethyl acetate solution (2 mL), and the mixture was concentrated under reduced pressure. The residue was crystallized from ethyl acetate to give the title compound as colorless crystals (yield 156 mg, 55%).

$^1$H-NMR (DMSO-d$_6$) δ: 1.82 (3H, s), 2.49 (3H, s), 3.29 (3H, s), 4.00 (2H, s), 6.45 (1H, d, J=1.8 Hz), 6.83-6.85 (1H, m), 7.11-7.21 (2H, m), 7.31-7.37 (1H, m), 7.78-7.89 (4H, m), 8.29-8.33 (1H, m), 9.31 (2H, br).

Example 170

N-Methyl-1-[1-(phenylsulfonyl)-5-(pyridin-2-yl)-1H-pyrrol-3-yl]methanamine oxalic acid salt 1-(Phenylsulfonyl)-5-(pyridin-2-yl)-1H-pyrrole-3-carbaldehyde (78 mg) was dissolved in methanol (10 mL), 40% methylamine methanol solution (100 mg) was added at room temperature, and the mixture was stirred for 30 min. Sodium borohydride (29 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3) and dissolved in ethyl acetate (10 mL). To the solution was added oxalic acid (50 mg) and the mixture was stirred for 15 min. The crystallized crystals were collected by filtration to give the title compound as colorless crystals (yield 47 mg, 45%).

$^{1}$H-NMR (DMSO-d$_{6}$) δ: 2.55 (3H, s), 4.02 (2H, s), 6.70 (1H, d, J=1.8 Hz), 7.33-7.38 (1H, m), 7.51-7.54 (1H, m), 7.63-7.68 (2H, m), 7.74-7.91 (5H, m), 8.44-8.46 (1H, m).

Example 171

1-{1-[(3,4-Difluorophenyl)sulfonyl]-5-(pyridin-2-yl)-1H-pyrrol-3-yl}-N-methylmethanamine dihydrochloride 1-[(3,4-Difluorophenyl)sulfonyl]-5-(pyridin-2-yl)-1H-pyrrole-3-carbaldehyde (100 mg) was dissolved in methanol (20 mL), 40% methylamine methanol solution (112 mg) was added at room temperature, and the mixture was stirred for 30 min. Sodium borohydride (33 mg) was added at room temperature, and the mixture was stirred for 10 min. 1 mol/L Hydrochloric acid (20 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent: ethyl acetate), and dissolved in methanol (5 mL). A 4 mol/L hydrogen chloride-ethyl acetate solution (1 mL) was added, and the mixture was concentrated under reduced pressure. The residue was crystallized from a mixed solvent (1:10) of methanol-tetrahydrofuran to give the title compound as colorless crystals (yield 89 mg, 71%).

$^{1}$H-NMR (DMSO-d$_{6}$) δ: 2.53 (3H, t, J=5.5 Hz), 4.00 (2H, t, J=5.5 Hz), 6.85 (1H, d, J=1.8 Hz), 7.39-7.43 (1H, m), 7.56-7.58 (1H, m), 7.73-7.94 (4H, m), 8.09-8.15 (1H, m), 8.48-8.50 (1H, m), 9.22 (2H, br).

Example 172

1-[1-(2,3-Dihydro-1,4-benzodioxin-5-ylsulfonyl)-4-methyl-5-phenyl-1H-pyrrol-3-yl]-N-methylmethanamine hydrochloride Using 1-(2,3-dihydro-1,4-benzodioxin-5-ylsulfonyl)-4-methyl-5-phenyl-1H-pyrrole-3-carbaldehyde (295 mg), 40% methylamine methanol solution (179 mg) and sodium borohydride (87 mg), a procedure as in Example 9 was performed. Recrystallization from a mixed solvent of ethyl acetate and ethanol gave the title compound as colorless crystals (yield 159 mg, 48%).

$^{1}$H-NMR (CDCl$_{3}$) δ: 1.90 (3H, s), 2.65 (3H, s), 4.02 (2H, s), 4.20-4.29 (4H, m), 6.73-6.76 (1H, m), 6.84-6.88 (2H, m), 7.04-7.08 (2H, m), 7.28-7.40 (3H, m), 7.72 (1H, s), 9.79 (2H, br).

Example 173

1-{1-[(2,5-Dimethoxyphenyl)sulfonyl]-4-methyl-5-phenyl-1H-pyrrol-3-yl}-N-methylmethanamine hydrochloride Using 1-[(2,5-dimethoxyphenyl)sulfonyl]-4-methyl-5-phenyl-1H-pyrrole-3-carbaldehyde (330 mg), 40% methylamine methanol solution (199 mg) and sodium borohydride (97 mg), a procedure as in Example 9 was performed. Recrystallization from a mixed solvent of ethyl acetate and ethanol gave the title compound as colorless crystals (yield 201 mg, 54%).

$^{1}$H-NMR (CDCl$_{3}$) δ: 1.90 (3H, s), 2.70 (3H, s), 3.51 (3H, s), 3.79 (3H, s), 4.07 (2H, s), 6.57 (1H, d, J=3.3 Hz), 6.82-6.89 (3H, m), 6.99-7.03 (1H, m), 7.15-7.30 (3H, m), 7.78 (1H, s), 9.79 (1H, br), 1H not detected.

Example 174

1-[1-(2,3-Dihydro-1,4-benzodioxin-6-ylsulfonyl)-4-methyl-5-phenyl-1H-pyrrol-3-yl]-N-methylmethanamine hydrochloride Using 1-(2,3-dihydro-1,4-benzodioxin-6-ylsulfonyl)-4-methyl-5-phenyl-1H-pyrrole-3-carbaldehyde (391 mg), 40% methylamine methanol solution (233 mg) and sodium borohydride (126 mg), a procedure as in Example 9 was performed. Recrystallization from a mixed solvent of ethyl acetate and ethanol gave the title compound as colorless crystals (yield 194 mg, 45%).

$^{1}$H-NMR (CDCl$_{3}$) δ: 1.90 (3H, s), 2.64 (3H, s), 4.02 (2H, s), 4.20-4.28 (4H, m), 6.73-6.76 (1H, m), 6.84-6.88 (2H, m), 7.04-7.07 (2H, m), 7.19-7.40 (3H, m), 7.71 (1H, m), 9.75 (1H, br), 1H not detected.

Example 175

1-(1-{[3-(Methylsulfonyl)phenyl]sulfonyl}-4-methyl-5-phenyl-1H-pyrrol-3-yl)-N-methylmethanamine hydrochloride Using 4-methyl-1-{[3-(methylsulfonyl)phenyl]sulfonyl}-5-phenyl-1H-pyrrole-3-carbaldehyde (191 mg), a procedure as in Example 134 was performed to give the title compound as a solid (yield 159 mg, 74%).

$^{1}$H-NMR (DMSO-d$_{6}$) δ: 1.78 (3H, s), 2.56 (3H, s), 3.28 (3H, s), 3.99 (2H, s), 6.99-7.03 (2H, m), 7.36-7.44 (3H, m), 7.75-7.88 (4H, m), 8.24-8.29 (1H, m), 8.92 (2H, br).

Example 176

N-Methyl-1-{4-methyl-5-phenyl-1-(3-thienylsulfonyl)-1H-pyrrol-3-yl}methanamine hydrochloride Using 4-methyl-5-phenyl-1-(3-thienylsulfonyl)-1H-pyrrole-3-carbaldehyde (290 mg), a procedure as in synthesis of Example 134 was performed to give the title compound as a solid (yield 208 mg, 62%).

$^{1}$H-NMR (DMSO-d$_{6}$) δ: 1.79 (3H, s), 2.57 (3H, s), 3.98 (2H, s), 6.98-7.04 (3H, m), 7.35-7.43 (3H, m), 7.69-7.73 (2H, m), 7.73-7.90 (1H, m), 8.93 (2H, br).

Example 177

N-Methyl-1-[4-methyl-1-(pyridin-3-ylsulfonyl)-5-phenyl-1H-pyrrol-3-yl]methanamine dihydrochloride Using 4-methyl-5-phenyl-1-(pyridin-3-ylsulfonyl)-1H-pyrrole-3-carbaldehyde (171 mg), a procedure as in Example 157 was performed to give the title compound (yield 110 mg, 50%).

$^1$H-NMR (DMSO-$d_6$) δ: 1.79 (3H, s), 2.57 (3H, s), 3.96-4.00 (2H, m), 6.98-7.01 (2H, m), 7.36-7.43 (3H, m), 7.55-7.60 (1H, m), 7.79-7.82 (2H, m), 8.43-8.44 (1H, m), 8.84-8.86 (1H, m), 9.13 (2H, br), 1H not detected.

Example 178

N-Methyl-1-[4-methyl-1-(pyridin-2-ylsulfonyl)-5-phenyl-1H-pyrrol-3-yl]methanamine hydrochloride 4-Methyl-5-phenyl-1-(pyridin-2-ylsulfonyl)-1H-pyrrole-3-carbaldehyde (262 mg) was dissolved in tetrahydrofuran (10 mL), a 2 mol/L solution (1.0 mL) of methylamine in tetrahydrofuran was added, and the mixture was stirred at room temperature for 4 hr. The reaction mixture was added to a solution (5 mL) of sodium borohydride (76 mg) in methanol, and the mixture was stirred at room temperature for 20 min. Water was added, and the mixture was extracted with ethyl acetate. The extract was washed with water and saturated brine, dried over anhydrous magnesium sulfate, and concentrated under reduced pressure. The residue was purified by silica gel column chromatography (eluent: ethyl acetate-methanol=1:0→1:1), and further purified by HPLC (ODS, 0.1% trifluoroacetic acid containing water-0.1% trifluoroacetic acid containing acetonitrile=9:1→0.1% trifluoroacetic acid containing acetonitrile) to give trifluoroacetate of the title compound. The obtained trifluoroacetate was neutralized with saturated aqueous sodium hydrogencarbonate solution, extracted with ethyl acetate, washed successively with saturated aqueous sodium hydrogencarbonate solution, water and saturated brine and dried over anhydrous magnesium sulfate, and the solvent was evaporated under reduced pressure. The residue was dissolved in ethyl acetate (3 mL), and a 4 mol/L hydrogen chloride-ethyl acetate solution (2 mL) was added, and the mixture was stood at room temperature for 30 min. The precipitated product was collected by filtration, and washed with ethyl acetate to give the title compound (yield 141 mg, 47%).

$^1$H-NMR (DMSO-$d_6$) δ: 1.79 (3H, s), 2.59 (3H, s), 4.01 (2H, s), 6.88-6.90 (2H, m), 7.27-7.45 (4H, m), 7.71-7.74 (2H, m), 7.95-7.99 (1H, m), 8.68-8.70 (1H, m), 8.88 (2H, br).

Example 179

1-{1-[(1,2-Dimethyl-1H-imidazol-4-yl)sulfonyl]-4-methyl-5-phenyl-1H-pyrrol-3-yl}-N-methylmethanamine dihydrochloride 1-[(1,2-Dimethyl-1H-imidazol-4-yl)sulfonyl]-4-methyl-5-phenyl-1H-pyrrole-3-carbaldehyde (294 mg) was dissolved in tetrahydrofuran (5 mL), a 2 mol/L solution (1.0 mL) of methylamine in tetrahydrofuran was added, and the mixture was stirred at room temperature for 1 hr. The mixture was heated to 40° C., and the mixture was further stirred for 4 hr. The reaction mixture was added to a solution (5 mL) of sodium borohydride (76 mg) in methanol, and the mixture was stirred at room temperature for 1 hr. Water was added, and the mixture was extracted with ethyl acetate. The extract was washed with water and saturated brine, dried over anhydrous magnesium sulfate, and concentrated under reduced pressure. The residue was purified by basic silica gel column chromatography (eluent: hexane-ethyl acetate=9:1→0:1) to give a free base of the title compound. To a solution (3 mL) of the obtained free base in ethyl acetate was added a 4 mol/L hydrogen chloride-ethyl acetate solution (1 mL). The mixture was stood at room temperature for 30 min, and the precipitated product was collected by filtration and washed with ethyl acetate to give the title compound (yield 196 mg, 53%).

$^1$H-NMR (DMSO-$d_6$) δ: 1.79 (3H, s), 2.25 (3H, s), 2.60 (3H, m), 3.45 (3H, s), 3.95-3.99 (2H, m), 4.86 (1H, br), 6.99-7.01 (2H, m), 7.13 (1H, s), 7.32-7.39 (3H, m), 7.59 (1H, s), 8.96 (2H, br).

Example 180

1-{1-[(5-Chloro-1,3-dimethyl-1H-pyrazol-4-yl)sulfonyl]-4-methyl-5-phenyl-1H-pyrrol-3-yl}-N-methylmethanamine hydrochloride Using 1-[(5-chloro-1,3-dimethyl-1H-pyrazol-4-yl)sulfonyl]-4-methyl-5-phenyl-1H-pyrrole-3-carbaldehyde (378 mg), a procedure as in Example 179 was performed to give the title compound as a solid (yield 238 mg, 55%).

$^1$H-NMR (DMSO-$d_6$) δ: 1.67 (3H, s), 1.79 (3H, s), 2.58 (3H, s), 3.67 (3H, s), 3.99 (2H, s), 6.97-6.99 (2H, m), 7.33-7.41 (3H, m), 7.73 (1H, s), 8.90 (2H, br).

Example 181

1-{1-[(1,3-Dimethyl-1H-pyrazol-4-yl)sulfonyl]-4-methyl-5-phenyl-1H-pyrrol-3-yl}-N-methylmethanamine hydrochloride Using 1-[(5-chloro-1,3-dimethyl-1H-pyrazol-4-yl)sulfonyl]-4-methyl-5-phenyl-1H-pyrrole-3-carbaldehyde (295 mg), a free base (297 mg) of the compound of Example 180 was obtained as an oil. The obtained oil was dissolved in toluene (10 mL) and methanol (10 mL), 10% palladium carbon (50% containing water, 30 mg) and 20% sodium ethoxide-ethanol solution (309 mg) were added, and the mixture was stirred under a hydrogen atmosphere at room temperature for 24 hr. The reaction mixture was filtrated, and the filtrate was concentrated under reduced pressure. The residue was dissolved in ethyl acetate solution (5 mL), and a 4 mol/L hydrogen chloride-ethyl acetate solution (1 mL) was added. The mixture was stood at room temperature for 30 min, and the precipitated product was collected by filtration and washed with ethyl acetate to give the title compound (yield 221 mg, 72%).

$^1$H-NMR (DMSO-$d_6$) δ: 1.80 (3H, s), 1.90 (3H, s), 2.59 (3H, m), 3.63 (3H, s), 3.99 (2H, s), 6.99-7.02 (2H, m), 7.35-7.40 (3H, m), 7.51 (1H, s), 7.66 (1H, s), 8.87 (2H, br).

Example 182

1-{1-[(2,4-Dimethyl-1,3-thiazol-5-yl)sulfonyl]-4-methyl-5-phenyl-1H-pyrrol-3-yl}-N-methylmethanamine trifluoroacetate To a solution (1 mL) of 1-[(2,4-dimethyl-1,3-thiazol-5-yl)sulfonyl]-4-methyl-5-phenyl-1H-pyrrole-3-carbaldehyde (27.7 mg) in tetrahydrofuran was added a 2 mol/L solution (0.1 mL) of methylamine in tetrahydrofuran, and the mixture was stirred at room temperature for 2 hr. The reaction mixture was added to a solution (1 mL) of sodium borohydride (7.6 mg) in methanol, and the mixture was stirred at room temperature for 20 min. Water was added to the reaction mixture, and the mixture was extracted with ethyl acetate. The extract was washed with saturated aqueous sodium hydrogencarbonate solution, water and saturated brine, dried over anhydrous magnesium sulfate, and concentrated under reduced pressure. The residue was purified by HPLC (ODS, 0.1% trifluoroacetic acid containing water-0.1% trifluoroacetic acid containing acetonitrile (97:3) →0.1% trifluoroacetic acid containing acetonitrile alone), and triturated with diisopropyl ether to give the title compound as a solid (yield 12.1 mg, 33%).

$^1$H-NMR (DMSO-d$_6$) δ: 1.80 (3H, s), 2.06 (3H, s), 2.58 (3H, s), 2.62 (3H, s), 4.03 (2H, s), 7.05-7.07 (2H, m), 7.37-7.44 (3H, m), 7.67 (1H, s), 8.62 (2H, br).

Example 183

[5-(2-Fluorophenyl)-4-methyl-1-(pyridin-3-ylsulfonyl)-1H-pyrrol-3-yl]-N-methylmethanamine hydrochloride To a solution of 5-(2-fluorophenyl)-4-methyl-1-(pyridin-3-ylsulfonyl)-1H-pyrrole-3-carbaldehyde (382 mg) in methanol (5 mL) and tetrahydrofuran (2 mL) was added 40% methylamine methanol solution (1.1 mL), and the mixture was stirred at room temperature for 4 hr. To the reaction mixture was added sodium borohydride (51 mg), and the mixture was further stirred for 15 min. The reaction mixture was concentrated under reduced pressure. Saturated aqueous sodium hydrogencarbonate solution (50 mL) was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by basic silica gel column chromatography (eluent: ethyl acetate) to give a free base of the title compound (yield 342 mg). To a solution of the obtained free base (336 mg) in ethanol (5 mL) was added a 4 mol/L hydrogen chloride-ethyl acetate solution (5.0 mL), and the mixture was stirred at room temperature for 30 min. The reaction mixture was concentrated under reduced pressure, and the residue was recrystallized from ethanol to give the title compound as white crystals (yield 197 mg, 46%).

$^1$H-NMR (DMSO-d$_6$) δ: 1.76 (3H, s), 2.59 (3H, t, J=5.4 Hz), 4.01 (2H, t, J=5.4 Hz), 7.03-7.08 (1H, m), 7.21-7.28 (2H, m), 7.51-7.64 (2H, m), 7.82-7.86 (2H, m), 8.53 (1H, d, J=2.4 Hz), 8.80-8.89 (3H, m).

Example 184

N-Methyl-[2-methyl-1-(phenylsulfonyl)-5-(3-pyridyl)-1H-pyrrol-3-yl]methanamine 0.5 oxalic acid salt To a solution of 2-methyl-1-(phenylsulfonyl)-5-(3-pyridyl)-1H-pyrrole-3-carbaldehyde (276 mg) in methanol (2 mL) and tetrahydrofuran (2 mL) were added 40% methylamine methanol solution (1.0 mL) and anhydrous magnesium sulfate (270 mg), and the reaction mixture was stirred at room temperature for 4 hr. To the reaction mixture was added sodium borohydride (43 mg) at room temperature and the mixture was stirred for 30 min. The reaction mixture was concentrated under reduced pressure, saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by basic silica gel column chromatography (eluent: ethyl acetate) to give a free base of the title compound as a yellow oil. To a solution (4 mL) of the obtained free base in ethanol was added a solution (2 mL) of oxalic acid (18 mg) in ethanol. The mixture was stirred at room temperature for 10 min, and concentrated under reduced pressure. The residue was recrystallized from ethanol to give the title compound as white crystals (yield 103 mg, 59%).

$^1$H-NMR (DMSO-d$_6$) δ: 2.28 (3H, s), 2.41 (3H, s), 3.64 (2H, s), 6.42 (1H, s), 7.40-7.46 (3H, m), 7.58 (2H, t, J=7.5 Hz), 7.70-7.75 (2H, m), 8.45 (1H, t, J=0.9 Hz), 8.54-8.57 (1H, m), 2H not detected.

Example 185

N-Methyl-[2-methyl-5-(1-methyl-1H-pyrazol-4-yl)-1-(phenylsulfonyl)-1H-pyrrol-3-yl]methanamine oxalic acid salt To a solution of 2-methyl-5-(1-methyl-1H-pyrazol-4-yl)-1-(phenylsulfonyl)-1H-pyrrole-3-carbaldehyde (386 mg) in methanol (5 mL) and tetrahydrofuran (5 mL) were added 40% methylamine methanol solution (1.5 mL) and anhydrous magnesium sulfate (319 mg), and the reaction mixture was stirred at room temperature for 12 hr. To the reaction mixture was added sodium borohydride (62 mg) at room temperature and the mixture was stirred for 30 min. The reaction mixture was concentrated under reduced pressure, saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by basic silica gel column chromatography (eluent: ethyl acetate) to give a free base of the title compound as a yellow oil. To a solution (4 mL) of the obtained free base in ethanol was added a solution (2 mL) of oxalic acid (29 mg) in ethanol. The mixture was stirred at room temperature for 10 min, and concentrated under reduced pressure. The residue was recrystallized from ethanol to give the title compound as white crystals (yield 59.6 mg, 44%).

$^1$H-NMR (DMSO-d$_6$) δ: 2.46 (3H, s), 2.48 (3H, s), 3.84 (3H, s), 3.90 (2H, s), 6.26 (1H, s), 7.25 (1H, s), 7.45-7.48 (2H, m), 7.53-7.60 (3H, m), 7.68-7.72 (1H, m), 3H not detected.

Example 186

N-Methyl-1-[4-methyl-1-(phenylsulfonyl)-5-(3-thienyl)-1H-pyrrol-3-yl]methanamine hydrochloride To a solution (10 mL) of 4-methyl-1-(phenylsulfonyl)-5-(3-thienyl)-1H-pyrrole-3-carbaldehyde (549 mg) in tetrahydrofuran was added a 2 mol/L solution (1.7 mL) of methylamine in tetrahydrofuran, and the mixture was stirred at room temperature for 4 hr. The reaction mixture was added to a solution (10 mL) of sodium borohydride (126 mg) in methanol, and the mixture was stirred at room temperature for 30 min. Water was added to the reaction mixture, and the mixture was extracted with ethyl acetate. The extract was washed with saturated aqueous sodium hydrogencarbonate solution, water and saturated brine, dried over anhydrous magnesium sulfate, and concentrated under reduced pressure. The residue was purified by basic silica gel column chromatography (eluent: ethyl acetate-methanol=1:0→4:1) to give a free base of the title compound. To a solution (10 mL) of the obtained free base in ethyl acetate was added a 4 mol/L hydrogen chloride-ethyl acetate solution (1 mL), and the mixture was stood at room temperature for 30 min. The precipitated product was collected by filtration, and recrystallized from ethanol to give the title compound as a colorless solid (yield 400 mg, 63%).

$^1$H-NMR (DMSO-d$_6$) δ: 1.81 (3H, s), 2.56 (3H, s), 3.96 (2H, s), 6.83-6.85 (1H, m), 7.19-7.21 (1H, m), 7.38-7.41 (2H, m), 7.50-7.60 (3H, m), 7.67-7.74 (2H, m), 9.01 (2H, br).

Example 187

1-[5-Phenyl-1-({4-[(trifluoromethyl)sulfonyl]phenyl}sulfonyl)-1H-pyrrol-3-yl]-N-methylmethanamine hydrochloride Under an argon atmosphere, 5-phenyl-1H-pyrrole-3-carbaldehyde (171 mg) was dissolved in tetrahydrofuran (10 mL), sodium hydride (60% in oil, 60 mg) was added, and the mixture was stirred at room temperature for 15 min. 15-Crown-5 (0.30 mL) was added and the mixture was further stirred at the same temperature for 15 min. 4-[(Trifluoromethyl)sulfonyl]benzenesulfonyl chloride (432 mg) was added and the reaction mixture was stirred at room temperature for 30 min. Water was added, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=9:1→4:1) to give 5-phenyl-1-({4-[(trifluoromethyl)sulfonyl]phenyl}sulfonyl)-1H-pyrrole-3-carbaldehyde (191 mg) as an orange solid. The obtained 5-phenyl-1-({4-[(trifluoromethyl)sulfonyl]phenyl}sulfonyl)-1H-pyrrole-3-carbaldehyde (191 mg) was subjected to a similar operation as in the synthesis of Example 179 to give the title compound as a solid (yield 86 mg, 40%).

$^1$H-NMR (DMSO-d$_6$) δ: 2.50 (3H, s), 4.00 (2H, s), 6.49 (1H, s), 7.08-7.10 (2H, m), 7.31-7.44 (3H, m), 7.75-7.81 (3H, m), 8.26-8.29 (2H, m), 8.89 (2H, br).

Example 188

1-[5-Phenyl-1-({3-[(trifluoromethyl)sulfonyl]phenyl}sulfonyl)-1H-pyrrol-3-yl]-N-methylmethanamine hydrochloride Using 3-[(trifluoromethyl)sulfonyl]benzenesulfonyl chloride, a procedure as in Example 187 was performed to give the title compound as a solid (yield 90 mg, 28%).

$^1$H-NMR (DMSO-d$_6$) δ: 2.50 (3H, s), 3.98 (2H, s), 6.50 (1H, s), 7.11-7.14 (2H, m), 7.33-7.45 (3H, m), 7.75 (1H, s), 7.82 (1H, s), 8.01-8.05 (1H, m), 8.12-8.15 (1H, m), 8.15-8.52 (1H, m), 8.91 (2H, br).

Example 189

1-[5-(2-Fluorophenyl)-1-({3-[(trifluoromethyl)sulfonyl]phenyl}sulfonyl)-1H-pyrrol-3-yl]-N-methylmethanamine hydrochloride Using 5-(2-fluorophenyl)-1H-pyrrole-3-carbaldehyde (189 mg) and 3-[(trifluoromethyl)sulfonyl]benzenesulfonyl chloride (432 mg), a procedure as in Example 187 was performed to give the title compound as a solid (yield 78 mg, 15%).

$^1$H-NMR (DMSO-d$_6$) δ: 2.50 (3H, s), 4.00 (2H, s), 6.58 (1H, s), 7.10-7.25 (3H, m), 7.51-7.60 (1H, m), 7.85 (1H, s), 7.90 (1H, s), 8.06-8.11 (1H, m), 8.22-8.25 (1H, m), 8.54-8.56 (1H, m), 8.91 (2H, br).

Example 190

N-Methyl-1-[4-methyl-5-phenyl-1-(phenylsulfonyl)-1H-pyrrol-3-yl]methanamine hydrochloride A solution (20 mL) of methyl 4-methyl-5-phenyl-1-(phenylsulfonyl)-1H-pyrrole-3-carboxylate (920 mg) in tetrahydrofuran was cooled to −78° C., a 1.5 mol/L toluene solution (6.3 mL) of diisobutylaluminum hydride was added dropwise, and the mixture was further stirred at −78° C. for 30 min. 1 mol/L Hydrochloric acid (25 mL) was added to the reaction mixture, and the mixture was extracted with ethyl acetate. The extract was washed with saturated brine, dried over anhydrous sodium sulfate, and concentrated under reduced pressure. A solution (20 mL) of the residue in acetonitrile was cooled to 0° C., tetra-n-propylammonium perruthenate (110 mg), N-methylmorpholine N-oxide (554 mg) and molecular sieves 4 A powder (2.0 g) were added, and the mixture was stirred at room temperature for 2 hr. The reaction mixture was concentrated under reduced pressure, the residue was suspended in ethyl acetate, and the mixture was filtered through celite. The filtrate was concentrated under reduced pressure, and the residue was purified by silica gel column chromatography (eluent: hexane-ethyl acetate=9:1→2:1) to give 4-methyl-5-phenyl-1-(phenylsulfonyl)-1H-pyrrole-3-carbaldehyde as a brown oil (yield 461 mg, 55%). 4-Methyl-5-phenyl-1-(phenylsulfonyl)-1H-pyrrole-3-carbaldehyde (460 mg) was dissolved in methanol (25 mL), and methylammonium chloride (952 mg) and sodium cyanoborohydride (266 mg) were added. The mixture was stirred at room temperature for 1 hr, and concentrated under reduced pressure. The residue was dissolved in water, and the solution was alkalized with a saturated aqueous sodium hydrogencarbonate solution and extracted with ethyl acetate. The extract was washed with saturated brine, and dried over anhydrous sodium sulfate, and the solvent was evaporated under reduced pressure. The residue was purified by basic silica gel column chromatography (eluent: hexane-ethyl acetate=9:1→-ethyl acetate). The obtained oil was dissolved in ethyl acetate (5 mL), and a 4 mol/L hydrogen chloride-ethyl acetate solution (0.5 mL) was added. The precipitated crystal was collected by filtration, and vacuum-dried to give the title compound as a colorless solid (yield 196 mg, 37%).

$^1$H-NMR (DMSO-d$_6$) δ: 1.78 (3H, s), 2.58 (3H, s), 3.99 (2H, s), 6.95-7.10 (2H, m), 7.20 (1H, m), 7.30-7.65 (6H, m), 7.70-7.90 (2H, m), 8.91 (2H, br).

Example 191

1-{1-[(3-Chlorophenyl)sulfonyl]-4-methyl-5-phenyl-1H-pyrrol-3-yl}-N-methylmethanamine hydrochloride A solution (15 mL) of methyl 1-[(3-chlorophenyl)sulfonyl]-4-methyl-5-phenyl-1H-pyrrole-3-carboxylate (700 mg) in tetrahydrofuran was cooled to −78° C., a 1.5 mol/L toluene solution (4.3 mL) of diisobutylaluminum hydride was added dropwise, and the mixture was further stirred at −78° C. for 30 min. 1 mol/L Hydrochloric acid (20 mL) was added to the reaction mixture, and the mixture was extracted with ethyl acetate. The extract was washed with saturated brine, dried over anhydrous sodium sulfate, and concentrated under reduced pressure. A solution (20 mL) of the residue in acetonitrile was cooled to 0° C., tetra-n-propylammonium perruthenate (76 mg), N-methylmorpholine N-oxide (377 mg) and molecular sieves 4 A powder (1.5 g) were added, and the mixture was stirred at room temperature for 2 hr. The reaction mixture was concentrated under reduced pressure, the residue was suspended in ethyl acetate, and the suspension was filtered through celite. The filtrate was concentrated under reduced pressure, and the residue was purified by silica gel column chromatography (eluent: hexane-ethyl acetate=9:1→2:1) to give 1-[(3-chlorophenyl)sulfonyl]-4-methyl-5-phenyl-1H-pyrrole-3-carbaldehyde as a brown solid (yield 565 mg, 88%). 1-[(3-Chlorophenyl)sulfonyl]-4-methyl-5-phenyl-1H-pyrrole-3-carbaldehyde (560 mg) was dissolved in methanol (25 mL), and methylammonium chloride (1.05 g) and sodium cyanoborohydride (294 mg) were added. The mixture was stirred at room temperature for 1 hr, and concentrated under reduced pressure. The residue was dissolved in water, and the solution was alkalized with a saturated aqueous sodium hydrogencarbonate solution and extracted with ethyl acetate. The extract washed with saturated brine, and dried over anhydrous sodium sulfate, and the solvent was evaporated under reduced pressure. The residue was purified by basic silica gel column chromatography (eluent: hexane-ethyl acetate=9:1→ethyl acetate). The obtained oil was dissolved in ethyl acetate (5 mL), and a 4 mol/L hydrogen chloride-ethyl acetate solution (0.5 mL) was added. The precipitated crystals were collected by filtration and vacuum-dried to give the title compound as a colorless solid (yield 154 mg, 24%).

$^1$H-NMR (DMSO-$d_6$) δ: 1.77 (3H, s), 2.56 (3H, s), 3.98 (2H, s), 6.95-7.05 (2H, m), 7.30-7.60 (6H, m), 7.65-7.80 (2H, m), 8.99 (2H, br).

Example 192

5-({4-[(Methylamino)methyl]-2-phenyl-1H-pyrrol-1-yl}sulfonyl)pyrimidine-2-amine

To a solution (4 mL) of 1-(2-chloropyrimidin-5-ylsulfonyl)-5-phenyl-1H-pyrrole-3-carbaldehyde (139 mg) in tetrahydrofuran was added a 0.5 mol/L oxane solution (4 mL) of ammonia was added. The mixture was stirred at room temperature for 1 hr, saturated aqueous sodium hydrogencarbonate solution was added, and the mixture was extracted with ethyl acetate. The extract was washed with saturated brine, dried over anhydrous magnesium sulfate, and concentrated under reduced pressure. The residue was dissolved in tetrahydrofuran solution (5 mL), a 2 mol/L tetrahydrofuran solution (0.75 mL) of methylamine was added, and the mixture was stirred overnight at room temperature. The reaction mixture was added to a solution (2 mL) of sodium borohydride (38 mg) in methanol, and the mixture was stirred at room temperature for 5 min. To the reaction mixture was added saturated aqueous sodium hydrogencarbonate solution, and the mixture was extracted with ethyl acetate. The extract was washed with saturated brine, dried over anhydrous magnesium sulfate, and concentrated under reduced pressure. The residue was purified by HPLC (ODS, 0.1% trifluoroacetic acid-containing water-0.1% trifluoroacetic acid-containing acetonitrile=9:1→0.1% trifluoroacetic acid-containing acetonitrile) to give trifluoroacetate of the title compound. The obtained trifluoroacetate was neutralized with saturated aqueous sodium hydrogencarbonate solution, and the mixture was extracted with ethyl acetate. The extract was washed successively with saturated aqueous sodium hydrogencarbonate solution, water and saturated brine, and dried over anhydrous magnesium sulfate. The solvent was evaporated under reduced pressure, and the crystals were washed with diisopropyl ether to give the title compound as a colorless solid (yield 23 mg, 17%).

$^1$H-NMR (DMSO-$d_6$) δ: 2.27 (3H, s), 3.52 (2H, s), 6.31 (1H, s), 7.26-7.40 (6H, m), 7.94 (2H, br), 8.00 (2H, s), 1H not detected.

Example 193

1-[(Imidazo[1,2-a]pyrimidin-6-ylsulfonyl)-5-phenyl-1H-pyrrol-3-yl]-N-methylmethanamine dihydrochloride Under a nitrogen atmosphere, a solution of ethyl 1-(imidazo[1,2-a]pyrimidin-6-ylsulfonyl)-5-phenyl-1H-pyrrole-3-carboxylate (242 mg) in tetrahydrofuran (10 mL) was cooled to −78° C., a 1.5 mol/L toluene solution (2.0 mL) of diisobutylaluminum was added with stirring. The mixture was stirred at the same temperature for 1 hr, and the temperature was raised to −20° C. over 1 hr. Water (30 mL) was added, the mixture was stirred at the same temperature for 5 min, and the temperature was raised to 0° C. over 10 min. Ethyl acetate (20 mL) was added, and the mixture was stirred at the same temperature for 15 min, and then at room temperature for 20 min. The gelated reaction product was filtered through celite, and the celite was washed with ethyl acetate. The organic layer was separated from the filtrate, washed with saturated brine, dried over anhydrous magnesium sulfate, and concentrated under reduced pressure. The residue was dissolved in tetrahydrofuran (50 mL), manganese dioxide (75% chemically-treated product, 2.0 g) was added, and the mixture was stirred at room temperature was for 2 hr. The reaction mixture was filtered through celite, and the celite was washed with ethyl acetate. The filtrate was concentrated under reduced pressure, and the residue was dissolved in absolute tetrahydrofuran (5 mL). A 2 mol/L tetrahydrofuran solution (0.6 mL) of methylamine was added, and the mixture was stirred at room temperature for 2 hr. The reaction mixture was added to a solution of sodium borohydride (45 mg) in methanol (2 mL), and the mixture was stirred at the same temperature for 20 min. The reaction mixture was diluted with ethyl acetate, washed with saturated brine, and dried over anhydrous magnesium sulfate, and the solvent was evaporated under reduced pressure. The residue was dissolved in tetrahydrofuran (10 mL), di-tert-butyl bicarbonate (0.22 g), sodium hydrogencarbonate (84 mg) and water (5 mL) were added, and the mixture was stirred at room temperature for 30 min. The reaction mixture was diluted with ethyl acetate, washed with saturated brine, and dried over anhydrous magnesium sulfate, and the solvent was evaporated under reduced pressure. The residue was dissolved in tetrahydrofuran (20 mL), manganese dioxide (75% chemically-treated product, 1.0 g) was added, and the mixture was stirred at room temperature for 2 days. The reaction mixture was filtered through celite, and the celite was washed with ethyl acetate. The filtrate was concentrated under reduced pressure, and the residue was purified by silica gel column chromatography (eluent: hexane-ethyl acetate=19:1→0:1) to give N-Boc compound of the title compound. The obtained N-Boc compound was dissolved in ethanol (1 mL), and a 4 mol/L hydrogen chloride-ethyl acetate solution (1 mL) was added. The mixture was stirred at room temperature for 2 hr, and the solvent was evaporated under reduced pressure. The residue was triturated with ethyl acetate-ethanol to give the title compound as a brown solid (yield 8.5 mg, 3%).

$^1$H-NMR (DMSO-d$_6$) δ: 2.50 (3H, s), 4.02-4.05 (2H, m), 6.49 (1H, s), 7.16-7.19 (2H, m), 7.32-7.44 (3H, m), 7.79 (1H, s), 7.92-7.99 (2H, m), 8.29-8.30 (1H, m), 8.97 (2H, br), 9.23-9.24 (1H, m), 1H not detected.

Example 194

N-Methyl-1-[1-(pyridazin-3-ylsulfonyl)-5-phenyl-1H-pyrrol-3-yl]methanamine fumarate Under a nitrogen atmosphere, a solution of ethyl 1-(pyridazin-3-ylsulfonyl)-5-phenyl-1H-pyrrole-3-carboxylate (567 mg) in tetrahydrofuran (16 mL) was cooled to −78° C., and a 1.5 mol/L toluene solution (6.4 mL) of diisobutylaluminum was added with stirring. The temperature of the reaction mixture was raised to −20° C. over 1 hr. Water (75 mL) was added, the mixture was stirred at the same temperature for 5 min, and the temperature was raised to 0° C. over 10 min. Ethyl acetate (75 mL) was added, and the mixture was stirred at the same temperature for 15 min, and then at room temperature for 20 min. The reaction mixture was filtered through celite, and the celite was washed with ethyl acetate. The organic layer was separated from the filtrate, washed with saturated brine, dried over anhydrous magnesium sulfate, and concentrated under reduced pressure. The residue was dissolved in tetrahydrofuran (30 mL), manganese dioxide (75% chemically-treated product, 5.0 g) was added, and the mixture was stirred at room temperature for 1 hr. The reaction mixture was filtered through celite, and the celite was washed with ethyl acetate. The filtrate was concentrated under reduced pressure, and the residue was dissolved in absolute tetrahydrofuran (15 mL). A 2 mol/L tetrahydrofuran solution (1.5 mL) of methylamine was added, and the mixture was stirred at room temperature overnight. The reaction mixture was added to a solution of sodium borohydride (66 mg) in methanol (5 mL), and the mixture was stirred at the same temperature for 20 min. To the reaction mixture was added saturated aqueous sodium hydrogencarbonate solution, and the mixture was extracted with ethyl acetate. The extract was washed with saturated brine, and dried over anhydrous magnesium sulfate, and the solvent was evaporated under reduced pressure. The residue was purified by HPLC (ODS, 0.1% trifluoroacetic acid-containing water-0.1% trifluoroacetic acid-containing acetonitrile=9:1→0.1% trifluoroacetic acid-containing acetonitrile) to give trifluoroacetate of the title compound. The obtained trifluoroacetate was neutralized with saturated aqueous sodium hydrogencarbonate solution, and the mixture was extracted with ethyl acetate. The extract was washed successively with saturated aqueous sodium hydrogencarbonate solution, water and saturated brine, and dried over anhydrous magnesium sulfate, and the solvent was evaporated under reduced pressure to give a free base (59 mg) of the title compound. The obtained free base (59 mg) was dissolved in methanol (2 mL) and ethyl acetate (2 mL), and fumaric acid (21 mg) was added. The solvent was evaporated under reduced pressure, and the residue was recrystallized from ethyl acetate-methanol to give the title compound as a pale-yellow solid (yield 41 mg, 6%).

$^1$H-NMR (DMSO-d$_6$) δ: 2.42 (3H, s), 3.82 (2H, s), 6.41 (1H, s), 6.47 (2H, s), 7.09-7.12 (2H, m), 7.29-7.38 (3H, m), 7.63 (1H, s), 7.80-7.83 (1H, m), 7.91-7.96 (1H, m), 9.48-9.50 (1H, m), 3H not detected.

Example 195

N,N-Dimethyl-1-[5-phenyl-1-(phenylsulfonyl)-1H-pyrrol-3-yl]methanamine hydrochloride To a solution (10 mL) of 5-phenyl-1H-pyrrole-3-carbaldehyde (140 mg) in tetrahydrofuran was added sodium hydride (60% in oil, 66 mg) at room temperature, and the mixture was stirred for 30 min. 15-Crown-5 (361 mg) was added dropwise, and the mixture was stirred for 30 min. Benzenesulfonyl chloride (217 mg) was added, and the mixture was further stirred for 1 hr. To the reaction mixture was added saturated brine, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=9:1→4:1) to give 5-phenyl-1-(phenylsulfonyl)-1H-pyrrole-3-carbaldehyde as a colorless oil. The obtained oil was dissolved in methanol (20 mL), a 2 mol/L tetrahydrofuran solution (4.1 mL) of dimethylamine was added at room temperature, and the mixture was stirred for 30 min. Sodium borohydride (93 mg) was added at room temperature, and the mixture was stirred for 10 min. 1 mol/L Hydrochloric acid (30 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by silica gel column chromatography (eluent: ethyl acetate-methanol=4:1), and dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 200 mg, 65%).

$^1$H-NMR (DMSO-d$_6$) δ: 2.67 (6H, s), 4.12 (2H, s), 6.48 (1H, br), 7.13-7.17 (2H, m), 7.32-7.43 (5H, m), 7.48-7.54 (2H, m), 7.58-7.73 (1H, m), 7.80 (1H, br).

Example 196

N,N-Dimethyl-1-[5-phenyl-1-(3-thienylsulfonyl)-1H-pyrrol-3-yl]methanamine hydrochloride To a solution (10 mL) of 5-phenyl-1H-pyrrole-3-carbaldehyde (100 mg) in tetrahydrofuran was added sodium hydride (60% in oil, 47 mg) at room temperature, and the mixture was stirred for 30 min. 15-Crown-5 (257 mg) was added dropwise, and the mixture was stirred for 30 min. (3-Thienyl)sulfonyl chloride (160 mg) was added, and the mixture was further stirred for 1 hr. Saturated brine was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→3:2) to give 5-phenyl-1-(3-thienylsulfonyl)-1H-pyrrole-3-carbaldehyde as a colorless oil. The obtained oil was dissolved in methanol (10 mL), a 2 mol/L tetrahydrofuran solution (2.1 mL) of dimethylamine was added at room temperature, and the mixture was stirred for 30 min. Sodium borohydride (47 mg) was added at room temperature, and the mixture was stirred for 10 min. 1 mol/L Hydrochloric acid (30 mL) was added, and the mixture was stirred for 5 min. The reaction mixture was alkalized with a saturated aqueous sodium hydrogencarbonate solution and extracted with ethyl acetate. The extract was washed with saturated brine, dried over anhydrous sodium sulfate, and concentrated under reduced pressure. The residue was purified by silica gel column chromatography (eluent: ethyl acetate-methanol=4:1), and dissolved in ethyl acetate (5 mL). A 4 mol/L hydrogen chloride-ethyl acetate solution (1 mL) was added, and the mixture was concentrated under reduced pressure. The residue was crystallized from ethyl acetate to give the title compound as colorless crystals (yield 70 mg, 45%).

$^1$H-NMR (DMSO-$d_6$) δ: 2.67 (6H, s), 4.12 (2H, s), 6.53 (1H, d, J=1.8 Hz), 7.00-7.02 (1H, m), 7.18-7.21 (2H, m), 7.33-7.44 (3H, m), 7.72-7.74 (1H, m), 7.76 (1H, d, J=1.8 Hz), 7.99-8.00 (1H, m), 10.84 (1H, br).

Example 197

N,N-Dimethyl-1-{5-phenyl-1-(3-pyridinesulfonyl)-1H-pyrrol-3-yl}methanamine dihydrochloride 5-Phenyl-1-(3-pyridinesulfonyl)-1H-pyrrole-3-carbaldehyde (230 mg) was dissolved in dichloromethane (20 mL), triethylamine (0.52 mL), dimethylamine hydrochloride (302 mg), sodium triacetoxyborohydride (1.06 g) were added, and the mixture was stirred at room temperature for 2 hr. The reaction mixture was diluted with ethyl acetate, washed successively with saturated aqueous sodium hydrogencarbonate solution, water and saturated brine, and dried over anhydrous magnesium sulfate. The solvent was evaporated under reduced pressure. The residue was purified by silica gel column chromatography (eluent: ethyl acetate-methanol=1:0→1:1) to give a free base of the title compound. The obtained free base was dissolved in ethyl acetate (3 mL), a 4 mol/L hydrogen chloride-ethyl acetate solution (1 ml) and ethanol (2 mL) were added, and the mixture was concentrated under reduced pressure. The residue was crystallized from ethanol to give the title compound (yield 138 mg, 45%).

$^1$H-NMR (DMSO-$d_6$) δ: 2.67-2.69 (6H, m), 4.12-4.14 (2H, m), 6.54 (1H, s), 7.16-7.18 (2H, m), 7.35-7.45 (3H, m), 7.54-7.59 (1H, m), 7.64-7.84 (2H, m), 8.48 (1H, s), 8.84-8.86 (1H, m), 10.50 (1H, br).

Example 198

1-[4-Ethyl-5-phenyl-1-(phenylsulfonyl)-1H-pyrrol-3-yl]-N-methylmethanamine hydrochloride Using tert-butyl {[4-ethyl-5-phenyl-1-(phenylsulfonyl)-1H-pyrrol-3-yl]methyl}methylcarbamate (589 mg), a procedure as in Example 33 was performed to give the title compound as a pale-yellow solid (yield 149 mg, 30%).

$^1$H-NMR (CDCl$_3$) δ: 0.87 (3H, t, J=7.5 Hz), 2.25 (2H, q, J=7.5 Hz), 2.71 (3H, brs), 4.09 (2H, brs), 6.97-7.00 (2H, m), 7.25-7.45 (7H, m), 7.49-7.54 (1H, m), 7.93 (1H, s), 9.92 (2H, brs).

Example 199

1-[4-Isopropyl-5-phenyl-1-(phenylsulfonyl)-1H-pyrrol-3-yl]-N-methylmethanamine hydrochloride Using tert-butyl {[4-isopropyl-5-phenyl-1-(phenylsulfonyl)-1H-pyrrol-3-yl]methyl}methylcarbamate (218 mg), a procedure as in Example 33 was performed to give the title compound as colorless crystals (yield 57 mg, 30%).

$^1$H-NMR (CDCl$_3$) δ: 0.96 (6H, d, J=7.2 Hz), 2.60-2.70 (1H, m), 2.83 (3H, s), 4.18 (2H, s), 6.92-6.96 (2H, m), 7.23-7.28 (2H, m), 7.32-7.40 (3H, m), 7.45-7.54 (3H, m), 8.02 (1H, s), 10.2 (1H, br), 1H not detected.

Example 200

2-({4-[(Methylamino)methyl]-2-phenyl-1H-pyrrol-1-yl}sulfonyl)benzoic acid hydrochloride 2-[(4-{[(tert-Butoxycarbonyl)(methyl)amino]methyl}-2-phenyl-1H-pyrrol-1-yl)sulfonyl]benzoic acid (256 mg) was dissolved in ethyl acetate (1 mL), and 4 mol/L hydrogen chloride-ethyl acetate solution (1 mL) was added at room temperature. After stirring at the same temperature for 3 hr, the reaction mixture was homogenized with methanol, activated carbon was added and the mixture was filtered through celite. The filtrate was concentrated under reduced pressure, and the residue was crystallized from ethyl acetate. The obtained crystal was recrystallized from a mixed solvent of ethyl acetate and ethanol to give the title compound as colorless crystals (yield 110 mg, 50%).

$^1$H-NMR (DMSO-$d_6$) δ: 2.49-2.55 (3H, m), 4.01 (2H, br), 6.50 (1H, d, J=1.8 Hz), 6.99 (1H, d, J=7.2 Hz), 7.07-7.10 (2H, m), 7.24-7.29 (2H, m), 7.33-7.38 (1H, m), 7.46-7.51 (1H, m), 7.62 (1H, d, J=1.8 Hz), 7.66-7.77 (2H, m), 9.15 (2H, br).

Example 201

3-({4-[(Methylamino)methyl]-2-phenyl-1H-pyrrol-1-yl}sulfonyl)benzoic acid hydrochloride Using 3-[(4-{[(tert-butoxycarbonyl)(methyl)amino]methyl}-2-phenyl-1H-pyrrol-1-yl)sulfonyl]benzoic acid (105 mg), a procedure as in Example 200 was performed to give the title compound as colorless crystals (yield 58 mg, 58%).

$^1$H-NMR (DMSO-$d_6$) δ: 2.50-2.51 (3H, m), 3.99 (2H, brs), 6.45 (1H, d, J=1.5 Hz), 7.11-7.13 (2H, m), 7.32-7.42 (3H, m), 7.64-7.66 (2H, m), 7.76 (1H, d, J=1.5 Hz), 7.81 (1H, s), 8.19-8.22 (1H, m), 8.95 (2H, br), 1H not detected.

Example 202

3-({4-[(Methylamino)methyl]-2-phenyl-1H-pyrrol-1-yl}sulfonyl)benzamide hydrochloride Using tert-butyl [(1-{[3-(aminocarbonyl)phenyl]sulfonyl}-5-phenyl-1H-pyrrol-3-yl)methyl]methylcarbamate (193 mg), a procedure as in Example 33 was performed to give the title compound as colorless crystals (yield 95 mg, 57%).

$^1$H-NMR (DMSO-$d_6$) δ: 2.49-2.51 (3H, m), 3.98 (2H, s), 6.45 (1H, d, J=1.8 Hz), 7.12 (2H, d, J=6.9 Hz), 7.32-7.47 (4H, m), 7.57-7.64 (2H, m), 7.77 (1H, d, J=1.2 Hz), 7.94 (1H, s), 8.14-8.21 (2H, m), 9.00 (2H, br).

Example 203

N-Cyclopropyl-3-({4-[(methylamino)methyl]-2-phenyl-1H-pyrrol-1-yl}sulfonyl)benzamide hydrochloride Using tert-butyl {[1-({3-[(cyclopropylamino)carbonyl]phenyl}sulfonyl)-5-phenyl-1H-pyrrol-3-yl]methyl}methylcarbamate (162 mg), a procedure as in Example 33 was performed to give the title compound as colorless crystals (yield 42 mg, 30%).

¹H-NMR (DMSO-d₆) δ: 0.57-0.74 (4H, m), 2.48 (3H, brs), 2.80-2.88 (1H, m), 3.97 (2H, brs), 6.46 (1H, d, J=1.8 Hz), 7.11-7.13 (2H, m), 7.32-7.48 (4H, m), 7.59 (1H, t, J=7.8 Hz), 7.77 (1H, s), 7.86 (1H, s), 8.11 (1H, d, J=7.8 Hz), 8.74 (1H, d, J=3.9 Hz), 9.12 (2H, br).

Example 204

N-Methyl-3-({4-[(methylamino)methyl]-2-phenyl-1H-pyrrol-1-yl}sulfonyl)benzamide hydrochloride Using tert-butyl methyl{[1-({3-[(methylamino)carbonyl]phenyl}sulfonyl)-5-phenyl-1H-pyrrol-3-yl]methyl}carbamate (157 mg), a procedure as in Example 33 was performed to give the title compound as colorless crystals (yield 59 mg, 43%).

¹H-NMR (DMSO-d₆) δ: 2.48-2.52 (3H, m), 2.78 (3H, d, J=4.5 Hz), 3.97 (2H, brs), 6.46 (1H, d, J=1.8 Hz), 7.10-7.13 (2H, m), 7.31-7.47 (4H, m), 7.60 (1H, t, J=7.8 Hz), 7.77 (1H, d, J=1.8 Hz), 7.91-7.92 (1H, m), 8.13 (1H, d, J=7.8 Hz), 8.75 (1H, q, J=4.5 Hz), 9.07 (2H, br).

Example 205

N,N-Dimethyl-3-({4-[(methylamino)methyl]-2-phenyl-1H-pyrrol-1-yl}sulfonyl)benzamide hydrochloride Using tert-butyl {[1-({3-[(dimethylamino)carbonyl]phenyl}sulfonyl)-5-phenyl-1H-pyrrol-3-yl]methyl}methylcarbamate (168 mg), a procedure as in Example 33 was performed to give the title compound as colorless crystals (yield 80 mg, 55%).

¹H-NMR (DMSO-d₆) δ: 2.49-2.51 (3H, m), 2.77 (3H, brs), 2.97 (3H, brs), 3.97 (2H, brs), 6.47 (1H, d, J=1.5 Hz), 7.13-7.16 (2H, m), 7.32-7.47 (5H, m), 7.55-7.60 (1H, m), 7.73-7.76 (2H, m), 9.02 (2H, br).

Example 206

N-Methyl-1-(1-{[3-(morpholin-4-ylcarbonyl)phenyl]sulfonyl}-5-phenyl-1H-pyrrol-3-yl)methanamine hydrochloride Using tert-butyl methyl[(1-{[3-(morpholin-4-ylcarbonyl)phenyl]sulfonyl}-5-phenyl-1H-pyrrol-3-yl)methyl]carbamate (164 mg), a procedure as in Example 33 was performed to give the title compound as colorless crystals (yield 95 mg, 66%).

¹H-NMR (CDCl₃) δ: 2.54 (3H, s), 3.26 (2H, br), 3.50-3.80 (6H, m), 3.96 (2H, s), 6.48 (1H, d, J=2.1 Hz), 7.15-7.18 (2H, m), 7.24-7.40 (5H, m), 7.48-7.49 (1H, m), 7.57-7.60 (1H, m), 7.69 (1H, d, J=2.1 Hz), 2H not detected.

Example 207

2-[3-({4-[(Methylamino)methyl]-2-phenyl-1H-pyrrol-1-yl]sulfonyl)phenyl}propan-2-ol To a solution of tert-butyl [1-(5-phenyl-1-{[3-(1-methyl-1-hydroxyethyl)phenyl]sulfonyl}-1H-pyrrol-3-yl)methyl]carbamate (334 mg) in ethanol (4 mL) was added 4 mol/L hydrogen chloride-ethyl acetate solution (4.0 mL) and the mixture was stirred at room temperature for 3 hr. After the reaction mixture was concentrated under reduced pressure, saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by basic silica gel column chromatography (eluent: ethyl acetate) to give the title compound as a white solid (yield 203 mg, 76%).

¹H-NMR (CDCl₃) δ: 1.44 (6H, s), 2.44 (3H, s), 3.59 (2H, s), 6.14 (1H, d, J=2.1 Hz), 7.23-7.37 (8H, m), 7.44-7.46 (1H, m), 7.59-7.62 (1H, m), 2H not detected.

Example 208

2-Fluoro-4-({4-[(methylamino)methyl]-2-phenyl-1H-pyrrol-1-yl}sulfonyl)benzonitrile hydrochloride Using tert-butyl ({1-[(4-Cyano-3-fluorophenyl)sulfonyl]-5-phenyl-1H-pyrrol-3-yl}methyl)carbamate (54.7 mg) and 4 mol/L hydrogen chloride-ethyl acetate solution (4 mL), a procedure as in Example 30 was performed to give the title compound as a white solid (yield 6.9 mg, 14%).

¹H-NMR (CDCl₃) δ: 2.65 (3H, brs), 4.01 (2H, brs), 6.49 (1H, d, J=1.8 Hz), 7.15-7.17 (3H, m), 7.31-7.35 (3H, m), 7.40-7.43 (1H, m), 7.60-7.65 (1H, m), 7.73 (1H, d, J=1.8 Hz), 9.93 (2H, brs).

Example 209

N-Methyl-1-(5-phenyl-1-{[3-(1H-tetrazol-5-yl)phenyl]sulfonyl}-1H-pyrrol-3-yl)methanamine hydrochloride To a solution (10 mL) of tert-butyl methyl[(5-phenyl-1-{[3-(1H-tetrazol-5-yl)phenyl]sulfonyl}-1H-pyrrol-3-yl)methyl]carbamate (52 mg) in methanol was added 4 mol/L hydrogen chloride-ethyl acetate solution (2 ml), and the mixture was stirred at 65° C. for 1.5 hr and concentrated under reduced pressure. The residue was crystallized from ethyl acetate to give the title compound as crystals (yield 42 mg, 86%).

¹H-NMR (DMSO-d₆) δ: 2.50 (3H, s), 4.00 (2H, t, J=5.6 Hz), 6.45 (1H, s), 7.12 (1H, d, J=1.7 Hz), 7.14 (1H, s), 7.27-7.37 (3H, m), 7.55 (1H, dd, J=1.1, 10.0 Hz), 7.72-7.81 (2H, m), 8.08 (1H, t, J=1.7 Hz), 8.37 (1H, d, J=8.3 Hz), 8.98 (2H, brs).

Example 210

2-({4-[(Methylamino)methyl]-2-(pyridin-3-yl)-1H-pyrrol-1-yl}sulfonyl)benzonitrile 0.5 oxalic acid salt Using tert-butyl {[(2-cyanophenyl)sulfonyl-5-(3-pyridyl)-1H-pyrrol-3-yl]methyl}methylcarbamate (178 mg), a procedure as in Example 30 was performed to give a free base of the title compound as a yellow oil. To a solution (4 mL) of the obtained free base in ethanol was added a solution (2 mL) of oxalic acid (10 mg) in ethanol, and reaction mixture was stirred at room temperature for 30 min. The reaction mixture was concentrated under reduced pressure, and the residue was recrystallized from methanol to give the title compound as a white solid (yield 49 mg, 32%).

¹H-NMR (DMSO-d₆) δ: 2.40 (3H, s), 3.77 (2H, s), 6.52 (1H, d, J=2.1 Hz), 7.32-7.39 (2H, m), 7.57-7.61 (1H, m), 7.67 (1H, s), 7.73-7.79 (1H, m), 7.86-7.92 (1H, m), 8.10-8.13 (1H, m), 8.23 (1H, d, J=2.1 Hz), 8.55-8.57 (1H, m), 2H not detected.

Example 211

N-Methyl-1-(1-{[3-(methylsulfonyl)phenyl]sulfonyl}-5-(3-thienyl)-1H-pyrrol-3-yl)methanamine hydrochloride Using tert-butyl methyl[(1-{[3-(methylsulfonyl)phenyl]sulfonyl}-5-(3-thienyl)-1H-pyrrol-3-yl)methyl]carbamate (302 mg), a procedure as in Example 33 was performed to give the title compound as a white solid (yield 46 mg, 18%).
$^1$H-NMR (DMSO-$d_6$) δ: 2.50 (3H, s), 3.27 (3H, s), 3.98 (2H, s), 6.98-7.00 (1H, m), 7.37-7.38 (1H, m), 7.56-7.59 (1H, m), 7.77-7.87 (4H, m), 8.25-8.28 (1H, m), 9.00 (2H, brs).

Example 212

N-Methyl-1-(1-{[3-(methylsulfonyl)phenyl]sulfonyl}-5-(pyridin-3-yl)-1H-pyrrol-3-yl)methanamine dihydrochloride Using tert-butyl methyl[(1-{[3-(methylsulfonyl)phenyl]sulfonyl}-5-(pyridin-3-yl)-1H-pyrrol-3-yl)methyl]carbamate (300 mg), a procedure as in Example 30 was performed to give the title compound as a white solid (yield 85 mg, 42%).
$^1$H-NMR (DMSO-$d_6$) δ: 2.46 (3H, t, J=5.4 Hz), 3.30 (3H, s), 3.99 (2H, t, J=5.4 Hz), 5.67 (1H, brs), 6.73 (1H, d, J=1.5 Hz), 7.66-7.70 (1H, m), 7.78 (1H, brs), 7.86-7.95 (4H, m), 8.28-8.32 (1H, m), 8.52 (1H, brs), 8.75-8.76 (1H, m), 9.31 (2H, brs).

Example 213

1-[1-(2-Chloropyridin-3-ylsulfonyl)-5-phenyl-1H-pyrrol-3-yl]-N-methylmethanamine hydrochloride To a solution (3 mL) of tert-butyl {[1-(2-chloro-3-pyridinesulfonyl)-5-phenyl-1H-pyrrol-3-yl]methyl}methylcarbamate (70 mg) in ethyl acetate was added 4 mol/L hydrogen chloride-ethyl acetate solution (1 mL), and the mixture was stirred at room temperature for 3 hr. The solvent was evaporated under reduced pressure, and the residue was crystallized from ethanol-ethyl acetate to give the title compound (yield 29 mg, 49%).
$^1$H-NMR (DMSO-$d_6$) δ: 2.56 (3H, s), 4.04 (2H, s), 6.48 (1H, s), 6.99-7.02 (2H, m), 7.25-7.36 (4H, m), 7.66-7.69 (1H, m), 7.83 (1H, s), 8.60-8.62 (1H, m), 8.79 (2H, br).

Example 214

N-Methyl-1-[1-(5-methyl-3-pyridinesulfonyl)-5-phenyl-1H-pyrrol-3-yl]methanamine fumarate To a solution (5 mL) of tert-butyl {[1-(6-chloro-5-methyl-3-pyridinesulfonyl)-5-phenyl-1H-pyrrol-3-yl]methyl}methylcarbamate (237 mg) in tetrahydrofuran was added hydrazine (160 mg) with stirring at room temperature. After stirring at the same temperature for 3 hr, saturated aqueous sodium hydrogencarbonate solution was added and the mixture was extracted with ethyl acetate. The extract was washed with water and saturated brine, dried over anhydrous magnesium sulfate, and concentrated under reduced pressure. The residue was dissolved in tetrahydrofuran (30 mL), manganese dioxide (75% chemically-treated product, 1.0 g) was added, the mixture was stirred at room temperature for 10 min. The reaction product was filtered through celite, and the celite was washed with ethyl acetate. The filtrate was concentrated under reduced pressure, and the residue was purified by silica gel column chromatography (eluent: hexane-ethyl acetate=19:1→1:1) to give N-Boc-compound (129 mg) of the title compound. The obtained N-Boc compound was dissolved in ethanol (2 mL), and a 4 mol/L hydrogen chloride-ethyl acetate solution (1 mL) was added. After stirring at room temperature for 2 hr, the solvent was evaporated under reduced pressure, saturated aqueous sodium hydrogencarbonate solution was added, and the mixture was extracted with ethyl acetate. The extract was washed with water and saturated brine, dried over anhydrous magnesium sulfate, and concentrated under reduced pressure. The residue (93 mg) was dissolved in methanol (3 mL), and fumaric acid (29 mg) was added. The mixture was stood at room temperature for 30 min, and the precipitated crystals were collected by filtration and washed with methanol to give the title compound as a colorless solid (yield 91 mg, 40%).
$^1$H-NMR (DMSO-$d_6$) δ: 2.27 (3H, s), 2.38 (3H, s), 3.75 (2H, s), 6.37 (1H, s), 6.47 (2H, s), 7.15-7.17 (2H, m), 7.36-7.45 (4H, m), 7.58 (1H, s), 8.28 (1H, s), 8.68 (1H, s), 3H not detected.

Example 215

5-({4-[(Methylamino)methyl]-2-phenyl-1H-pyrrol-1-yl}sulfonyl)pyridin-2-ol hydrochloride tert-Butyl {[1-(6-chloro-3-pyridinesulfonyl)-5-phenyl-1H-pyrrol-3-yl]methyl}methylcarbamate (175 mg) was dissolved in tetrahydrofuran (10 mL), 8 mol/L aqueous sodium hydroxide solution (3.8 mL) was added, and the mixture was stirred at 50° C. for 2 days. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→0:1) to give a free base of the title compound. To a solution (1 mL) of the obtained free base in ethanol was added a 4 mol/L hydrogen chloride-ethyl acetate solution (2 mL). After stirring at room temperature for 4 hr, the solvent was evaporated under reduced pressure, and the residue was crystallized from ethanol-ethyl acetate to give the title compound (yield 40 mg, 27%).
$^1$H-NMR (DMSO-$d_6$) δ: 2.50 (3H, s), 3.97-4.01 (2H, m), 6.32-6.36 (1H, m), 6.47 (1H, s), 7.20-7.23 (4H, m), 7.37-7.48 (3H, m), 7.66 (1H, s), 8.94 (2H, br), 12.35 (1H, br).

Example 216

5-({4-[(Methylamino)methyl]-2-phenyl-1H-pyrrol-1-yl}sulfonyl)pyridine-2-carbonitrile hydrochloride Under an argon atmosphere, a mixture of tert-butyl {[1-(6-chloro-3-pyridinesulfonyl)-5-phenyl-1H-pyrrol-3-yl]methyl}methylcarbamate (100 mg), zinc (II) cyanide (51 mg), tetrakis(triphenylphosphine)palladium (50 mg) and N,N-dimethylformamide (4 mL) was stirred at 100° C. for 2 hr. The reaction mixture was diluted with ethyl acetate, and washed successively saturated aqueous sodium hydrogencarbonate solution, water and saturated brine. The mixture was dried over anhydrous magnesium sulfate, and the solvent was evaporated under reduced pressure. The residue was purified by silica gel column chromatography (eluent: hexane-ethyl acetate=19:1→7:3) to give N-Boc compound of the title compound. The obtained N-Boc compound was dissolved in ethyl acetate (2 mL), and a 4 mol/L hydrogen chloride-ethyl acetate solution (2 mL) was added. The mixture was stirred at room temperature for 1 hr, and the solvent was evaporated under reduced pressure. The residue was crystallized from ethanol to give the title compound (yield 57 mg, 68%).

$^1$H-NMR (DMSO-d$_6$) δ: 2.50 (3H, s), 3.98 (2H, s), 6.52 (1H, s), 7.15-7.17 (2H, m), 7.37-7.47 (3H, m), 7.79 (1H, s), 8.04-8.07 (1H, m), 8.22-8.24 (1H, m), 8.61-8.62 (1H, m), 9.03 (2H, br).

Example 217

N-Methyl-1-{1-[(6-methylpyridin-3-yl)sulfonyl]-5-phenyl-1H-pyrrol-3-yl}methanamine dihydrochloride tert-Butyl ({[1-(6-methylpyridin-3-yl)sulfonyl]-5-phenyl-1H-pyrrol-3-yl}methyl)methylcarbamate (113 mg, 0.26 mmol) was dissolved in ethanol (2 mL), 4 mol/L hydrogen chloride-ethyl acetate solution (1 mL) was added, and the mixture was stirred at room temperature for 1 hr. The solvent was evaporated under reduced pressure, and the residue was recrystallized from ethanol to give the title compound (yield 40 mg, 38%).

$^1$H-NMR (DMSO-d$_6$) δ: 2.50-2.53 (6H, m), 3.97-3.99 (2H, m), 6.46 (1H, s), 7.16-7.18 (2H, m), 7.38-7.44 (4H, m), 7.65-7.75 (2H, m), 8.34 (1H, s), 8.98 (2H, br), 1H not detected.

Example 218

N-Methyl-1-[1-(pyridin-3-ylsulfonyl)-5-(3-thienyl)-1H-pyrrol-3-yl]methanamine hydrochloride Using tert-butyl {[1-(pyridin-3-ylsulfonyl)-5-(3-thienyl)-1H-pyrrol-3-yl]methyl}methylcarbamate (182 mg), a procedure as in Example 217 was performed to give the title compound as colorless crystals (yield 64 mg, 41%).

$^1$H-NMR (CDCl$_3$) δ: 2.60 (3H, s), 3.98 (2H, brs), 6.57 (1H, brs), 7.00 (1H, brd, J=4.5 Hz), 7.16 (1H, brs), 7.26-7.31 (2H, m), 7.70 (2H, brs), 8.61 (1H, brs), 8.73 (1H, brs), 9.86 (2H, brs).

Example 219

1-[5-(4-Fluorophenyl)-1-(pyridin-3-ylsulfonyl)-1H-pyrrol-3-yl]-N-methylmethanamine dihydrochloride tert-Butyl {[5-(4-fluorophenyl)-1-(pyridin-3-ylsulfonyl)-1H-pyrrol-3-yl]methyl}methylcarbamate (293 mg) was dissolved in dichloromethane (1 mL), trifluoroacetic acid (1 mL) was added at 0° C., and the mixture was stirred at room temperature for 3 hr. The reaction solution was basified by the dropwise addition to 6% aqueous sodium hydrogencarbonate solution, and the mixture was extracted with ethyl acetate. The organic layer was washed with saturated brine, dried over anhydrous sodium sulfate, and concentrated under reduced pressure. The residue was purified by basic silica gel column chromatography (eluent: hexane-ethyl acetate=1:1→1:9) to give a free base of the title compound as a pale-yellow oil. The obtained free base was dissolved in ethyl acetate (5 mL). A 4 mol/L hydrogen chloride-ethyl acetate solution (1 mL) was added, and the mixture was concentrated under reduced pressure. The residue was recrystallized from ethyl acetate-ethanol to give the title compound as colorless crystals (yield 110 mg, 40%).

$^1$H-NMR (DMSO-d$_6$) δ: 2.47-2.51 (3H, m), 3.97 (2H, t, J=6.0 Hz), 6.52-6.53 (1H, m), 7.15-7.26 (4H, m), 7.57-7.61 (1H, m), 7.79-7.85 (2H, m), 8.00 (1H, d, J=2.4 Hz), 8.85-8.87 (1H, m), 9.22 (2H, br), 1H not detected.

Example 220

N-Methyl-1-[5-(2-methylphenyl)-1-(pyridin-3-ylsulfonyl)-1H-pyrrol-3-yl]methanamine dihydrochloride Using tert-butyl methyl{[5-(2-methylphenyl)-1-(pyridin-3-ylsulfonyl)-1H-pyrrol-3-yl]methyl}carbamate (210 mg), a procedure as in Example 219 was performed to give the title compound as colorless crystals (yield 67 mg, 34%).

$^1$H-NMR (DMSO-d$_6$) δ: 1.80 (3H, s), 2.49-2.53 (3H, m), 4.00 (2H, t, J=5.4 Hz), 6.46 (1H, d, J=2.4 Hz), 6.83 (1H, d, J=7.8 Hz), 7.13-7.22 (2H, m), 7.33-7.39 (1H, m), 7.59-7.63 (1H, m), 7.80-7.85 (2H, m), 8.46 (1H, d, J=2.4 Hz), 8.88-8.90 (1H, m), 9.27 (2H, br), 1H not detected.

Example 221

1-[5-(4-Fluoro-2-methylphenyl)-1-(pyridin-3-ylsulfonyl)-1H-pyrrol-3-yl]-N-methylmethanamine dihydrochloride Using tert-butyl {[5-(4-fluoro-2-methylphenyl)-1-(pyridin-3-ylsulfonyl)-1H-pyrrol-3-yl]methyl}methylcarbamate (216 mg), a procedure as in Example 219 was performed to give the title compound as colorless crystals (yield 81 mg, 40%).

$^1$H-NMR (DMSO-d$_6$) δ: 1.80 (3H, s), 2.49-2.51 (3H, m), 4.00 (2H, t, J=6.0 Hz), 6.47 (1H, d, J=2.1 Hz), 6.85-6.90 (1H, m), 6.98-7.12 (2H, m), 7.61-7.65 (1H, m), 7.81-7.88 (2H, m), 8.51 (1H, d, J=2.7 Hz), 8.89-8.91 (1H, m), 9.29 (2H, br), 1H not detected.

Example 222

N-Methyl-1-[5-(4-methyl-3-thienyl)-1-(pyridin-3-ylsulfonyl)-1H-pyrrol-3-yl]methanamine dihydrochloride Using tert-butyl methyl{[5-(4-methyl-3-thienyl)-1-(pyridin-3-ylsulfonyl)-1H-pyrrol-3-yl]methyl}carbamate (200 mg), a procedure as in Example 219 was performed to give the title compound as colorless crystals (yield 125 mg, 67%).

$^1$H-NMR (DMSO-d$_6$) δ: 1.71 (3H, s), 2.49-2.51 (3H, m), 3.98 (2H, t, J=5.7 Hz), 6.49 (1H, d, J=2.1 Hz), 7.16-7.23 (2H, m), 7.58-7.62 (1H, m), 7.79-7.86 (2H, m), 8.50-8.51 (1H, m), 8.87-8.89 (1H, m), 9.30 (2H, br), 1H not detected.

Example 223

3-[4-[(Methylamino)methyl]-1-(pyridin-3-ylsulfonyl)-1H-pyrrol-2-yl]benzonitrile hydrochloride Using tert-butyl {[5-(3-Cyanophenyl)-1-(pyridin-3-ylsulfonyl)-1H-pyrrol-3-yl]methyl}methylcarbamate (298 mg), a procedure as in Example 219 was performed to give the title compound as colorless crystals (yield 132 mg, 52%).

$^1$H-NMR (DMSO-d$_6$) δ: 2.48-2.51 (3H, m), 3.98 (2H, brs), 6.65 (1H, d, J=1.8 Hz), 7.51-7.65 (4H, m), 7.85-7.95 (3H, m), 8.55 (1H, d, J=2.4 Hz), 8.88-8.90 (1H, m), 9.25 (2H, br).

Example 224

1-[5-(2-Chlorophenyl)-1-(pyridin-3-ylsulfonyl)-1H-pyrrol-3-yl]-N-methylmethanamine dihydrochloride Using tert-butyl {[5-(2-chlorophenyl)-1-(pyridin-3-ylsulfonyl)-1H-pyrrol-3-yl]methyl}methylcarbamate (171 mg), a procedure as in Example 219 was performed to give the title compound as colorless crystals (yield 74 mg, 46%).

$^1$H-NMR (DMSO-$d_6$) δ: 2.50 (3H, br), 4.01 (2H, t, J=6.0 Hz), 5.40 (1H, br), 6.55 (1H, d, J=2.1 Hz), 7.13-7.16 (1H, m), 7.35-7.40 (1H, m), 7.47-7.51 (2H, m), 7.61-7.65 (1H, m), 7.84-7.93 (2H, m), 8.57 (1H, d, J=2.1 Hz), 8.89-8.91 (1H, m), 9.23 (2H, br).

Example 225

1-[5-(2,4-Difluorophenyl)-1-(pyridin-3-ylsulfonyl)-1H-pyrrol-3-yl]-N-methylmethanamine dihydrochloride Using tert-butyl {[5-(2,4-difluorophenyl)-1-(pyridin-3-ylsulfonyl)-1H-pyrrol-3-yl]methyl}methylcarbamate (110 mg), a procedure as in Example 219 was performed to give the title compound as colorless crystal (yield 58 mg, 56%).

$^1$H-NMR (DMSO-$d_6$) δ: 2.48-2.51 (3H, m), 3.98 (2H, t, J=5.7 Hz), 6.62 (1H, d, J=1.8 Hz), 7.13-7.17 (2H, m), 7.28-7.36 (1H, m), 7.62-7.66 (1H, m), 7.86-7.95 (2H, m), 8.61 (1H, d, J=2.4 Hz), 8.89-8.91 (1H, m), 9.31 (2H, br), 1H not detected.

Example 226

1-[5-(2,5-Difluorophenyl)-1-(pyridin-3-ylsulfonyl)-1H-pyrrol-3-yl]-N-methylmethanamine hydrochloride Using tert-butyl {[5-(2,5-difluorophenyl)-1-(pyridin-3-ylsulfonyl)-1H-pyrrol-3-yl]methyl}methylcarbamate (105 mg), a procedure as in Example 219 was performed to give the title compound as colorless crystals (yield 39 mg, 43%).

$^1$H-NMR (DMSO-$d_6$) δ: 2.50-2.51 (3H, m), 3.99 (2H, brs), 6.62 (1H, d, J=1.8 Hz), 7.00-7.06 (1H, m), 7.27-7.44 (2H, m), 7.63-7.67 (1H, m), 7.86 (1H, br), 7.94-7.97 (1H, m), 8.65 (1H, d, J=2.7 Hz), 8.90-8.92 (1H, m), 9.08 (2H, m).

Example 227

1-[5-(4-Chloro-2-fluorophenyl)-1-(pyridin-3-ylsulfonyl)-1H-pyrrol-3-yl]-N-methylmethanamine dihydrochloride Using tert-butyl {[5-(4-chloro-2-fluorophenyl)-1-(pyridin-3-ylsulfonyl)-1H-pyrrol-3-yl]methyl}methylcarbamate (103 mg), a procedure as in Example 219 was performed to give the title compound as colorless crystals (yield 32 mg, 33%).

$^1$H-NMR (DMSO-$d_6$) δ: 2.47-2.52 (3H, m), 3.97 (2H, t, J=6.0 Hz), 5.10 (1H, br), 6.64 (1H, brs), 7.15 (1H, t, J=7.8 Hz), 7.34-7.36 (1H, m), 7.50-7.53 (1H, m), 7.62-7.67 (1H, m), 7.88 (1H, brs), 7.95-7.98 (1H, m), 8.64 (1H, d, J=2.4 Hz), 8.90 (1H, d, J=4.8 Hz), 9.33 (2H, br).

Example 228

1-[5-(3-Fluorophenyl)-1-(pyridin-3-ylsulfonyl)-1H-pyrrol-3-yl]-N-methylmethanamine hydrochloride tert-Butyl {[5-(3-fluorophenyl)-1-(pyridin-3-ylsulfonyl)-1H-pyrrol-3-yl]methyl}methylcarbamate (280 mg) was dissolved in ethyl acetate (3 mL), 4 mol/L hydrogen chloride-ethyl acetate solution (6 mL) was added, and the mixture was stirred at room temperature for 16 hr. The reaction solution was basified by the dropwise addition to 6% aqueous sodium hydrogencarbonate solution, and the mixture was extracted with ethyl acetate. The organic layer was washed with saturated brine, dried over anhydrous sodium sulfate, and concentrated under reduced pressure. The residue was purified by basic silica gel column chromatography (eluent: ethyl acetate-hexane=1:1→9:1) to give a free base of the title compound as a pale-yellow oil. The obtained free base was dissolved in ethyl acetate. A 4 mol/L hydrogen chloride-ethyl acetate solution was added, and the mixture was concentrated under reduced pressure. The residue was crystallized from ethyl acetate and hexane, and recrystallized from ethyl acetate-ethanol to give the title compound as colorless crystals (yield 84 mg, 35%).

$^1$H-NMR (DMSO-$d_6$) δ: 2.49-2.51 (3H, m), 3.97 (2H, s), 6.57 (1H, d, J=1.8 Hz), 6.98-7.02 (2H, m), 7.27-7.33 (1H, m), 7.40-7.47 (1H, m), 7.58-7.62 (1H, m), 7.80-7.87 (2H, m), 8.54 (1H, d, J=2.7 Hz), 8.86-8.88 (1H, m), 9.06 (2H, br).

Example 229

N-Methyl-1-[1-(phenylsulfonyl)-5-(pyrimidin-5-yl)-1H-pyrrol-3-yl]methanamine hydrochloride tert-Butyl {[5-bromo-1-(phenylsulfonyl)-1H-pyrrol-3-yl]methyl}methylcarbamate (170 mg), pyrimidin-5-ylboronic acid (123 mg), sodium carbonate (147 mg) and tetrakis(triphenylphosphine)palladium (46 mg) was added to 1,2-dimethoxyethane (10 mL) and water (5 mL), and the mixture was stirred at 90° C. for 3 hr. After the reaction mixture was cooled to room temperature, water was added, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=4:1→1:3) to give N-Boc compound of the title compound as a colorless oil. The obtained oil was dissolved in methanol (20 mL), a 4 mol/L hydrogen chloride-ethyl acetate solution (2 mL) was added, and the mixture was stirred at 70° C. for 30 min, and concentrated under reduced pressure. The residue was suspended in ethyl acetate and collected by filtration to give the title compound as a colorless powder (yield 42 mg, 29%).

$^1$H-NMR (DMSO-$d_6$) δ: 2.50 (3H, m), 4.00 (2H, t, J=5.8 Hz), 6.71 (1H, d, J=1.8 Hz), 7.44-7.47 (2H, m), 7.55-7.60 (2H, m), 7.73-7.78 (1H, m), 7.89 (1H, d, J=1.8 Hz), 8.62 (2H, s), 9.18 (2H, br), 9.23 (1H, s).

Example 230

N-Methyl-1-[1-(phenylsulfonyl)-5-(pyridin-3-yl)-1H-pyrrol-3-yl]methanamine dihydrochloride tert-Butyl {[5-bromo-1-(phenylsulfonyl)-1H-pyrrol-3-yl]methyl}methylcarbamate (170 mg), pyridin-3-ylboronic acid (244 mg), sodium carbonate (294 mg) and tetrakis(triphenylphosphine)palladium (92 mg) were added to 1,2-dimethoxyethane (10 mL) and water (5 mL), and the mixture was stirred at 90° C. for 4 hr. After the reaction mixture was cooled to room temperature, water was added and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=1:1→1:3) to give N-Boc compound of the title compound as a colorless oil. The obtained oil was dissolved in methanol (20 mL), a 4 mol/L hydrogen chloride-ethyl acetate solution (4 mL) was added, and the mixture was stirred at 70° C. for 30 min and concentrated under reduced pressure. The residue was suspended in a mixed solvent of methanol and tetrahydrofuran and collected by filtration to give the title compound as a colorless powder (yield 77 mg, 49%).

$^1$H-NMR (DMSO-d$_6$) δ: 2.47 (3H, t, J=5.5 Hz), 3.98 (2H, t, J=5.5 Hz), 6.72 (1H, d, J=1.8 Hz), 7.45-7.58 (4H, m), 7.70-7.76 (2H, m), 7.88 (1H, d, J=1.3 Hz), 7.95-7.98 (1H, m), 8.53 (1H, d, J=1.8 Hz), 8.76 (1H, dd, J=1.3, 5.3 Hz), 9.34 (2H, br).

Example 231

{1-[5-(2-Fluorophenyl)-2-methyl-1-(pyridin-3-ylsulfonyl)-1H-pyrrol-3-yl]-N-methylmethanamine fumarate A suspension of tert-butyl {1-[5-bromo-2-methyl-1-(pyridin-3-ylsulfonyl)-1H-pyrrol-3-yl]methyl}methylcarbamate (369 mg), (2-fluorophenyl)boronic acid (234 mg), sodium carbonate (265 mg) and tetrakis(triphenylphosphine)palladium (48.9 mg) in 1,2-dimethoxyethane (15 mL) and water (7.5 mL) was stirred at 105° C. for 12 hr. After cooling to room temperature, water was added and the mixture was extracted with ethyl acetate. The extract was washed with saturated aqueous sodium hydrogencarbonate solution, water and saturated brine, dried over anhydrous magnesium sulfate, filtered, concentrated under reduced pressure. The residue was purified by silica gel column chromatography (eluent: hexane-ethyl acetate=1:4) to give N-Boc compound of the title compound. This was dissolved in ethanol (5 mL), and a 4 mol/L hydrogen chloride-ethyl acetate solution (2 mL) was added and the mixture was stirred at room temperature for 4 hr. The reaction mixture was concentrated under reduced pressure, and the residue was neutralized with saturated aqueous sodium hydrogencarbonate solution (50 mL). The mixture was extracted with ethyl acetate, and the extract was washed with saturated aqueous sodium hydrogencarbonate solution, water, saturated brine, and dried over anhydrous sodium sulfate. The solvent was evaporated under reduced pressure. The residue was purified by basic silica gel column chromatography (eluent: ethyl acetate), and further purified by HPLC(ODS, 0.1% trifluoroacetic acid containing water-0.1% trifluoroacetic acid containing acetonitrile=9:1→0.1% trifluoroacetic acid containing acetonitrile) to give trifluoroacetate of the title compound. The obtained trifluoroacetate was neutralized with saturated aqueous sodium hydrogencarbonate solution, and the mixture was extracted with ethyl acetate. The extract was washed successively with saturated aqueous sodium hydrogencarbonate solution, water and saturated brine, dried over anhydrous magnesium sulfate, and the solvent was evaporated under reduced pressure to give a free base of the title compound (yield 65 mg). The free base (62 mg) was dissolved in ethyl acetate (2 mL), a solution of fumaric acid (17 mg) in methanol (2 mL) was added, and the mixture was stirred for 10 min. The reaction mixture was concentrated under reduced pressure, and the residue was recrystallized from ethanol to give the title compound as white crystals (yield 25 mg, 7%).

$^1$H-NMR (DMSO-d$_6$) δ: 2.35 (3H, s), 2.40 (3H, s), 3.75 (2H, s), 6.46 (3H, s), 7.20-7.28 (3H, s), 7.44-7.52 (1H, m), 7.63-7.67 (1H, m), 7.88-7.92 (1H, m), 8.61 (1H, d, J=2.4 Hz), 8.88-8.90 (1H, m), 3H not detected.

Example 232

2,2,2-Trifluoro-N-({1-[(4-methylphenyl)sulfonyl]-5-phenyl-1H-pyrrol-3-yl}methyl)ethanamine trifluoroacetate A solution (15 mL) of 2,2,2-trifluoro-N-({1-[(4-methylphenyl)sulfonyl]-5-phenyl-1H-pyrrol-3-yl}methyl)acetamide (300 mg) in tetrahydrofuran was cooled at 0° C., 1 mol/L tetrahydrofuran solution of borane (2.84 mL) was added, and the mixture was stirred at room temperature for 5 hr and then at 50° C. for 3 hr. Water was added to the reaction mixture, the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=9:1→2:1), and the obtained oil was purified by preparative HPLC. The purified product was concentrated under reduced pressure, and the crystals precipitated during the process were collected by filtration. The crystals were recrystallized from ethyl acetate to give the title compound as colorless crystals (yield 70 mg, 20%).

$^1$H-NMR (CDCl$_3$) δ: 2.35 (3H, s), 3.37 (2H, q, J=7.0 Hz), 4.02 (2H, s), 4.80 (2H, br), 6.22 (1H, d, J=1.8 Hz), 7.05-7.40 (9H, m), 7.50 (1H, d, J=1.8 Hz).

The structures of the compounds described in the Examples are shown in Table 25-Table 33.

TABLE 25

| Ex. No. | $R^{1b}$ | $R^{2b}$ | $R^{3b}$ | $R^{4b}$ | $R^{5b}$ | addition salt |
|---|---|---|---|---|---|---|
| 117 | F$_3$C—⟨⟩—SO$_2$ | 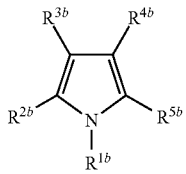 | | H | CH$_2$NHMe | Cl | HCl |

TABLE 25-continued
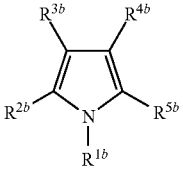
| Ex. No. | R$^{1b}$ | R$^{2b}$ | R$^{3b}$ | R$^{4b}$ | R$^{5b}$ | addition salt |
|---|---|---|---|---|---|---|
| 118 | 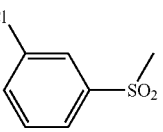 | 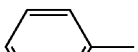 | H | CH$_2$NHMe | Me | HCl |
| 119 |  | 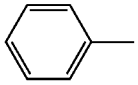 | H | CH$_2$NHMe | H | HCl |
| 120 | 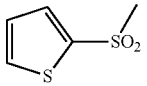 | 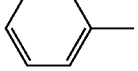 | H | CH$_2$NHMe | H | HCl |
| 121 | 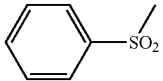 | 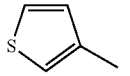 | H | CH$_2$NHMe | Me | HCl |
| 122 | 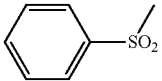 |  | H | CH$_2$NHMe | Me | HCl |
| 123 | 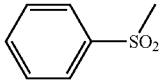 |  | H | CH$_2$NHEt | Me | HCl |
| 124 | 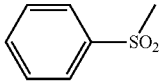 | 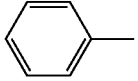 | Me | CH$_2$NHMe | Me | HCl |
| 125 | 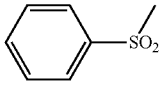 | 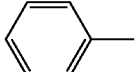 | n-Pr | CH$_2$NHMe | Me | HCl |
| 126 | 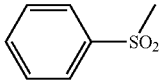 | 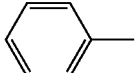 | 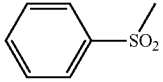 | CH$_2$NHMe | H | — |
| 127 | 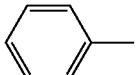 | 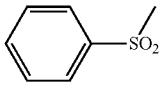 | H | CH$_2$NHMe | Cl | HCl |
| 128 | 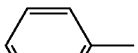 | 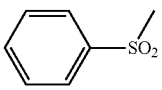 | H | CH$_2$NHMe | F | HCl |
| 129 | 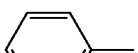 | 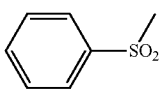 | F | CH$_2$NHMe | Cl | HCl |
| 130 | 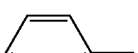 | | F | CH$_2$NHMe | H | HCl |

TABLE 25-continued
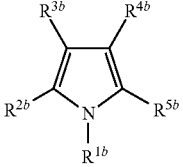
| Ex. No. | R[1b] | R[2b] | R[3b] | R[4b] | R[5b] | addition salt |
|---|---|---|---|---|---|---|
| 131 | 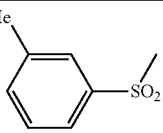 | 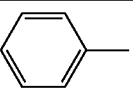 | H | CH$_2$NHMe | Me | HCl |
| 132 | 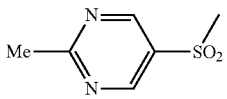 | 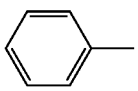 | H | CH$_2$NHMe | H | 2HCl |
| 133 | 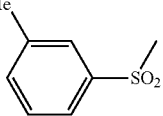 | 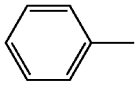 | Me | CH$_2$NHMe | H | HCl |
| 134 | 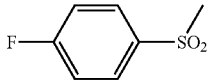 | 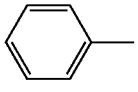 | Me | CH$_2$NHMe | H | HCl |
continued on Table 26
TABLE 26
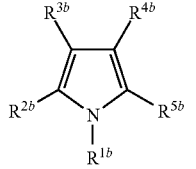
| Ex. No. | R[1b] | R[2b] | R[3b] | R[4b] | R[5b] | addition salt |
|---|---|---|---|---|---|---|
| 135 | 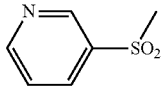 | 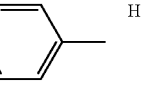 | H | CH$_2$NHMe | Me | 2HCl |
| 136 | 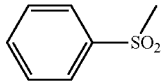 | 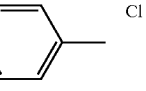 | Cl | CH$_2$NHMe | Me | HCl |
| 137 | 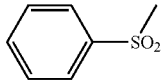 | n-Bu | H | CH$_2$NHMe | H | HCl |
| 138 | 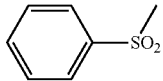 | 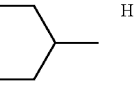 | H | CH$_2$NHMe | H | HCl |
| 139 | 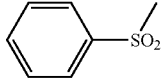 | 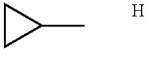 | H | CH$_2$NHMe | H | HCl |

TABLE 26-continued

[Pyrrole core structure with substituents R$^{1b}$ (N), R$^{2b}$, R$^{3b}$, R$^{4b}$, R$^{5b}$]

| Ex. No. | R$^{1b}$ | R$^{2b}$ | R$^{3b}$ | R$^{4b}$ | R$^{5b}$ | addition salt |
|---|---|---|---|---|---|---|
| 140 | 3-(MeO$_2$S)-phenyl-SO$_2$- | phenyl | H | CH$_2$NHMe | H | HCl |
| 141 | 3-(EtO$_2$S)-phenyl-SO$_2$- | phenyl | H | CH$_2$NHMe | H | HCl |
| 142 | 2,3-dihydro-1,4-benzodioxin-6-yl-SO$_2$- | phenyl | H | CH$_2$NHMe | H | HCl |
| 143 | 2-CN-phenyl-SO$_2$- | phenyl | H | CH$_2$NHMe | H | HCl |
| 144 | 4-NC-phenyl-SO$_2$- | phenyl | H | CH$_2$NHMe | H | HCl |
| 145/146 | 2-(CO$_2$Me)-phenyl-SO$_2$- | phenyl | H | CH$_2$NHMe | H | —/HCl |
| 147/148 | 3-(MeO$_2$C)-phenyl-SO$_2$- | phenyl | H | CH$_2$NHMe | H | —/HCl |
| 149 | 4-Cl-3-CN-phenyl-SO$_2$- | phenyl | H | CH$_2$NHMe | H | HCl |
| 150 | benzothiazol-6-yl-SO$_2$- | phenyl | H | CH$_2$NHMe | H | (COOH)$_2$ |
| 151 | 2,3-dihydro-1,1-dioxo-benzothiophen-6-yl-SO$_2$- | phenyl | H | CH$_2$NHMe | H | — |

TABLE 26-continued

Structure: pyrrole with R²ᵇ, R³ᵇ, R⁴ᵇ, R⁵ᵇ on ring carbons and R¹ᵇ on N

| Ex. No. | R¹ᵇ | R²ᵇ | R³ᵇ | R⁴ᵇ | R⁵ᵇ | addition salt |
|---|---|---|---|---|---|---|
| 152 | benzothiophen-2-yl-SO₂- | phenyl | H | CH₂NHMe | H | HCl | continued on Table 27

TABLE 27

Structure: pyrrole with R²ᵇ, R³ᵇ, R⁴ᵇ, R⁵ᵇ on ring carbons and R¹ᵇ on N

| Ex. No. | R¹ᵇ | R²ᵇ | R³ᵇ | R⁴ᵇ | R⁵ᵇ | addition salt |
|---|---|---|---|---|---|---|
| 153 | 4-(MeO₂)-C₆H₄-SO₂- | phenyl | H | CH₂NHMe | H | HCl |
| 154 | 3-(MeCO)-C₆H₄-SO₂- | phenyl | H | CH₂NHMe | H | 0.5(COOH)₂ |
| 155 | 3-(O₂N)-C₆H₄-SO₂- | phenyl | H | CH₂NHMe | H | HCl |
| 156 | pyridin-3-yl-SO₂- | phenyl | H | CH₂NHMe | H | 2HCl |
| 157 | 6-MeO-pyridin-3-yl-SO₂- | phenyl | H | CH₂NHMe | H | HCl |
| 158 | 6-MeHN-pyridin-3-yl-SO₂- | phenyl | H | CH₂NHMe | H | 2HCl |
| 159 | 2-MeHN-pyridin-3-yl-SO₂- | phenyl | H | CH₂NHMe | H | 2HCl |

TABLE 27-continued

[Pyrrole core structure with substituents R$^{1b}$, R$^{2b}$, R$^{3b}$, R$^{4b}$, R$^{5b}$]

| Ex. No. | R$^{1b}$ | R$^{2b}$ | R$^{3b}$ | R$^{4b}$ | R$^{5b}$ | addition salt |
|---|---|---|---|---|---|---|
| 160 | 2-(MeHN)-pyrimidin-5-yl-SO$_2$-CH$_2$- | phenyl | H | CH$_2$NHMe | H | HCl |
| 161 | 3-(MeO$_2$S)-phenyl-SO$_2$-CH$_2$- | 2-F-phenyl | H | CH$_2$NHMe | H | HCl |
| 162 | 3-(EtO$_2$S)-phenyl-SO$_2$-CH$_2$- | 2-F-phenyl | H | CH$_2$NHMe | H | HCl |
| 163 | 2-CN-phenyl-SO$_2$-CH$_2$- | 2-F-phenyl | H | CH$_2$NHMe | H | HCl |
| 164 | 4-NC-phenyl-SO$_2$-CH$_2$- | 2-F-phenyl | H | CH$_2$NHMe | H | HCl |
| 165 | 2-F-phenyl-SO$_2$-CH$_2$- | 2-F-phenyl | H | CH$_2$NHMe | H | HCl | continued on Table 28

TABLE 28

[Pyrrole core structure with substituents R$^{1b}$, R$^{2b}$, R$^{3b}$, R$^{4b}$, R$^{5b}$]

| Ex. No. | R$^{1b}$ | R$^{2b}$ | R$^{3b}$ | R$^{4b}$ | R$^{5b}$ | addition salt |
|---|---|---|---|---|---|---|
| 166 | pyridin-3-yl-SO$_2$-CH$_2$- | 2-F-phenyl | H | CH$_2$NHMe | H | fumaric acid |

TABLE 28-continued

| Ex. No. | R¹ᵇ | R²ᵇ | R³ᵇ | R⁴ᵇ | R⁵ᵇ | addition salt |
|---|---|---|---|---|---|---|
| 167 | 3-(MeO₂S)-C₆H₄-SO₂-CH₂- | 2-CF₃-C₆H₄-CH₂- | H | CH₂NHMe | H | HCl |
| 168 | pyridin-3-yl-SO₂-CH₂- | 2-CF₃-C₆H₄-CH₂- | H | CH₂NHMe | H | 2HCl |
| 169 | 3-(MeO₂S)-C₆H₄-SO₂-CH₂- | 2-Me-C₆H₄-CH₂- | H | CH₂NHMe | H | HCl |
| 170 | C₆H₅-SO₂-CH₂- | pyridin-2-yl-CH₂- | H | CH₂NHMe | H | (COOH)₂ |
| 171 | 3,4-diF-C₆H₃-SO₂-CH₂- | pyridin-2-yl-CH₂- | H | CH₂NHMe | H | 2HCl |
| 172 | 2,3-dihydro-1,4-benzodioxin-5-yl-SO₂-CH₂- | C₆H₅-CH₂- | Me | CH₂NHMe | H | HCl |
| 173 | 2,5-diMeO-C₆H₃-SO₂-CH₂- | C₆H₅-CH₂- | Me | CH₂NHMe | H | HCl |
| 174 | 2,3-dihydro-1,4-benzodioxin-6-yl-SO₂-CH₂- | C₆H₅-CH₂- | Me | CH₂NHMe | H | HCl |
| 175 | 3-(MeO₂S)-C₆H₄-SO₂-CH₂- | C₆H₅-CH₂- | Me | CH₂NHMe | H | HCl |
| 176 | thien-3-yl-SO₂-CH₂- | C₆H₅-CH₂- | Me | CH₂NHMe | H | HCl |

TABLE 28-continued

| Ex. No. | R$^{1b}$ | R$^{2b}$ | R$^{3b}$ | R$^{4b}$ | R$^{5b}$ | addition salt |
|---|---|---|---|---|---|---|
| 177 | pyridin-3-yl-SO$_2$-CH$_2$- | phenyl | Me | CH$_2$NHMe | H | 2HCl | continued on Table 29

TABLE 29

| Ex. No. | R$^{1b}$ | R$^{2b}$ | R$^{3b}$ | R$^{4b}$ | R$^{5b}$ | addition salt |
|---|---|---|---|---|---|---|
| 178 | pyridin-2-yl-SO$_2$-CH$_2$- | phenyl | Me | CH$_2$NHMe | H | HCl |
| 179 | 1,2-dimethyl-imidazol-4-yl-SO$_2$-CH$_2$- | phenyl | Me | CH$_2$NHMe | H | 2HCl |
| 180 | 5-chloro-1,3-dimethyl-pyrazol-4-yl-SO$_2$-CH$_2$- | phenyl | Me | CH$_2$NHMe | H | HCl |
| 181 | 1,3-dimethyl-pyrazol-4-yl-SO$_2$-CH$_2$- | phenyl | Me | CH$_2$NHMe | H | HCl |
| 182 | 2,4-dimethyl-thiazol-5-yl-SO$_2$-CH$_2$- | phenyl | Me | CH$_2$NHMe | H | CF$_3$COOH |
| 183 | pyridin-3-yl-SO$_2$-CH$_2$- | 2-fluorophenyl | Me | CH$_2$NHMe | H | HCl |

TABLE 29-continued

| Ex. No. | R$^{1b}$ | R$^{2b}$ | R$^{3b}$ | R$^{4b}$ | R$^{5b}$ | addition salt |
|---|---|---|---|---|---|---|
| 184 | phenyl-SO$_2$-Me | 3-pyridyl | H | CH$_2$NHMe | Me | 0.5(COOH)$_2$ |
| 185 | phenyl-SO$_2$-Me | 1-Me-pyrazol-4-yl | H | CH$_2$NHMe | Me | (COOH)$_2$ |
| 186 | phenyl-SO$_2$-Me | 3-thienyl | Me | CH$_2$NHMe | H | HCl |
| 187 | 4-(F$_3$CO$_2$S)-phenyl-SO$_2$-Me | phenyl | H | CH$_2$NHMe | H | HCl |
| 188 | 3-(F$_3$CO$_2$S)-phenyl-SO$_2$-Me | phenyl | H | CH$_2$NHMe | H | HCl |
| 189 | 3-(F$_3$CO$_2$S)-phenyl-SO$_2$-Me | 2-F-phenyl | H | CH$_2$NHMe | H | HCl | continued on Table 30

TABLE 30

| Ex. No. | R$^{1b}$ | R$^{2b}$ | R$^{3b}$ | R$^{4b}$ | R$^{5b}$ | addition salt |
|---|---|---|---|---|---|---|
| 190 | phenyl-SO$_2$-Me | phenyl | Me | CH$_2$NHMe | H | HCl |
| 191 | 3-Cl-phenyl-SO$_2$-Me | phenyl | Me | CH$_2$NHMe | H | HCl |

TABLE 30-continued
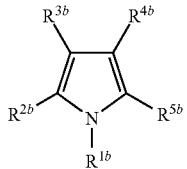
| Ex. No. | R¹ᵇ | R²ᵇ | R³ᵇ | R⁴ᵇ | R⁵ᵇ | addition salt |
|---|---|---|---|---|---|---|
| 192 | 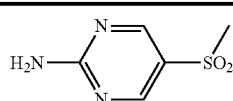 | 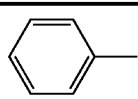 | H | CH₂NHMe | H | — |
| 193 | 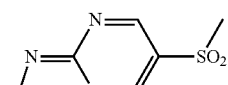 | 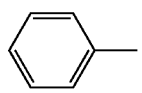 | H | CH₂NHMe | H | 2HCl |
| 194 | 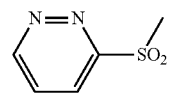 | 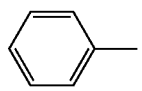 | H | CH₂NHMe | H | HO₂C–CH=CH–CO₂H |
| 195 |  | 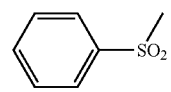 | H | CH₂NMe₂ | H | HCl |
| 196 | 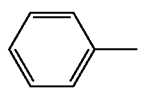 | 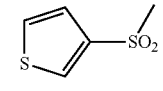 | H | CH₂NMe₂ | H | HCl |
| 197 | 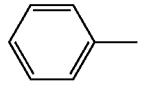 | 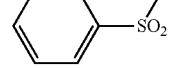 | H | CH₂NMe₂ | H | 2HCl |
| 198 | 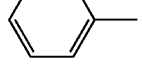 | 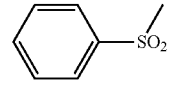 | Et | CH₂NHMe | H | HCl |
| 199 | 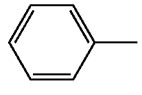 | 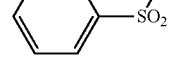 | i-Pr | CH₂NHMe | H | HCl |
| 200 | 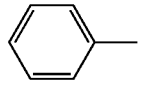 | 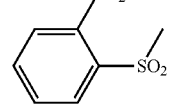 | H | CH₂NHMe | H | HCl |
| 201 | 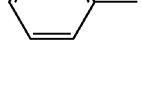 | 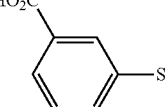 | H | CH₂NHMe | H | HCl |
| 202 | 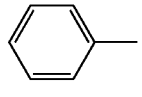 | 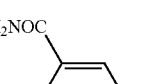 | H | CH₂NHMe | H | HCl | continued on Table 31

TABLE 31

[Pyrrole core structure with substituents R^1b (N), R^2b, R^3b, R^4b, R^5b]

| Ex. No. | R^1b | R^2b | R^3b | R^4b | R^5b | addition salt |
|---|---|---|---|---|---|---|
| 203 | 3-(MeSO₂)-phenyl with CONHcyclopropyl | phenyl | H | CH₂NHMe | H | HCl |
| 204 | 3-(MeSO₂)-phenyl with CONHMe | phenyl | H | CH₂NHMe | H | HCl |
| 205 | 3-(MeSO₂)-phenyl with CONMe | phenyl | H | CH₂NHMe | H | HCl |
| 206 | 3-(MeSO₂)-phenyl with CO-morpholine | phenyl | H | CH₂NHMe | H | HCl |
| 207 | 3-(MeSO₂)-phenyl with C(Me)₂OH | phenyl | H | CH₂NHMe | H | — |
| 208 | 4-(MeSO₂)-2-F-phenyl with CN | phenyl | H | CH₂NHMe | H | HCl |
| 209 | 3-(MeSO₂)-phenyl with 1H-tetrazol-5-yl | phenyl | H | CH₂NHMe | H | HCl |
| 210 | 2-(MeSO₂)-phenyl with CN | pyridin-3-yl | H | CH₂NHMe | H | 0.5(COOH)₂ |

TABLE 31-continued
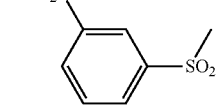
| Ex. No. | R$^{1b}$ | R$^{2b}$ | R$^{3b}$ | R$^{4b}$ | R$^{5b}$ | addition salt |
|---|---|---|---|---|---|---|
| 211 | 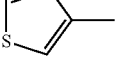 | 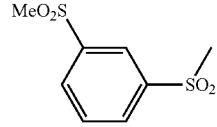 | H | CH$_2$NHMe | H | HCl |
| 212 | 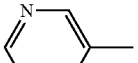 | 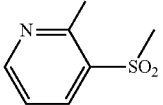 | H | CH$_2$NHMe | H | 2HCl |
| 213 | 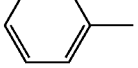 | 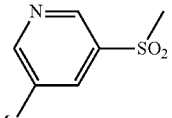 | H | CH$_2$NHMe | H | HCl |
| 214 | 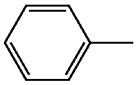 |  | H | CH$_2$NHMe | H | 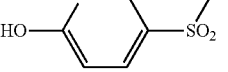 |
continued on Table 32
TABLE 32
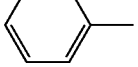
| Ex. No. | R$^{1b}$ | R$^{2b}$ | R$^{3b}$ | R$^{4b}$ | R$^{5b}$ | addition salt |
|---|---|---|---|---|---|---|
| 215 | 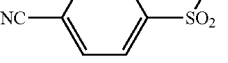 | 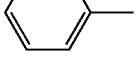 | H | CH$_2$NHMe | H | HCl |
| 216 | 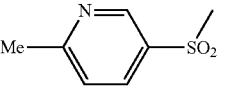 | 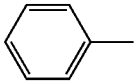 | H | CH$_2$NHMe | H | HCl |
| 217 | 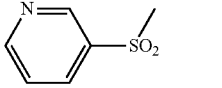 | 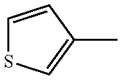 | H | CH$_2$NHMe | H | 2HCl |
| 218 | 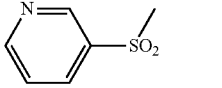 | 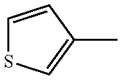 | H | CH$_2$NHMe | H | HCl |

TABLE 32-continued
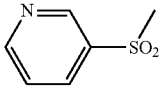
| Ex. No. | R$^{1b}$ | R$^{2b}$ | R$^{3b}$ | R$^{4b}$ | R$^{5b}$ | addition salt |
|---|---|---|---|---|---|---|
| 219 | 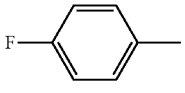 | 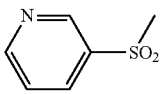 | H | CH$_2$NHMe | H | 2HCl |
| 220 | 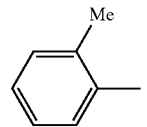 | 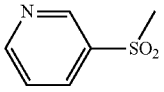 | H | CH$_2$NHMe | H | 2HCl |
| 221 | 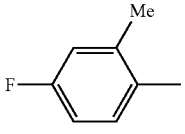 | 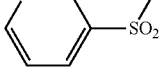 | H | CH$_2$NHMe | H | 2HCl |
| 222 | 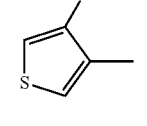 | 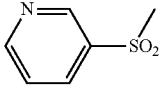 | H | CH$_2$NHMe | H | 2HCl |
| 223 | 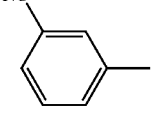 | 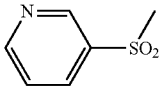 | H | CH$_2$NHMe | H | HCl |
| 224 | 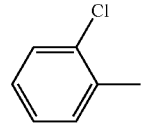 | 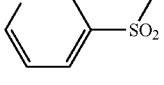 | H | CH$_2$NHMe | H | 2HCl |
| 225 | 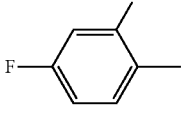 | 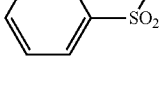 | H | CH$_2$NHMe | H | 2HCl |
| 226 | 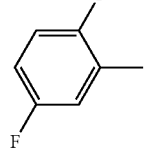 | 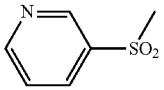 | H | CH$_2$NHMe | H | HCl |
| 227 | 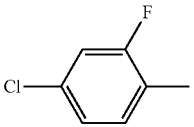 | | H | CH$_2$NHMe | H | 2HCl | continued on Table 33

TABLE 33

[Pyrrole core structure with substituents $R^{1b}$ (on N), $R^{2b}$, $R^{3b}$, $R^{4b}$, $R^{5b}$]

| Ex. No. | $R^{1b}$ | $R^{2b}$ | $R^{3b}$ | $R^{4b}$ | $R^{5b}$ | addition salt |
|---|---|---|---|---|---|---|
| 228 | 3-pyridyl-SO₂- | 3-fluorophenyl | H | CH₂NHMe | H | HCl |
| 229 | phenyl-SO₂- | 5-pyrimidinyl | H | CH₂NHMe | H | HCl |
| 230 | phenyl-SO₂- | 3-pyridyl | H | CH₂NHMe | H | HCl |
| 231 | 3-pyridyl-SO₂- | 2-fluorophenyl | H | CH₂NHMe | Me | HO₂C–CH=CH–CO₂H |
| 232 | 4-Me-phenyl-SO₂- | phenyl | H | CH₂NHCH₂CF₃ | H | CF₃COOH |

Experimental Example 1

Proton Potassium-adenosine Triphosphatase ($H^+,K^+$-ATPase) Inhibitory Activity Test According to the method [*Biochem. Biophys. Acta.*, 728, 31 (1983)] of Wallmark et al., a gastric mucous membrane microsomal fraction was prepared from the stomach of swine. First, the stomach was removed, washed with tap water, immersed in 3 mol/L brine, and the surface of the mucous membrane was wiped with a paper towel. The gastric mucous membrane was detached, chopped, and homogenized in a 0.25 mol/L saccharose solution (pH 6.8) containing 1 mmol/L EDTA and 10 mmol/L tris-hydrochloric acid using polytron (Kinematica). The obtained homogenate was centrifuged at 20,000×g for 30 min and the supernatant was centrifuged at 100,000×g for 90 min. The precipitate was suspended in 0.25 mol/L saccharose solution, superimposed on a 0.25 mol/L saccharose solution containing 7.5% Ficoll, and centrifuged at 100,000×g for 5 hr. The fraction containing the interface between the both layers was recovered, and centrifugally washed with 0.25 mol/L saccharose solution.

The obtained microsomal fraction was used as a proton, potassium-adenosine triphosphatase standard product.

To 40 μL of a 50 mmol/L HEPES-tris buffer (5 mmol/L magnesium chloride, 10 mmol/L potassium chloride, 10 μmol/L valinomycin, pH=6.5) containing 2.5 μg/mL (based on the protein concentration) of the enzyme standard product was added a test compound (5 μL) dissolved in a 10% aqueous dimethyl sulfoxide solution, and the mixture was incubated at 37° C. for 30 min. The enzyme reaction was started by adding 5 μL of a 2 mmol/L adenosine triphosphate tris salt solution (50 mmol/L HEPES-tris buffer (5 mmol/L magnesium chloride, pH 6.5)). The enzyme reaction was carried out at 37° C. for 20 min, and 15 μL of a malachite green solution (0.12% malachite green solution in sulfuric acid (2.5 mol/L), 7.5% ammonium molybdate and 11% Tween 20 were mixed at a ratio of 100:25:2) was added to quench the reaction. After allowing to stand at room temperature for 15 min, the resulting reaction product of inorganic phosphorus with malachite green was colorimetrically determined at a wavelength of 610 nm. In addition, the amount of the inorganic phosphoric acid in the reaction solution free of potassium chloride was measured in the same manner, which was subtracted from the inorganic phosphoric acid amount in the presence of potassium chloride to determine the proton, potassium-adenosine triphosphatase activity. The inhibitory rate (%) was determined from the activity value of the control and the activity values of various concentrations of the test compound, and the 50% inhibitory concentration ($IC_{50}$) of the proton, potassium-adenosine triphosphatase was determined. The results are shown in Tables 34 and 35.

TABLE 34

| Example compound | IC$_{50}$ (μM) |
|---|---|
| 7 | 0.091 |
| 11 | 0.051 |
| 12 | 0.71 |

TABLE 35

| Example No. | H$^+$/K$^+$-ATPase inhibitory activity (IC$_{50}$, nM) |
|---|---|
| 30 | 4.2 |
| 43 | 51 |
| 140 | 78 |
| 152 | 33 |
| 157 | 13 |
| 161 | 62 |
| 165 | 9.0 |
| 166 | 22 |
| 204 | 86 |
| 220 | 36 |
| 225 | 8.9 |

From the results of Tables 34 and 35, it is clear that compound (I) of the present invention has a superior H$^+$/K$^+$-ATPase inhibitory activity.

INDUSTRIAL APPLICABILITY

Since compound (I) shows a superior proton pump inhibitory effect, it can provide a clinically useful pharmaceutical agent for the prophylaxis and/or treatment of peptic ulcer, Zollinger-Ellison syndrome, gastritis, reflux esophagitis, gastroesophageal reflux disease (Symptomatic Gastroesophageal Reflux Disease (symptomatic GERD)) free of esophagitis, NUD (Non Ulcer Dyspepsia), gastric cancer, stomach MALT lymphoma, ulcer caused by non-steroidal anti-inflammatory agents or gastric hyperacidity and ulcer due to postoperative stress, and the like; a *Helicobacter pylori* eradicating agent; an inhibitor of upper gastrointestinal hemorrhage due to peptic ulcer, acute stress ulcer, hemorrhagic gastritis or invasive stress. Since compound (I) shows low toxicity and is superior in water-solubility, in vivo kinetics and efficacy expression, it is useful as a pharmaceutical. Moreover, since compound (I) is stable even under acidic conditions, which enables oral administration of the compound as a conventional tablet and the like without formulating an enteric-coated preparation. This has a consequence that the preparation of tablet and the like can be made smaller, which is advantageous in that it is easily taken by patients having difficulty in swallowing, particularly the elderly and children. In addition, since a sustained release effect afforded by enteric-coated preparations is absent, expression of a gastric acid secretion-suppressive action is rapid, and alleviation of symptoms such as pain and the like is rapid.

This application is based on patent application Nos. 2004-289169 and 2005-44740 filed in Japan, the contents of which are incorporated in full herein by this reference.

The invention claimed is:
1. A compound represented by the formula (II-a)

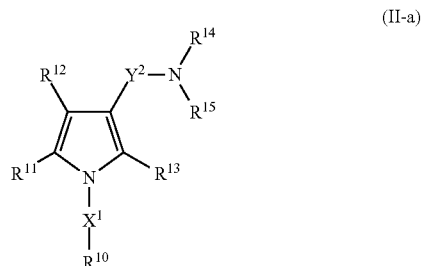

(II-a)

wherein X$^1$ is —SO$_2$—,
Y$^1$ is an optionally substituted alkylene group wherein a substituent of Y$^1$ does not include an oxo group,
R$^{10}$ is an optionally substituted phenyl group,
R$^{11}$ is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group,
R$^{12}$ is a halogen atom or an optionally substituted hydrocarbon group,
R$^{13}$ is a halogen atom or an optionally substituted hydrocarbon group,
R$^{14}$ is a hydrogen atom or a methyl group, and
R$^{15}$ is a methyl group,
wherein the hydrocarbon group, for R$^{11}$, R$^{12}$ and R$^{13}$, is selected from C$_{1-6}$ alkyl, C$_{2-6}$ alkenyl, C$_{2-6}$ alkynyl, C$_{3-7}$ cycloalkyl, C$_{6-14}$ aryl, and C$_{7-16}$ aralkyl;
wherein each of C$_{1-6}$ alkyl, C$_{2-6}$ alkenyl, and C$_{2-6}$ alkynyl, for R$^{11}$, R$^{12}$ and R$^{13}$, may independently optionally be substituted by 1 to 3 substituents selected from (1) a halogen atom, (2) nitro, (3) cyano, (4) hydroxy, (5) C$_{1-6}$ alkoxy optionally having 1 to 3 halogen atoms, (6) C$_{6-14}$ aryloxy, (7) C$_{7-16}$ aralkyloxy, (8) mercapto, (9) C$_{1-6}$ alkylthio optionally having 1 to 3 halogen atoms, (10) C$_{6-14}$ arylthio, (11) C$_{7-16}$ aralkylthio, (12) amino, (13) mono-C$_{1-6}$ alkylamino, (14) mono-C$_{6-14}$ arylamino, (15) mono-C$_{7-16}$ aralkylamino, (16) di-C$_{1-6}$ alkylamino, (17) di-C$_{6-14}$ arylamino, (18) di-C$_{7-16}$ aralkylamino, (19) formyl, (20) C$_{1-6}$ alkyl-carbonyl, (21) C$_{6-14}$ aryl-carbonyl, (22) carboxyl, (23) C$_{1-6}$ alkoxy-carbonyl, (24) C$_{6-14}$ aryloxy-carbonyl, (25) carbamoyl, (26) thiocarbamoyl, (27) mono-C$_{1-6}$ alkyl-carbamoyl, (28) di-C$_{1-6}$ alkyl-carbamoyl, (29) C$_{6-14}$ aryl-carbamoyl, (30) C$_{1-6}$ alkylsulfonyl, (31) C$_{6-14}$ arylsulfonyl, (32) C$_{1-6}$ alkylsulfinyl, (33) C$_{6-14}$ arylsulfinyl, (34) formylamino, (35) C$_{1-6}$ alkyl-carbonylamino, (36) C$_{6-14}$ aryl-carbonylamino (, (37) C$_{1-6}$ alkoxy-carbonylamino, (38) C$_{1-6}$ alkylsulfonylamino, (39) C$_{6-14}$ arylsulfonylamino, (40) C$_{1-6}$ alkyl-carbonyloxy, (41) C$_{6-14}$ aryl-carbonyloxy, (42) C$_{1-6}$ alkoxy-carbonyloxy, (43) mono-C$_{1-6}$ alkyl-carbamoyloxy, (44) di-C$_{1-6}$ alkyl-carbamoyloxy, (45) C$_{6-14}$ aryl-carbamoyloxy, (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group containing, besides carbon atom, 1 or 2 kinds of 1 to 4 hetero atoms selected from a nitrogen atom, a sulfur atom and an oxygen atom, (48) $C_{1-3}$ alkylenedioxy, and (49) $C_{3-7}$ cycloalkyl;

wherein each of $C_{3-7}$ cycloalkyl, $C_{6-14}$ aryl, and $C_{7-16}$ aralkyl, for $R^{11}$, $R^{12}$ and $R^{13}$, and phenyl for $R^{10}$ may independently optionally be substituted by 1 to 5 substituents selected from (1) a halogen atom, (2) nitro, (3) cyano, (4) hydroxy, (5) $C_{1-6}$ alkoxy optionally having 1 to 3 halogen atoms, (6) $C_{6-14}$ aryloxy, (7) $C_{7-16}$ aralkyloxy, (8) mercapto, (9) $C_{1-6}$ alkylthio optionally having 1 to 3 halogen atoms, (10) $C_{6-14}$ arylthio, (11) $C_{7-16}$ aralkylthio, (12) amino, (13) mono-$C_{1-6}$ alkylamino, (14) mono-$C_{6-14}$ arylamino, (15) mono-$C_{7-16}$ aralkylamino, (16) di-$C_{1-6}$ alkylamino, (17) di-$C_{6-14}$ arylamino, (18) di-$C_{7-16}$ aralkylamino, (19) formyl, (20) $C_{1-6}$ alkyl-carbonyl, (21) $C_{6-14}$ aryl-carbonyl, (22) carboxyl, (23) $C_{1-6}$ alkoxy-carbonyl, (24) $C_{6-14}$ aryloxy-carbonyl, (25) carbamoyl, (26) thiocarbamoyl, (27) mono-$C_{1-6}$ alkyl-carbamoyl, (28) di-$C_{1-6}$ alkyl-carbamoyl, (29) $C_{6-14}$ aryl-carbamoyl, (30) $C_{1-6}$ alkylsulfonyl optionally having 1 to 3 halogen atoms, (31) $C_{6-14}$ arylsulfonyl, (32) $C_{1-6}$ alkylsulfinyl, (33) $C_{6-14}$ arylsulfinyl, (34) formylamino, (35) $C_{1-6}$ alkyl-carbonylamino, (36) $C_{6-14}$ aryl-carbonylamino, (37) $C_{1-6}$ alkoxy-carbonylamino, (38) $C_{1-6}$ alkylsulfonylamino, (39) $C_{6-14}$ arylsulfonylamino, (40) $C_{1-6}$ alkyl-carbonyloxy, (41) $C_{6-14}$ aryl-carbonyloxy, (42) $C_{1-6}$ alkoxy-carbonyloxy, (43) mono-$C_{1-6}$ alkyl-carbamoyloxy, (44) di-$C_{1-6}$ alkyl-carbamoyloxy, (45) $C_{6-14}$ aryl-carbamoyloxy, (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group containing, besides carbon atom, 1 or 2 kinds of 1 to 4 hetero atoms selected from a nitrogen atom, a sulfur atom and an oxygen atom, (48) $C_{1-3}$ alkylenedioxy, (49) $C_{3-7}$ cycloalkyl, (50) $C_{1-6}$ alkyl group optionally having 1 to 3 halogen atoms or hydroxy groups, (51) a $C_{2-6}$ alkenyl group optionally having 1 to 3 halogen atoms, (52) a $C_{2-6}$ alkynyl group, (53) mono-$C_{3-7}$ cycloalkyl-carbamoyl, and (54) a 5 to 10-membered heterocyclyl-carbonyl containing, besides carbon atom, one or two kinds of 1 to 4 heteroatoms selected from a nitrogen atom, a sulfur atom and an oxygen atom;

wherein benzo[b]thienyl group, for $R^{11}$, may optionally be substituted by 1 to 5 substituents selected from (1) a halogen atom, (2) nitro, (3) cyano, (4) hydroxy, (5) $C_{1-6}$ alkoxy optionally having 1 to 3 halogen atoms, (6) $C_{6-14}$ aryloxy, (7) $C_{7-16}$ aralkyloxy, (8) mercapto, (9) $C_{1-6}$ alkylthio optionally having 1 to 3 halogen atoms, (10) $C_{6-14}$ arylthio, (11) $C_{7-16}$ aralkylthio, (12) amino, (13) mono-$C_{1-6}$ alkylamino, (14) mono-$C_{6-14}$ arylamino, (15) mono-$C_{7-16}$ aralkylamino, (16) di-$C_{1-6}$ alkylamino, (17) di-$C_{6-14}$ arylamino, (18) di-$C_{7-16}$ aralkylamino, (19) formyl, (20) $C_{1-6}$ alkyl-carbonyl, (21) $C_{6-14}$ aryl-carbonyl, (22) carboxyl, (23) $C_{1-6}$ alkoxy-carbonyl, (24) $C_{6-14}$ aryloxy-carbonyl, (25) carbamoyl, (26) thiocarbamoyl, (27) mono-$C_{1-6}$ alkyl-carbamoyl, (28) di-$C_{1-6}$ alkyl-carbamoyl, (29) $C_{6-14}$ aryl-carbamoyl, (30) $C_{1-6}$ alkylsulfonyl optionally having 1 to 3 halogen atoms, (31) $C_{6-14}$ arylsulfonyl, (32) $C_{1-6}$ alkylsulfinyl, (33) $C_{6-14}$ arylsulfinyl, (34) formylamino, (35) $C_{1-6}$ alkyl-carbonylamino, (36) $C_{6-14}$ aryl-carbonylamino, (37) $C_{1-6}$ alkoxy-carbonylamino, (38) $C_{1-6}$ alkylsulfonylamino, (39) $C_{6-14}$ arylsulfonylamino, (40) $C_{1-6}$ alkyl-carbonyloxy, (41) $C_{6-14}$ aryl-carbonyloxy, (42) $C_{1-6}$ alkoxy-carbonyloxy, (43) mono-$C_{1-6}$ alkyl-carbamoyloxy, (44) di-$C_{1-6}$ alkyl-carbamoyloxy, (45) $C_{6-14}$ aryl-carbamoyloxy, (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group containing, besides carbon atom, 1 or 2 kinds of 1 to 4 hetero atoms selected from a nitrogen atom, a sulfur atom and an oxygen atom, (48) $C_{1-3}$ alkylenedioxy, (49) $C_{3-7}$ cycloalkyl, (50) $C_{1-6}$ alkyl group optionally having 1 to 3 halogen atoms or hydroxy groups, (51) a $C_{2-6}$ alkenyl group optionally having 1 to 3 halogen atoms, (52) a $C_{2-6}$ alkynyl group, (53) mono-$C_{3-7}$ cycloalkyl-carbamoyl, and (54) a 5 to 10-membered heterocyclyl-carbonyl containing, besides carbon atom, one or two kinds of 1 to 4 heteroatoms selected from a nitrogen atom, a sulfur atom and an oxygen atom; and wherein each of thienyl group, furyl group, pyridyl group, pyrazolyl group, and pyrimidinyl group, for $R^{11}$, may optionally be substituted by 1 to 3 substituents selected from (1) a halogen atom, (2) nitro, (3) cyano, (4) hydroxy, (5) $C_{1-6}$ alkoxy optionally having 1 to 3 halogen atoms, (6) $C_{6-14}$ aryloxy, (7) $C_{7-16}$ aralkyloxy, (8) mercapto, (9) $C_{1-6}$ alkylthio optionally having 1 to 3 halogen atoms, (10) $C_{6-14}$ arylthio, (11) $C_{7-16}$ aralkylthio, (12) amino, (13) mono-$C_{1-6}$ alkylamino, (14) mono-$C_{6-14}$ arylamino, (15) mono-$C_{7-16}$ aralkylamino, (16) di-$C_{1-6}$ alkylamino, (17) di-$C_{6-14}$ arylamino, (18) di-$C_{7-16}$ aralkylamino, (19) formyl, (20) $C_{1-6}$ alkyl-carbonyl, (21) $C_{6-14}$ aryl-carbonyl, (22) carboxyl, (23) $C_{1-6}$ alkoxy-carbonyl, (24) $C_{6-14}$ aryloxy-carbonyl, (25) carbamoyl, (26) thiocarbamoyl, (27) mono-$C_{1-6}$ alkyl-carbamoyl, (28) di-$C_{1-6}$ alkyl-carbamoyl, (29) $C_{6-14}$ aryl-carbamoyl, (30) $C_{1-6}$ alkylsulfonyl optionally having 1 to 3 halogen atoms, (31) $C_{6-14}$ arylsulfonyl, (32) $C_{1-6}$ alkylsulfinyl, (33) $C_{6-14}$ arylsulfinyl, (34) formylamino, (35) $C_{1-6}$ alkyl-carbonylamino, (36) $C_{6-14}$ aryl-carbonylamino, (37) $C_{1-6}$ alkoxy-carbonylamino, (38) $C_{1-6}$ alkylsulfonylamino, (39) $C_{6-14}$ arylsulfonylamino, (40) $C_{1-6}$ alkyl-carbonyloxy, (41) $C_{6-14}$ aryl-carbonyloxy, (42) $C_{1-6}$ alkoxy-carbonyloxy, (43) mono-$C_{1-6}$ alkyl-carbamoyloxy, (44) di-$C_{1-6}$ alkyl-carbamoyloxy, (45) $C_{6-14}$ aryl-carbamoyloxy, (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group containing, besides carbon atom, 1 or 2 kinds of 1 to 4 hetero atoms selected from a nitrogen atom, a sulfur atom and an oxygen atom, (48) $C_{1-3}$ alkylenedioxy, (49) $C_{3-7}$ cycloalkyl, (50) $C_{1-6}$ alkyl group optionally having 1 to 3 halogen atoms or hydroxy groups, (51) a $C_{2-6}$ alkenyl group optionally having 1 to 3 halogen atoms, (52) a $C_{2-6}$ alkynyl group, (53) mono-$C_{3-7}$ cycloalkyl-carbamoyl, and (54) a 5 to 10-membered heterocyclyl-carbonyl containing, besides carbon atom, one or two kinds of 1 to 4 heteroatoms selected from a nitrogen atom, a sulfur atom and an oxygen atom; or a salt thereof.

2. A pharmaceutical composition comprising the compound of claim 1 and a pharmacologically acceptable carrier.

3. A method for the treatment of peptic ulcer, Zollinger-Ellison syndrome, gastritis, reflux esophagitis, Symptomatic Gastroesophageal Reflux Disease, ulcer caused by a non-steroidal anti-inflammatory agent or gastric hyperacidity and ulcer due to postoperative stress in a mammal, which comprises administering an effective amount of the compound of claim 1 to the mammal.

* * * * *